US011105817B2

(12) United States Patent
Van Eyk et al.

(10) Patent No.: US 11,105,817 B2
(45) Date of Patent: Aug. 31, 2021

(54) ROLE OF CITRULLINATION IN DIAGNOSING DISEASES

(71) Applicant: Cedars-Sinai Medical Center, Los Angeles, CA (US)

(72) Inventors: Jennifer Van Eyk, Los Angeles, CA (US); Justyna Fert-Bober, Sherman Oaks, CA (US); Erin Crowgey, Newark, DE (US); Ronald Holewinski, Sherman Oaks, CA (US); Benjamin Phillip Berman, Culver City, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/575,697

(22) PCT Filed: Jun. 20, 2016

(86) PCT No.: PCT/US2016/038439
§ 371 (c)(1),
(2) Date: Nov. 20, 2017

(87) PCT Pub. No.: WO2016/205828
PCT Pub. Date: Dec. 22, 2016

(65) Prior Publication Data
US 2018/0299467 A1 Oct. 18, 2018

Related U.S. Application Data

(60) Provisional application No. 62/387,149, filed on Dec. 23, 2015, provisional application No. 62/233,231, filed on Sep. 25, 2015, provisional application No. 62/181,665, filed on Jun. 18, 2015.

(51) Int. Cl.
*G01N 33/50* (2006.01)
*G01N 33/68* (2006.01)

(52) U.S. Cl.
CPC ..... *G01N 33/6893* (2013.01); *G01N 33/6896* (2013.01); *G01N 2440/18* (2013.01); *G01N 2800/28* (2013.01); *G01N 2800/2814* (2013.01); *G01N 2800/2835* (2013.01); *G01N 2800/32* (2013.01)

(58) Field of Classification Search
None
See application file for complete search history.

(56) References Cited

U.S. PATENT DOCUMENTS

| 8,519,096 B2 | 8/2013 | Ling et al. |
| 10,309,974 B2 | 6/2019 | Fert-Bober et al. |
| 2001/0041680 A1 | 11/2001 | Schwarz |
| 2004/0265849 A1 | 12/2004 | Cargill et al. |
| 2006/0205708 A1 | 9/2006 | Eggenweiler et al. |
| 2011/0244492 A1 | 10/2011 | Ossetrova |
| 2014/0308676 A1 | 10/2014 | Fert-Bober et al. |
| 2017/0328915 A1 | 11/2017 | Fert-Bober et al. |
| 2018/0136232 A1 | 5/2018 | Fert-Bober et al. |

FOREIGN PATENT DOCUMENTS

| CA | 2817847 A1 | 5/2012 |
| CN | 107923917 A | 4/2018 |
| EP | 2638401 A2 | 9/2013 |
| EP | 2638401 BI | 2/2017 |
| EP | 3311176 A2 | 4/2018 |
| IN | 201817001039 A | 3/2018 |
| JP | 2007524100 A | 8/2007 |
| JP | 2009510464 A | 3/2009 |
| JP | 2009-155226 A | 7/2009 |
| JP | 2014503795 A | 2/2014 |
| JP | 2015021739 A | 2/2015 |
| JP | 5701994 B2 | 4/2015 |
| JP | 2018-524575 A | 8/2018 |
| WO | 2009/103988 A1 | 8/2009 |
| WO | 2010/104964 A1 | 9/2010 |
| WO | 2012/065176 A2 | 5/2012 |
| WO | 2014/016584 A | 1/2014 |
| WO | 2014/037911 A | 3/2014 |
| WO | 2016/205828 A2 | 12/2016 |

OTHER PUBLICATIONS

Choi et al., Abnormal-Accumulation of citrullinated proteins in Scrapie-Infected mouse brain, Alzheimer's & Dementia, The Journal of the Alzheimer's Association, Jul. 2006, vol. 2, Issue 3, Supplemental p. S551. (Year: 2006).*
Moscarello et al., The Role of Citrullinated Proteins Suggests a Novel Mechanism in the Pathogenesis of Multiple Sclerosis, Neurochem Res, 2007, 32, pp. 251-256. (Year: 2007).*
Ishigami et al., Abnormal Accumulation of Citrullinated Proteins Catalyzed by Peptidylargine Deiminase in Hippocampal Extracts from Patients with Alzheimer's Disease, Journal of Neuroscience Research 80, 2005, pp. 120-128. (Year: 2005).*
Bennike et al., Optimizing the Identification of Citrulllinated Peptides by Mass Spectrometry: Utilizing teh Inability of Trypsin to Cleave after Citrullinated Amino Acids, J Proteomics Bioinform 2013, 6:12, pp. 288-295. (Year: 2013).*
Almer et al., Inducible Nitric Oxide Synthase Up-Regulation in Transgenic Mouse Model of Familial Amyotrophic Lateral Sclerosis, Journal of Neurochemistry, 1999, pp. 2415-2425.

(Continued)

*Primary Examiner* — Gary Counts
(74) *Attorney, Agent, or Firm* — Linda B. Huber; Nixon Peabody LLP

(57) ABSTRACT

Provided herein are methods and markers for diagnosing cardiovascular disease and/or neurodegenearative diseases in a subject. The methods include obtaining a biological sample from a subject in need of diagnosis and detecting the amount of a citrullinated protein or a citrullinated peptide in the biological sample obtained from said subject.

7 Claims, 20 Drawing Sheets

Specification includes a Sequence Listing.

(56) References Cited

OTHER PUBLICATIONS

Amador et al., Serum Lactic Dehydrogenase Activity: An Analytical Assessment of Current Assays, Clinical Chemistry, 1963, vol. 9(4), pp. 391-399.

Avasthi et al., Serum Lipid Profile and Lipoprotein Lipase Activity in Patients of Ischaemic Heart Disease, Indian Journal of Clinical BioChemistry, 1992, vol. 7(2), pp. 199-202; Abstract Only.

Backs et al., Control of Cardiac Growth by Histone Acetylation/Deacetylation, Circulation Research, 2006, vol. 98, pp. 15-24.

Chang et al., Citrullination of Fibronectin in Rheumatoid Arthritis Synovial Tissue, Rheumatology, 2005, vol. 44(11), pp. 1374-1382.

Chang et al., Increased PADI4 Expression in Blood and Tissues of Patients with Malignant Tumors, BMC Cancer, 2009, vol. 9(1), pp. 40.

Gabriel et al., The Epidemiology of Rheumatoid Arthritis in Rochester, Minnesota, 1955-1985, Arthritis and Rheumatology, 1999, vol. 42(3), pp. 415-420.

Giles et al., Left Ventricular Structure and Function in Patients with Rheumatoid Arthritis, as Assessed by Cardiac Magnetic Resonance Imaging, Arthritis and Rheumatism, 2010, vol. 62, pp. 940-951.

Hermansson et al., Mass Spectrometric Analysis of Rheumatoid Arthritic Synovial Tissue Identifies Specific Citrullinaiton Siteson Fibrinogen, Proteomics, 2010.

Holm et al., Specific Modification of Peptide-Bound Citrulline Residues, Analytical Biochemistry, 2006, vol. 352, pp. 68-76.

Inagaki et al., Ca2+-Dependent Deimination-Induced Disassembly of Intermediate Filaments Involves Specific Modification of the Amino-Terminal Head Domain, Journal of Biological Chemistry, 1989, vol. 264, pp. 18119-18127.

Ishida-Yamamoto et al., Sequential Reorganization of Cornified Cell Keratin Filaments Involving Filaggrin-Mediated Compaction and Keratin 1 Deimination, Journal of Investigative Dermatology, 2002, vol. 118(2), pp. 282-287.

Jacquet et al., Identification of Cardiac Myosin-Binding Protein C as a Candidate Biomarker of Myocardial Infarction by Proteomics Analysis, Molecular Cell Proteomics, 2009, vol. 8(12), pp. 2687-2699.

Jaffe et al., Comparative Sensitivity of Cardiac Troponin I and Lactate Dehydrogenase Isoenzymes for Diagnosing Acute Myocardial Infarction, The American Association for Clinical Chemistry, 1996, vol. 42(11), pp. 1770-1776.

Kane et al., Subfraction of Heart Tissue: The "In Sequence" Myofilament Protein Extraction of Myocardial TissueCardiovascular Proteomics, 2007, vol. 357, pp. 87-90.

Kidd et al., Epitope Spreading to Cirullinated Antigens in Mouse Models of Autoimmune Arthritis and Demyelination, Arthritis Research and Therapy, 2008, vol. 10(5), pp. 1-12.

Levy et al., Incidence and Risk of Fatal Myocardial Infarction and Stroke Events in Rheumatoid Arthritis Patients, Clin Exp Rheumatol, 2008, vol. 4, pp. 673-679.

Lofberg et al., Myosin Heavy-Chain Fragments and Cardiac Troponins in the Serum in Rhabdomyolysis, Diagnostic Specificity of New BioChemical Markers, Arch Neurology, 1995, vol. 52(12), pp. 1210-1214; Abstract Only.

Lopez-Longo et al., Association Between Anti-Cyclic Citrullinated Peptide Antibodies and Ischemic Heart Disease in Patients with Rheumatoid Arthritis, Arthritis and Rheumatism, 2009, vol. 61(4), pp. 419-424.

Lundberg et al., Antibodies to Citrullinated α-Enolase Peptide 1 are Specific for Rheumatoid Arthritis and Cross-React with Bacterial Enolase, Arthritis and Rheumatology, 2008, vol. 58(10), pp. 3009-3019.

Makrygiannakis et al., Citrullination is an Inflammation-Dependent Process, Annals of Rheumatic Disease, 2006, vol. 65(9), pp. 1219-1222.

Martinez-Amat et al., Release of α-actin into Serum after Skeletal Muscle Damage, Br J Sports Medicine, 2005, vol. 39, pp. 830-834.

Mastronardi et al., Increased Citrullination of Histone H3 in Multiple Sclerosis Brain and Animal Models of Demyelination: A Role for Tumor Necrosis Factor-Induced Peptidylarginine Deiminase 4 Translocation, Journal of Neuroscience, 2006, vol. 26(44), pp. 11387-11396.

Nadareishvili et al., Cardiovascular, Rheumatologic and Pharmacologic Predictors of Stroke in Patients with Rheumatoid Arthritis, A Nested, Case-Control Study, Arthritis Care and Research, 2008, vol. 59(8), pp. 1090-1096.

Nicholas et al., Immunohistochemical Localization of Citrullinated Proteins in Adult Rat Brain, Journal of Comparative Neurology, 2003, vol. 459, pp. 251-266.

Okamoto et al., Serum Alpha 1-Antichimotrypsin Levels and Cardiovascular Risk Factors in the Japanese Elderly Population, J. Epidemiol., 1998, vol. 8(2), pp. 94-98.

Prion 2008 Conference Abstract Book retrieved from http://www.neuroprion.org/resources/pdf_docs/conferences/prion2008/abstract-book-prion2008.pdf on Jan. 24, 2014.

Raptopoulou et al., Anti-Citrullinated Antibodies in the Diagnosis and Prognosis of Rheumatoid Arthritis: Evolving Concepts, Critical Reviews in Clinical Lab Sciences, 2007, vol. 44(4), pp. 339-363.

Shevchenko et al., Mass Spectrometric Sequencing of Proteins from Silver-Stained Polyacrylamide Gels, Analytical Chemistry, 1996, vol. 68(5), pp. 850-858.

Shibata et al., Anti-Cyclic Citrullinated Peptide Antibodies and IL-23p19 in Psoriatic Arthritis, Journal of Dermatological Science, 2009, vol. 53(1), pp. 34-39.

Sihvonen et al., Death Rates and Causes of Death in Patients with Rheumatoid Arthritis: A Population-Based Study, Scandinavian Journal of Rheumatology, 2004, vol. 33(4), pp. 221-227.

Spencer et al., Role of Covalent Modifications of Histones in Regulating Gene Expression, Gene, 1999, vol. 240(1), pp. 1-12.

Stensland et al., Targeted Analysis of Protein Citrullination using Chemical Modification and Tandem Mass Spectrometry, Rapid Communication in Mass Spectrometry, 2009, vol. 23(17), pp. 2754-2762.

Strongin, Laboratory Diagnosis of Viral Infections, Sensetivity, Specificity and Predictive Value of Diagnostic Tests: Definitions and Clinical Applications, 1992, pp. 211-219.

Tarcsa et al., Protein Unfolding by Peptidylarginine Deiminase, Journal of Biological Chemistry, 1996, vol. 271(48), pp. 30709-30716.

Taub et al., Biomarkers of Heart Failure, Congestive Heart Failure, 2010, vol. 16, pp. S19-S24.

Torzewski et aL, Animal Models of C-Reactive Protein, Mediators of Inflammation, 2014, vol. 2014, pp. 1-7.

Turesson et al., Severe Extra-Articular Disease Manifestations are Associated with an Increased Risk of First Ever Cardiovascular Events in Patients with Rheumatoid Arthritis, Annals of Rheumatic Disease, 2007, vol. 66(1), pp. 70-75.

Van Der Vekiens et al., Human and Equine Cardiovascular Endocrinology: Beware to Compare, Cardiovascular Endocrinology, 2013, vol. 2(4), pp. 67-76.

Van Gaalen et al., Association between HLA Class II Genes and Autoantibodies to Cyclic Citrullinated Peptides (CCPs) Influences the Severity of Rheumatoid Arthritis, Arthritis and Rheumatology, 2004, vol. 50(7), pp. 2113-2121.

Wolfe et al., The Risk of Myocardial Infarction and Pharmacologic and Nonpharmacologic Myocardial Infarction Predictors in Rheumatoid Arthritis, Arthritis Rheumatism, 2008, vol. 58(9), pp. 2612-2621.

Yamada et al., Citrulline and Anti-Cyclic Citrullinated Peptide Antibodies in Rheumatoid Arthritis, Future Rheumatology, 2006, vol. 1(2), pp. 249-258.

Zhang et al., Proteomic Profiling of the Silkworm Skeletal Muscle Proteins during Larval-Pupal Metamorphosis, Journal of Proteome Research, 2007, vol. 6(6), pp. 2295-2303.

EP 11840460.7 Extended Search Report dated Feb. 14, 2014, 10 pages.

PCT/US2011/060640 International Preliminary Report on Patentability dated May 14, 2013, 4 pages.

PCT/US2011/060640 Written Opinion dated May 8, 2012, 3 pages.

PCT/US2016/038439 International Search Report and Written Opinion dated Dec. 8, 2016, 11 pages.

(56) References Cited

OTHER PUBLICATIONS

EP 16812648.0 Extended Search Report dated Oct. 19, 2018, 19 pages.
Jang et al., Accumulation of Citrullinated Proteins by Up-Regulated Peptidylarginine Deiminase 2 in Brains of Scrapie-Infecte d Mice, American Journal of Pathology, 2008, vol. 173 (4), pp. 1129-1142.
Jang et al., Peptidylarginine deiminase modulates the physiological roles of enolase via citrullination: links between altered multifunction of enolase and neurodegenerative diseases, Biochemical Journal, 2012, vol. 445 (2), pp. 183-192.
Jang et al., Peptidylarginine deiminase and protein citrullination in prion diseases: Strong evidence of neurodegeneration, Prion, 2013, vol. 7 (1), pp. 42-46.
Nicholas, Dual immunofluorescence study of citrullinated proteins in Parkinson diseased substantia nigra, Neuroscience Letters, 2011, vol. 495 (1), pp. 26-29.
Turner et al., Biomarkers in amyotrophic lateral sclerosis, Lancet Neurology, 2009, vol. 8 (1), pp. 94-109.
PCT/US2016/038439 International Preliminary Report on Patentability dated Dec. 19, 2017, 7 pages.
EP 16812648.0 Extended Search Report dated Feb. 13, 2019, 19 pages.
Fert-Bober et al., Citrullination of myofilament proteins in heart failure, Cardiovascular Research, 2015, 108, pp. 232-242.
Baka et al., Citrullination under physiological and pathological conditions. Joint Bone Spine 2012, 79:431-436.
Crowgey et al., An integrated approach for analyzing clinical genomic variant data from next-generation sequencing. J Biomol Tech 2015, 26:19-28.
De Ceuleneer et al. In Vivo relevance of citrullinated protines and the challenges in their detection. Proteomics, 2012, 12:752-760.
Demoruelle et al., Antibodies to citrullinated protein antigens (ACPAs): clinical and pathophysiologic significance. Curr Rheumatol Rep 2011, 13:421-430.
Eaton et al., Tropomyosin binding to F-actin induced by myosin heads. Science 1976, 192:1337-1339.
Escher et al., Using iRT, a normalized retention time for more targeted measurement of peptides. Proteomics 2012, 12:1111-1121.
Fert-Bober et al., Citrullination in Actin-Tropomyosin-Myosin Complex: Novel Regulatory Mechanism, Abstract, American Heart Association, Scientific Sessions 2014, Nov. 15-19, 2014, Chicago, Illinois.
Fert-Bober et al., Citrullination in Actin-Tropomyosin-Myosin Complex: Novel Regulatory Mechanism, Final Program, American Heart Association, Scientific Sessions 2014, Nov. 15-19, 2014, Chicago, Illinois.
Fert-Bober et al., SWATH-MS Technology for Citrullination: A Target for Neurodegenerative Diseases, Abstract Book, 14th Human Proteome Organization (HUPO) World Congress, Sep. 27-30, 2015, Vancouver, Canada.
Fert-Bober et al., SWATH-MS Technology for Citrullination: A Target for Neurodegenerative Diseases, Poster Presentation (P19.16), 14th Human Proteome Organization (HUPO) World Congress, Sep. 27-30, 2015, Vancouver, Canada.
Salinska et al., The C terminus of cardiac troponin I stabilizes the Ca2+-activated state of tropomyosin on actin filaments. Circ Res 2010, 106:705-711.
Gillet et al., Targeted data extraction of the MS/MS spectra generated by data-independent acquisition: a new concept for consistent and accurate proteome analysis. Mol Cell Proteomics 2012, 11:O111 016717.
Hensen et al., Methods for the detection of peptidylarginine diminase (PAD) activity and protein citrullination. Mol Cell Proteomics 2014, 13:388-396.
Hensen et al., Phenylglyoxal-based visualization of citrullinated proteins on Western blots. Molecules 2015, 20:6592-6600.
Kirk et al., Cardiac resynchronizaiton sensitizes the sarcomere to calcium by reactivating GSK-3beta. J Clin Invest. 2014, 1:129-38.
Liu et al., Mass spectrometric protein maps for biomarker discovery and clinical research. Expert Rev Mol Diagn 2013, 13:811-825.
Matt et al., Biomarker discovery: proteome fractionation and separation in biological samples. Physiol Genomics 2008, 33: 12-17.
Nascimento et al.Enzymatic characterization and functional domain mapping of brain myosin-V. J Biol Chem 1996, 271:17561-17569.
Natale et al., Protein Ontology: a controlled structured network of protein entities. Nucleic Acids Res 2014, 42: D415-421.
Okada et al., Genetics of rheumatoid arthritis contributes to biology and drug discovery. Nature 2014, 506:376-381.
Raijmakers et al., Elevated levels of fibrinogen-derived endogenous citrullinated peptides in synovial fluid of rheumatoid arthritis patients. Arthritis Res Ther 2012, 14:R114.
Ren et al., PhosSNP for systematic analysis of genetic polymorphisms that influence protein phosphorylation. Mol. Cell. Proteomics, 2010, 9:623-634.
Ryu et al., Genome-wide analysis to predict protein sequence variations that change phosphorylation sites or their corresponding kinases. Nucleic Acids Res., 2009, 37: 1297-1307.
Saito et al., A travel guide to Cytoscape plugins. Nat Methods 2012, 9:1069-1076.
Skorzewski et al., Effect of actin C-terminal modification on tropomyosin isoforms binding and thin filament regulation. Biochim Biophys Acta, 2009, 2: 237-243.
Sliwinska et al., role of actin C-terminus in regulation of striated muscle thin filament. Biophys J. 2008, 4: 1341.
Stahl et al., Data-controlled automation of liquid chromatography/tandem mass spectrometry analysis of peptide mixtures. J Am Soc Mass Spectrom 1996, 7: 532-540.
Tauhata et al., High affinity binding of brain myosin-Va to F-actin induced by calcium in the presence of ATP. J Biol Chem 2001, 276:39812-39818.
Uysal et al. Antibodies to citrullinated proteins: molecular interactions and arthritogenicity. Immunol Rev 2010, 233:9-33.
White et al. Special instrumentation and techniques for kinetic studies of contractile systems. Methods Enzymol 1982, 85: 698-708.
Yates et al., Method to correlate tandem mass spectra of modified peptides to amino acid sequences in the protein database. Anal Chem 1995, 67:1426-1436.
Zhang et al., Multiple reaction monitoring to identify site-specific troponin I phsphorylated residues in the failing human heart. Circulation 2012, 126: 1828-1837.
Jin et al., Identification and Characterization of Citrulline-Modified Brain Proteins by Combining HCD and CID Fragmentation, Proteomics, 2013, vol. 13, pp. 2682-2691.
Olsson et al., CSF and blood biomarkers for the diagnosis of Alzheimer's disease: a systematic review and meta-analysis, Lancet Neural, 2016, vol. 15, pp. 673-684.
Mattsson et al. Plasma tau in Alzheimer disease, American Academy of Neurology, 2016, pp. 1827-1835.
Goemaere et al., Peroxiredoxin Distribution in the Mouse Brain With Emphasis on Neuronal Populations Affected in Neurodegenerative Disorders, The Journal of Comparative Neurology, 2012, vol. 520, pp. 258-280.
Beckelman et al., Dysregulation of Elongation Factor 1A Expression is Correlated with Synaptic Plasticity Impairments in Alzheimer's Disease, J. Alzheimers Dis., 2016, vol. 54(2), pp. 669-678.

\* cited by examiner

| Gel view | MS/MS ID* | Accession Number | Coverage % | Observed pI/MW | Theoretical pI/MW | P<0.05 |
|---|---|---|---|---|---|---|
| 1 | Fatty acid binging protein heart | P05413 | 63.2 | 6.0/ 14.500 | 6.29/ 14.858 | 0.20* |
| 2 | L-lactate dehydrogenase B chain | P07195 | 35.9 | 5.8/ 36.00 | 5.71/ 36.638 | 0.13* |
| 3 | Vinculin | P18206 | 4.5 | 6.2/ 170.00 | 5.83/ 123.799 | 0.19* |
| 4 | Actin, alpha cardiac | P62736 | 30.1 | 5.5/ 44.00 | 5.24/ 42.009 | 0.020 |
| 5 | Tropomyosin | P09493 | 6.2 | 4.6/ 38.000 | 4.69/ 32.709 | 0.0020 |
| 6 | Myosin light chain | P08590 | 32 | 5.0/ 24.000 | 5.03/ 21.932 | 0.021 |
| 7 | Myosin regulatory light chain 2 | P10916 | 39.8 | 4.9/ 18.000 | 4.92/ 18.789 | 0.0018 |

* Not statistical significant

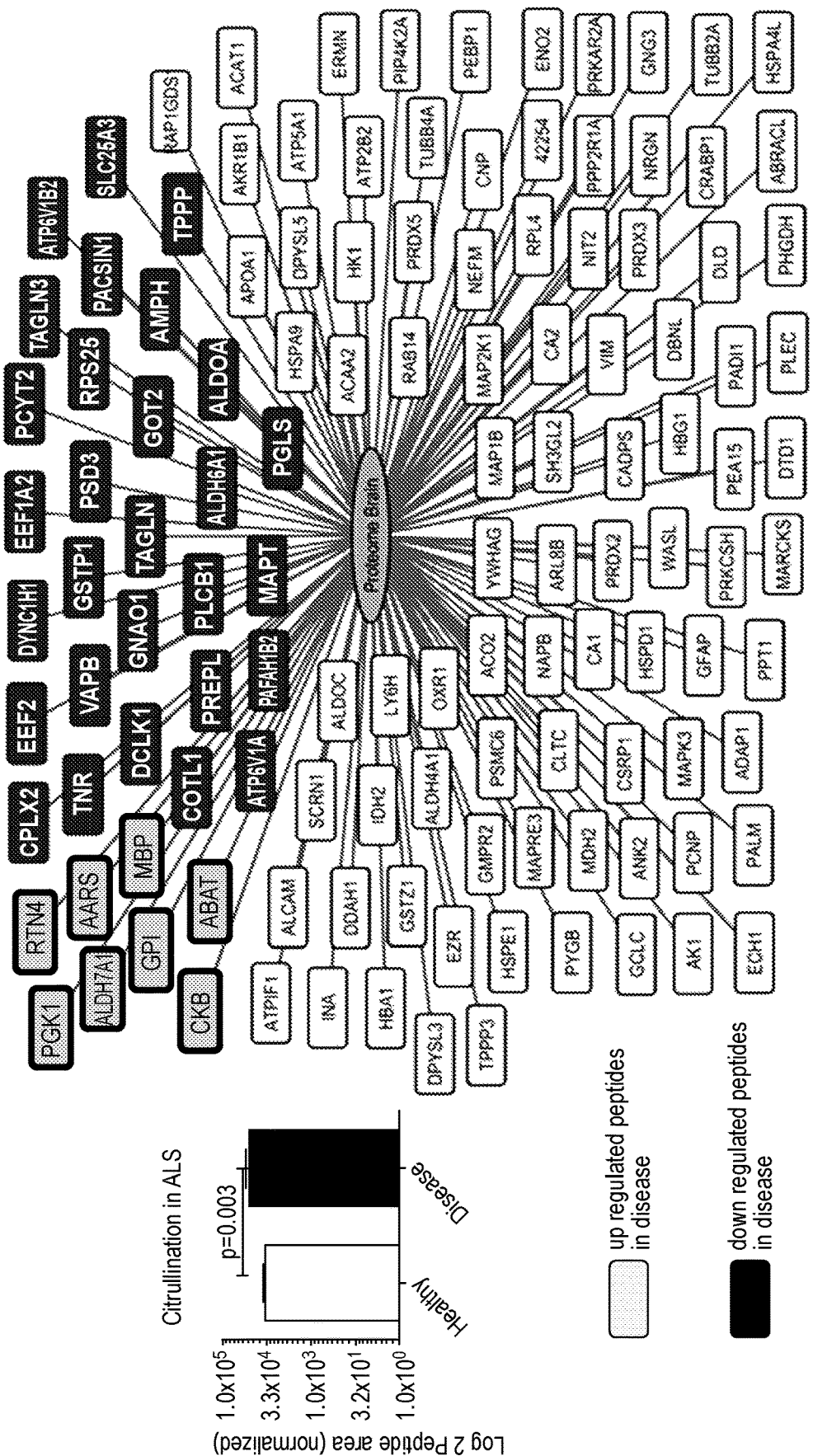
FIG. 8E Citrullination: A Target for ASL and other neurodegenerative disease

FIG. 8F

Protein of interest

| Protein name | Protein function |
|---|---|
| Glial fibrillary acidic protein | Class-III intermediate filament, is a cell-specific marker that, during the development of the central nervous system, distinguishes astrocytes from other glial cells. |
| Glucose-6-phosphate isomerase | GPI is a neurotrophic factor (Neuroleukin) for spinal and sensory neurons. |
| Vimentin | Vimentin is attached to the nucleus, endoplasmic reticulum, and mitochondria, either laterally or terminally. |
| Endophilin-A1 | Implicated in synaptic vesicle endocytosis. May recruit other proteins to membranes with high curvature. |
| Myelin basic protein | Role in formation and stabilization of myelin membrane in the CNS. |
| Delta-1-pyrroline-5-carboxylate dehydrogenase, mitochondrial | Irreversible conversion of delta-1-pyrroline-5-carboxylate(P5C), derived either from proline or ornithine, to glutamate. This is a necessary step in the pathway interconnecting the urea and tricarboxylic acid cycles. |
| Peroxiredoxin-5, mitochondrial | Reduces hydrogen peroxide and alkyl hydroperoxides with reducing equivalents provided through the thioredoxin system. Involved in intracellular redox signaling. |
| Neurogranin | Acts as a "third messenger" substrate of protein kinase C-mediated molecular cascades during synaptic development and remodeling. Binds to calmodulin in the absence of calcium. |
| Dual specificity mitogen-activated protein kinase kinase 1 | Dual specificity protein kinase which acts as an essential component of the MAP kinase signal transduction pathway |
| Tublin polymerization-promoting protein family member 3 | Binds tubulin and has microtubule bundling activity. May play a role in cell proliferation and mitosis |
| Delta(3,5)-Delta(2,4)- dienoyl-CoA isomerase, mitochondrial | This protein is involved in the pathway fatty acid beta-oxidation, which is part of Lipid metabolism. |
| Cysteine and glycine-rich protein 1 | Could play a role in neuronal development. |
| Cellular retinoic acid-binding protein 1 | Cytosolic CRABPs may regulate the access of retinoic acid to the nuclear retinoic acid receptors. |
| GMP reductase 2 | Catalyzes the irreversible NADPH-dependent deamination of GMP to IMP. |
| Guanine nucleotide-binding protein G(1)/G(S)/G(O) subunit gamma-3 | Guanine nucleotide-binding proteins (G proteins) are involved as a modulator or transducer in various transmembrane signaling systems. |

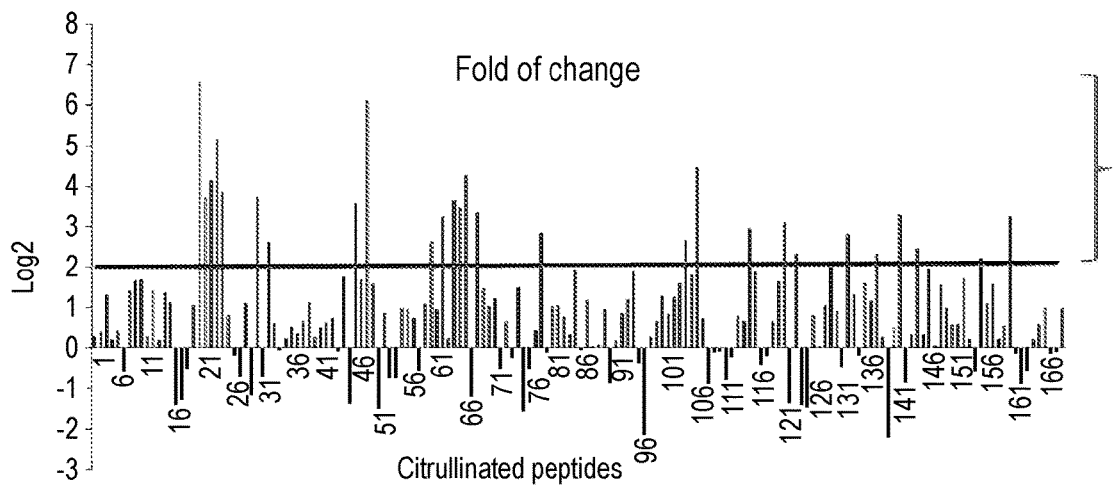

Disassembly of intermediate filaments by citrullination

ROLE OF CITRULLINATION IN DIAGNOSING DISEASES

CROSS-REFERENCE TO RELATED APPLICATIONS

This application is a National Phase of International Application No. PCT/US2016/38439 filed Jun. 20, 2016, which designated the U.S. and that International Application was published under PCT Article 21(2) in English, which also includes a claim of priority under 35 U.S.C. § 119(e) to U.S. provisional patent application No. 62/181,665 filed Jun. 18, 2015, U.S. provisional patent application No. 62/233,231 filed Sep. 25, 2015, U.S. provisional patent application No. 62/387,149 filed Dec. 23, 2015, the entirety of each of which are hereby incorporated by reference.

STATEMENT REGARDING FEDERALLY SPONSORED RESEARCH OR DEVELOPMENT

This invention was made with government support under Grant Nos. HL112586, HL077180 and HHSN268201000032C awarded by the National Institutes of Health. The government has certain rights in the invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Citrullination, the irreversible post-translational modification (PTM) involving the conversion of arginine to citrulline by the family of enzymes peptidylarginine deiminase (PAD), is associated with several diseases. Citrullination appears to be a generalized process; autoantibodies targeting citrullinated proteins are relatively specific for rheumatoid arthritis (RA) and, although occasionally observed in other autoimmune conditions, are uncommonly observed in healthy individuals. In our previous study, elevated levels of autoantibodies to citrullinated protein antigens were found in the myocardium of RA patients. PADs were detected in cardiomyocytes, resident inflammatory cells, endothelial cells and vascular smooth muscle cells.

Citrullination results in a small increase in molecular mass (+0.984 Da) but converts the positively charged guanidine group on an arginine residue into the neutrally charged ureido group on the citrulline amino acid. The loss of charge from an arginine to a citrulline can have dramatic consequences on protein structure, proteolytic susceptibility, protein-protein interactions and intracellular signaling. Since citrullination can lead to profound changes in protein structure and function, it is not surprising that citrullination and the PAD enzymes are found in numerous chronic diseases. Furthermore, the conversion of arginine to citrulline is catalyzed in a Ca2+-dependent manner with relatively high intracellular concentration of calcium. Because the cytosolic and nucleoplasmic calcium concentrations are relatively low, PADs should be inactive under normal conditions. However PADs become activated in injured and dying cells, when calcium concentrations increase because of the influx of calcium ions from the extracellular environment and release from intracellular calcium stores.

The actual proteins that are citrullinated in myocardium is unknown as is whether i) myocardial citrullinated proteins are immune targets for circulating autoantibodies, ii) myocardial citrullinated proteins can themselves induce an autoimmune response, and iii) citrullinated proteins directly mediate phenotypic modifications to cardiac structure or function. There is precedent for PTMs of myocardial proteins leading to changes in cardiac contractility and structure in heart failure (HF). Phosphorylation, oxidation, and acetylation of sarcomeric proteins cause morphologic changes to proteins that lead to decreased contractile performance and adverse cardiac remodeling with HF. However, it is unknown whether citrullination of myocardial proteins plays a similar role.

The framework of health information on neurodegenerative diseases sometimes includes brain diseases, defined as pathologic conditions also affecting the brain (composed of the intracranial components of the central nervous system). This includes (but is not limited to) the cerebral cortex, intracranial white matter, basal ganglia, thalamus, hypothalamus, brain stem, and cerebellum (MeSH definition). It is important to note that not all individuals with a family history of neurodegenerative disease will have an identifiable gene mutation. This could be because the responsible gene has not yet been identified, or because the disease is not actually due to a gene mutation.

There have been challenges in identification of citrullinated proteins and the modified amino acid residues. Here, the inventors provide examples of cirtullinated proteins and peptides showing modified amino acid residues which may serve as markers for cardiovascular diseases and neurodegenerative diseases.

SUMMARY

The following embodiments and aspects thereof are described and illustrated in conjunction with systems, compositions and methods which are meant to be exemplary and illustrative, not limiting in scope Provided herein are method for diagnosing and predicting cardiovascular diseases. The methods include obtaining a biological sample from a subject in need of diagnosing cardiovascular disease and detecting the amount of a citrullinated protein or a citrullinated peptide in the biological sample obtained from said subject. In some embodiments a change in the level of the citrullinated protein or the citrullinated peptide relative to a reference value is indicative of increase risk of cardiovascular disease. In one embodiment, the change in citrullination levels is an increase in the levels of the citrullinated protein or the citrullinated peptide relative to a reference value is indicative of increased risk of cardiovascular disease. In another embodiment, the change in citrullination levels is a decrease in the levels of the citrullinated protein or the citrullinated peptide relative to a reference value is indicative of increased risk of cardiovascular disease. In exemplary embodiments, presence of one or more citrullinated proteins or peptides shown in Table 1A, Table 1B, Table 1C, Table 1D and/or Table 1E is indicative of increased risk of cardiovascular disease. In exemplary embodiments, a change in the levels of citrullinated proteins or peptides shown in Table 1A, Table 1B, Table 1C, Table 1D and/or Table 1E is indicative of increased risk of cardiovascular diseases. In exemplary embodiments, the change in the levels is an increase in the levels of citrullination of proteins or peptides shown in Table 1A, Table 1B, Table 1C, Table 1D and/or Table 1E which is indicative of increased risk of cardiovascular diseases. In exemplary embodiments, the change in the levels is a decrease in the levels of citrullination of proteins or peptides shown in Table 1A, Table 1B, Table 1C, Table 1D and/or Table 1E which is indicative of increased risk of cardiovascular diseases. In some embodiments, an increase in citrullination levels of some peptides shown in Table 1A, Table 1B, Table 1C, Table 1D and/or Table 1E and a decrease in citrullination of some peptides shown in Table 1A, Table 1B, Table 1C, Table 1D and/or Table 1E is indicative of increased risk of cardiovascular disease. In various embodiments, citrullination is at the Arginine residues, as indicated as "Dea" in Table 1A, Table 1B, Table 1C, Table 1D and/or Table 1E. In exemplary embodiments, cardiovascular diseases are any one or more of ischemic heart disease (ISHD), idiopathic myopathy (IDCM) or combinations thereof.

Also provided herein are methods for treating cardiovascular diseases in a subject in need thereof. The methods include diagnosing cardiovascular diseases by the methods set forth herein and administering an effective amount of a therapeutic agent to the subject diagnosed with cardiovascular diseases so as to treat cardiovascular diseases in the subject. In exemplary embodiments, cardiovascular diseases are any one or more of ischemic heart disease (ISHD), idiopathic myopathy (IDCM) or combinations thereof.

Provided herein are methods for diagnosing and/or predicting amyotropic lateral sclerosis (ALS). The methods include obtaining a biological sample from a subject in need of diagnosing ALS and detecting citrullinated protein or citrullinated peptide in the biological sample obtained from said subject. In some embodiments, presence of citrullinated proteins or citrullnated peptides is indicative of increased risk of ALS. In some embodiments a change in the level of the citrullinated protein or the citrullinated peptide relative to a reference value is indicative of increased risk of ALS. In one embodiment, an increase in the levels of the citrullinated protein or the citrullinated peptide relative to a reference value is indicative of increased risk of ALS. In another embodiment, a decrease in the levels of the citrullinated protein or the citrullinated peptide relative to a reference value is indicative of increased risk of ALS. In an exemplary embodiment, presence of citrullinated peptides shown in Table 2 is indicative of ALS. In exemplary embodiments, presence of one or more citrullinated peptides shown in Tables 2, 3 or 4 is indicative of increased risk of ALS. In exemplary embodiments, a change in the levels of citrullinated peptides shown in Tables 2, 3 or 4 is indicative of increased risk of ALS. In exemplary embodiments, a change in the amount of citrullination of peptides shown in Tables 2, 3 or 4 is indicative of increased risk of neurodegenerative diseases. In various embodiments, citrullination is at the Arginine residues, as indicated as "Dea" in Table 2, 3 or 4.

Also provided herein are methods for treating ALS in a subject in need thereof. The methods include diagnosing ALS by the methods set forth herein and administering an effective amount of a therapeutic agent to the subject diagnosed with ALS so as to treat ALS in the subject.

Provided herein are methods for diagnosing and/or predicting chronic neurodegenerative disease. The methods include obtaining a biological sample from a subject in need of diagnosing chronic neurodegenerative disease and detecting citrullinated proteins or citrullinated peptides in the biological sample obtained from said subject. In some embodiments, presence of citrullinated proteins or citrullinated peptides is indicative of increased risk of chronic neurodegenerative disease. In some embodiments a change in the level of the citrullinated protein or the citrullinated peptide relative to a reference value is indicative of increased risk of chronic neurodegenerative disease. In one embodiment, an increase in the levels of the citrullinated protein or the citrullinated peptide relative to a reference value is indicative of increased risk of chronic neurodegenerative disease. In another embodiment, a decrease in the levels of the citrullinated protein or the citrullinated peptide relative to a reference value is indicative of increased risk of chronic neurodegenerative disease. In exemplary embodiments, a change in the levels of one or more citrullinated proteins or citrullinated peptides shown in Tables 5A-5B is indicative of increased risk of neurodegenerative diseases. In exemplary embodiments, the change in the cirullination levels is an increase in the levels of citrullination of one or more peptides or proteins shown in Tables 5A-5B which is indicative of increased risk of neurodegenerative diseases. In exemplary embodiments, the change in the citrullination levels is a decrease in the levels of citrullination of one or more peptides or proteins shown in Tables 5A-5B which is indicative of increased risk of chronic neurodegenerative diseases. In some embodiments, an increase in citrullination levels of some peptides shown in Table 5A-5B and a decrease in citrullination of some peptides shown in Tables 5A-5B is indicative of increased risk of chronic neurodegenerative disease. In exemplary embodiments, examples of neurodegenerative diseases include but are not limited to acquired brain injury, chronic neurodegenerative disease Alzheimer disease, Parkinson disease, Lewy body dementia, frontotemporal dementia, amyotrophic lateral sclerosis, Huntington disease, Friedreich's ataxia, spinal muscular atrophy, prion diseases, multiple sclerosis, stroke, degenerative nerve diseases, encephalitis, spinal muscular dystrophy and/or Creutzfeld-Jakob disease.

Also provided herein are methods for treating chronic neurodegenerative diseases in a subject in need thereof. The methods include diagnosing chronic neurodegenerative diseases by the methods set forth herein and administering an effective amount of a therapeutic agent to the subject diagnosed with chronic neurodegenerative disease so as to treat chronic neurodegenerative disease in the subject. In exemplary embodiments, examples of neurodegenerative diseases include but are not limited to acquired brain injury, chronic neurodegenerative disease Alzheimer disease, Parkinson disease, Lewy body dementia, frontotemporal dementia, amyotrophic lateral sclerosis, Huntington disease, Friedreich's ataxia, spinal muscular atrophy, prion diseases, multiple sclerosis, stroke, degenerative nerve diseases, encephalitis, spinal muscular dystrophy and/or Creutzfeld-Jakob disease.

Provided herein are methods for diagnosing and/or predicting acquired brain injury. The methods include obtaining a biological sample from a subject in need of diagnosing acquired brain injury and detecting citrullinated proteins or citrullinated peptides in the biological sample obtained from said subject. In some embodiments, presence of citrullinated proteins or citrullinated peptides is indicative of increased risk of acquired brain injury. In some embodiments a change in the level of the citrullinated protein or the citrullinated peptide relative to a reference value is indicative of increased risk of acquired brain injury. In one embodiment, an increase in the levels of the citrullinated protein or the citrullinated peptide relative to a reference value is indicative of increased risk of acquired brain injury. In another embodiment, a decrease in the levels of the citrullinated protein or the citrullinated peptide relative to a reference value is indicative of increased risk of acquired brain injury. In exemplary embodiments, presence of one or more citrullinated proteins or citrullinated peptides shown in Tables 6A-6B is indicative of increased risk of acquired brain injury. In exemplary embodiments, a change in the levels of one or more citrullinated proteins or citrullinated peptides shown in Tables 6A-6B is indicative of increased risk of acquired brain injury. In exemplary embodiments, the change in the levels of citrullination is an increase in the levels of one or more peptides or proteins shown in Tables 6A-6B which is indicative of increased risk of acquired brain injury. In exemplary embodiments, the change in the citrullination levels is a decrease in the levels of citrullination of one or more peptides or proteins shown in Tables 6A-6B which is indicative of increased risk of acquired brain injury. In some embodiments, an increase in citrullination levels of some peptides shown in Table 6A-6B and a decrease in citrullination of some peptides shown in Tables 6A-6B is indicative of increased risk of acquired brain injury. In exemplary embodiments, acquired brain injury includes but is not limited to traumatic brain injuries (TBI's), strokes, brain illness, tumor, hemorrhage, and any other kind of brain injury acquired after birth.

Also provided herein are methods for treating acquired brain injury in a subject in need thereof. The methods include diagnosing acquired brain injury by the methods set forth herein and administering an effective amount of a therapeutic agent to the subject diagnosed with acquired brain injury so as to treat acquired brain injury in the subject. In exemplary embodiments, acquired brain injury includes but is not limited to traumatic brain injuries (TBI's), strokes, brain illness, tumor, hemorrhage, and any other kind of brain injury acquired after birth.

BRIEF DESCRIPTION OF THE FIGURES

Exemplary embodiments are illustrated in referenced figures. It is intended that the embodiments and figures disclosed herein are to be considered illustrative rather than restrictive FIG. 1A (FIG. 1C) Detection of citrullinated proteins in heart obtained from control and HF patients (ISHD, IDCM) using 4-12% SDS PAGE. Densitometry analysis revealed that there was no significant change between groups.

(FIG. 2A) Samples labeled with Cy2 (internal control), Cy3 (untreated) and Cy5 (treated) as described in methods section. (FIG. 2B) Proteins described by the network: contractility and energy production. Citrullinated proteins up and down regulated in ischemia were mapped onto the human STRING database of known human protein interactions. Red, protein marked as down regulated, green, proteins up-regulated and blue=protein-protein interacting partner. The following abbreviations were used: FLNC: Filamin C; LDB3: LIM domain-binding protein 3; MYBPC: Myosin-binding protein C, cardiac-type; MYOZ2: Myozenin-2; TNNI3: Troponin I; MYH: Myosin; CRYAB: Alpha-crystallin B chain; VIM: ATP synthase subunit alpha; AHNAK: Neuroblast differentiation-associated protein; HSP9OAA1: Heat shock protein HSP 90-alpha; HSPD1: 60 kDa heat shock protein; PPIA: Peptidyl-prolyl cis-trans isomerase A; FABP3: Fatty acid-binding protein.

FIG. 4A) Regulation of the actomyosin HMM-ATPase activity by citrullinated F-actin and/or citrullinated HMM. FIG. 4B) Inhibition of actomyosin HMM-ATPase activity by TM. ATPase activity was measured as a function of TM concentration. The results are the average of four independent experiments for each protein at each TM concentration. Assay conditions: 0.2 mg/ml F-actin, 0.02 mg/ml HMM, 0-2.0 uM TM in 10 mM Hepes, pH 7.5, 30 mM NaCl, 5 mM MgCl2, 4 mM ATP. PAD2 treatment reduced myofilament calcium sensitivity. FIG. 4C) Force-calcium relationships for untreated membrane-permeabilized myocytes from untreated control (n=8 myocytes from 3 mice, gray circles) and PAD2 treated (n=8 myocytes from 3 mice, open circles) groups. FIG. 4D) There was no difference in maximal calcium activated force (Fmax) between the two groups. FIG. 4E) PAD2 treatment caused a significant (p=0.009) increase in EC50 (calcium required to generate 50% Fmax), indicating a decrease in calcium sensitivity. FIG. 4F) While the hill coefficient (nH) trended to be decreased by PAD2 treatment (see steepness of curve in panel C), the difference was not significant (p=0.34).

FIG. 8A-FIG. 8G depicts in accordance with various embodiments of the invention, the use of SWATH-MS (Sequential Window Acquisition of all Theoretical Fragment Ion Spectra—Mass Spectrometry) technology to identify citrullination of protein involved in neurodegenerative diseases.

DETAILED DESCRIPTION

Figure 1A:
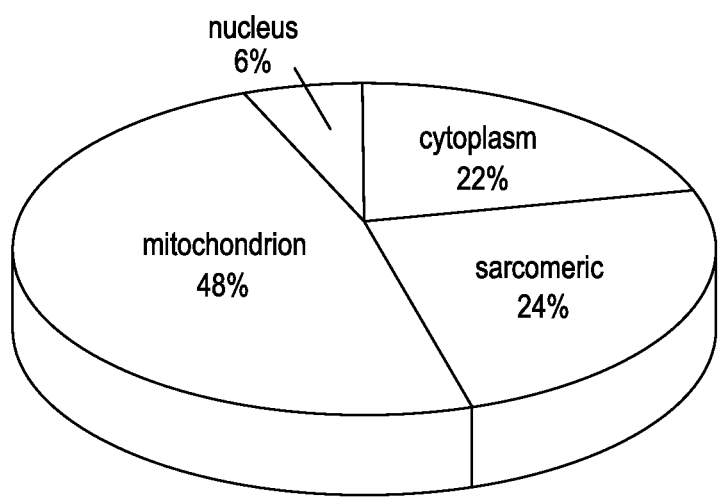
-FIG. 1C depicts in accordance with various embodiments of the invention, the cardiac citrullinated proteome. Diagrams show citrullinated proteins with significant p value group by (FIG. 1A) cellular component and by (FIG. 1B) molecular function. Details can be found in Tables 1A-F.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul., 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "marker" or "biomarker" are used interchangeably herein, and in the context of the present invention refer to a protein or peptide that has specific citrullinated amino acid residues or the enzyme itself, PAD 1, PAD2, PAD3 or PAD4 (of a particular specific identity or apparent molecular weight) which is differentially present in a sample taken from patients having a specific disease or disorder as compared to a control value, the control value consisting of, for example, average or mean values in comparable samples taken from control subjects (e.g., a person with a negative diagnosis, normal or healthy subject). Biomarkers may be determined as specific peptides or proteins (Tables 1-10) which may be detected by antibodies or mass spectroscopy. In some applications, for example, a mass spectroscopy or other profile or multiple antibodies may be used to determine multiple biomarkers, and differences between individual biomarkers and/or the partial or complete profile may be used for diagnosis. This can include detection of the enzyme or a protein it has citrullinated, alone or in combination.

The term "differentially present" or "change in level" refers to differences in the quantity and/or the frequency of a marker present in a sample taken from patients having a specific disease or disorder as compared to a control subject. For example, a marker can be present at an elevated level or at a decreased level in samples of patients with the disease or disorder compared to a control value (e.g. determined from samples of control subjects). Alternatively, a marker can be detected at a higher frequency or at a lower frequency in samples of patients compared to samples of control subjects. A marker can be differentially present in terms of quantity, frequency or both as well as a ratio of differences between two or more specific modified amino acid residues and/or the enzyme itself. In one embodiment, an increase in the ratio of modified to unmodified proteins and peptides described herein is diagnostic of any one or more of the diseases described herein. In an embodiment, an increase in citrullination of proteins and peptides as described herein refers to an increase in ratio of modified (citrullinated) to unmodified (non-citrullinated) proteins and/or peptides described herein. In one embodiment, a decrease in the ratio of modified to unmodified proteins and peptides described herein is diagnostic of any one or more of the diseases described herein. In an embodiment, a decrease in citrullination of proteins and peptides as described herein refers to a decrease in ratio of modified (citrullinated) to unmodified (non-citrullinated) proteins and/or peptides described herein.

A marker, compound, composition or substance is differentially present in a sample if the amount of the marker, compound, composition or substance in the sample is statistically significantly different from the amount of the marker, compound, composition or substance in another sample, or from a control value. For example, a compound is differentially present if it is present at least about 120%, at least about 130%, at least about 150%, at least about 180%, at least about 200%, at least about 300%, at least about 500%, at least about 700%, at least about 900%, or at least about 1000% greater or less than it is present in the other sample (e.g. control), or if it is detectable in one sample and not detectable in the other.

Alternatively or additionally, a marker, compound, composition or substance is differentially present between samples if the frequency of detecting the marker, etc. in samples of patients suffering from a particular disease or disorder, is statistically significantly higher or lower than in the control samples or control values obtained from healthy individuals. For example, a biomarker is differentially present between the two sets of samples if it is detected at least about 10%, at least about 20%, at least about 30%, at least about 40%, at least about 50%, at least about 60%, at least about 70%, at least about 80%, at least about 90%, or at least about 100% more frequently or less frequently observed in one set of samples than the other set of samples. These exemplary values notwithstanding, it is expected that a skilled practitioner can determine cut-off points, etc. that represent a statistically significant difference to determine whether the marker is differentially present.

"Diagnostic" means identifying the presence or nature of a pathologic condition and includes identifying patients who are at risk of developing a specific disease or disorder.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g. when positive assay results are obtained). In the latter context, "detecting" and "diagnosing" are considered synonymous.

By "indicative of" or "at risk of" is intended to mean at increased risk of, compared to a normal subject, or compared to a control group, e.g. a patient population. Thus a subject carrying a particular marker may have an increased risk for a specific disease or disorder, and be identified as needing further testing. "Increased risk" or "elevated risk" mean any statistically significant increase in the probability, e.g., that the subject has the disorder. The risk is preferably increased by at least 10%, more preferably at least 20%, and even more preferably at least 50% over the control group with which the comparison is being made.

A "test amount" of a marker refers to an amount of a marker present in a sample being tested. A test amount can be either in absolute amount (e.g., .mu.g/ml) or a relative amount (e.g., relative intensity of signals).

A "diagnostic amount" of a marker refers to an amount of a marker in a subject's sample that is consistent with a diagnosis of a particular disease or disorder. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person who does not suffer from the disease or disorder sought to be diagnosed. A control amount can be either in absolute amount (e.g., µg/ml) or a relative amount (e.g., relative intensity of signals).

The terms "polypeptide," "peptide" and "protein" are used interchangeably herein to refer to a polymer of .alpha.-amino acid residues, in particular, of naturally-occurring .alpha.-amino acids. The terms apply to amino acid polymers in which one or more amino acid residue is an analog or mimetic of a corresponding naturally-occurring amino acid, as well as to naturally-occurring amino acid polymers. Polypeptides can be modified, e.g., by the addition of carbohydrate residues to form glycoproteins, phosphorylation to form phosphoproteins, and a large number of chemical modifications (oxidation, deamidation, amidation, methylation, formylation, hydroxymethylation, guanidination, for example) as well as degraded, reduced, or cross-linked. The terms "polypeptide," "peptide" and "protein" include all unmodified and modified forms of the protein. A peptide would have a citrullinated residue or is part of the PAD enzyme.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct analysis by mass spectrometry of intact protein or peptides (one or more peptide can be assessed) that has a potential citrullinated residue or part of the PAD enzyme. Citrullinated Arg as part of a protein or peptide can be detected directly by MS or via chemical derivatization. Any capture reagent including but not limited to antibodies and aptamers may be used to detect cirullinated peptides described herein.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'.sub.2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution. Further, chemical binding to the citrullinated residue can occur directly.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

Methods for detecting citrullination refer to the mass spectrometry (MS) based methods used to detect citrullinated peptides, polypeptides and proteins. The methods include but are not restricted to neutral loss of 1 Da when deimination occurs on Arg; neutral loss of isocyanic acid from unmodified citrulline and used this ion as a diagnostic marker for detecting protein citrullination; derivatization when chemical modification of 238 Da or 239 Da occurs on Cit residue (can be monitored at the peptide and protein level); enrichment of citrullinated peptides (or proteins) that is based on the specific reaction of glyoxal derivatives that is immobilized on beads/column/matrix reacts exclusively with the ureido group of the citrulline residue at low pH. As well, MS using a targeted method like multiple or selective reaction monitoring can be used to quantify the modified peptide directly. In some embodiments, a labeled (e.g. labeled with $^{15}$N or chemically labeled with additional stable isotopes) peptide of known concentration is added to the sample and compared directly to the endogenous (unlabeled) corresponding peptide allowing for quantification (based on a ratio of the endogenous peptide to the isotopic labeled peptides or absolute concentration if the exact amount of the isotopic labeled peptide is known).

The terms "subject", "patient" or "individual" generally refer to a human, although the methods of the invention are not limited to humans, and should be useful in other animals (e.g. birds, reptiles, amphibians, mammals), particularly in mammals, since albumin is homologous among species.

"Sample" is used herein in its broadest sense. A sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Subject samples usually comprise derivatives of blood products, including blood, plasma and serum.

The term "modulation of specific PAD isoforms" includes but is not limited to, increasing or decreasing the activity of endogenous PAD isoforms using gene therapy, siRNA, known inhibitors of PADs, or site-directed mutagenesis.

The term "peptide" as used herein refers to a polymer of amino acid residues typically ranging in length from 2 to about 30, or to about 40, or to about 50, or to about 60, or to about 70 residues. In certain embodiments the peptide ranges in length from about 2, 3, 4, 5, 7, 9, 10, or 11 residues to about 60, 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an a-ester, a f3-ester, a thioamide, phosphonamide, carbamate, hydroxylate, and the like (see, e.g., Spatola, (1983) Chern. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn eta/., (1990) Pp. 969-970 in Proc. 11th American Peptide Symposium, ESCOM Science Publishers, The Netherlands, and the like)).

Citrullination (also called deimination) is a post-translational protein modification catalyzed by PADs that involves conversion of the amino acid arginine to citrulline within proteins. The involvement of citrullinated proteins in the pathogenesis of a number of autoimmune diseases has been established. For example, protein citrullination has been directly linked to the generation of autoantibodies contributing to rheumatoid arthritis (RA). However, the exact circumstances and underlying purpose of PAD activation and consequent protein citrullination within cells are not fully understood. In addition, the production of autoantibodies targeting citrullinated proteins has been implicated in many other autoimmune diseases such as multiple sclerosis, psoriasis, sporadic Creutzfeld-Jakob disease, Parkinson's disease and Alzheimer's disease (AD). The knowledge of citrullinated proteins and citrullinated sites in protein sequences can provide invaluable information about the etiological importance and function of these citrullinated proteins. Provided herein are new biomarkers predictive of cardiovascular diseases and neurodegenerative diseases which include citrullinated proteins and peptides.

Citrullination is linked to autoantigen and autoantibody response which may be used for detection or measurement of ratios of autoantigen (unmodified/not-citrullinated) to autoantigen (modified/citrullinated) to detect heart disease (citrullinated autoantibody/autoantigens as biomarker). Further, detection of citrullinated auoantibody can be used as risk stratification factor. Risk of developing heart failure (HF) and succumbing to myocardial infraction increases with age. Citrullination is known to increase with age and an increase in citrullination may be predictive of heart failure. Inhibition (eg. drug inhibition) of PAD enzyme responsible for citrullination may be a therapeutic target.

Protein citrullination plays a role in the generation of autoantibodies during the pathogenesis of specific neurodegenerative diseases such as Alzheimer's disease (AD). Since citrullination alters the overall charge distribution within a protein, potentially modifying tertiary structure, many citrullinated proteins in these PAD-expressing cells may be in a non-native conformation that is potentially immunogenic, especially if they are released from the cell and thus become accessible to immune surveillance.

Citrullination is linked to autoantigen and autoantibody response which may be used for detection or measurement of ratios of autoantigen (unmodified/not-citrullinated) to autoantigen (modified/citrullinated) to detect neurodegenerative disease (citrullinated autoantibody/autoantigens as biomarker). Citrullination is known to increase with age and an increase in citrullination may be predictive of neurodegenerative diseases. Inhibition (eg. drug inhibition) of PAD enzyme responsible for citrullination may be a therapeutic target.

Detection of Peptidyl-Citrulline—Comparison with Other Methods

Current research on citrullination focuses on its role in auto-immune diseases such as multiple sclerosis and rheumatoid arthritis (RA) [Baka Z, et al. Citrullination under physiological and pathological conditions. *Joint Bone Spine* 2012, 79:431-436; De Ceuleneer M, et al. In vivo relevance of citrullinated proteins and the challenges in their detection. *Proteomics* 2012, 12:752-760]. In this context, the exact knowledge of citrullination sites in a protein can provide invaluable information about the etiological importance of these citrullinated proteins. However, few techniques exist that can accurately detect citrullination at the peptide level in a high-throughput format.

In general analysis of PTMs by MS is a difficult task and dependent on PTM profound effect on local peptide characteristics, like: (i) the mass shift in the peptide molecular weight induced by the PTM, (ii) the overall abundance of the modified peptide, (iii) the stability of the modification during MS and MS/MS analysis, and (iv) the effect of the modification on the peptide's ionization efficiency. Citrullination is complicated as citrullinated proteins/peptides are difficult to discern from their non-PTM forms because citrullination leads to an additional mass of nominally 0.9802 Dalton compared to regular arginine residues, which prone to false positives. The commonly applied shotgun type liquid chromatography tandem MS (LC-MS/MS) methods depend on automated database screening which in this case may cause misidentification of $^{13}C$ isotopes or misidentification of other modifications that lead to a similar mass increase (in particular the commonly occurring deamidation of glutamine or asparagine residues). Misidentification of 13C isotopes can be avoided by searching the database that has a small enough parent mass tolerance (<5 ppm), because $^{13}C$ leads to a slightly larger mass increase (1.0036 Da) than the conversion of arginine into citrulline (0.9802 Da) [De Ceuleneer M, et al. In vivo relevance of citrullinated proteins and the challenges in their detection. *Proteomics* 2012, 12:752-760; Raijmakers R, et al. Elevated levels of fibrinogen-derived endogenous citrullinated peptides in synovial fluid of rheumatoid arthritis patients. *Arthritis Res Ther* 2012, 14:R114]. Deamidation, however, cannot be discriminated from citrullination based on mass alone. Deamidation does not change the number of charged residues in the peptide (under the acidic conditions used for LC-MS), whereas the conversion of arginine to citrulline neutralizes a positive charge. Citrullination results in a loss of positive charge that causing a shift in the isoelectric point from 11.41 for arginine to 5.91 for citrulline. Therefore, citrullination increases the overall hydrophobicity of a peptide compared to the non-modified and/or deamidated peptide resulting in a shift in retention time, which is a proof for a peptide being citrullinated rather than deamidated [Raijmakers R, et al. Elevated levels of fibrinogen-derived endogenous citrullinated peptides in synovial fluid of rheumatoid arthritis patients. *Arthritis Res* Ther 2012, 14:R114.]. However, with the current methods it remains challenging to rapidly, consistently, reproducibly, accurately, and sensitively detect and quantify citrullinated peptides across multiple samples.

Advantages of SWATH MS (Sequential Window Acquisition of all Theoretical Fragment Ion Spectra Mass Spectrometry) Over Other Strategies for Citrullinated-Targeted Protein Detection The most commonly used mass spectrometry-based method for high-throughput protein citrullination analysis is data-dependent acquisition (DDA) [tahl DC, S et al. Data-controlled automation of liquid chromatography/tandem mass spectrometry analysis of peptide mixtures. *J Am Soc Mass Spectrom* 1996, 7:532-540; Yates J R, 3rd, Eng J K, McCormack A L, Schieltz D. Method to correlate tandem mass spectra of modified peptides to amino acid sequences in the protein database. *Anal Chem* 1995, 67:1426-1436]. However, stochastic precursor selection and dependence on MS1 ions for quantification impede comprehensive. To overcome this limitation a few years ago Aebersold's group came up with SWATH MS (Sequential Window Acquisition of all Theoretical Fragment Ion Spectra Mass Spectrometry) as a targeting method similar to multiple reaction monitoring (MRM). SWATH MS (Sequential Window Acquisition of all Theoretical Fragment Ion Spectra Mass Spectrometry) is a technique that combines data-independent acquisition (DIA) with targeted data extraction, which together gives quantitative accuracy, reproducibility, dynamic range, and extends the number of quantifiable peptides [Gillet LC1 NP TS, Röst H, Selevsek N, Reiter L, Bonner R, Aebersold R. Targeted data extraction of the MS/MS spectra generated by data-independent acquisition: a new concept for consistent and accurate proteome analysis. *Mol Cell Proteomics* 2012; Liu Y, et al. Mass spectrometric protein maps for biomarker discovery and clinical research. *Expert Rev Mol Diagn* 2013, 13:811-825]. Creation of highly citrullinated library improves the sensitivity and quantitative accuracy.

Cardiovascular Diseases

Provided herein are method for diagnosing and/or predicting cardiovascular diseases. The methods include obtaining a biological sample from a subject in need of diagnosing cardiovascular disease and detecting the amount of a citrullinated protein or a citrullinated peptide in the biological sample obtained from said subject. In some embodiments a change in the level of the citrullinated protein or the citrullinated peptide relative to a reference value is indicative of increased risk of cardiovascular disease. In one embodiment, an increase in the levels of the citrullinated protein or the citrullinated peptide relative to a reference value is indicative of increased risk of cardiovascular disease. In another embodiment, a decrease in the levels of the citrullinated protein or the citrullinated peptide relative to a reference value is indicative of increased risk of cardiovascular disease. In exemplary embodiments, change in cirullination levels of one or more proteins or peptides shown in Tables 1A, 1B, 1C, 1D and/or 1E is indicative of increased risk of of cardiovascular diseases. In some embodiments, an increase in citrullination of the proteins shown in Table 1C, 1D, 1E and 1F as indicated by "up" in Table 1C, 1D, 1E and 1F is indicative of increased risk of cardiovascular disease. In some embodiments, a decrease in citrullination of the proteins shown in Table 1C, 1D, 1E and 1F as indicated by "down" in Table 1C, 1D, 1E and 1F is indicative of increased risk of cardiovascular disease. In some embodiments, change in citrullination refers to 'differentially present' citrullunation as defined herein In some embodiments, a subject has ischemic heart disease (ISHD) or is at an increased risk of ISHD if the sample from the subject has an increase in citrullination in any one or more of the proteins in Table 1C, as indicated by 'up' in ischemic heart disease column (T). In some embodiments, the subject has or is at increased risk of ISHD if the sample from the subject has the presence of citrullination or an increase in citrullination of any one or more of the peptides in Table 1A. In some embodiments, the subject has or is at an increased risk of ISHD if the sample from the subject has the absence of citrullination or a decrease in citrullination of any one or more of the peptides in Table 1A. In some embodiments, a subject has or is at an increased risk of ISHD if the sample from the subject has an increase in cirullination in any one or more of ES1 protein homolog, aconitate hydratase or citrullinated fragments thereof, glyceraldehyde-3-phosphate dehydrogenase or citrullinated fragments thereof, delta-1-pyrroline-5-carboxylate dehydrogenase or citrullinated fragments thereof, vimentin or citrullinated fragments thereof, neuroblast differentiation-associated protein AHNAK or citrullinated fragments thereof, serum deprivation-response protein or citrullinated fragments thereof, enoyl-CoA hydratase or citrullinated fragments thereof, aconitate hydratase or citrullinated fragments thereof, or combinations thereof.

In some embodiments, a subject has idiopathic cardiomyopathy (IDCM) or is at increased risk of IDCM if the sample from the subject has an increase in citrullination in any one or more of the proteins in Table 1D, as indicated by 'up' in IDCM column ('ID'). In some embodiments, the subject has or is at increased risk of IDCM if the sample from the subject has the presence of citrullination or an increase in citrullination of any one or more of the peptides in Table 1A. In some embodiments, the subject has or is at an increased risk of IDCM if the sample from the subject has the absence of citrullination or a decrease in citrullination of any one or more of the peptides in Table 1A. In some exemplary embodiments, a subject has or is at an increased risk of IDCM if the sample from the subject has an increase in citrullination in any one or more of ATP synthase subunit alpha or citrullinated fragments thereof, Myozenin-2 or citrullinated fragments thereof, Glyceraldehyde-3-phosphate dehydrogenase or citrullinated fragments thereof, ES1 protein homolog or citrullinated fragments thereof and/or combinations thereof.

In some embodiments, the subject has or is at increased risk of having cardiovascular disease (ISHD, IDCM or both ISHD and IDCM) if the sample from the subject has an increase in citrullination in any one or more of the proteins or peptides set forth in Tables 1A-1F. In some embodiments, the subject has or is at increased risk of having cardiovascular disease (ISHD, IDCM or both ISHD and IDCM) if the sample from the subject has an increase in citrullination in any one or more of ATP synthase subunit alpha or citrullinated fragments thereof, glyceraldehyde-3-phosphate dehydrogenase or citrullinated fragments thereof, ES1 protein homolog or citrullinated fragments thereof, delta-1-pyrroline-5-carboxylate dehydrogenase or citrullinated fragments thereof, enoyl-CoA hydratase or citrullinated fragments thereof, voltage-dependent anion-selective channel protein 1 or citrullinated fragments thereof, aconitate hydratase or citrullinated fragments thereof, pyruvate dehydrogenase E1 component subunit alpha, somatic form or citrullinated fragments thereof, vimentin or citrullinated fragments thereof, trifunctional enzyme subunit beta or citrullinated fragments thereof, myosin-binding protein C, cardiac-type or citrullinated fragments thereof, chloride intracellular channel protein 4 or citrullinated fragments thereof, heat shock protein HSP 90-alpha or citrullinated fragments thereof, serum deprivation-response protein or citrullinated fragments thereof, alcohol dehydrogenase 1B or citrullinated fragments thereof, succinate dehydrogenase [ubiquinone] iron-sulfur subunit or citrullinated fragments thereof, dual specificity protein phosphatase 3 or citrullinated fragments thereof or combinations thereof (Table 1E). In some embodiments, the subject has or is at increased risk of having cardiovascular disease (ISHD, IDCM or both ISHD and IDCM) if the sample from the subject has a decrease in citrullination in any one or more of Troponin I, Alpha-crystalline B chain, ATP-synthase-coupling factor 6, beta-enolase, adenylate kinase isoenzyne I or combination thereof (Table 1F). In some embodiments, change in citrullination refers to 'differentially present' citrullination as defined herein.

Also provided herein is a method comprising obtaining a biological sample from a subject in need of diagnosing cardiovascular disease, using a peptide to assay the biological sample to detect the presence or absence of an antibody capable of binding specifically to the peptide, determining the presence of cardiovascular disease when the presence of the antibody capable of binding specifically to the peptide is detected and directing the subject to treatment of cardiovascular disease when the presence of the antibody capable of binding specifically to the peptide is detected. In various embodiments, presence of the antibody capable of binding specifically to the peptide is indicative of any one or more of ISHD, IDCM, heart failure or a combination thereof. In some embodiments, the peptide is a fragment of Troponin I, Vimentin, Myosin-7 or a combination thereof. In various embodiments, the peptide is citrullinated. In exemplary embodiments, the peptide comprises, consists of or consists essentially of the amino acid sequence NIDALSGMEGRK (SEQ ID NO: 18), PRSFMPNLVPPK (SEQ ID NO: 20), ESLDLRAHLK (SEQ ID NO: 19), AEETQRSVNDLTSQRAK (SEQ ID NO: 24) or FADLSEAANRNNDALRQAK (SEQ ID NO: 22). In exemplary embodiments, the peptide sequence of the citrullinated peptides in the sample from the subject is at least 95%, 90%, 80%, 70% or 60% identical to peptides set forth in any of Table 1A-1F. In exemplary embodiments, the peptide sequence of the citrullinated peptides in the sample from the subject is at least 95%, 90%, 80%, 70% or 60% identical to NIDALSGMEGRK (SEQ ID NO: 18), PRSFMPNLVPPK (SEQ ID NO: 20), ESLDLRAHLK (SEQ ID NO: 19), AEETQRSVNDLTSQRAK (SEQ ID NO: 24) or FADLSEAANRNNDALRQAK (SEQ ID NO: 22). In various embodiments, the length of the peptide is optimized to bind the antibody in the sample. In various embodiments, citrullinated peptides are detected using mass spectrometry, high resolution mass spectrometry, tandem mass spectrometry, binding assay, immunoassay, SDS page electrophoresis, Western blot analysis, conformation on mass spectrometry, including SWATH (Sequential Window Acquisition of all Theoretical Fragment Ion Spectra).

In various embodiments, the methods further comprise prescribing treatment to the subject diagnosed with cardiovascular disease. In various embodiments, treatments include but are not limited to any one or more of therapeutic lifestyle changes, therapeutic agents, surgical treatments or a combination thereof. In exemplary embodiments, lifestyle changes include any one or more of healthy diet, physical activity, weight management, stress management, not smoking or a combination thereof. In exemplary embodiments, therapeutic agents include any one or more of Angiotensin-converting enzyme (ACE) inhibitors, Angiotensin II receptor blockers (ARBs), Beta-blockers, Aldosterone antagonists, Cardiac glycosides, Diuretics, Vasodilators, Antiarrhythmics, Human B-type natriuretic peptide, Inotropic agent, Anticoagulants, inhibitors of peptidyl arginine deiminase (PAD) enzymes or a combination thereof. In exemplary embodiments, surgical treatments include any one or more of use of left ventricular assist devices, cardiac resynchronization therapy (biventricular pacing), automatic implantable cardioverter-defibrillators, ventricular restoration surgery, heart transplantation, angioplasty, stents, atherectomy, radiation therapy, coronary artery bypass grafting or a combination thereof. Appropriate therapies will be apparent to one skilled in the art.

In various embodiments of the processes, assays and methods described herein, the reference value is based on the change in the level of citrullinated proteins or citrullinated peptides, as set forth in, for example, Tables 1A, 1B, 1C, 1D, 1E and/or 1F. In one embodiment, the change in the level of citrullinated proteins or citrullinated peptides is in a cardiomyocyte. In another embodiment, the change in the level of citrullinated proteins or citrullinated peptides is in a non-cardiac cell. In an additional embodiment, the change in the level of citrullinated proteins or citrullinated peptidesis in any cell. In an additional embodiment, the change in the level of citrullinated proteins or citrullinated peptidesis in any bodily fluid. In some embodiments, the reference value is the mean or median change in level of citrullinated proteins or citrullinated peptides in a population of subjects that do not have cardiovascular disease. In other embodiments, the reference value is the mean or median change in level of citrullinated proteins or citrullinated peptides in a population of subjects that have cardiovascular diseases but have undergone treatment and show no or reduced expression of citrullinated proteins or citrullinated peptides. In additional embodiments, the reference value is the change in expression level of citrullinated proteins or citrullinated peptides in a sample obtained from the subject from a different (for example, an earlier) time point, such as during diagnosis, before treatment, after treatment or a combination thereof. In some embodiments, cardiovascular disease is any one or more of ISHD, IDCM, heart failure or a combination thereof. In some embodiments, change in citrullination refers to 'differentially present' citrullination as defined herein.

In various embodiments, the change in the level of citrullinated proteins or citrullinated peptides in the subject having or suspected of having cardiovascular disease compared to the reference value is increased by at least or about 10%, 20%, 30%, 40%, 50%, 60%, 70%, 80%, 90% or 100%. In various embodiments, the change in the level of citrullinated proteins or citrullinated peptides in the subject having or suspected of having cardiovascular disease compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

In various embodiments, the change in the level of citrullinated proteins or citrullinated peptides in the subject having or suspected of having cardiovascular disease compared to the reference value is decreased by at least or about 10%, 20%, 30%, 40%, 50%, 60%, 70%, 80%, 90% or 100%. In various embodiments, the change in the level of citrullinated proteins or citrullinated peptides in the subject having or suspected of having cardiovascular disease compared to the reference value is decreased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Neurodegenerative Diseases

Provided herein are methods for diagnosing and/or predicting chronic neurodegenerative diseases and/or acquired brain injury and/or acute brain disease. The methods include obtaining a biological sample from a subject in need of a diagnosis and detecting citrullinated protein or citrullinated peptide in the biological sample obtained from said subject. In some embodiments, presence of citrullinated proteins or citrullinated peptides is indicative of neurodegenerative diseases. In some embodiments a change in the level of the citrullinated protein or the citrullinated peptide relative to a reference value is indicative of neurodegenerative disease and/or acquired brain injury and/or acute brain disease. In one embodiment, an increase in the levels of the citrullinated protein or the citrullinated peptide relative to a reference value is indicative of neurodegenerative disease and/or acquired brain injury and/or acute brain disease. In another embodiment, a decrease in the levels of the citrullinated protein or the citrullinated peptide relative to a reference value is indicative of neurodegenerative disease and/or acquired brain injury and/or acute brain disease. In exemplary embodiments, a change in the levels of one or more citrullinated peptides or citrullinated proteins shown in Tables 2-10 is indicative of neurodegenerative diseases. In exemplary embodiments, a change in the amount of citrullination of one or more peptides or proteins shown in Tables 2-10 is indicative of neurodegenerative diseases. In some embodiments, the change in the level is an increase in the level of one or more citrullinated peptides or citrullinated proteins shown in Tables 2-10 which is indicative of chronic neurodegenerative disease. In some embodiments, the change in the level is a decrease in the level of one or more citrullinated peptides or citrullinated proteins shown in Tables 2-10 which is indicative of chronic neurodegenerative disease. In some embodiments, change in citrullination refers to 'differentially present' citrullination as defined herein.

In exemplary embodiments, examples of neurodegenerative diseases include but are not limited to Alzheimer disease, Parkinson disease, Lewy body dementia, frontotemporal dementia, amyotrophic lateral sclerosis, Huntington disease, Friedreich's ataxia, spinal muscular atrophy, prion diseases, multiple sclerosis, stroke, degenerative nerve diseases, encephalitis, Motor neurone diseases (MND, Spinocerebellar ataxia (SCA), Spinal muscular atrophy (SMA) or Creutzfeld-Jacob disease.

In some embodiments, the biological sample is any one or more of blood, plasma, serum, urine or tissue (tissue biopsy).

In various embodiments, the level of the citrullinated protein or citrullinated peptide is detected using mass spectrometry, high resolution mass spectrometry, tandem mass spectrometry, binding assay, immunoassay, antibody binding or immunohistochemistry.

Provided herein is a method for diagnosing ALS in a subject in need thereof. The method includes obtaining a biological sample from a subject in need of a diagnosis and detecting citrullinated protein or citrullinated peptide in the biological sample obtained from the said subject. In some embodiments, presence of citrullinated proteins or citrullinated peptides is indicative of ALS. In some embodiments a change in the level of the citrullinated protein or the citrullinated peptide relative to a reference value is indicative of ALS. In one embodiment, an increase in the levels of citrullination of protein or citrullination of peptide relative to a reference value is indicative of ALS. In one embodiment, the subject has ALS or is at increased risk of having ALS if the sample from the subject has an increase in citrullination in any one or more of the proteins in Table 2, Table 3 or Table 4. In another embodiment, the subject has ALS or is at increased risk of having ALS if the sample from the subject has an increase in citrullination in any one or more of the peptides PSGVQMDPCCRALYDFEPENEGELGFK (SEQ ID NO: 306), QYMRRSTCTINYSK (SEQ ID NO: 307), LILIARNK (SEQ ID NO: 308), VIVVWVGTNNHENTAEEVAGGIEAIVQLINTRQPQAK (SEQ ID NO: 309), EVDVGLAADVGTLQRLPK (SEQ ID NO: 310), HEEAPGHRPTTNPNASK (SEQ ID NO: 311), GETPVNSTMSIGQARK (SEQ ID NO: 312), VRIQTQPGYANTLRDAAPK (SEQ ID NO: 313), NVGCLQEALQLATSFAQLRLGDVK (SEQ ID NO: 314) or combinations thereof. In exemplary embodiments, the citrullination sites in peptides having the sequence set forth in SEQ ID Nos. 306-314 are shown in Table 2. In a further embodiment, the subject has ALS or is at increased risk of having ALS if the sample from the subject has an increase in citrullination in any one or more of the peptides having the sequence set forth in any one or more of SEQ ID NO.: 315, SEQ ID NO.: 316, SEQ ID NO.: 317, SEQ ID NO.: 318, SEQ ID NO.: 319, SEQ ID NO.: 320, SEQ ID NO.: 321, SEQ ID NO.: 322, SEQ ID NO.: 323, SEQ ID NO.: 324, SEQ ID NO.: 325, SEQ ID NO.: 326, SEQ ID NO.: 327, SEQ ID NO.: 328, SEQ ID NO.: 329, SEQ ID NO.: 330, SEQ ID NO.: 331, SEQ ID NO.: 332, SEQ ID NO.: 333, SEQ ID NO.: 334, SEQ ID NO.: 335, SEQ ID NO.: 336, SEQ ID NO.: 337, SEQ ID NO.: 338, or combinations thereof. In exemplary embodiments, the citrullination sites in peptides having the sequence set forth in SEQ ID Nos. 315-338 are shown in Table 3. In exemplary embodiments, each of the citrullinated peptide sequences in the sample obtained from the subject is at least 100% 95%, 90%, 80%, 70% or 60% identical to the sequences set forth in any of SEQ ID Nos. 306-338. In some embodiments, the subject has ALS or is at increased risk of having ALS if the sample from the subject has an increase in citrullination in any one or more of the peptides having the sequence set forth in any one or more of SEQ ID Nos. 339-474. In exemplary embodiments, each of the peptide sequence in the sample obtained from the subject is at least 100%, 95%, 90%, 80%, 70% or 60% identical to the sequences set forth in any of SEQ ID Nos. 339-474. In some embodiments, change in citrullination refers to 'differentially present' citrullination as defined herein.

Provided herein is a method for diagnosing chronic neurodegenerative disease in a subject in need thereof. The method includes obtaining a biological sample from a subject in need of a diagnosis and detecting citrullinated protein or citrullinated peptide in the biological sample obtained from the said subject. In some embodiments, presence of citrullinated proteins or citrullinated peptides is indicative of chronic neurodegenerative disease. In some embodiments a change in the level of the citrullinated protein or the citrullinated peptide relative to a reference value is indicative of chronic neurodegenerative disease. In one embodiment, an increase in the levels of citrullination of protein or citrullination of peptide relative to a reference value is indicative of chronic neurodegenerative disease. In one embodiment, a decrease in the levels of citrullination of protein or citrullination of peptide relative to a reference value is indicative of chronic neurodegenerative disease. In one embodiment, the subject has chronic neurodegenerative disease or is at increased risk of having chronic neurodegenerative disease if the sample from the subject has a change in in citrullination in any one or more of the proteins in Table 5A. In some embodiments, the citrullinated peptides are brain specific. In some embodiments, the citrullinated peptides are not brain specific. In a further embodiment, the subject has chronic neurodegenerative disease or is at increased risk of having chronic neurodegenerative disease if the sample from the subject has a change in citrullination in any one or more of the peptides having the sequence set forth in any one or more of SEQ ID NO.: 355, SEQ ID NO.: 402, SEQ ID NO.: 1, SEQ ID NO.: 348, SEQ ID NO.: 363, SEQ ID NO.: 428, SEQ ID NO.: 373, SEQ ID NO.: 315, SEQ ID NO.: 316, SEQ ID NO.: 340, SEQ ID NO.: 377, SEQ ID NO.: 331, SEQ ID NO.: 332, SEQ ID NO.: 325, SEQ ID NO.: 375, SEQ ID NO.: 429, SEQ ID NO.: 414, SEQ ID NO.: 313, SEQ ID NO.: 366, SEQ ID NO.: 360, SEQ ID NO.: 423, SEQ ID NO.: 405, SEQ ID NO.: 439, SEQ ID NO.: 321, SEQ ID NO.: 475, SEQ ID NO.: 476, SEQ ID NO.: 477, SEQ ID NO.: 478, SEQ ID NO.: 479, SEQ ID NO.: 480, SEQ ID NO.: 481, SEQ ID NO.: 482, SEQ ID NO.: 483, SEQ ID NO.: 484, SEQ ID NO.: 485, SEQ ID NO.: 486, SEQ ID NO.: 487, SEQ ID NO.: 488, SEQ ID NO.: 489, SEQ ID NO.: 490, SEQ ID NO.: 491, SEQ ID NO.: 492, SEQ ID NO.: 493, SEQ ID NO.: 494, SEQ ID NO.: 495, SEQ ID NO.: 496, SEQ ID NO.: 497, SEQ ID NO.: 498, SEQ ID NO.: 499, SEQ ID NO.: 500, or combinations thereof (Table 5A). In exemplary embodiments, the citrullination sites in peptides having the sequence set forth in SEQ ID Nos. above are shown in Table 5A. In exemplary embodiments, each of the citrullinated peptide sequences in the sample from the subject is at least 95%, 90%, 80%, 70% or 60% identical to the sequences set forth Table 5A. In exemplary embodiments, peptides that may be used for diagnosing chronic neurodegenerative disease are brain specific and comprises, consists of or consists essentially of any one or more of the sequences shown in Table 5A. In exemplary embodiments, peptides that may be used for diagnosing chronic neurodegenerative disease are not brain specific and comprises, consists of or consists essentially of sequences set forth in SEQ ID Nos. 501, 502, 503, 506 or combinations thereof (Table 5B). In exemplary embodiments, chronic neurodegenerative disease include buy are not limited to any one or more of Alzheimer's disease (AD) and other dementias, Parkinson's disease (PD) and PD-related disorders, Prion disease, Motor neurone diseases (MND), Huntington's Disease (HD), Spinocerebellar ataxia (SCA), spinal muscular atrophy (SMA) or combinations thereof. In some embodiments, change in citrullination refers to 'differentially present' citrullination as defined herein.

Provided herein is a method for diagnosing acquired brain injury in a subject in need thereof. The method includes obtaining a biological sample from a subject in need of a diagnosis and detecting citrullinated protein or citrullinated peptide in the biological sample obtained from the said subject. In some embodiments, presence of citrullinated proteins or citrullinated peptides is indicative of acquired brain injury. In some embodiments a change in the level of the citrullinated protein or the citrullinated peptide relative to a reference value is indicative of acquired brain injury. In one embodiment, an increase in the levels of citrullination of protein or citrullination of peptide relative to a reference value is indicative of acquired brain injury. In one embodiment, a decrease in the levels of citrullination of protein or citrullination of peptide relative to a reference value is indicative of acquired brain injury. In a further embodiment, the subject has acquired brain injury or is at increased risk of having acquired brain injury if the sample from the subject has a change in citrullination in any one or more of the peptides having the sequence set forth in any one or more of SEQ ID NO.: 125, SEQ ID NO.: 265, SEQ ID NO.: 285, SEQ ID NO.: 505, SEQ ID NO.: 506, SEQ ID NO.: 507, SEQ ID NO.: 508, SEQ ID NO.: 509, SEQ ID NO.: 510, SEQ ID NO.: 511, SEQ ID NO.: 512, SEQ ID NO.: 513, SEQ ID NO.: 514, SEQ ID NO.: 515, SEQ ID NO.: 516, SEQ ID NO.: 517, SEQ ID NO.: 518, SEQ ID NO.: 519, SEQ ID NO.: 520, SEQ ID NO.: 521, SEQ ID NO.: 522, SEQ ID NO.: 523, SEQ ID NO.: 524, SEQ ID NO.: 525, SEQ ID NO.: 526, SEQ ID NO.: 527, SEQ ID NO.: 528, SEQ ID NO.: 529, SEQ ID NO.: 530, SEQ ID NO.: 531, SEQ ID NO.: 532, SEQ ID NO.: 533, SEQ ID NO.: 534, SEQ ID NO.: 535, SEQ ID NO.: 536, SEQ ID NO.: 537, SEQ ID NO.: 538, SEQ ID NO.: 539, SEQ ID NO.: 540, SEQ ID NO.: 541, SEQ ID NO.: 542, SEQ ID NO.: 543, SEQ ID NO.: 544, SEQ ID NO.: 545, SEQ ID NO.: 546, SEQ ID NO.: 547 or combinations thereof. In a further embodiment, the subject has acquired brain injury or is at increased risk of having acquired brain injury if the sample from the subject has a change in citrullination in any one or more of the peptides having the sequence set forth in Tables 6A and/or 6B. In exemplary embodiments, each of the citrullinated peptide sequence in the sample obtained from the subject is at least 95%, 90%, 80%, 70% or 60% identical to the sequences set forth in any of Tables 6A and/or 6B. In exemplary embodiments, acquired brain injury includes but is not limited to traumatic brain injuries (TBI's), strokes, brain illness, tumor, hemorrhage, and any other kind of brain injury acquired after birth. In some embodiments, change in citrullination refers to 'differentially present' citrullination as defined herein.

Provided herein is a method for diagnosing chronic brain disease in a subject in need thereof. The method includes obtaining a biological sample from a subject in need of a diagnosis and detecting citrullinated protein or citrullinated peptide in the biological sample obtained from the said subject. In some embodiments, presence of citrullinated proteins or citrullinated peptides is indicative of chronic brain disease. In some embodiments a change in the level of the citrullinated protein or the citrullinated peptide relative to a reference value is indicative of chronic brain disease. In one embodiment, an increase in the levels of citrullination of protein or citrullination of peptide relative to a reference value is indicative of chronic brain disease. In one embodiment, a decrease in the levels of citrullination of protein or citrullination of peptide relative to a reference value is indicative of chronic brain disease. In one embodiment, the subject has chronic brain disease or is at increased risk of having chronic brain disease if the sample from the subject has a change in citrullination in any one or more of the secreted proteins in Table 7. In one embodiment, the subject has chronic brain disease or is at increased risk of having chronic brain disease if the sample from the subject has a change in citrullination in any one or more of the non-secreted proteins in Table 8. In a further embodiment, the subject has chronic brain disease or is at increased risk of having chronic brain disease if the sample from the subject has a change in citrullination in any one or more of secreted proteins selected from Syntaxin-binding protein 1 or citrullinated fragments thereof, Histone H4 or citrullinated fragments thereof, Cytoplasmic dynein 1 heavy chain 1 or citrullinated fragments thereof, Dynamin-1 or citrullinated fragments thereof, Gamma-enolase or citrullinated fragments thereof, Endoplasmin precursor or citrullinated fragments thereof, Heat shock 70 kDa protein 12A or citrullinated fragments thereof, Serine/threonine-protein phosphatase PP1-alpha catalytic subunit or citrullinated fragments thereof, Calreticulin precursor or citrullinated fragments thereof, Coronin-1A or citrullinated fragments thereof, Electron transfer flavoprotein subunit beta or citrullinated fragments thereof, Hemoglobin subunit beta or citrullinated fragments thereof, Mitogen-activated protein kinase 1 or citrullinated fragments thereof, Mitogen-activated protein kinase 3 or citrullinated fragments thereof, 26S proteasome non-ATPase regulatory subunit 12 or citrullinated fragments thereof, 60S ribosomal protein L4 or citrullinated fragments thereof, 60S acidic ribosomal protein P2 or citrullinated fragments thereof, Septin-7 or citrullinated fragments thereof, Alanine-tRNA ligase, cytoplasmic or citrullinated fragments thereof or combinations thereof. In a further embodiment, the subject has chronic brain disease or is at increased risk of having chronic brain disease if the sample from the subject has a change in citrullination in any one or more of non-secreted proteins selected from Synapsin-1 or citrullinated fragments thereof, Aconitate hydratase or citrullinated fragments thereof, Complexin-1 or citrullinated fragments thereof, Complexin-2 or citrullinated fragments thereof, Band 4.1-like protein 3 or citrullinated fragments thereof, Synapsin-2 or citrullinated fragments thereof, AP2-associated protein kinase 1 or citrullinated fragments thereof, Alpha-adducin or citrullinated fragments thereof, AP-2 complex subunit beta or citrullinated fragments thereof, Serine/threonine-protein kinase DCLK1 or citrullinated fragments thereof, Glutaminase kidney isoform or citrullinated fragments thereof, Isocitrate dehydrogenase [NAD] subunit alpha or citrullinated fragments thereof, Serine/threonine-protein phosphatase 2B catalytic subunit alpha isoform or citrullinated fragments thereof or combinations thereof. In some embodiments, change in citrullination refers to 'differentially present' citrullination as defined herein.

Provided herein is a method for diagnosing acute brain disease in a subject in need thereof. The method includes obtaining a biological sample from a subject in need of a diagnosis and detecting citrullinated protein or citrullinated peptide in the biological sample obtained from the said subject. In some embodiments, presence of citrullinated proteins or citrullinated peptides is indicative of acute brain disease. In some embodiments a change in the level of the citrullinated protein or the citrullinated peptide relative to a reference value is indicative of acute brain disease. In one embodiment, an increase in the levels of citrullination of protein or citrullination of peptide relative to a reference value is indicative of acute brain disease. In one embodiment, a decrease in the levels of citrullination of protein or citrullination of peptide relative to a reference value is indicative of acute brain disease. In one embodiment, the subject has acute brain disease or is at increased risk of having acute brain disease if the sample from the subject has a change in citrullination in any one or more of the secreted proteins in Table 9. In one embodiment, the subject has acute brain disease or is at increased risk of having acute brain disease if the sample from the subject has a change in citrullination in any one or more of the non-secreted proteins in Table 10. In a further embodiment, the subject has acute brain disease or is at increased risk of having acute brain disease if the sample from the subject has a change in citrullination in any one or more of secreted proteins selected from Cullin-associated NEDD8-dissociated protein 1 or citrullinated fragments thereof, Peroxiredoxin-5 or citrullinated fragments thereof or combinations thereof. In a further embodiment, the subject has acute brain disease or is at increased risk of having acute brain disease if the sample from the subject has an increase in citrullination Guanine nucleotide-binding protein G(I)/G(S)/G(0) subunit gamma-3 precursor or citrullinated fragments thereof. In some embodiments, change in citrullination refers to 'differentially present' citrullination as defined herein.

Also provided herein are methods for treating neurodegenerative diseases in a subject in need thereof. The methods include diagnosing a neurodegenerative disease by the methods set forth herein and administering an effective amount of a therapeutic agent to the subject diagnosed with the neurodegenerative disease so as to treat neurodegenerative disease in the subject. In exemplary embodiments, examples of neurodegenerative diseases include but are not limited to Alzheimer disease, Parkinson disease, Lewy body dementia, frontotemporal dementia, amyotrophic lateral sclerosis, Huntington disease, Friedreich's ataxia, spinal muscular atrophy, prion diseases, multiple sclerosis, stroke, degenerative nerve diseases, encephalitis or Creutzfeld-Jacob disease. In various embodiments, treatments include but are not limited to any one or more of therapeutic lifestyle changes, therapeutic agents, surgical treatments or a combination thereof. In exemplary embodiments, lifestyle changes include any one or more of healthy diet, physical activity, weight management, stress management, not smoking or a combination thereof.

In exemplary embodiments, therapeutic agents for Alzheimer's disease include but are not limited to cholinesterase inhibitors (such as Donepezil, Rivastigmine, Galantamine), memantine (Namenda), Vitamin E, alternative treatments (for example, Caprylic acid and coconut oil, Concerns, Coenzyme Q10, Coral calcium, *Ginkgo biloba*, Huperzine A, Omega-3 fatty acids, Phosphatidylserine, Tramiprosate), or combinations thereof. Appropriate therapies and dosages will be apparent to one skilled in the art.

In exemplary embodiments, therapeutic agents for Parkinson's disease include but are not limited to carbidopa/levodopa, dopamine agonists, monoamine oxidase inhibitors, anticholinergics, surgery, lifestyle changes, alternative treatments (for example, Antioxidants Vitamin C and E, the Mediterranean Diet, Calcium and Vitamin D, Coenzyme Q10, Folate (Folic Acid), Ginger (*Zingiber Officinalis*), Gingko Biloba, Green Tea Polyphenols (GTPs), Milk Thistle (*Silybum Marianum*), St. John's Wort (*Hypericum Perforatum*), Vitamin B12) or combinations thereof. Appropriate therapies and dosages will be apparent to one skilled in the art.

In exemplary embodiments, treatments for Huntinton's disease include therapeutic agents and therapies including psychotherapy, speech therapy, physical therapy, occupation therapy or combinations thereof. Exemplary, therapeutic agents for Huntington's disease include but are not limited to Tetrabenazine (Xenazine), Antipsychotic drugs, (such as haloperidol (Haldol)), amantadine, levetiracetam (Keppra), clonazepam (Klonopin) or combinations thereof. Appropriate therapies and dosages will be apparent to one skilled in the art.

In exemplary embodiments, therapeutic agents for ataxia include but are not limited to riluzole, antiglutaminergic medication, nicotine receptor agonists, serotonergic therapy, GABAergic therapy, cholinergic therapy, channel stabilizing treatments (such as carbonic anhydrase inhibitors), insulin-like growth factors, supplements (such as Vitamin E) or combinations thereof. Appropriate therapies and dosages will be apparent to one skilled in the art.

In exemplary embodiments, treatments for spinal muscular atrophy include proper nutrition, therapeutic agents and therapies including psychotherapy, speech therapy, physical therapy, occupation therapy or combinations thereof. Therapeutic agents for spinal muscular atrophy include but are not limited to muscle relaxants such as baclofen, tizanidine, and the benzodiazepines to reduce spasticity, Botulinum toxin to treat jaw spasms or drooling, amitriptyline, glycopyolate, and atropine or by botulinum injections into the salivary glands to treat excessive saliva, antidepressants to treat depression. Appropriate therapies and dosages will be apparent to one skilled in the art.

In exemplary embodiments, therapeutic agents for prion disease include but are not limited to quinacrine, pentosan polysulfate (PPS), tetracyclic compounds or combinations thereof.

In various embodiments of the processes, assays and methods described herein, the reference value is based on the change in the level of citrullinated proteins or citrullinated peptides as set forth in, for example Tables 2-10. In one embodiment, the change in the level of citrullinated proteins or citrullinated peptides is in a neuronal cell. In another embodiment, the change in the level of citrullinated proteins or citrullinated peptides is in a non-neuronal cell. In an additional embodiment, the change in the level of citrullinated proteins or citrullinated peptides is in any cell. In an additional embodiment, the change in the level of citrullinated proteins or citrullinated peptides is in any bodily fluid. In some embodiments, the reference value is the mean or median expression level of citrullinated proteins or citrullinated peptides in a population of subjects that do not have neurodegenerative disease. In other embodiments, the reference value is the mean or median expression level of citrullinated proteins or citrullinated peptides in a population of subjects that have neurodegenerative diseases but have undergone treatment and show no or reduced expression of citrullinated proteins or citrullinated peptides. In additional embodiments, the reference value is the expression level of citrullinated proteins or citrullinated peptides in a sample obtained from the subject from a different (for example, an earlier) time point, such as during diagnosis of neurodegenerative disease, before treatment of neurodegenerative disease, after treatment of neurodegenerative diseaseor a combination thereof. In exemplary embodiments, neurodegenerative diseases include but are not limited to ALS, Alzheimer's disease, brain stroke, chronic brain disease, acute brain disease or combinations thereof. In some embodiments, change in citrullination refers to 'differentially present' citrullination as defined herein.

In various embodiments, the expression level of citrullinated proteins or citrullinated peptides in the subject having or suspected of having neurodegenerative disease compared to the reference value is increased by at least or about 10%, 20%, 30%, 40%, 50%, 60%, 70%, 80%, 90% or 100%. In various embodiments, the expression level of citrullinated proteins or citrullinated peptides in the subject having or suspected of having neurodegenerative disease compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof. In exemplary embodiments, neurodegenerative diseases include but are not limited to ALS, Alzheimer's disease, brain stroke, chronic brain disease, acute brain disease or combinations thereof.

In various embodiments, the expression level of citrullinated proteins or citrullinated peptides in the subject having or suspected of having neurodegenerative disease compared to the reference value is decreased by at least or about 10%, 20%, 30%, 40%, 50%, 60%, 70%, 80%, 90% or 100%. In various embodiments, the expression level of citrullinated proteins or citrullinated peptides in the subject having or suspected of having neurodegenerative disease compared to the reference value is decreased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof. In exemplary embodiments, neurodegenerative diseases include but are not limited to ALS, Alzheimer's disease, brain stroke, chronic brain disease, acute brain disease or combinations thereof.

Example 1: Experimental Methods

Reagents and Materials

The following reagents were obtained: rabbit skeletal muscle PAD cocktail (PAD) (SignalChem); PAD2 (Sigma), heavy meromyosin (HMM), tropomyosin (TM) (Sigma);

F-actin (Cytoskeleton. Inc), cardiac troponin (TnI) (Abeam), anti-modified citrulline antibody (Millipore); sequencing grade Lys-C protease (WAKO), and protease inhibitor cocktail (Roche).

Human Heart Tissue

Left ventricular tissue samples were obtained from Cris Dos Remedios, University of Sydney, Australia after informed consent and with approval of the local Ethical Committee. The samples were acquired during heart transplantation surgery, from patients with HF (Ischemic Heart Disease (ISHD) and Idiopathic Cardiomyopathy (IDCM), n=10 each) and non-failing donor hearts (n=10) as previously described [Zhang P et al., Multiple reaction monitoring to identify site-specific troponin I phosphorylated residues in the failing human heart. *Circulation* 2012, 126:1828-1837].

Mouse Heart Tissue and Neonatal Myocytes

Male C57BL/6 mice (n=3) (5 days old neonatal mice, Jackson Laboratories) were obtained. Animal study was approved by The Johns Hopkins University Animal Care and Use Committee and followed established NIH guidelines. Briefly, Primary cultured ventricular myocytes were isolated from neonatal mice. Collagenase-digested isolated myocytes were incubated in buffer with increasing concentrations of $Ca^{2+}$, achieving a final concentration of 1.2 mM $Ca^{2+}$ as in the MEM culture media. Cells were seeded at 25,000 rod-shaped myocytes/ml on 6-well plates or 60-mm dishes coated with laminin. After 1 hour incubation in 37° C., 5% $CO_2$, the culture media was replaced to remove unattached cells.

Protein Extraction and SWATH MS (Sequential Window Acquisition of all Theoretical Fragment Ion Spectra Mass Spectrometry)

Hearts were fractionated into myofilament- and cytosolic-enriched fractions using the IN Sequence protocol [Kane L A et al. Subfractionation of heart tissue: the "in sequence" myofilament protein extraction of myocardial tissue. *Methods Mol Biol* 2007, 357:87-90]. Protein extraction and generation of LysC peptides from subfractions was performed using a filter-aided sample preparation (FASP) protocol [24]. When needed recombinant proteins or the In Sequence fractions were incubated with PAD's cocktail at a ratio of 1:20 for 2 hr. at 37° C. in 100 mM Tris, pH 7.6, 5 mM DTT, 10 mM $CaCl_2$. The reaction was stopped by addition of 5 mM EDTA prior to digestion. A TripleTOF 6600 mass spectrometer (Sciex) was used for both data dependent acquisition to build peptide spectral ion library and SWATH-MS (Sequential Window Acquisition of all Theoretical Fragment Ion Spectra—Mass Spectrometry) (data independent acquisition) for each individual sample analysis. The raw data was searched with ProteinPilot™ Software 5.0 to create a spectral ion library. Individual SWATH-MS (Sequential Window Acquisition of all Theoretical Fragment Ion Spectra—Mass Spectrometry) runs were matched against the spectral library created in the presence or absence of PAD (plus and minus PAD) for both the myofilament- and cytosolic-enriched protein fractions (see Data Supplement).

Preparation of Citrullinated Samples

Recombinant proteins and the fractions obtained from IN Sequence were incubated with PAD2 at a ratio of 1:20 for 2 hr. at 37° C. in working buffer (100 mM Tris, pH 7.6, 5 mM DTT, 10 mM $CaCl_2$). The reaction was stopped by addition of 5 mM EDTA.

Statistical Validation Peptides, Proteins and Citrullination Residues: Acceptance Criteria.

Bioinformatics Analysis was performed with the workflow described in data supplement. The peptide normalization used in this study was based on the iRT peptide retention time [Escher C, et al. Using iRT, a normalized retention time for more targeted measurement of peptides. *Proteomics* 2012, 12:1111-1121] and normalized values were used for downstream analysis. Ensemble protein ID accession numbers were mapped back to their associated encoding Ensemble gene entries. Data analysis and mining were performed using iProXpress (proteininformationresource.org/iproxpress2) [Natale D A et al. Protein Ontology: a controlled structured network of protein entities. *Nucleic Acids Res* 2014, 42:D415-421] and Cytoscape [Saito R et al. A travel guide to Cytoscape plugins. *Nat Methods* 2012, 9:1069-1076]. The Kruskal-Wallis test (non-parametric one way ANOVA) for each peptide was used to calculate p-values. The significance of the biochemical changes was determined by performing a t-test ($p \leq 0.05$) on the differences for all paired data. Unless otherwise stated all biochemical assays were replicated three times.

SDS-PAGE Immunoblot for Citrullination

A 1:2000 diluted of the anti-citrulline (Modified) antibody was used for the 1 DE western blot (see Data Supplement).

Two-Dimensional Gel Electrophoresis (2DE)

The independent verification of proteomics data was performed with fluorescence 2DE gel electrophoresis (2D-DIGE, pI range and SDS PAGE range) as reported previously [Matt P et al. Biomarker discovery: proteome fractionation and separation in biological samples. *Physiol Genomics* 2008, 33:12-17]. The treatment of sample with PAD2 enzyme, which removes a guanidino group from specific arginine residues within the modified protein, can be used to identify citrullinated proteins based on the change in charge of the protein after treatment (see Data Supplement).

Membrane-Permeabilized Myocytes

Left ventricular tissue from C57BL/6 mice was flash frozen in liquid nitrogen and stored at −80° C. For analysis, tissue was homogenized in the presence of 0.3% Triton X-100, and protease and phosphatase inhibitors, as described [Kirk J A et al. Cardiac resynchronization sensitizes the sarcomere to calcium by reactivating GSK-3beta. *J Clin Invest.* 2014, 1:129-38]. Myocytes were washed without Triton X-100 to remove the detergent, and resuspended in isolation buffer. PAD2 was activated in 10 mM $Ca^{2+}$ and 50 mM DTT for 60 minutes at 37° C. PAD2 treated myocytes were then exposed to a 1:10 dilution of activated PAD2 in isolation buffer for 30 minutes at room temperature. Myocytes were then glued with silicone to the tips of 150 µm diameter minutia pins attached to a force transducer and motor arm (Aurora Scientific Inc., Aurora, ON, Canada). Sarcomere length was monitored by video camera (Imperx, Boca Raton, Fla.) and calculated by the High-speed Video Sarcomere Length Program (Aurora Scientific Inc.). Myocyte sarcomere length was set at 2.1 µm. A complete activation of the myocyte occurred at the beginning and end of the experiment, and the myocyte discarded if there was >10% rundown, as described [Kirk J A et al. Cardiac resynchronization sensitizes the sarcomere to calcium by reactivating GSK-3beta. *J Clin Invest.* 2014, 1:129-38].

ATPase Activity

The HMM-ATPase activity was analyzed at three separate experiments described previously [White HD. Special instrumentation and techniques for kinetic studies of contractile systems. *Methods Enzymol* 1982, 85:698-708; Tauhata S B, et al. High affinity binding of brain myosin-Va to F-actin induced by calcium in the presence of ATP. *J Biol Chem* 2001, 276:39812-39818]. First experiment was carried at constant HMM and F-actin concentration with citrullinated or non-citrullinated HMM and/or F-actin. Second, MINI-ATPase activity was determined at increasing TM concentrations (citrullinated or non-citrullinated). Third experiment HMM-ATPase activity was determined at constant HMM, F-actin and TM concentration with citrullinated or non-citrullinated TnI. Each experiment was done in triplicate and three separate times.

Actin Binding Experiments

Various concentrations of citrullinated and non-citrullinated HMM, TM and/or TnI were added to F-actin and centrifuged to determine extent of binding. Pellet and supernatant were analyzed using 10% SDS PAGE, and amount of each protein quantified by densitometry as previously described [Skorzewski R et al. Effect of actin C-terminal modification on tropomyosin isoforms binding and thin filament regulation. *Biochim Biophys Acta* 2009, 2: 237-243; Nascimento A A et al. Enzymatic characterization and functional domain mapping of brain myosin-V. *J Biol Chem* 1996, 271:17561-17569]. Each assay was carried out in triplicate.

Reverse Transcription-Polymerase Chain Reaction (RT-PCR)

Total mRNA from mouse neonatal cardiac myocytes was extracted using TRI-reagent (Sigma) according to the manufacturer's protocols. Complementary DNA (cDNA) was generated using the SuperScript III First-Standard Synthesis System (Invitrogen) according to the instructions of the manufacturer. RT-PCR was performed using primers specific for the PAD1, PAD2, PAD3, PAD4 and β-actin. The PCR products were separated by electrophoresis on a 1.8% agarose gel and visualized under UV light. Each assay was done in duplicate.

ID-PAGE and Western Blot

Proteins bug per well were separated by ID-PAGE using 12-well 4-12% NuPAGE Bis-Tris gels and blotted onto PVDF membranes according to manufacturer's instruction. After staining the blotted membrane with Direct Blue followed by scanning images, membranes were incubated with modification reagent [1 vol of 1% diacetyl monoxime/0.5% antipyrine/1 N acetic acid, and 2 vol of a mixture of 85% $H_3PO_4$/98% $H_2SO_4/H_2O$ (20/25/55) containing 0.025% $FeCl_3$] overnight at 37° C., protected from light. The membrane was blocked, probed overnight at 4° C. with an anti-modified citrulline antibody at 1:2000 (Millipore, Billerica, Mass.) and followed by washes incubated with the secondary antibody for 1 hour (goat polyclonal antirabbit IgG, 1:10000 dilution). Bound antibodies were visualized by chemiluminescent substrate as described by the manufacturer (Amersham Biosciences, Piscataway, N.J.). When developed, films were scanned with Epson Expression 10000 XL scanner (Epson, US) and imported into GraphPad Prism tools. A student's t-test was used to determine statistical difference between the groups. A p-value <0.05 was considered statistically significant.

Sample Deimination, Cy Labeling, 2-DE Separation

Heart samples, weighing approximately 150 mg, were subfractionated as described earlier. For deimination of each fraction was treated with 1.5 mg bacterial PAD2 in 200 mM Tris-HCl pH 7.5/10 mM dithiothreitol (DTT)/20 mMCaCl$_2$ in a total volume of 100 uL. The same amount of each sample was treated at the same condition but without enzyme. After incubating the samples at 50° C. for 2 hours samples were mixed with DIGE labeling buffer (7 M urea/2 M thiourea/4% CHAPS/30 mM Tris pH 8.5) at a final concentration of 70 ug/110 uL. Cy dyes were added (3200 pmol/400 mg aliquot) and aliquots were incubated at RT in the dark for 30 min. Reactions were stopped by adding 1 mL 10 mM lysine per 400 pmol dye. Pooled standard was labeled with Cy2, samples no PAD2 treated were labeled with Cy3, and samples treated with PAD2 were labeled with Cy5. A 150 ug aliquot of pooled standard, sample +PAD2 and sample—PAD2, labeled as stated above, were mixed together and diluted in IEF buffer (7 M urea/2 M thiourea/4% CHAPS/1% DTT/1% 3-10 ampholytes) to final volume 350 ul. Prepared samples were applied to 18 cm immobilized linear pH gradients (4-7) strips (IPG, BioRad), with active rehydration for 12 h at 20° C. For isoelectrofocusing (IEF), the BioRad Protean IEF cell was used with the following conditions at 20° C.: Step 1:1 hr with end voltage at 200 V; Step 2: 1 h ramping with end voltage at 500 V; Step 3: 1 hr with end voltage 500V; Step 4: 1 hr ramping with end voltage at 1000 V; Step 5: 2 hr with end voltage 1000V; Step 6: 2 hrs. ramping with end voltage at 1000 V; Step 7: 50000V/h (approximately 6 hrs). After IEF, the strips were equilibrated according to the manufacturer's instructions. Second dimension of 2-DE was then carried out with 10% gels and electrophoresed at constant voltage (80 V) for 30-60 min, followed by constant power (200V, 200 mA) for 6 hours. The DIGE gels were scanned using a Typhoon 9410 (GE Healthcare) at different emission wavelengths, which allows the differentially expressed proteins to be viewed as changed in color. Preparative gels were stained with silver staining and scanned with the Typhoon 9410.

Image Analysis

Small gels were scanned using an Epson Expression 10000 XL (Epson America), and large gels were scanned using an Amersham Typhoon 9410 (GE Healthcare). Differentially expressed proteins (treated vs. no treated with PAD2) were identified using Ludesi REDFIN analysis (Ludesi, www.ludesi.com) for spot detection, matching, and analysis. Ludesi REDFIN analysis was performed in two steps: differential in-gel analysis (DIA) followed by biological variation analysis (BVA). DIA quantifies protein volume from fluorescence intensity for Cy2, Cy3 and Cy5 and calculates the ratios Cy3/Cy2 (no PAD2 treated to internal standard) and Cy5/Cy2 (PAD2 treated to internal standard). Values are then normalized based on the assumption that the amount of protein per image is the same. 2-DE gel images were analyzed in REDFINA (www.ludesi.com) using student's t-test to determine statistical difference between the groups. A p-value <0.05 was considered statistically significant. Spots of interest were then excised from gel, destined and in-gel digested with trypsin. Digested samples were used for LC-MS/MS analysis as described below.

In Gel Protein Digestion and Peptide Identification

Spots of interest were picked out from the gels with a shortened pipette tip, placed in small eppendorf tubes and distained by using a 30 mM potassium ferricyanide and 100 mM sodium thiosulfate. After a further washing with bi-distilled water, gel plugs were dried and rehydrated directly in reducing and alkylate reagent follow by digestion of 0.1 μg/μl trypsin in 50 mM $NH_4HCO_3$ pH 8.8 solution (Trypsin ultra grade sequencing grade, Promega, Wis., USA). Digestion was performed 1 hr on ice; next the extra solution was removed and gel plugs were cover with 100 ul 50 mM $NH_4HCO_3$ and incubate overnight at 37° C. Peptides were desalted by ZipTip and analyzed by nanoflow LC-MS/MS by using an LTQ ion trap MS (Thermo Fisher Scientific) interfaced with an Agilent 1200 nanoLC system.

Mass Spectrometry

Each human heart was fractionated into myofilament- and cytosolic-enriched fractions using IN Sequence protocol [Kane L A, et al. Subfractionation of heart tissue: the "in sequence" myofilament protein extraction of myocardial tissue. *Methods Mol Biol* 200, 357:87-90]. Protein extracts were denatured, reduced and alkylated prior to digestion with LysC (1:20) using a filter-aided sample preparation (FASP) protocol (www.biochem.mpg.de/226356/FASP). Exogenous internal retention time standards (IRT, company and reference [Escher C, et al. Using iRT, a normalized retention time for more targeted measurement of peptides. *Proteomics* 2012, 12:1111-1121]) were added to each peptide fraction. To maximize the citrullinated proteome depth in vitro citrulllination, using PADs cocktail, of cardiac tissue lysates was performed followed by the proteins digestion with LysC. Spectral ion libraries were constructed by data dependent acquisition on an AB Sciex 6600 TripleTOF and the raw data was searched with ProteinPilot™ Software 5.0 to create a spectral ion library. The two fractions from each individual were sequentially analyzed using data independent acquisition (SWATH-MS) (Sequential Window Acquisition of all Theoretical Fragment Ion Spectra—Mass Spectrometry) on the 6600 Triple TOF. The peptide data were kept for further analysis if they contained at least one high confidence citrulline-peptide/spectrum assignment (>95% confidence) and the confidence level of the protein to which it mapped was >95%. Peptide and ProteinProphet thresholds, the global false discovery rates for this study, obtained from a search of the reversed human database, were estimated to be on the order of <0.1% at the peptide and protein levels respectively. Importantly, transitions of each citrullinated peptide were selected and verified to provide accurate sensitivity and specificity for these targeted proteomics experiments. SWATH-MS (Sequential Window Acquisition of all Theoretical Fragment Ion Spectra—Mass Spectrometry) fragment ion maps were created (from the endogenous samples) between 400-1250 m/z using 200 variable SWATH (Sequential Window Acquisition of all Theoretical Fragment Ion Spectra) windows with a dwell time of 20 ms for each window. Source conditions were as follows for DDA and SWATH (Sequential Window Acquisition of all Theoretical Fragment Ion Spectra) experiments: Spray voltage was set to 2.4 kV, source gas was set to 5, curtain gas was set to 30, interface heater temperature was set to 80, and declustering potential was set to 100. Rolling collision energy was used for MS2 experiments in the DDA runs. For both DDA and SWATH (Sequential Window Acquisition of all Theoretical Fragment Ion Spectra) runs peptides were separated using an Eksigent Ekspert™ 415 nanoLC equipped with Ekspert™ cHiPLC and Ekspert™ nanoLC 400 autosampler. Samples were loaded onto a trap column (nano cHiPLC Trap 200 μm×0.5 mm ChromXP C18-CL 3 μm 120 Å) for 10 minutes at a flow rate of 2 μL/min in 100% solvent A (0.1% formic acid in water) after which point they were separated using a nano cHiPLC 75×15 cm ChromXP C18-CL 3 μm 120 Å column using a flow rate of 300 nL/min and a linear gradient of 5-35% solvent B (0.1% formic acid in acetonitrile) for 120 min, 35-85% B for 2 minutes, holding at 85% for 5 minutes, then re-equilibration at 5% B for 17 minutes.

Construction of a Verified Citrullinated Spectral Ion Library

A verified citrullinated peptide ion library was constructed based on the retention time (RT) difference between pairs of peptides that had un-modified (non-citrullinated) and citrullinated forms present in the ion library and between peptides that had N/Q deaminated and citrullinated forms. Based on our data we observed that the difference in RT between the unmodified and citrullinated form of the same peptide sequence (in the absence of any other modifications) was on average 10 minutes, with the citrullinated peptide having the longer retention time, whereas N/Q deamidation resulted in a RT shift on average of about 2.5 minutes. Therefore, for citrullinated peptide sequences that had paired unmodified forms or paired N/Q deamidation forms and the RT difference was greater than 5 minutes we did not alter the selected transition ions in the ion library. For citrullinated peptides where the RT was less than 5 minutes between the pairs or if there was no unmodified form to use as a reference we manually selected transition ions that would unambiguously distinguish the citrullinated peptide from the unmodified or N/Q deaminated form and any transitions that did not unambiguously distinguish the citrullination site were removed from the ion library. For this subset of peptides five unique transitions were required for a citrullinated peptide to be included in the library. In addition to the verified citrullinated peptides for each protein, a maximum of 10 unmodified peptides were incorporated into the library for total protein quantification.

SWATH (Sequential Window Acquisition of all Theoretical Fragment Ion Spectra) Data Analysis The verified ion library was imported into PeakView v2.1 and SWATH (Sequential Window Acquisition of all Theoretical Fragment Ion Spectra) files were loaded into the SWATH (Sequential Window Acquisition of all Theoretical Fragment Ion Spectra) microapp version 2.0. Extraction settings were as follows: 30 peptides per protein, 5 transitions per peptide, 95% peptide confidence cutoff, an FDR threshold of 1%, an XIC extraction window of 5 min and tolerance of 0.05 Da.

Co-Sedimentation Assay

Binding assays were performed by TM cosedimentation (0-2 uM) with 5 uM F-actin essentially as described earlier [Skorzewski R, et al. Effect of actin C-terminal modification on tropomyosin isoforms binding and thin filament regulation. *Biochim Biophys Acta*, 2009, 2:237-243], with the following modifications. Binding of TM alone was assayed in 40 mM Tris HCl, pH 7.6, 1 mM DTT, 5 mM MgCl2, and 100 mM NaCl. After mixing of all assay components, samples were incubated at room temperature for ~0.5 h to ensure attainment of the steady-state. Protein mixtures were ultracentrifuged for 25 min at 60,000 rpm in Beckman rotor TLA 100.2. The composition of the proteins in pellets and the amount of free TM left in the supernatant were examined on 4-12% SDS-PAGE. The gels stained with Coomassie Blue were scanned and quantified. Intensities of SDS-gel bands of pelleted F-actin were similar. TM bound to actin was calculated as TM/actin band intensity ratio normalized to the maximum ratio reached at saturation. The concentration of unbound TM was calculated from band intensities of TM left in the supernatant.

Myosin HMM-Induced Binding of TM to F-Actin

F-actin (5 μM) and TM (1 μM, citrullinated or control) in 30 mM NaCl, 0.5 mM MgCl2, 1 mM DTT, 5 mM imidazole, pH 7.0, were mixed with HMM (0-3.5 μM). The mixture was incubated at room temperature for 30 min and then centrifuged in a TLA-100.2 rotor for 25 min, at 60,000 rpm at 15° C. The composition of proteins sedimented in pellets was analyzed by SDS-PAGE and densitometry [Sliwinska M, et al. Role of actin C-terminus in regulation of striated muscle thin filament. *Biophys J.* 2008, 4:1341-].

HMM-ATPase assays. The assays were performed as described by White [White HD. Special instrumentation and techniques for kinetic studies of contractile systems. *Methods Enzymol* 1982, 85:698-708] with several modifications. All assays were carried out at 22° C. in a buffer containing 30 mM NaCl, 5 mM MgCl2, and 10 mM Hepes, pH 7.5 with F-actin 0.2 mg/ml and HMM 0.02 mg/ml final concentrations. When present, non-citrullinated or citrullinated TM was added to F-actin to a final molar concentrations between 0-2 μM TM. HMM-Actin-TM-TnI assay was carried as above with citrullinated or not citrullinated TnI at F-actin: TM:TnI molar ration 7:1:1 respectively. To assess the sensitivity of the regulated acto-S1 system, all assays were done in parallel both in the presence (0.5 mM CaCl2) and the absence (2 mM EGTA) of calcium. All reactions were initiated by addition of 4 mM ATP. The amount of liberated phosphate was determined calorimetrically at 650 nm. All assays were carried out within the linear range and each assay was done in triplicate.

Example 2

Identification of Myocardial Citrullinated Proteins.

To identify citrullinated targets in the heart we assessed the citrullinome in three groups, ISHD, IDCM and non-failing donor hearts (n=10 per group) using SWATH-MS (Sequential Window Acquisition of all Theoretical Fragment Ion Spectra—Mass Spectrometry) [34]. SWATH-MS (Sequential Window Acquisition of all Theoretical Fragment Ion Spectra—Mass Spectrometry) allowed for the quantification. 53 citrullinated sites were altered with HF compared to the non-failing controls (p<0.05) and are listed in Table 1A.

TABLE 1A

List of citrullinated protein (p = 0.05) with citrullinated peptides sequence. "Dea" is Citrullination or deamination. "CAM" is carbamidomethylation. Citrullinated proteins were grouped by cellular component. UP identifier = Universal Protein (UP)Resource protein ID; p_kw = p value for Kruskal-Wallis test (statistic)

| Protein | Peptide | UniProtKB Accessions | p_kw |
|---|---|---|---|
| Adenylate kinase isoenzyme 1 | RGETSGR[Dea]VDDNEETIK (SEQ ID NO: 1) | Q5T9B7 | 0.03 |
| Alcohol dehydrogenase 1B | AAGAAR[Dea]IIAVDINK (SEQ ID NO: 2) | ADH1B | 0.04 |
| Beta-enolase | SPDDPAR[Dea]HITGEK (SEQ ID NO: 3) | ENOB | 0.00 |
| Carbonic anhydrase 3 | DIR[Dea]HDPSLQPWSVSYDGGSAK (SEQ ID NO: 4) | CAH3 | 0.01 |
| Fatty acid-binding protein, heart | LILTLTHGTAVC[CAM]TR[Dea]TYEK (SEQ ID NO: 5) | FABPH | 0.04 |
| Peptidyl-prolyl cis-trans isomerase A | TAENFR[Dea]ALSTGEK (SEQ ID NO: 6) | PPIA | 0.01 |
| Serum deprivation-response protein | FQHPGSDMR[Dea]QEK (SEQ ID NO: 7) | SDPR | 0.01 |
| Serum deprivation-response protein | VSPLTFGR[Dea]K (SEQ ID NO: 8) | SDPR | 0.01 |
| Heat shock protein beta-7 | RHPHTEHVQQTFR[Dea]TEIK (SEQ ID NO: 9) | HSPB7 | 0.05 |
| Alpha-crystallin B chain | GLSEMR[Dea]LEK (SEQ ID NO: 10) | CRYAB | 0.01 |
| Actin* | C[CAM]DIDIR[Dea]K (SEQ ID NO: 11) | ACTA1 | >0.05 |
| Actin* | QEYDEAGPSIVHR[Dea]K (SEQ ID NO: 12) | ACTA2 | >0.05 |
| Filamin-C | SSSSR[Dea]GSSYSSIPK (SEQ ID NO: 13) | FLNC | 0.03 |
| LIM domain-binding protein 3 | TSPEGAR[Dea]DLLGPK (SEQ ID NO: 14) | LDB3 | 0.00 |
| Myosin-binding protein C, cardiac-type | EPVFIPR[Dea]PGITYEPPNYK (SEQ ID NO: 15) | A8MXZ9 | 0.03 |
| Myozenin-2 | R[Dea]VATPFGGFEK (SEQ ID NO: 16) | MYOZ2 | 0.01 |
| Myozenin-2 | AELPDYR[Dea]SFNR[Dea]VATPFGGFEK (SEQ ID NO: 17) | MYOZ2 | 0.02 |
| Troponin I, cardiac muscle | NIDALSGMEGR[Dea]K (SEQ ID NO: 18) | TNNI3 | 0.02 |
| Troponin I, cardiac muscle | ESLDLR[Dea]AHLK (SEQ ID NO: 19) | TNNI3 | 0.02 |
| Troponin I, cardiac muscle | PR[Dea]SFMPNLVPPK (SEQ ID NO: 20) | E7EPW4 | 0.01 |
| Tropomyosin** | ETR[Dea]AEFAESVTKLEK (SEQ ID NO: 21) | TPM1 | 0.002 |
| Vimentin | FADLSEAAN[Dea]RNNDALR[Dea]QAK (SEQ ID NO: 22) | VIME | 0.03 |
| Glyceraldehyde-3-phosphate dehydrogenase | LWR[Dea]D[Dhy]GRGALQN[Oxi]IIPASTGAAK (SEQ ID NO: 23) | G3P | 0.01 |
| Myosin-7 | AEETQR[Dea]SVNDLTSQR[Dea]AK (SEQ ID NO: 24) | MYH7 | 0.05 |
| Aconitate hydratase, | SYLR[Dea]LRPDRVAMQDATAQ[Dea]M[Oxi]AMLQFISSGLSK (SEQ ID NO: 25) | ACON | 0.01 |
| Aconitate hydratase, | ANSVR[Dea]NAVTQEFGPVPDTAR[Dea]YYK (SEQ ID NO: 26) | ACON | 0.03 |
| Aconitate hydratase, | IVYGHLDDPASQEIER[Dea]GK (SEQ ID NO: 27) | ACON | 0.03 |
| Adenylate kinase 4, | LLR[Dea]AVILGPPGSGK (SEQ ID NO: 28) | KAD4 | 0.00 |
| Alcohol dehydrogenase class-3 | VAGASR[Dea]IIGVDINK (SEQ ID NO: 29) | ADHX | 0.05 |
| ATP synthase subunit alpha, | R[Dea]TGAIVDVPVGEELLGR[Dea]VVDALGNAIDGK (SEQ ID NO: 30) | ATPA | 0.00 |

TABLE 1A-continued

List of citrullinated protein (p = 0.05) with citrullinated peptides sequence.
"Dea" is Citrullination or deamination. "CAM" is carbamidomethylation. Citrullinated
proteins were grouped by cellular component. UP identifier = Universal Protein
(UP)Resource protein ID; p_kw = p value for Kruskal-Wallis test (statistic)

| Protein | Peptide | UniProtKB Accessions | p_kw |
|---|---|---|---|
| ATP synthase subunit alpha, | AIEEQVAVIYAGVR[Dea]GYLDK (SEQ ID NO: 31) | ATPA | 0.01 |
| ATP synthase subunit alpha, | GIRPAINVGLSVSR[Dea]VGSAAQ[Dea]TRAMK (SEQ ID NO: 32) | ATPA | 0.01 |
| ATP synthase subunit alpha, | QGQYSPMAIEEQVAVIYAGVR[Dea]GYLDK (SEQ ID NO: 33) | ATPA | 0.03 |
| ATP synthase-coupling factor 6 | SGGPVDASSEYQQELER[Dea]ELFK (SEQ ID NO: 34) | ATP5J | 0.00 |
| Chloride intracellular channel protein 4 | YR[Dea]NFDIPK (SEQ ID NO: 35) | CLIC4 | 0.04 |
| Cytochrome c (Fragment) | EER[Dea]ADLIAYLK (SEQ ID NO: 36) | C9JFR7 | 0.01 |
| Delta-1-pyrroline-5-carboxylate dehydrogenase, | VLR[Dea]NAAGNFYINDK (SEQ ID NO: 37) | AL4A1 | 0.00 |
| Delta-1-pyrroline-5-carboxylate dehydrogenase, | AADMLSGPR[Dea]R[Dea]AEILAK (SEQ ID NO: 38) | AL4A1 | 0.01 |
| Delta-1-pyrroline-5-carboxylate dehydrogenase, | VANEPVLAFTQGSPER[Dea]DALQK (SEQ ID NO: 39) | AL4A1 | 0.03 |
| Enoyl-CoA hydratase, | EMVLTGDR[Dea]SAQDAK (SEQ ID NO: 40) | ECHM | 0.01 |
| ES1 protein homolog, | VLR[Dea]GVEVTVGHEQEEGGK (SEQ ID NO: 41) | ES1 | 0.00 |
| Heat shock protein HSP 90-alpha | HLEINPDHSIIETLR[Dea]QK (SEQ ID NO: 42) | HS90A | 0.04 |
| NAD(P) transhydrogenase, | AATITPFR[Dea]K (SEQ ID NO: 43) | NNTM | 0.05 |
| Phosphate carrier protein, | VYFR[Dea]LPRPPPPEMPESLK (SEQ ID NO: 44) | MPCP | 0.00 |
| Pyruvate dehydrogenase E1 component subunit alpha, somatic form, | C[CAM]DLHR[Dea]LEEGPPVTTVLTR[Dea]EDGLK (SEQ ID NO: 45) | ODPA | 0.01 |
| Succinate dehydrogenase [ubiquinone] iron-sulfur subunit, | FAIYR[Dea]WDPDK (SEQ ID NO: 46) | SDHB | 0.05 |
| Succinyl-CoA ligase [ADP/GDP-forming] subunit alpha, | TR[Dea]LIGPNC[CAM]PGVINPGEC[CAM]K (SEQ ID NO: 47) | SUCA | 0.02 |
| Succinyl-CoA:3-ketoacid coenzyme A transferase 1, | ADR[Dea]AGNVIFR[Dea]K (SEQ ID NO: 48) | SCOT1 | 0.04 |
| Voltage-dependent anion-selective channel protein 1 | SR[Dea]VTQSNFAVGYK (SEQ ID NO: 49) | VDAC1 | 0.02 |
| 60 kDa heat shock protein, | FDR[Dea]GYISPYFINTSK (SEQ ID NO: 50) | CH60 | 0.04 |
| Trifunctional enzyme subunit beta, | PNIR[Dea]NVVVVDGVR[Dea]TPFLLSGTSYK (SEQ ID NO: 51) | ECHB | 0.02 |
| Aconitate hydratase, | TGR[Dea]EDIANLADEFK (SEQ ID NO: 52) | ACON | 0.00 |
| Aconitate hydratase, | R[Dea]LQLLEPFDK (SEQ ID NO: 53) | ACON | 0.01 |
| Dual specificity protein phosphatase 3 | LGITHVLNAAEGR[Dea]SFMHVNTNANFYK (SEQ ID NO: 54) | DUS3 | 0.01 |

TABLE 1A-continued

List of citrullinated protein (p = 0.05) with citrullinated peptides sequence. "Dea" is Citrullination or deamination. "CAM" is carbamidomethylation. Citrullinated proteins were grouped by cellular component. UP identifier = Universal Protein (UP)Resource protein ID; p_kw = p value for Kruskal-Wallis test (statistic)

| Protein | Peptide | UniProtKB Accessions | p_kw |
|---|---|---|---|
| Neuroblast differentiation-associated protein AHNAK | FGVSTGR[Dea]EGQTPK (SEQ ID NO: 55) | AHNK | 0.01 |
| Collagen alpha-3 (VI) chain | DVVFLLDGSEGVR[Dea]SGFPLLK (SEQ ID NO: 56) | E7ENL6 | 0.03 |

Figure 1B:
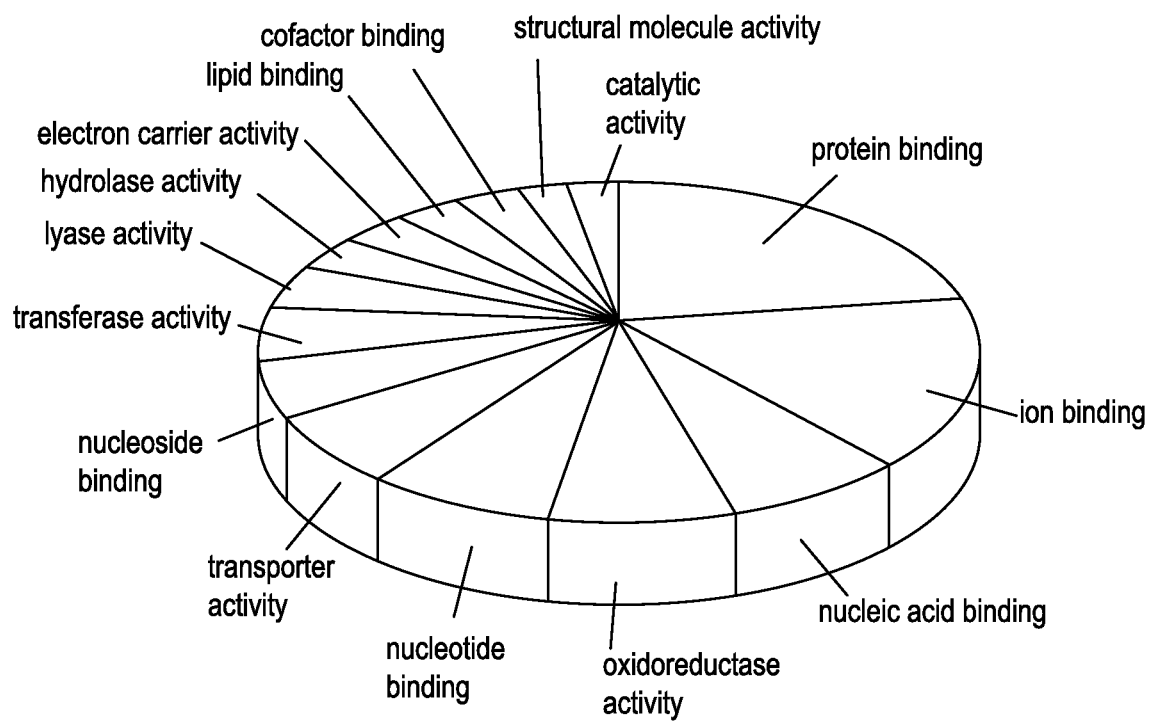
Figure 1C:
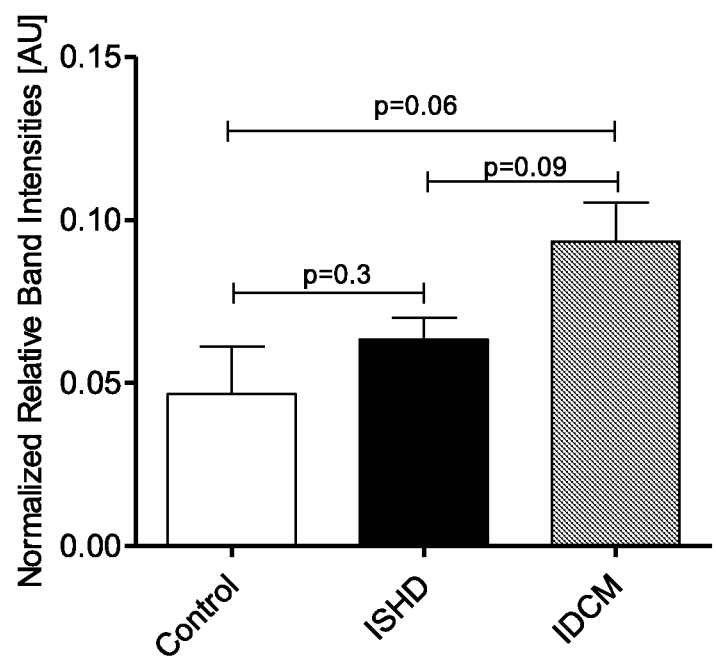

Table 1B shows all citrullinated peptides found in this study. These were proteins with diverse cellular functions, including the regulators of transcription and chromatin structure, cytoskeletal and contraction, cellular signaling processes and metabolism (FIG. 1A-FIG. 1C).

TABLE 1B all citrullinated peptides found in this study. "Dea" is Citrullination or deamination. "CAM" is carbamidomethylation.

| Protein | Peptide | UniProtKB Accessions | p_kw |
|---|---|---|---|
| Cysteine-rich protein 2 | GVNTGAVGSYIYDR (SEQ ID NO: 57) | P52943 | 0.58 |
| Adenylate kinase isoenzyme 1 | RGETSGR (SEQ ID NO: 1) | Q5T9B7 | 0.03 |
| Adenylate kinase isoenzyme 1 | R[Dea]GETSGR[Dea]VDDNEETIK (SEQ ID NO: 58) | Q5T9B7 | 0.15 |
| Adenylate kinase isoenzyme 1 | YGYTHLSTGDLLR[Dea]SEVSSGSAR[Dea]GK (SEQ ID NO: 59) | Q5T9B7 | 0.57 |
| Adenylate kinase isoenzyme 1 | LLR[Dea]SEVSSGSAR[Dea]GK (SEQ ID NO: 60) | Q5T9B7 | 0.68 |
| Adenylate kinase isoenzyme 1 | YGYTHLSTGDLLR[Dea]SEVSSGSARGK (SEQ ID NO: 61) | Q5T9B7 | 0.74 |
| Alcohol dehydrogenase 1B | AAGAAR[Dea]IIAVDINK (SEQ ID NO: 2) | P00325 | 0.04 |
| Aldose reductase | PEDPSLLEDPR[Dea]IK (SEQ ID NO: 62) | P15121 | 0.18 |
| Alpha-crystallin B chain | GLSEMR[Dea]LEK (SEQ ID NO: 10) | P02511 | 0.01 |
| Alpha-crystallin B chain | QVSGPER[Dea]TIPITREEK (SEQ ID NO: 63) | P02511 | 0.23 |
| Alpha-crystallin B chain | YR[Dea]IPADVDPLTITSSLSDGVLTVNGPR[Dea]K (SEQ ID NO: 64) | P02511 | 0.41 |
| Alpha-crystallin B chain | SPFYLR[Dea]PPSFLR[Dea]APSWFDTGLSEMRLEK (SEQ ID NO: 65) | P02511 | 0.51 |
| Alpha-crystallin B chain | SPFYLRPPSFLR[Dea]APSWFDTGLSEMRLEK (SEQ ID NO: 66) | P02511 | 0.55 |
| Alpha-crystallin B chain | QVSGPER[Dea]TIPITR[Dea]EEK (SEQ ID NO: 67) | P02511 | 0.97 |
| Aspartate aminotransferase, | HIYLLPSGR[Dea]INVSGLTTK (SEQ ID NO: 68) | P17174 | 0.84 |
| ATP-dependent 6-phosphofructokinase | LLAHVR[Dea]PPVSK (SEQ ID NO: 69) | P08237 | 0.53 |
| ATP-dependent 6-phosphofructokinase | NVLGHMQQGGSPTPFDR[Dea]NFATK (SEQ ID NO: 70) | P08237 | 0.80 |
| ATP-dependent 6-phosphofructokinase | [1Ac]-MDADDSR[Dea]APK (SEQ ID NO: 71) | Q01813 | 0.55 |
| Beta-enolase | SPDDPAR[Dea]HITGEK (SEQ ID NO: 3) | P13929 | 0.00 |
| Carbonic anhydrase 3 | DIR[Dea]HDPSLQPWSVSYDGGSAK (SEQ ID NO: 4) | P07451 | 0.01 |
| Creatine kinase M-type | ELFDPIISDR[Dea]HGGYK (SEQ ID NO: 72) | P06732 | 0.20 |

TABLE 1B-continued all citrullinated peptides found in this study. "Dea" is Citrullination or deamination. "CAM" is carbamidomethylation.

| Protein | Peptide | UniProtKB Accessions | p_kw |
| --- | --- | --- | --- |
| Creatine kinase M-type | GGDDLDPNYVLSSR[Dea]VR[Dea]TGR[Dea]SIK (SEQ ID NO: 73) | P06732 | 0.36 |
| Creatine kinase M-type | PIISDR[Dea]HGGYKPTDK (SEQ ID NO: 74) | P06732 | 0.47 |
| Creatine kinase M-type | ELFDPIISDR[Dea]HGGYKPTDK (SEQ ID NO: 75) | P06732 | 0.51 |
| Creatine kinase M-type | GGDDLDPNYVLSSRVR[Dea]TGRSIK (SEQ ID NO: 76) | P06732 | 0.66 |
| Creatine kinase M-type | FEEILTR[Dea]LRLQK (SEQ ID NO: 77) | P06732 | 0.82 |
| Fatty acid-binding protein | LILTLTHGTAVC[CAM]TR[Dea]TYEK (SEQ ID NO: 5) | P05413 | 0.04 |
| Glyceraldehyde-3-phosphate dehydrogenase | LWR[Dea]D[Dhy]GRGALQN[Oxi]IIPSTGAAK (SEQ ID NO: 23) | P04406 | 0.01 |
| Glycogen phosphorylase | VAIQLNDTHPALSIPELMR[Dea]ILVDVEK (SEQ ID NO: 78) | P11216 | 0.39 |
| Glycogen phosphorylase | QISVR[Dea]GLAGLGDVAEVRK (SEQ ID NO: 79) | P11216 | 0.63 |
| Hemoglobin subunit alpha | LR[Dea]VDPVN[Dea]FK (SEQ ID NO: 80) | P69905 | 0.91 |
| Hemoglobin subunit alpha | VGAHAGEYGAEALER[Dea]MFLSFPT (SEQ ID NO: 81) | P69905 | 0.93 |
| Hemoglobin subunit alpha | LER[Dea]MFLSFPTTK (SEQ ID NO: 82) | P69905 | 0.93 |
| Hemoglobin subunit alpha | R[Dea]VDPVNFK (SEQ ID NO: 83) | P69905 | 0.93 |
| Hemoglobin subunit beta | VNVDEVGGEALGRLLVVYPWTQ[Dea]R[Dea]FFESFGDLSTPDAVM[Oxi]GNPK (SEQ ID NO: 84) | P68871 | 0.40 |
| Hemoglobin subunit beta | VNVDEVGGEALGR[Dea]LLV (SEQ ID NO: 85) | P68871 | 0.46 |
| Hemoglobin subunit beta | VNVDEVGGEALGR[Dea]LLVVYPWTQ[Dea]RFFWSFGDLSTPDAVMGNPK (SEQ ID NO: 86) | P68871 | 0.67 |
| Hemoglobin subunit beta | R[Dea]FFESFGDLSTPDAVMGNPK (SEQ ID NO: 87) | P68871 | 0.82 |
| Hemoglobin subunit beta | VNVDEVGGEALGR[Dea]L (SEQ ID NO: 88) | P68871 | 0.90 |
| Peptidyl-prolyl cis-trans isomerase A | TAENFR[Dea]ALSTGEK (SEQ ID NO: 6) | P62937 | 0.01 |
| Phosphatidylethanolamine-binding protein 1 | VLVLTDPDAPSR[Dea]KDPK (SEQ ID NO: 89) | P30086 | 0.12 |
| Phosphatidylethanolamine-binding protein 1 | C[CAM]DEPILSN[Dea]RSGDHR[Dea]GK (SEQ ID NO: 90) | P30086 | 0.55 |
| Phosphoglycerate kinase 1 | SVVLMSHLGR[Dea]PDGVPMPDK (SEQ ID NO: 91) | P00558 | 0.26 |
| Phosphoglycerate kinase 1 | R[Dea]VVMR[Dea]VDFNVPMK (SEQ ID NO: 92) | P00558 | 0.27 |
| Serum albumin | YLYEIARR[Dea]H[AAS]P[Oxi]YFYAPELLFFAK (SEQ ID NO: 93) | P02768 | 0.06 |
| Serum albumin | VPQVSTPTLVEVSR[Dea]N (SEQ ID NO: 94) | P02768 | 0.31 |
| Serum albumin | WAVAR[Dea]LSQR[Dea]FPK (SEQ ID NO: 95) | P02768 | 0.40 |
| Serum albumin | FGER[Dea]AFK (SEQ ID NO: 96) | P02768 | 0.46 |
| Serum albumin | RESLVNR[Dea]RPC[CAM] (SEQ ID NO: 97) | P02768 | 0.49 |
| Serum albumin | AWAVAR[Dea]LSQR[Dea]FPK (SEQ ID NO: 98) | P02768 | 0.64 |
| Serum albumin | DDNPNLPRLVR[Dea]PEVDVMC[CAM]TAFHDNEETFLK (SEQ ID NO: 99) | P02768 | 0.66 |
| Serum albumin | TPVSDR[Dea]VTK (SEQ ID NO: 100) | P02768 | 0.69 |
| Serum albumin | ALLVR[Dea]YTK (SEQ ID NO: 101) | P02768 | 0.70 |

TABLE 1B-continued all citrullinated peptides found in this study. "Dea" is Citrullination or deamination. "CAM" is carbamidomethylation.

| Protein | Peptide | UniProtKB Accessions | p_kw |
| --- | --- | --- | --- |
| Serum albumin | SEVAHR[Dea]FK (SEQ ID NO: 102) | P02768 | 0.72 |
| Serum albumin | LVEVSR[Dea]NLGK (SEQ ID NO: 103) | P02768 | 0.74 |
| Serum albumin | R[Dea]MPC[CAM]AEDYLSVVLNQLC[CAM]VLHEK (SEQ ID NO: 104) | P02768 | 0.82 |
| Serum albumin | DDNPNLPR[Dea]LVR[Dea]PEVDVMC[CAM]TAFHDNEETFLK (SEQ ID NO: 105) | P02768 | 0.84 |
| Serum albumin | [CRM]-YLYEIAR[Dea]RHPYFYAPELLFFAK (SEQ ID NO: 106) | P02768 | 0.93 |
| Serum albumin | C[CAM]C[CAM]TESLVNR[Dea]RPC[CAM] (SEQ ID NO: 107) | P02768 | 0.93 |
| Serum deprivation-response protein | FQHPGSDMR[Dea]QEK (SEQ ID NO: 7) | O95810 | 0.01 |
| Serum deprivation-response protein | VSPLTFGR[Dea]K (SEQ ID NO: 8) | O95810 | 0.01 |
| Transgelin | R[Dea]EFTESQLQEGK (SEQ ID NO: 108) | Q01995 | 0.22 |
| Translationally-controlled tumor protein | MIIYR[Dea]DLISHDEMFSDIYK (SEQ ID NO: 109) | Q5W0H4 | 0.14 |
| Tumor protein D54 | TSAALSTVGSAISR[Dea]K (SEQ ID NO: 110) | O43399 | 0.08 |
| Malate dehydroenase | FVEGLPINDFSR[Dea]EK (SEQ ID NO: 111) | P40925 | 0.17 |
| Actin, alpha skeletal muscle | C[CAM]DIDIR[Dea]K (SEQ ID NO: 11) | Q5T8M8 | 0.11 |
| Actin, alpha skeletal muscle | QEYDEAGPSIVHR[Dea]K (SEQ ID NO: 12) | Q5T8M8 | 0.16 |
| Desmin | EEAENNLAAFR[Dea]ADVDAATLAR (SEQ ID NO: 112) | P17661 | 0.06 |
| Desmin | SR[Dea]LGTTR[Dea]TPSSYGAGELLDFSLADAVNQEFLTTRTNEK (SEQ ID NO: 113) | P17661 | 0.08 |
| Desmin | NFRETSPEQR[Dea]GSEVHTK (SEQ ID NO: 114) | P17661 | 0.23 |
| Desmin | MALDVEIATYR[Dea]K (SEQ ID NO: 115) | P17661 | 0.23 |
| Desmin | SR[Dea]LGTTRTPSSYGAGELLDFSLADAVNQEFLTTRTNEK (SEQ ID NO: 116) | P17661 | 0.31 |
| Desmin | VDVER[Dea]DNLLDDLQRLK (SEQ ID NO: 117) | P17661 | 0.39 |
| Desmin | NFR[Dea]ETSPEQR[Dea]GSEVHTK (SEQ ID NO: 118) | P17661 | 0.43 |
| Desmin | TIETR[Dea]DGEVVSEATQQHEVL (SEQ ID NO: 119) | P17661 | 0.55 |
| Desmin | SSPVFPR[Dea]AGFGSK (SEQ ID NO: 120) | P17661 | 0.88 |
| Desmin | [1Ac]-ASGVQVADEVC[CAM]R[Dea]IFYDMK (SEQ ID NO: 121) | P60981 | 0.78 |
| Filamin-C | SSSR[Dea]GSSYSSIPK (SEQ ID NO: 13) | Q14315 | 0.03 |
| Four and a half LIM domains protein 2 | EPITTGGVTYR[Dea]EQPWHK (SEQ ID NO: 122) | Q14192 | 0.08 |
| Fructose-bisphosphate aldolase A | ELSDIAHR[Dea]IVAPGK (SEQ ID NO: 123) | P04075 | 0.55 |
| Glyceraldehyde-3-phosphate dehydrogenase | LVIN[Dea]GNPITIFQER[Dea]DPSK (SEQ ID NO: 124) | P04406 | 0.66 |
| Glyceraldehyde-3-phosphate dehydrogenase | R[Dea]VIISAPSADAPMFVMGVNHEK (SEQ ID NO: 125) | P04406 | 0.68 |
| Glyceraldehyde-3-phosphate dehydrogenase | AFRVPTAN[Dea]VSVVDLTC[CAM]R[Dea]LEK (SEQ ID NO: 126) | P04406 | 0.88 |

TABLE 1B-continued all citrullinated peptides found in this study. "Dea" is Citrullination or deamination. "CAM" is carbamidomethylation.

| Protein | Peptide | UniProtKB Accessions | p_kw |
|---|---|---|---|
| Glyceraldehyde-3-phosphate dehydrogenase | VSVVDLTC[CAM]R[Dea]LEKPAK (SEQ ID NO: 127) | P04406 | 0.93 |
| Glyceraldehyde-3-phosphate dehydrogenase | LWR[Dea]DGR[Dea]GALQNIIPASTGAAK (SEQ ID NO: 128) | P04406 | 0.99 |
| LIM domain-binding protein 3 | TSPEGAR[Dea]DLLGPK (SEQ ID NO: 14) | O75112 | 0.00 |
| Moesin | DR[Dea]SEEER[Dea]TTEAEK (SEQ ID NO: 129) | P26038 | 0.28 |
| Myomesin-1 | HVSGITDTEEER[Dea]IK (SEQ ID NO: 130) | P52179 | 0.07 |
| Myomesin-1 | SPR[Dea]FALFDLAEGK (SEQ ID NO: 131) | P52179 | 0.57 |
| Myosin light chain 3 | LGQNPTQAEVLR[Dea]VLGKPRQEELNTK (SEQ ID NO: 132) | P08590 | 0.09 |
| Myosin light chain 3 | LGKPR[Dea]QEELNTK (SEQ ID NO: 133) | P08590 | 0.16 |
| Myosin light chain 3 | [CRM]-EAFMLFDR[Dea]TPK (SEQ ID NO: 134) | P08590 | 0.39 |
| Myosin light chain 3 | EAFMLFDR[Dea]TPK (SEQ ID NO: 135) | P08590 | 0.41 |
| Myosin light chain 3 | VLGKPR[Dea]QEELNTK (SEQ ID NO: 136) | P08590 | 0.42 |
| Myosin light chain 3 | ALGQNPTQAEVLR[Dea]VLGK (SEQ ID NO: 137) | P08590 | 0.59 |
| Myosin light chain 3 | LGQNPTQAEVLR[Dea]VLGKPRQ[Dea]EELNTK (SEQ ID NO: 138) | P08590 | 0.79 |
| Myosin light chain 3 | LGQNPTQAEVLR[Dea]VLGK (SEQ ID NO: 139) | P08590 | 0.71 |
| Myosin light chain 3 | EAFM[Oxi]LFDR[Dea]TPK (SEQ ID NO: 140) | P08590 | 0.86 |
| Myosin light chain 4 | MLDFETFLPILQHISR[Dea]NK (SEQ ID NO: 141) | P12829 | 0.28 |
| Myosin light chain 4 | EQGTYEDFVEGLR[Dea]VFDK (SEQ ID NO: 142) | P12829 | 0.74 |
| Myosin regulatory light chain 2 | NDLRDTFAALGR[Dea]VNVK (SEQ ID NO: 143) | P10916 | 0.71 |
| Myosin regulatory light chain 2 | EAFTIMDQNR[Dea]DGFIDK (SEQ ID NO: 144) | P10916 | 0.77 |
| Myosin-7 | AEETQR[Dea]SVNDLTSQR[Dea]AK (SEQ ID NO: 24) | P12883 | 0.05 |
| Myosin-7 | [1Ac]-GDSEMAVFGAAAPYLR[Dea]K (SEQ ID NO: 145) | P12883 | 0.18 |
| Myosin-7 | VR[Dea]ELENELEAEQK (SEQ ID NO: 146) | P12883 | 0.27 |
| Myosin-7 | R[Dea]YR[Dea]ILNPAAIPEGQFIDSRK (SEQ ID NO: 147) | P12883 | 0.28 |
| Myosin-7 | RNHLR[Dea]VVDSLQT (SEQ ID NO: 148) | P12883 | 0.31 |
| Myosin-7 | R[Dea]VR[Dea]ELENELEAEQK (SEQ ID NO: 149) | P12883 | 0.40 |
| Myosin-7 | AVFGAAAPYLR[Dea]K (SEQ ID NO: 150) | P12883 | 0.42 |
| Myosin-7 | LEAR[Dea]VR[Dea]ELENELEAEQK (SEQ ID NO: 151) | P12883 | 0.43 |
| Myosin-7 | YR[Dea]ILNPAAIPEGQFIDSRK (SEQ ID NO: 152) | P12883 | 0.51 |
| Myosin-7 | RYR[Dea]ILNPAAIPEGQFIDSRK (SEQ ID NO: 153) | P12883 | 0.52 |
| Myosin-7 | NFELNALNAR[Dea]IEDEQALGSQLQK (SEQ ID NO: 154) | P12883 | 0.58 |
| Myosin-7 | AEETQRSVNDLTSQR[Dea]AK (SEQ ID NO: 155) | P12883 | 0.60 |
| Myosin-7 | RSVNDLTSQR[Dea]AK (SEQ ID NO: 156) | P12883 | 0.74 |
| Myosin-7 | R[Dea]VRELENELEAEQK (SEQ ID NO: 157) | P12883 | 0.76 |
| Myosin-7 | YRILNPAAIPEGQFIDSR[Dea]K (SEQ ID NO: 158) | P12883 | 0.81 |

TABLE 1B-continued all citrullinated peptides found in this study. "Dea" is Citrullination or deamination. "CAM" is carbamidomethylation.

| Protein | Peptide | UniProtKB Accessions | p_kw |
|---|---|---|---|
| Myosin-7 | RVIQYFAVIAAIGDR[Dea]SK (SEQ ID NO: 159) | P12883 | 0.86 |
| Myosin-7 | RYR[Dea]ILNPAAIPEGQFIDSR[Dea]K (SEQ ID NO: 160) | P12883 | 0.96 |
| Myosin-binding protein C | EPVFIPR[Dea]PGITYEPPNYK (SEQ ID NO: 15) | A8MXZ9 | 0.03 |
| Myosin-binding protein C | VRWQR[Dea]GGSDISASNK (SEQ ID NO: 161) | A8MXZ9 | 0.09 |
| Myosin-binding protein C | PR[Dea]PQVTWTK (SEQ ID NO: 162) | A8MXZ9 | 0.21 |
| Myozenin-2 | R[Dea]VATPFGGFEK (SEQ ID NO: 16) | Q9NPC6 | 0.01 |
| Myozenin-2 | AELPDYR[Dea]SFNR[Dea]VATPFGGFEK (SEQ ID NO: 17) | Q9NPC6 | 0.02 |
| Phosphoglucomutase-1 | SGEHDFGAAFDGDGDR[Dea]NMILGK (SEQ ID NO: 163) | P36871 | 0.86 |
| Phosphoglucomutase-1 | DLEALMFDR[Dea]SFVGK (SEQ ID NO: 164) | P36871 | 0.87 |
| Plastin-2 | VNDDIIVNWVNETLR[Dea]EAKK (SEQ ID NO: 165) | P13796 | 0.45 |
| Profilin-1 | C[CAM]SVIR[Dea][Dea]DS[Dhy]LLQDGEFSMDLRTK (SEQ ID NO: 166) | P07737 | 0.18 |
| Titin | C[CAM]DVS[Dhy]R[Dea]GDWVTALASVTK (SEQ ID NO: 167) | Q8WZ42 | 0.17 |
| Tropomyosin* | ETR[Dea]AEFAERSVTKLEK (SEQ ID NO: 21) | Z7Z596 | 0.002* |
| Troponin I | NIDALSGMEGR[Dea]K (SEQ ID NO: 18) | P19429 | 0.02 |
| Troponin I | ESLDLR[Dea]AHLK (SEQ ID NO: 19) | P19429 | 0.02 |
| Troponin I | YR[Dea]AYATEPHAK (SEQ ID NO: 168) | P19429 | 0.09 |
| Troponin I | [PGQ]-QELEREAEER[Dea]R[Dea]GEK (SEQ ID NO: 169) | P19429 | 0.49 |
| Troponin T | PR[Dea]SFMPNLVPPK (SEQ ID NO: 20) | E7EPW4 | 0.01 |
| Troponin T | GERVDFDDIHR[Dea]K (SEQ ID NO: 170) | E7EPW4 | 0.06 |
| Troponin T | EAEDGPMEESKPKPR[Dea] (SEQ ID NO: 171) | E7EPW4 | 0.23 |
| Troponin T | AEAETEETR[Dea]AEEDEEEEEAK (SEQ ID NO: 172) | A7EPW4 | 0.66 |
| Tubulin alpha-1B chain | HVPR[Dea]AVFVDLEPTVIDEVR[Dea]TGTYR[Dea]QLFHPEQLITGK (SEQ ID NO: 173) | P68363 | 0.43 |
| Tubulin alpha-4A chain | HVPR[Dea]AVFVDLEPTVIDEIRN[Dea]GPYRQ[Dea]LFHPEQLITGK (SEQ ID NO: 174) | P68366 | 0.26 |
| Tubulin alpha-8 chain | EDAANNYAR[Dea]GHYTVGK (SEQ ID NO: 176) | C9J2C0 | 0.37 |
| Vimentin | FADLSEAAN[Dea]RNNDALR[Dea]QAK (SEQ ID NO: 22) | P08670 | 0.03 |
| Vimentin | TVETR[Dea]DGQVINETSQHHDDLE (SEQ ID NO: 177) | P08670 | 0.09 |
| Heat shock protein beta-1 | LATQSNEITIPVTFESR[Dea]AQLGGPEAAK (SEQ ID NO: 178) | P04792 | 0.34 |
| Heat shock protein beta-7 | RHPHTEHVQQTFR[Dea]TEIK (SEQ ID NO: 9) | Q9UBY9 | 0.05 |
| Leucine-rich PPR motif-containing protein | IPENIYRGIR[Dea]N[Dea]LLESYHVPELIK (SEQ ID NO: 179) | P42704 | 0.55 |
| Troponin C | SEEELSDLFR[Dea]MFDK (SEQ ID NO: 180) | P63316 | 0.69 |
| Alpha-1-antitrypsin | ELDR[Dea]DTVFALVN[Dea]YIFFK (SEQ ID NO: 181) | P01009 | 0.61 |
| Apolipoprotein A-I | [PGE]-EN[Dea]GGAR[Dea]LAEYHAK (SEQ ID NO: 182) | P02647 | 0.58 |
| Apolipoprotein A-I | DSGR[Dea]DYVSQFEGSALGK (SEQ ID NO: 183) | P02647 | 0.90 |
| Apolipoprotein A-I | AKPALEDLR[Dea]QGLLPVLESFK (SEQ ID NO: 184) | P02647 | 0.96 |
| Calreticulin | PR[Dea]QIDNPDYK (SEQ ID NO: 185) | P27797 | 0.17 |

TABLE 1B-continued all citrullinated peptides found in this study. "Dea" is Citrullination or deamination. "CAM" is carbamidomethylation.

| Protein | Peptide | UniProtKB Accessions | p_kw |
| --- | --- | --- | --- |
| Calreticulin | TEREQFVEFR[Dea]DK (SEQ ID NO: 186) | O43852 | 0.06 |
| Sarcalumenin | IER[Dea]AITQELPGLLGSLGLGK (SEQ ID NO: 187) | Q86TD4 | 0.24 |
| Sarcalumenin | TIEGIVMAADSAR[Dea]SFSPLEK (SEQ ID NO: 188) | Q86TD4 | 0.60 |
| Decorin | ISR[Dea]VDAASLK (SEQ ID NO: 189) | P07585 | 0.25 |
| Beta-2-glycoprotein 1 | ATVVYQGER[Dea]VK (SEQ ID NO: 190) | P02749 | 0.55 |
| Cathepsin D | VER[Dea]QVFGEATK (SEQ ID NO: 191) | P07339 | 0.14 |
| Lumican | YLYLR[Dea]NNQIDHIDEK (SEQ ID NO: 192) | P51884 | 0.66 |
| Myoglobin | ALELFR[Dea]K (SEQ ID NO: 193) | P02144 | 0.11 |
| Ubiquitin carboxyl-terminal hydrolase 5 | EEDPATGTGDPPR[Dea]K (SEQ ID NO: 194) | P45974 | 0.50 |
| 2,4-dienoyl-CoA reductase | GAFSR[Dea]LDPTGTFEK (SEQ ID NO: 195) | B7Z6B8 | 0.26 |
| 28S ribosomal protein S36 | PNVSEALR[Dea]SAGLPSHSSVISQHSK (SEQ ID NO: 196) | P82909 | 0.29 |
| 3-ketoacyl-CoA thiolase | YALQSQQR[Dea]WK (SEQ ID NO: 197) | P42765 | 0.55 |
| 3-ketoacyl-CoA thiolase | VSPETVDSVIMGNVLQSSSDAIYLAR[Dea]HVGLR[Dea]VGIPK (SEQ ID NO: 198) | P42765 | 0.28 |
| Acetyl-CoA acetyltransferase | EVVIVSATR[Dea]TPIGSFLGSLSLLPATK (SEQ ID NO: 199) | P24752 | 0.07 |
| Aconitate hydratase | SYLR[Dea]LRPDRVAMQDAT[Dhy]AQ[Dea]M[Oxi]AMLQFISSGLSK (SEQ ID NO: 25) | Q99798 | 0.01 |
| Aconitate hydratase, | ANSVR[Dea]NAVTQEFGPVPDTAR[Dea]YYK (SEQ ID NO: 26) | Q99798 | 0.03 |
| Aconitate hydratase, | IVYGHLDDPASQEIER[Dea]GK (SEQ ID NO: 27) | Q99798 | 0.03 |
| Aconitate hydratase | SYLRLR[Dea]PDRVAMQDATAQMAMLQFISSGLSK (SEQ ID NO: 200) | Q99798 | 0.14 |
| Aconitate hydratase | FR[Dea]GHLDNISNNLLIGAINIEN[Dea]GK (SEQ ID NO: 201) | Q99798 | 0.19 |
| Acyl-Coenzyme A dehydrogenase, C-4 to C-12 straight chain, isoform CRA_a | AFTGFIVEADTPGIQGR[Dea]K (SEQ ID NO: 202) | Q5T4U5 | 0.15 |
| Acyl-Coenzyme A dehydrogenase, C-4 to C-12 straight chain, isoform CRA_a | FAR[Dea]EEIIPVAAEYDK (SEQ ID NO: 203) | Q5T4U5 | 0.26 |
| Acyl-Coenzyme A dehydrogenase, C-4 to C-12 straight chain, isoform CRA_a | TR[Dea]PVVAAGAVGLAQRALDEATK (SEQ ID NO: 204) | Q5T4U5 | 0.93 |
| Adenylate kinase 4 | LLR[Dea]AVILGPPGSGK (SEQ ID NO: 28) | P27144 | 0.00 |
| Adenylate kinase isoenzyme 1 | KR[Dea]GETSGR[Dea]VDDNEETIK (SEQ ID NO: 205) | Q5T9B7 | 0.95 |
| Alcohol dehydrogenase class-3 | VAGASR[Dea]IIGVDINK (SEQ ID NO: 29) | P11766 | 0.05 |
| Aldehyde dehydrogenase | VAFTGSTEIGR[Dea]VIQVAAGSSNLK (SEQ ID NO: 206) | P05091 | 0.08 |
| Aldehyde dehydrogenase | SR[Dea]VVGNPFDSK (SEQ ID NO: 207) | P05091 | 0.55 |
| Aspartate aminotransferase | PYVLPSVR[Dea]K (SEQ ID NO: 208) | P00505 | 0.22 |
| ATP synthase subunit alpha | R[Dea]TGAIVDVPVGEELLGR[Dea]VVDALGNAIDGK (SEQ ID NO: 30) | P25705 | 0.00 |
| ATP synthase subunit alpha | AIEEQVAVIYAGVR[Dea]GYLDK (SEQ ID NO: 31) | P25705 | 0.01 |

TABLE 1B-continued all citrullinated peptides found in this study. "Dea" is Citrullination or deamination. "CAM" is carbamidomethylation.

| Protein | Peptide | UniProtKB Accessions | p_kw |
| --- | --- | --- | --- |
| ATP synthase subunit alpha | GIRPAINVGLSVSR[Dea]VGSAAQ[Dea]TRAMK (SEQ ID NO: 32) | P25705 | 0.01 |
| ATP synthase subunit alpha | QGQYSPMAIEEQVAVIYAGVR[Dea]GYLDK (SEQ ID NO: 33) | P25705 | 0.03 |
| ATP synthase subunit beta | IPVGPETLGRIMNVIGEPIDER[Dea]GPIK (SEQ ID NO: 209) | P06576 | 0.26 |
| ATP synthase subunit beta | IPVGPETLGR[Dea]IMNVIGEPIDER[Dea]GPIK (SEQ ID NO: 210) | P06576 | 0.51 |
| ATP synthase subunit beta | IQR[Dea]FLSQPFQVAEVFTGHMGK (SEQ ID NO: 211) | P06576 | 0.70 |
| ATP synthase subunit beta | AHGGYSVFAGVGERTR[Dea]EGN[Dea]DLYHEMIESGVINLK (SEQ ID NO: 212) | P06576 | 0.87 |
| ATP synthase subunit e | PRAEEER[Dea]R[Dea]IAAEEK (SEQ ID NO: 213) | P56385 | 0.32 |
| ATP synthase-coupling factor 6, | SGGPVDASSEYQQELER[Dea]ELFK (SEQ ID NO: 34) | P18859 | 0.00 |
| Chloride intracellular channel protein 4 | YR[Dea]NFDIPK (SEQ ID NO: 35) | Q9Y696 | 0.04 |
| Citrate synthase | SQLSAAVTALNSESN[Dea]FARAYAQGISR[Dea]TK (SEQ ID NO: 214) | B4DJV2 | 0.34 |
| Citrate synthase | TVVGQITVDMMYGGMR[Dea]GMK (SEQ ID NO: 215) | B4DJV2 | 0.75 |
| Creatine kinase B-type | LR[Dea]FPAEDEFPDLSAHNNHMAK (SEQ ID NO: 216) | P12277 | 0.33 |
| Creatine kinase B-type | EVFTR[Dea]FC[CAM]TGLTQIETLFK (SEQ ID NO: 217) | P12277 | 0.82 |
| Creatine kinase S-type, | C[CAM]TR[Dea]AER[Dea]R[Dea]EVENVAITALEGLK (SEQ ID NO: 218) | P17540 | 0.31 |
| Creatine kinase S-type, | TR[Dea]AER[Dea]R[Dea]EVENVAITALEGLK (SEQ ID NO: 219) | P17540 | 0.59 |
| Creatine kinase S-type, | EVREQ[Dea]PR[Dea]LFPPSADYPDLRK (SEQ ID NO: 220) | P17540 | 0.72 |
| Cytochrome C | EER[Dea]ADLIAYLK (SEQ ID NO: 36) | C9JFR7 | 0.01 |
| Cytochrome C | KEER[Dea]ADLIAYLK (SEQ ID NO: 221) | C9JFR7 | 0.01 |
| Cytochrome c oxidase subunit 5A, | EIYPYVIQELR[Dea]PTLNELGISTPEELGLDKV (SEQ ID NO: 222) | P20674 | 0.07 |
| Cytochrome c oxidase subunit 5A, | SHGSQETDEEFDARWVTYFN[Dea]KPDIDAWELR[Dea]K (SEQ ID NO: 223) | P20674 | 0.18 |
| Cytochrome c oxidase subunit 5A, | ASGGGVPTDEEQATGLER[Dea]FIMLAAK (SEQ ID NO: 224) | P10606 | 0.49 |
| Delta-1-pyrroline-5-carboxylate dehydrogenase | VLR[Dea]NAAGNFYINDK (SEQ ID NO: 37) | P30038 | 0.00 |
| Delta-1-pyrroline-5-carboxylate dehydrogenase | AADMLSGPR[Dea]R[Dea]AEILAK (SEQ ID NO: 38) | P30038 | 0.01 |
| Delta-1-pyrroline-5-carboxylate dehydrogenase | VANEPVLAFTQGSPER[Dea]DALQK (SEQ ID NO: 39) | P30038 | 0.03 |
| Delta-1-pyrroline-5-carboxylate dehydrogenase | TVIQAEIDAAAELIDFFR[Dea]FNAK (SEQ ID NO: 225) | P30038 | 0.12 |
| Dihydrolipoyl dehydrotenase | NFQR[Dea]ILQK (SEQ ID NO: 226) | P09622 | 0.87 |
| Electron transfer flavoprotein subunit alpha | VVVSGGR[Dea]GLK (SEQ ID NO: 227) | P13804 | 0.18 |
| Electron transfer flavoprotein subunit alpha | VFSVR[Dea]GTSFDAAATSGGSASSEK (SEQ ID NO: 228) | P13804 | 0.18 |
| Electron transfer flavoprotein subunit alpha | LLYDLADQLHAAVGASR[Dea]AAVDAGFVPNDMQVGQTGK (SEQ ID NO: 229) | P13804 | 0.48 |

TABLE 1B-continued all citrullinated peptides found in this study. "Dea" is Citrullination or deamination. "CAM" is carbamidomethylation.

| Protein | Peptide | UniProtKB Accessions | p_kw |
| --- | --- | --- | --- |
| Electron transfer flavoprotein subunit beta | VEREIDGGLETLR[Dea]LK (SEQ ID NO: 230) | P38117 | 0.17 |
| Electron transfer flavoprotein subunit beta | LSVISVEDPPQR[Dea]TAGVK (SEQ ID NO: 231) | P38117 | 0.70 |
| Elongation factor Tu, | PFLLPVEAVYSVPGR[Dea]GTVVTGTLER[Dea]GILK (SEQ ID NO: 232) | P49411 | 0.34 |
| Elongation factor Tu, | SLERAEAGDN[Dea]LGALVR[Dea]GLK (SEQ ID NO: 233) | P49411 | 0.53 |
| Elongation factor Tu, | NIR[Dea]TVVTGIEMFHK (SEQ ID NO: 234) | P49411 | 0.58 |
| Elongation factor Tu, | PFLLPVEAVYSVPGR[Dea]GTVVTGTLERGILK (SEQ ID NO: 235) | P49411 | 0.80 |
| Elongation factor Tu, | SLERAEAGDNLGALVR[Dea]GLK (SEQ ID NO: 236) | P49411 | 0.80 |
| Enoyl-CoA hydratase, | EMVLTGDR[Dea]ISAQDAK (SEQ ID NO: 40) | P30084 | 0.01 |
| Enoyl-CoA hydratase, | AQFAQPEILIGTIPGAGGTQ[Dea]RLTR[Dea]AVGK (SEQ ID NO: 237) | P30084 | 0.11 |
| ES1 protein homolog, | VLR[Dea]GVEVTVGHEQEEGGK (SEQ ID NO: 41) | P30042 | 0.00 |
| Fumarate hydratase, | IANDIRFLGSGPR[Dea]SGLGELILPEN[Dea]EPGSSIMPGK (SEQ ID NO: 238) | P07954 | 0.19 |
| Fumarate hydratase, | YYGAQTVR[Dea]STMNFK (SEQ ID NO: 239) | P07954 | 0.55 |
| Glutathione S-transferase kappa 1 | DSGNKPPGLLPR[Dea]K (SEQ ID NO: 240) | Q9Y2Q3 | 0.95 |
| Glutathione S-transferase P | DQQEAALVDMVNDGVEDLR[Dea]C[CAM]K (SEQ ID NO: 241) | P09211 | 0.63 |
| Heat shock 70 kDa protein 1A/1B | AQIHDLVLVGGSTR[Dea]IPK (SEQ ID NO: 242) | P08107 | 0.68 |
| Heat shock 70 kDa protein 1A/1B | DAGVIAGLNVLRIIN[Dea]EPTAAAIAYGLDR[Dea]TGK (SEQ ID NO: 243) | P08107 | 0.74 |
| Heat shock protein HSP 90-alpha | HLEINPDHSIIETLR[Dea]QK (SEQ ID NO: 42) | P07900 | 0.04 |
| Heat shock protein HSP 90-alpha | EQVANSAFVERVR[Dea]K (SEQ ID NO: 244) | P08238 | 0.60 |
| Isocitrate dehydrogenase [NAD] subunit alpha, | ANIMR[Dea]MSDGLFLQK (SEQ ID NO: 245) | P50213 | 0.84 |
| Isocitrate dehydrogenase [NADP], | IWYEHR[Dea]LIDDMVAQVLK (SEQ ID NO: 246) | [48735 | 0.13 |
| Isocitrate dehydrogenase [NADP], | SNLDR[Dea]ALGRQ (SEQ ID NO: 247) | P48735 | 0.19 |
| Isocitrate dehydrogenase [NADP], | ATDFVADR[Dea]AGTFK (SEQ ID NO: 248) | P48735 | 0.35 |
| Isocitrate dehydrogenase [NADP], | PITIGR[Dea]HAHGDQYK (SEQ ID NO: 249) | P48735 | 0.58 |
| Isocitrate dehydrogenase [NADP], | TIEAEAAHGTVTR[Dea]HYREHQK (SEQ ID NO: 250) | P48735 | 0.73 |
| Ketimine reductase mu-crystallin | HR[Dea]GYLGVMPAYSAAEDALTTK (SEQ ID NO: 251) | Q14894 | 0.21 |
| Ketimine reductase mu-crystallin | PGAHINAVGASR[Dea]PDWR[Dea]ELDDELMK (SEQ ID NO: 252) | Q14894 | 0.49 |
| L-lactate dehydrogenase A chain | GEMMDLQHGSLFLR[Dea]TPK (SEQ ID NO: 253) | P00338 | 0.23 |

TABLE 1B-continued all citrullinated peptides found in this study. "Dea" is Citrullination or deamination. "CAM" is carbamidomethylation.

| Protein | Peptide | UniProtKB Accessions | p_kw |
|---|---|---|---|
| L-lactate dehydrogenase B chain | HR[Dea]VIGSGC[CAM]NLDSAR[Dea]FR[Dea]YLMAEK (SEQ ID NO: 254) | P01795 | 0.87 |
| L-lactate dehydrogenase B chain | IVVVTAGVRQQEGESR[Dea]LNLVQRN[Dea]VNVFK (SEQ ID NO: 255) | P07195 | 0.87 |
| Lon protease homolog, | LQQ[Dea]RLGR[Dea]EVEEK (SEQ ID NO: 256) | K7EKE6 | 0.97 |
| Malate dehydrogenase, | GC[CAM]DVVVIPAGVPR[Dea]K (SEQ ID NO: 257) | P40926 | 0.49 |
| Malate dehydrogenase, | NSPLVSR[Dea]LTLYDIAHTPGVAADLSHIETK (SEQ ID NO: 258) | P40926 | 0.97 |
| Methylcrotonoyl-CoA carboxylase subunit alpha, | QEGIIFIGPPPSAIR[Dea]DMGIK (SEQ ID NO: 259) | Q96RQ3 | 0.31 |
| Methylmalonate-semialdehyde dehydrogenase [acylating], | NLR[Dea]VNAGDQPGADLGPLITPQAK (SEQ ID NO: 260) | Q02252 | 0.70 |
| NAD(P) transhydrogenase | AATITPFR[Dea]K (SEQ ID NO: 43) | Q13423 | 0.05 |
| NAD(P) transhydrogenase | SMGAIVR[Dea]GFDTR[Dea]AAALEQFK (SEQ ID NO: 261) | Q13423 | 0.11 |
| NADH dehydrogenase [ubiquinone] 1 alpha subcomplex subunit 6 | PIFSR[Dea]DMNEAK (SEQ ID NO: 262) | P56556 | 0.16 |
| Peroxiredoxin-1 | R[Dea]TIAQDYGVLK (SEQ ID NO: 263) | Q06830 | 0.21 |
| Peroxiredoxin-2 | EGGLGPLNIPLLADVTR[Dea]R[Dea]LSEDYGVLK (SEQ ID NO: 264) | P32119 | 0.16 |
| Peroxiredoxin-5 | VR[Dea]LLADPTGAFGK (SEQ ID NO: 265) | P30044 | 0.16 |
| Peroxiredoxin-6 | LPFPIIDDR[Dea]NR[Dea]ELAILLGMLDPAEK (SEQ ID NO: 266) | P30041 | 0.68 |
| Phosphate carrier protein, | VYFR[Dea]LPRPPPPEMPESLK (SEQ ID NO: 44) | Q00325 | 0.00 |
| Pyruvate dehydrogenase E1 component subunit alpha, somatic form, | C[CAM]DLHR[Dea]LEEGPPVTTVLTR[Dea]EDGLK (SEQ ID NO: 45) | P08559 | 0.01 |
| Pyruvate dehydrogenase E1 component subunit alpha, somatic form, | DR[Dea]MVNSNLASVEELK (SEQ ID NO: 267) | P08559 | 0.60 |
| Pyruvate dehydrogenase protein X component | HSLDASQGTATGPR[Dea]GIFTK (SEQ ID NO: 268) | O00330 | 0.37 |
| Short-chain specific acyl-CoA dehydrogenase | SAAVVFASTDR[Dea]ALQNK (SEQ ID NO: 269) | P16219 | 0.54 |
| Stress-70 protein, | SDIGEVILVGGMTR[Dea]MPK (SEQ ID NO: 270) | P38646 | 0.11 |
| Stress-70 protein, | IVR[Dea]ASN[Dea]GDAWVEAHGK (SEQ ID NO: 271) | P38646 | 0.16 |
| Succinate dehydrogenase [ubiquinone] flavoprotein subunit, | VTLEYR[Dea]PVIDK (SEQ ID NO: 272) | P31040 | 0.07 |
| Succinate dehydrogenase [ubiquinone] flavoprotein subunit, | IYQR[Dea]AFGGQSLK (SEQ ID NO: 273) | P31040 | 0.40 |
| Succinate dehydrogenase [ubiquinone] iron-sulfur subunit, | FAIYR[Dea]WDPDK (SEQ ID NO: 46) | P21912 | 0.05 |
| Succinyl-CoA ligase [ADP/GDP-forming] subunit alpha, | TR[Dea]LIGPNC[CAM]PGVINPGEC[CAM]K (SEQ ID NO: 47) | P53597 | 0.02 |

TABLE 1B-continued all citrullinated peptides found in this study. "Dea" is Citrullination or deamination. "CAM" is carbamidomethylation.

| Protein | Peptide | UniProtKB Accessions | p_kw |
|---|---|---|---|
| Succinyl-CoA ligase [ADP/GDP-forming] subunit alpha, | PVVSFIAGLTAPPGR[Dea]R[Dea]MGHAGAIIAGGK (SEQ ID NO: 274) | P53597 | 0.09 |
| Succinyl-CoA ligase [ADP-forming] subunit beta, | INFDSNSAYR[Dea]QK (SEQ ID NO: 275) | Q9P2R7 | 0.27 |
| Succinyl-CoA ligase [ADP-forming] subunit beta, | GRIC[CAM]N[Dea]QVLVC[CAM]ER[Dea]K (SEQ ID NO: 276) | Q9P2R7 | 0.39 |
| Succinyl-CoA ligase [ADP-forming] subunit beta, | IFDLQDWTQEDER[Dea]DK (SEQ ID NO: 277) | Q9P2R7 | 0.73 |
| Succinyl-CoA: 3-ketoacid coenzyme A transferase 1, | ADR[Dea]AGNVIFR[Dea]K (SEQ ID NO: 48) | P55809 | 0.04 |
| Succinyl-CoA: 3-ketoacid coenzyme A transferase 1, | GLTAVSNNAGVDNFGLGLLLR[Dea]SK (SEQ ID NO: 278) | P55809 | 0.93 |
| Thioredoxin-dependent peroxide reductase, | HLSVNDLPVGR[Dea]SVEETLRLVK (SEQ ID NO: 279) | P30048 | 0.18 |
| Thioredoxin-dependent peroxide reductase, | HLSVNDLPVGR[Dea]SVEETLR[Dea]LVK (SEQ ID NO: 280) | P30048 | 0.68 |
| Trifunctional enzyme subunit alpha, | ALTSFER[Dea]DSIFSNLTGQLDYQGFEK (SEQ ID NO: 281) | P40939 | 0.99 |
| Very long-chain specific acyl-CoA dehydrogenase, | SDSHPSDALTR[Dea]K (SEQ ID NO: 282) | P49748 | 0.32 |
| Very long-chain specific acyl-CoA dehydrogenase, | ITAFVVER[Dea]GFGGITHGPPEK (SEQ ID NO: 283) | P49748 | 0.55 |
| Very long-chain specific acyl-CoA dehydrogenase, | ALVER[Dea]GGVVTSNPLGF (SEQ ID NO: 284) | P49748 | 0.87 |
| Voltage-dependent anion-selective channel protein 1 | SR[Dea]VTQSNFAVGYK (SEQ ID NO: 49) | P21796 | 0.02 |
| 60 kDa heat shock protein, | FDR[Dea]GYISPYFINTSK (SEQ ID NO: 50) | P10809 | 0.04 |
| 61 kDa heat shock protein, | VVR[Dea]TALLDAAGVASLLTTAEVVVTEIPK (SEQ ID NO: 285) | P10809 | 0.07 |
| 62 kDa heat shock protein, | LVQDVANNTNEEAGDGTTTATVLAR[Dea]SIAK (SEQ ID NO: 286) | P10809 | 0.14 |
| 63 kDa heat shock protein, | GANPVEIR[Dea]R[Dea]GVMLAVDAVIAELK (SEQ ID NO: 287) | P10809 | 0.22 |
| 64 kDa heat shock protein, | GR[Dea]TVIIEQSWGSPK (SEQ ID NO: 288) | P10809 | 0.55 |
| 65 kDa heat shock protein, | GANPVEIRR[Dea]GVMLAVDAVIAELK (SEQ ID NO: 289) | P10809 | 0.58 |
| 66 kDa heat shock protein, | FGADAR[Dea]ALMLQGVDLLADAVAVTMGPK (SEQ ID NO: 290) | P10809 | 0.93 |
| Cytoplasmic aconitate hydratase | PAR[Dea]VILQDFTGVPAVVDFAAMR[Dea]DAVK (SEQ ID NO: 291) | P21399 | 0.77 |
| Polymerase I and transcript release factor | TVRGSLER[Dea]QAGQIK (SEQ ID NO: 292) | Q6NZI2 | 0.09 |
| Polymerase I and transcript release factor | TVR[Dea]GSLER[Dea]QAGQIK (SEQ ID NO: 293) | Q6NZI2 | 0.34 |
| Trifunctional enzyme subunit beta, | PNIR[Dea]NVVVVDGVR[Dea]TPFLLSGTSYK (SEQ ID NO: 51) | P55084 | 0.02 |
| Aconitate hydratase, | TGR[Dea]EDIANLADEFK (SEQ ID NO: 52) | Q99798 | 0.00 |
| Aconitate hydratase, | R[Dea]LQLLEPFDK (SEQ ID NO: 53) | Q99798 | 0.01 |
| Dual specificity protein phosphatase 3 | LGITHVLNAAEGR[Dea]SFMHVNTNANFYK (SEQ ID NO: 54) | P51452 | 0.01 |

TABLE 1B-continued all citrullinated peptides found in this study. "Dea" is Citrullination or deamination. "CAM" is carbamidomethylation.

| Protein | Peptide | UniProtKB Accessions | p_kw |
|---|---|---|---|
| Elongation factor 1-alpha 2 | ASGVSLLEALDTILPPTR[Dea]PTDK (SEQ ID NO: 294) | Q05639 | 0.45 |
| Elongation factor 1-alpha 2 | IGGIGTVPVGR[Dea]VETGILR[Dea]PGMVVTFAPVNITTEVK (SEQ ID NO: 295) | Q05639 | 0.80 |
| Elongation factor 2 | VNFTVDQIR[Dea]AIMDK (SEQ ID NO: 296) | P13639 | 0.09 |
| Eukaryotic translation initiation factor 4B | VAPAQPSEEGPGR[Dea]K (SEQ ID NO: 297) | E7EX17 | 0.95 |
| Histone H2B type 1-M | AVR[Dea]LLLPGELAK (SEQ ID NO: 298) | Q99879 | 0.99 |
| Histone H3 (Fragment) | LPFQR[Dea]LVR[Dea]EIAQDFK (SEQ ID NO: 299) | K7EK07 | 0.36 |
| Histone H4 | RISGLIYEETR[Dea]GVLK (SEQ ID NO: 300) | P62805 | 0.65 |
| Histone H4 | VFLENVIR[Dea]DAVTYTEHAK (SEQ ID NO: 301) | P62805 | 0.74 |
| Neuroblast differentiation-associated protein AHNAK | FGVSTGR[Dea]EGQTPK (SEQ ID NO: 55) | Q09666 | 0.01 |
| Fibrinogen alpha chain | ESSSHHPGIAEFPSR[Dea]GK (SEQ ID NO: 302) | P02671 | 0.39 |
| Fibrinogen alpha chain | R[Dea]LDGSVDFK (SEQ ID NO: 303) | C9JEU5 | 0.62 |
| Haptoglobin | LR[Dea]TEGDGVYTLNNEK (SEQ ID NO: 304) | P00738 | 0.40 |
| Serotransferrin | DYELLC[CAM]LDGTR[Dea]K (SEQ ID NO: 305) | P02787 | 0.10 |
| Collagen alpha-3(VI) chain | DVVFLLDGSEGVR[Dea]SGFPLLK (SEQ ID NO: 56) | E7ENL6 | 0.03 |

TABLE 1C

Citrullinated peptides that are upregulated or downregulated in healthy versus ischemic and healthy versus IDCM subjects.

| Protein | I/N | I |
|---|---|---|
| ES1 protein homolog | 10.32617915 | up |
| Aconitate hydratase | 8.871956482 | up |
| Glyceraldehyde-3-phosphate dehydrogenase | 7.914843955 | up |
| Delta-1-pyrroline-5-carboxylate dehydrogenase | 7.552745345 | up |
| Vimentin | 6.886890573 | up |
| Neuroblast differentiation-associated protein AHNAK | 6.631800512 | up |
| Serum deprivation-response protein | 5.310526396 | up |
| Enoyl-CoA hydratase | 5.304039413 | up |
| Aconitate hydratase | 5.18248378 | up |
| Peptidyl-prolyl cis-trans isomerase A | 4.691862761 | up |
| Delta-1-pyrroline-5-carboxylate dehydrogenase | 4.531765219 | up |
| Chloride intracellular channel protein 4 | 4.143020683 | up |
| Alcohol dehydrogenase 1B | 3.979284116 | up |
| Adenylate kinase 4 | 3.954001114 | up |
| Fatty acid-binding protein | 3.891772332 | up |
| Myosin-binding protein C | 3.770886194 | up |
| Aconitate hydratase | 3.740779581 | up |
| Aconitate hydratase,\ | 3.54332942 | up |
| Delta-1-pyrroline-5-carboxylate dehydrogenase | 3.484011583 | up |
| Dual specificity protein phosphatase 3 | 3.348178139 | up |
| Pyruvate dehydrogenase E1 component subunit alpha, somatic form | 3.336292196 | up |
| Voltage-dependent anion-selective channel protein 1 | 3.075867039 | up |
| Heat shock protein HSP 90-alpha | 3.018162117 | up |
| Succinate dehydrogenase [ubiquinone] iron-sulfur subunit | 2.797967329 | up |
| Aconitate hydratase | 2.646902712 | up |
| Carbonic anhydrase 3 | 2.393105549 | up |
| Serum deprivation-response protein | 2.181113303 | up |
| ATP synthase subunit alpha | 2.125964715 | up |
| Succinyl-CoA:3-ketoacid coenzyme A transferase 1 | 2.02609809 | up |
| Alcohol dehydrogenase class-3 | 1.955112799 | up |
| Succinyl-CoA ligase [ADP/GDP-forming] subunit alpha | 1.813434217 | up |
| Troponin I, cardiac muscle | 1.770629108 | up |
| ATP synthase subunit alpha | 1.757665967 | up |

TABLE 1C-continued

Citrullinated peptides that are upregulated or downregulated in healthy versus ischemic and healthy versus IDCM subjects.

| Protein | I/N | I |
| --- | --- | --- |
| ATP synthase subunit alpha | 1.716317069 | up |
| Filamin-C | 1.707322518 | up |
| 60 kDa heat shock protein | 1.691322503 | up |
| Heat shock protein beta-7 | 1.659329245 | up |
| Myozenin-2 | 1.640224333 | up |
| Cytochrome c (Fragment) | 1.516000483 | up |
| LIM domain-binding protein 3 | 1.456615429 | up |
| Trifunctional enzyme subunit beta | 1.262914035 | up |
| Phosphate carrier protein | 0.90684035 | down |
| ATP synthase subunit alpha | 0.821046528 | down |
| Collagen alpha-3(VI) chain | 0.787448747 | down |
| Myozenin-2 | 0.750016161 | down |
| Troponin I | 0.707050891 | down |
| NAD(P) transhydrogenase | 0.689499324 | down |
| Alpha-crystallin B chain | 0.574071929 | down |
| ATP synthase-coupling factor 6 | 0.558912444 | down |
| Troponin T, cardiac muscle (Fragment) | 0.474388613 | down |
| Beta-enolase | 0.324050919 | down |
| Adenylate kinase isoenzyme 1 | 0.134886108 | down |

I: Ischemic Heart Disease (ISHD);
I/N = ischemia vs. normal (healthy);
ID = Idiopathic Cardiomyopathy (IDCM);
ID/N = IDCM vs. control (healthy).

TABLE 1D

Citrullinated peptides that are upregulated or downregulated in healthy versus ischemic and healthy versus IDCM subjects.

| Protein | ID/N | ID |
| --- | --- | --- |
| ATP synthase subunit alpha | 18.47537571 | up |
| ATP synthase subunit alpha | 15.31631115 | up |
| Myozenin-2 | 14.27029851 | up |
| Glyceraldehyde-3-phosphate dehydrogenase | 12.08226474 | up |
| ATP synthase subunit alpha | 9.229219757 | up |
| ATP synthase subunit alpha | 7.956015709 | up |
| ES1 protein homolog | 6.450987219 | up |
| Delta-1-pyrroline-5-carboxylate dehydrogenase | 4.442955018 | up |
| Enoyl-CoA hydratase | 3.92858654 | up |
| Voltage-dependent anion-selective channel protein 1 | 3.872789427 | up |
| Aconitate hydratase | 3.868674325 | up |
| Phosphate carrier protein | 3.29840839 | up |
| Pyruvate dehydrogenase E1 component subunit alpha, somatic form | 3.241986763 | up |
| Aconitate hydratase | 3.202560876 | up |
| Vimentin | 3.18977634 | up |
| NAD(P) transhydrogenase | 3.087350045 | up |
| Trifunctional enzyme subunit beta | 3.078371104 | up |
| Aconitate hydratase | 3.033531051 | up |
| Myosin-binding protein C | 2.938608028 | up |
| Chloride intracellular channel protein 4 | 2.768865949 | up |
| Aconitate hydratase | 2.733376766 | up |
| Heat shock protein HSP 90-alpha | 2.673523729 | up |
| Delta-1-pyrroline-5-carboxylate dehydrogenase | 2.570795078 | up |
| Collagen alpha-3(VI) chain | 2.444430998 | up |
| Serum deprivation-response protein | 2.396582653 | up |
| Delta-1-pyrroline-5-carboxylate dehydrogenase | 2.194292783 | up |
| Alcohol dehydrogenase 1B | 1.513050932 | up |
| Aconitate hydratase | 1.359569141 | up |
| Succinate dehydrogenase [ubiquinone] iron-sulfur subunit | 1.182430989 | up |
| Dual specificity protein phosphatase 3 | 1.089131195 | up |
| Serum deprivation-response protein | 1.05734493 | up |
| 60 kDa heat shock protein | 0.676500721 | down |
| Heat shock protein beta-7 | 0.569844647 | down |
| Filamin-C | 0.543903731 | down |
| Alcohol dehydrogenase class-3 | 0.539343446 | down |
| Adenylate kinase 4 | 0.516646378 | down |
| Fatty acid-binding protein | 0.500998082 | down |
| Myozenin-2 | 0.483486835 | down |
| Neuroblast differentiation-associated protein AHNAK | 0.440092248 | down |
| Cytochrome c (Fragment) | 0.256014197 | down |
| Succinyl-CoA ligase [ADP/GDP-forming] subunit alpha | 0.234602593 | down |

TABLE 1D-continued

Citrullinated peptides that are upregulated or downregulated in healthy versus ischemic and healthy versus IDCM subjects.

| Protein | ID/N | ID |
|---|---|---|
| Peptidyl-prolyl cis-trans isomerase A | 0.231427358 | down |
| Carbonic anhydrase 3 | 0.230059909 | down |
| LIM domain-binding protein 3 | 0.21853459 | down |
| Troponin I | 0.188118204 | down |
| Troponin I | 0.184373163 | down |
| Troponin T | 0.153543871 | down |
| Alpha-crystallin B chain | 0.145172906 | down |
| Succinyl-CoA:3-ketoacid coenzyme A transferase 1 | 0.121733077 | down |
| ATP synthase-coupling factor 6 | 0.076789945 | down |
| Adenylate kinase isoenzyme 1 | 0.023786955 | down |
| Beta-enolase | 0.013231973 | down |

I: Ischemic Heart Disease (ISHD);
I/N = ischemia vs. normal (healthy);
ID = Idiopathic Cardiomyopathy (IDCM);
ID/N = IDCM vs. control (healthy)

TABLE 1E

Proteins that were up in both I and ID groups.

| Protein | I/N | I | ID/N | ID |
|---|---|---|---|---|
| ATP synthase subunit alpha | 2.125964715 | up | 18.47537571 | up |
| ATP synthase subunit alpha | 1.757665967 | up | 15.31631115 | up |
| Glyceraldehyde-3-phosphate dehydrogenase | 7.914843955 | up | 12.08226474 | up |
| ATP synthase subunit alpha | 1.716317069 | up | 7.956015709 | up |
| ES1 protein homolog | 10.32617915 | up | 6.450987219 | up |
| Delta-1-pyrroline-5-carboxylate dehydrogenase | 4.531765219 | up | 4.442955018 | up |
| Enoyl-CoA hydratase | 5.304039413 | up | 3.92858654 | up |
| Voltage-dependent anion-selective channel protein 1 | 3.075867039 | up | 3.872789427 | up |
| Aconitate hydratase | 3.54332942 | up | 3.868674325 | up |
| Pyruvate dehydrogenase E1 component subunit alpha, somatic form | 3.336292196 | up | 3.241986763 | up |
| Aconitate hydratase | 8.871956482 | up | 3.202560876 | up |
| Vimentin | 6.886890573 | up | 3.18977634 | up |
| Trifunctional enzyme subunit beta | 1.262914035 | up | 3.078371104 | up |
| Aconitate hydratase | 5.18248378 | up | 3.033531051 | up |
| Myosin-binding protein C | 3.770886194 | up | 2.938608028 | up |
| Chloride intracellular channel protein 4 | 4.143020683 | up | 2.768865949 | up |
| Aconitate hydratase | 3.740779581 | up | 2.733376706 | up |
| Heat shock protein HSP 90-alpha | 3.018162117 | up | 2.673523729 | up |
| Delta-1-pyrroline-5-carboxylate dehydrogenase | 7.552745345 | up | 2.570795078 | up |
| Serum deprivation-response protein | 2.181113303 | up | 2.396582653 | up |
| Delta-1-pyrroline-5-carboxylate dehydrogenase | 3.484011583 | up | 2.194292783 | up |
| Alcohol dehydrogenase 1B | 3.979284116 | up | 1.513050932 | up |
| Aconitate hydratase | 2.646902712 | up | 1.359569141 | up |
| Succinate dehydrogenase [ubiquinone] iron-sulfur subunit | 2.797967329 | up | 1.182430989 | up |
| Dual specificity protein phosphatase 3 | 3.348178139 | up | 1.089131195 | up |
| Serum deprivation-response protein | 5.310526396 | up | 1.05734493 | up |

I: Ischemic Heart Disease (ISHD);
I/N = ischemia vs. normal (healthy);
ID = Idiopathic Cardiomyopathy (IDCM);
ID/N = IDCM vs. control (healthy).

TABLE 1F

Proteins that were down in both I and ID groups.

| Protein | I/N | I | ID/N | ID |
|---|---|---|---|---|
| Troponin I | 0.707051 | down | 0.188118 | down |
| Alpha-crystallin B chain | 0.574072 | down | 0.145173 | down |
| ATP synthase-coupling factor 6 | 0.558912 | down | 0.07679 | down |
| Troponin T, cardiac muscle (Fragment) | 0.474389 | down | 0.153544 | down |
| Beta-enolase | 0.324051 | down | 0.013232 | down |
| Adenylate kinase isoenzyme 1 | 0.134886 | down | 0.023787 | down |

I: Ischemic Heart Disease (ISHD);
I/N = ischemia vs. normal (healthy);
ID = Idiopathic Cardiomyopathy (IDCM);
ID/N = IDCM vs. control (healthy).

Western blotting of myofilament- and cytosolic-enriched fractions obtained from ISHD, IDCM and non-failing donor hearts (n=10/group) using an anti-modified citrulline antibody confirmed that citrullination occurs to intracellular proteins. Although there was no difference (FIG. 1B) in the overall immunoreactivity between groups with regard to the number of bands or band density per blot, in-gel digestion and subsequent mass spectrometry of the immuno-reactive bands identified the major sarcomeric proteins at their expected molecular weight (e.g. myosin heavy and light chains and actin. It must be noted that quantitative assessment by immuno-IDE was confounded by the presence of other proteins in the gel bands and challenges of direct site-specific assessment using mass spectrometry.

Figure 2A:
FIG. 2A-FIG. 2B depicts in accordance with various embodiments of the invention, 2DE DIGE analysis with samples treated with PAD2.
Figure 2B:
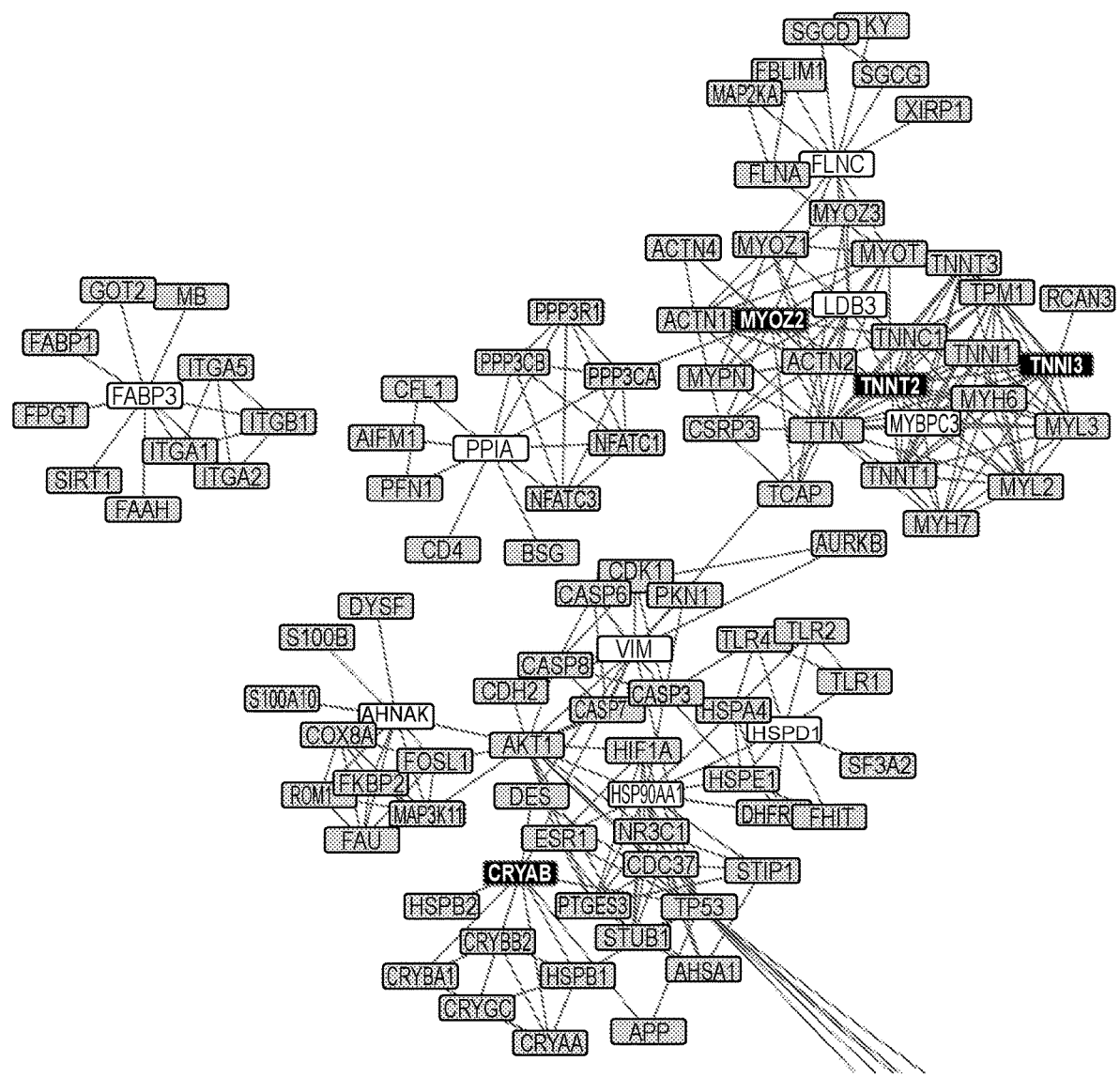

To further validate citrullination of the high abundant sarcomeric proteins, DIGE 2D gel electrophoresis (pH 4-7, 10% SDS PAGE) was carried out. Myofilament- and cytosolic-enriched fractions of ISHD, IDCM and non-failing donor hearts (n=4/group) were pretreated with PAD2 to induce maximum citrullination, combined at a 1:1 ratio with the matching untreated samples and simultaneously resolved by 2D gel electrophoresis. The sarcomeric proteins, including actin, TM and myosin light chains were shown to be citrullinated with ectopic treatment of PAD2 (FIG. 2A-FIG. 2B).

Biochemical Assessment of Modified Sarcomeric Proteins.

Figure 3A:
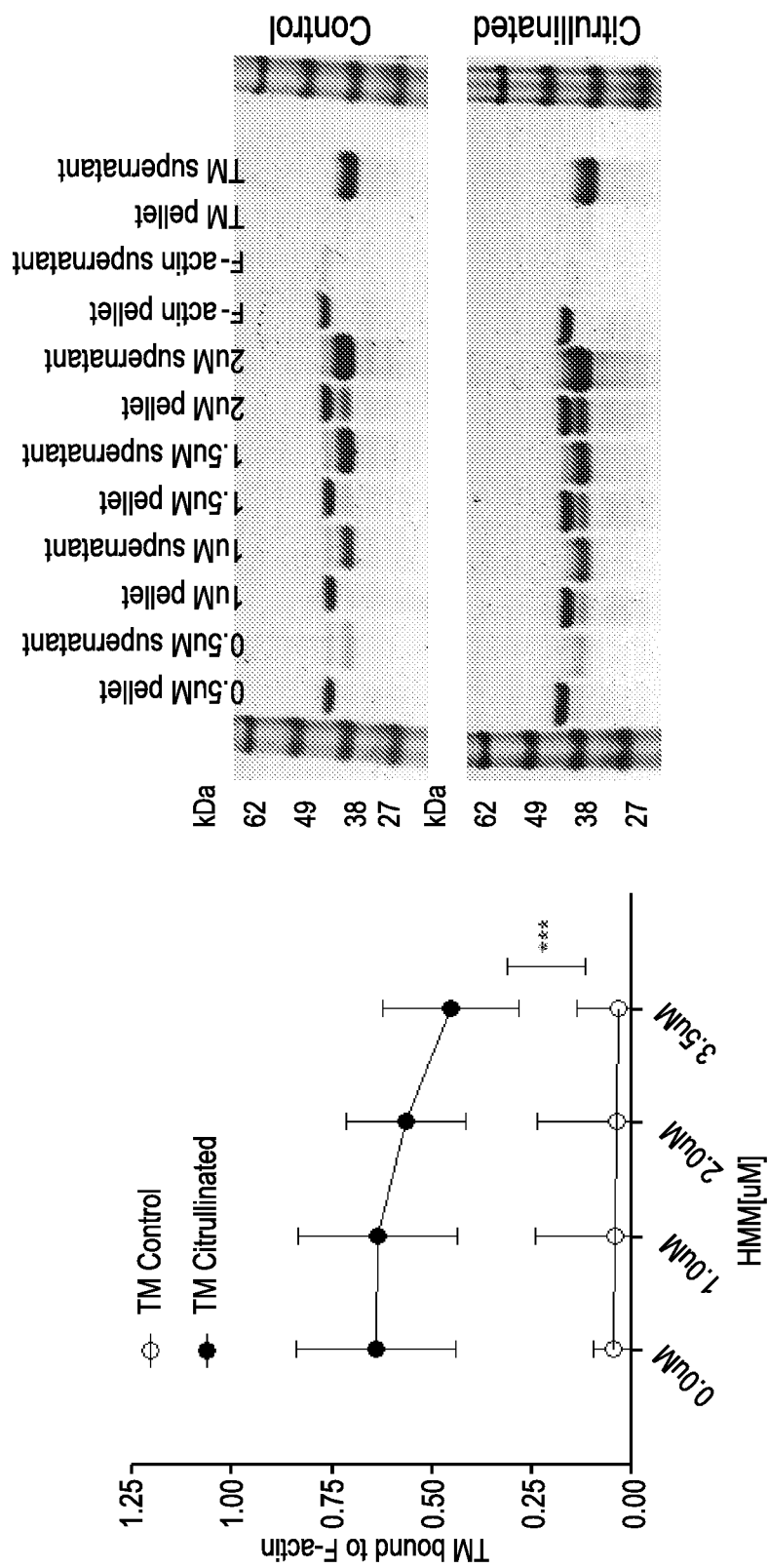
FIG. 3A-FIG. 3C depicts in accordance with various embodiments of the invention, actin-binding studies. Increasing concentrations of FIG. 3A) TM (0.5 uM to 2 uM) were incubated with F-actin or FIG. 3B) actin-HMM and FIG. 3C) TnI (0.5 uM to 2 uM) in buffer containing 40 mM Tris-HCl (pH 7.6), 100 mM NaCl, 5 mM MgCl2, and 1 mM DTT. Binding of TM to F-actin was carried out at 25° C. for 30 min and ultracentrifuged at 60,000 rpm for 25 min, 20° C., in a Beckman model TL-100.2. Both pellet and supernatant (unbound protein) were analyzed. Representative silver-stained gels show proteins composition of the supernatants and pellets. A triplicate set of gels, were analyzed by densitometry. Each data point is an average (and range) of the values obtained from the three sets of gels.
Figure 3B:
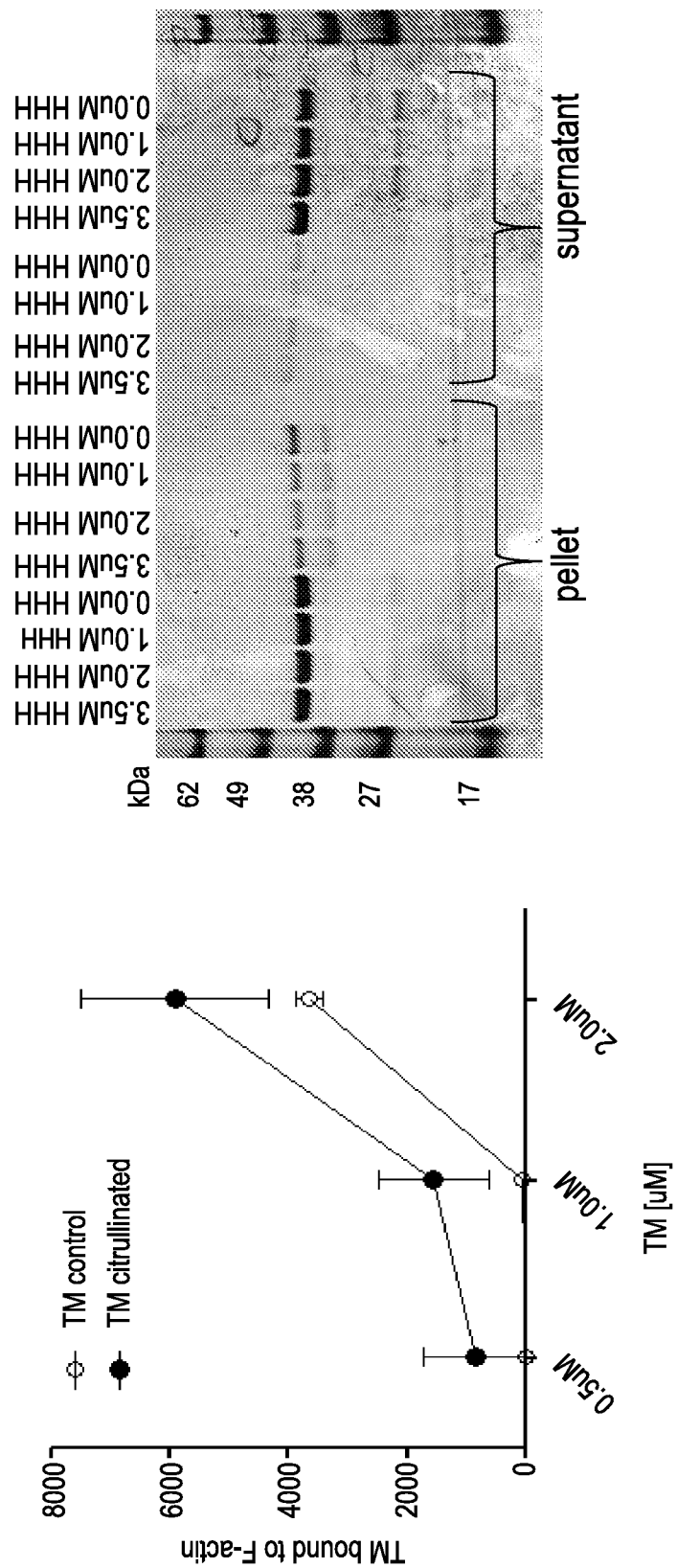
Figure 3C:
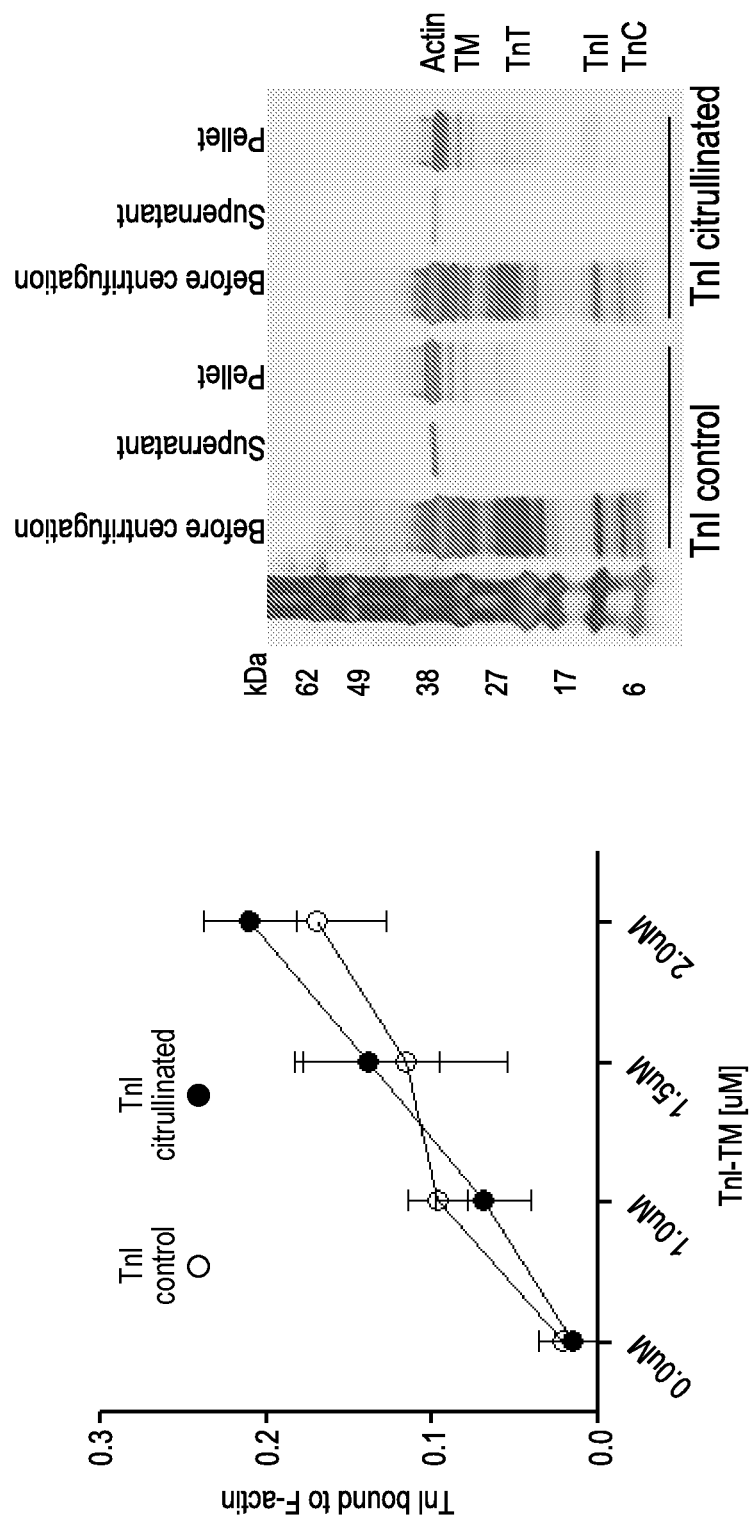

To test whether citrullination can affect sarcomeric protein function, actin, HMM, TM and troponin were citrullinated by ectopic PAD2 and then compared to respective unmodified recombinant proteins to determine if citrullination affects their biochemical, structural, or enzymatic properties. The binding of citrullinated or untreated MINI, TM or TM-TnI to F-actin was determined using classical co-sedimentation assays (FIG. 3A-FIG. 3C). Citrullination of actin did not alter F-actin formation and over 95% of the actin was pelleted upon centrifugation. Binding of citrullinated TM to F-actin was enhanced compared to unmodified TM (FIG. 3A). Since TM and HMM can affect binding of each other to F-actin in a cooperative manner [Galinska A et al. The C terminus of cardiac troponin I stabilizes the Ca2+-activated state of tropomyosin on actin filaments. *Circ Res* 2010, 106:705-711], we tested for cooperativity under conditions in which binding of TM alone to F-actin is poor, but increased upon the binding of myosin heads to F-actin [Eaton BL. Tropomyosin binding to F-actin induced by myosin heads. *Science* 1976, 192:1337-1339]. As illustrated in FIG. 3B, at low salt concentration citrullinated TM in the presence of HMM was able to bind to F-actin.

The binding of cardiac TnI to F-actin in the presence of TM was performed by co-sedimenting citrullinated TnI in the presence of F-actin and TM. It was found that both citrullinated and non-citrullinated forms of cardiac TnI bound to F-actin equally well (FIG. 3C)

Inhibition of HMM ATPase Activity.

Figure 4A:
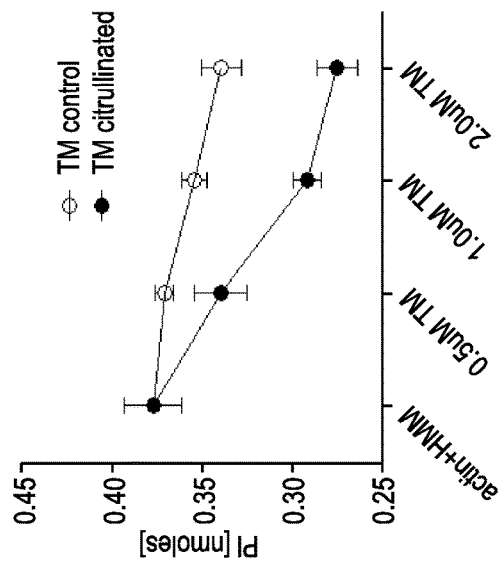
FIG. 4A-FIG. 4F depicts in accordance with various embodiments of the invention, citrullination of sarcomeric proteins, biochemical and physiological effects.
Figure 4B:
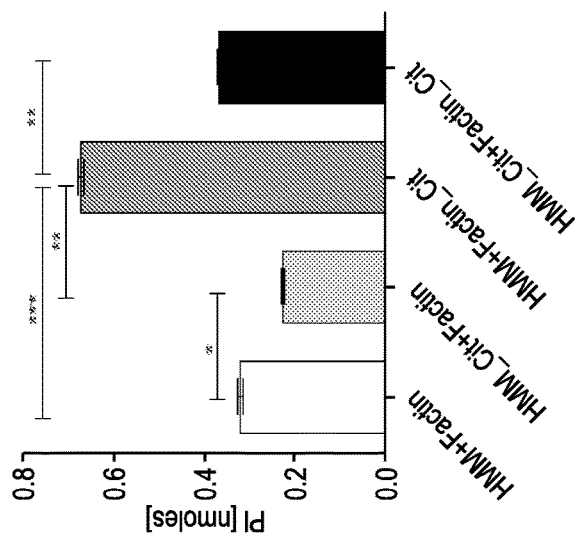

To verify a possible modulation of the actomyosin HMM-ATPase activity by citrullination of sarcomeric proteins, experiments were performed in the presence of citrullinated HMM, F-actin and TM. The data summarized in FIG. 4A show that, in the presence of citrullinated HMM (0.5 µmol/L HMM and 7 µmol/L F-actin), the actomyosin HMM-ATPase activity decreased from 0.32±0.01 nmol Pi to 0.22±0.002 nmol Pi, corresponding to 30% decrease in the enzyme activity. In contrast, citrullination of F-actin enhanced actomyosin HMM-ATPase activity up to 55% on the enzyme activity (FIG. 4A). When both F-actin and HMM were citrullinated, the rate of ATP hydrolysis remained greater than control (0.368±0.005 nmol Pi to 0.32±0.01 nmol Pi). FIG. 4B showed that actomyosin HMM-ATPase activity was affected by TM citrullination. The inhibition of actomyosin HMM-ATPase conferred by non-citrullinated and citrullinated TnI was compared. Addition of non-citrullinated TnI to HMM-F-actin-TM caused a decrease in the ATPase rate at 37° C. Citrullinated TnI acted similar to non-citrullinated TnI and caused a decrease in the ATPase with no significant deference to non-citrullinated form.

PAD2 Reduces Calcium Sensitivity in Skinned Myocytes

Chemically skinned cardiomyocytes isolated from the left ventricle of wild-type C57B16 male mice were exposed to varying concentrations of calcium (n=8 myocytes from 3 mice per group, FIG. 4C-FIG. 4F). PAD2 treatment had no effect either maximal calcium activated force ($F_{max}$) or hill coefficient (nH). However, PAD2 caused a rightward shift in the force-calcium relationship that indicates an increase in $EC_{50}$, or a decrease in calcium-sensitivity (p=0.009, FIG. 4C). This suggests that citrullination of myofilament proteins causes a loss-of-function phenotype, reducing its ability to generate force in response to intracellular calcium.

Analysis of PAD mRNA Expression.

Figure 5:
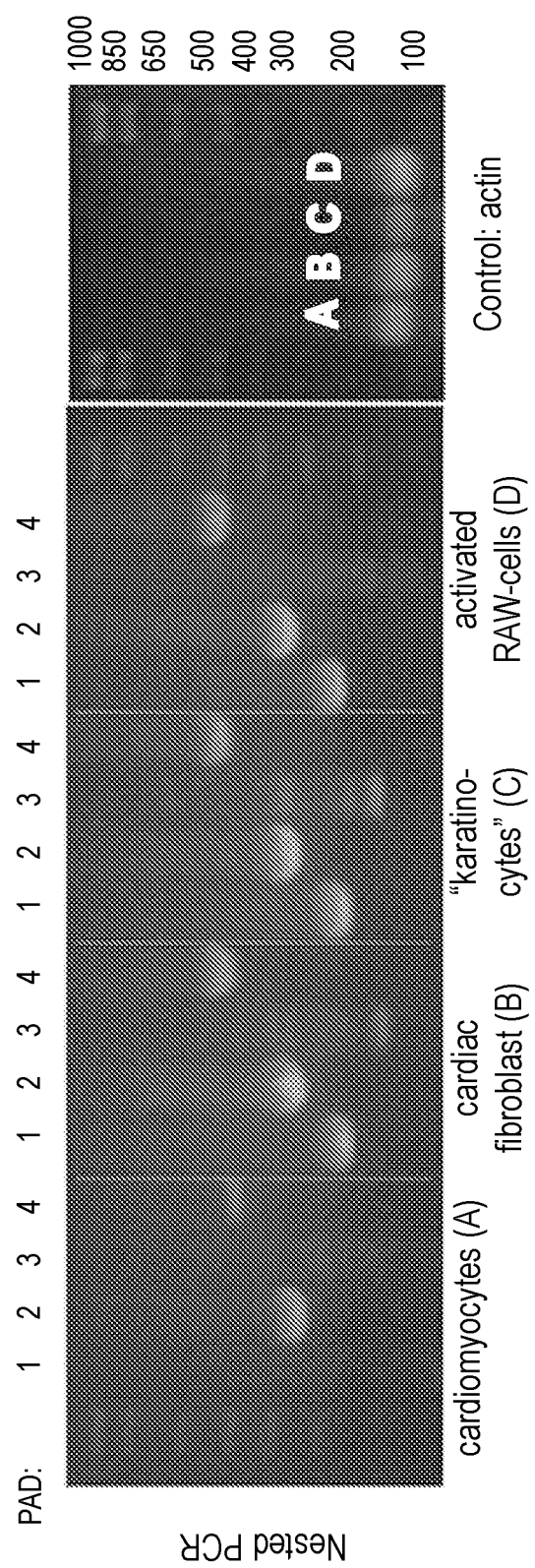
FIG. 5 depicts in accordance with various embodiments of the invention, RT-PCR analysis of expression level of PAD isoforms in A, B) heart from control mouse, C) mouse keratinocytes and D) mouse macrophage cell line activated by lipopolysaccharide. The PCR product PAD2 is seen in all types of samples; PAD4 and PAD1 is seen in cardiac fibroblast, keratinocytes and macrophage cell line. PAD3 has not been detected. (MW: PAD1 285 bp; PAD2 390 bp; PAD3 200 bp; PAD4 550 bp).

To determine the cell specificity of the PAD isoform expression in the myocardium, mRNA expression level was determined using isoform specific primers by Nested-PCR on isolated cardiac myocytes and fibroblasts (FIG. 5). PAD2 was the primary isoform expressed in both cardiomyocytes and cardiac fibroblasts, although fibroblasts also had significant expression of PAD1 and PAD4 mRNA. In contrast, PAD3 mRNA was not detected in any of the cell types and conditions tested (FIG. 5, note no band at 200 bp, see online supplement for more details).

Example 3

Figure 6:
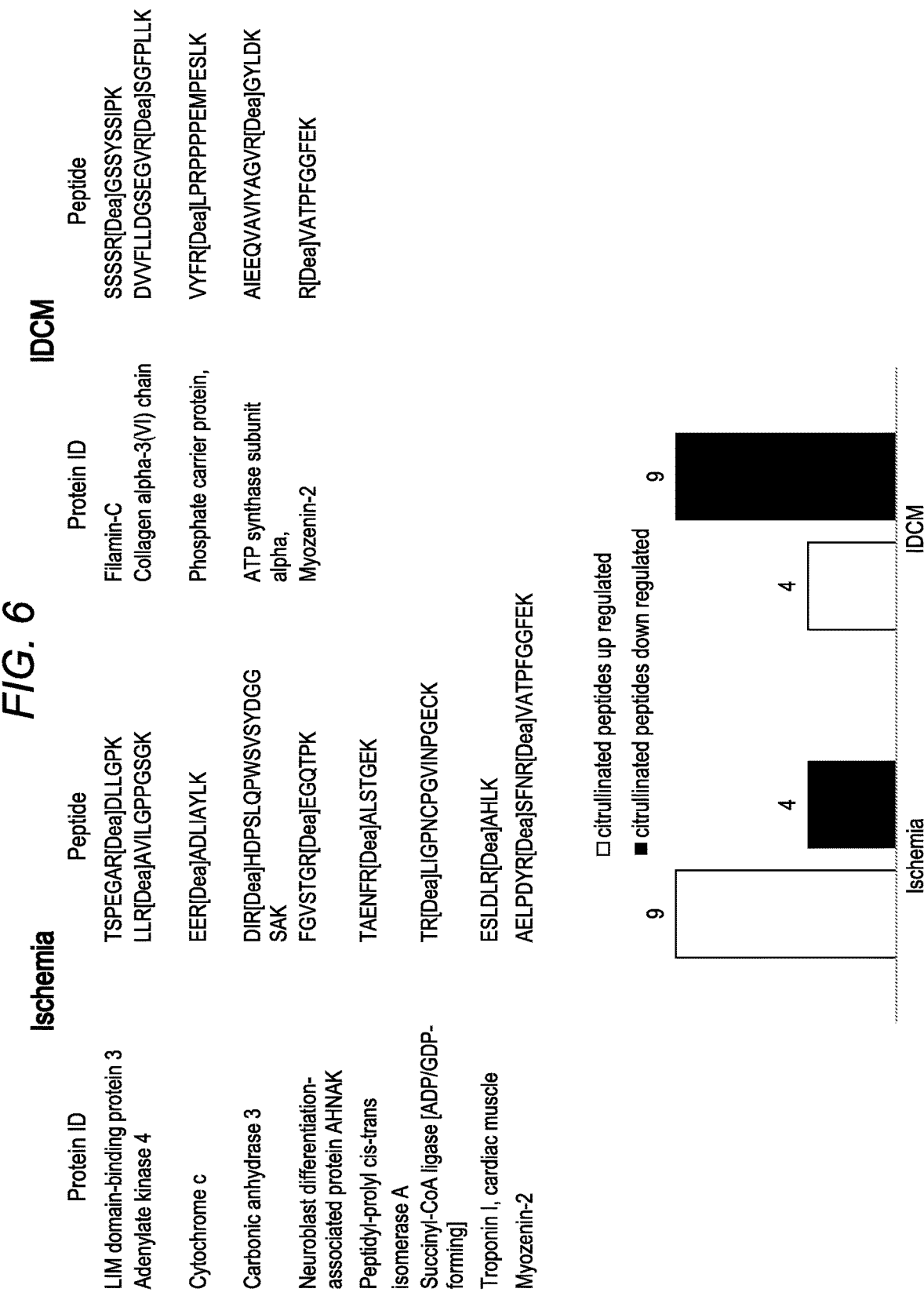
FIG. 6 depicts in accordance with various embodiments of the invention, a citrullinated protein up/down regulated between heart failure groups, ischemia and IDCM.

Our experimental findings characterize citrullinated proteins in the normal and HF myocardium. The analysis revealed that citrullination is enriched in the mitochondria and sarcomere subproteomes. Protein citrullination has broad cellular distribution (FIG. 1A) but is highly enriched in the mitochondria and sacromeric subproteome. A close connection between these two subproteomes is not unexpected due to the high energetic requirements of the sarcomere. We speculated that citrullination, similar to phosphorylation and acetylation, could potentially regulate muscle-contractile proteins in a coordinated manner. Interestingly, the multiple enzymes involved in metabolic pathways/metabolism were up regulated in ischemia but down regulated in IDCM (FIG. 6). To understand the topology and functional annotation of citrullinated protein—protein interaction in the heart system the protein network was constructed using the STRING database (FIG. 2B). The entire protein network consisted of high scoring interaction partners (STRING relevant confidence score ≥0.5, ischemia/IDCM vs. control). The visual analysis of this sub-network showed that citrullinated proteins are interacted to each other and are involved in the metabolism and respiratory chain targets, contraction and signal transduction systems. As an initial assessment to understand potential functional consequences of the citrullination, recombinant sarcomere proteins HMM, F-actin, TM and TnI were used as model proteins to study the interactions that govern the thick and thin filament function and by measured the contractile properties of single skinned myocytes treated with PAD2.

$Ca^{2+}$-dependent alterations to Tn alter an azimuthal movement of TM on the actin surface, which allows myosin binding and cross-bridge isomerization to strong binding, force-producing states and muscle contraction. At low intracellular $Ca^{2+}$, Tn-TM sterically blocks myosin binding sites on actin (blocked state), while in presence of elevated $Ca^{2+}$ Tn-TM moves and partially exposes the myosin binding sites on F-actin (closed state). Myosin binding in the presence of $Ca^{2+}$ is required for full activation. It is a combination of $Ca^{2+}$-induced TnI conformational change which is, in part, transmitted via TnT to TM (especially the T1 region that binds along TM) as well as myosin binding that influence the exact positioning of TM on the actin filament. Based on our MS data, citrullination sites on myosin, actin, TM, TnI and TnT are in regions what can influence these interactions and thus, the actomyosin HMM-ATPase activity and contraction. Below outlines the potential impact based on the biochemical and physiological experiments presented in this manuscript.

Figure 7:
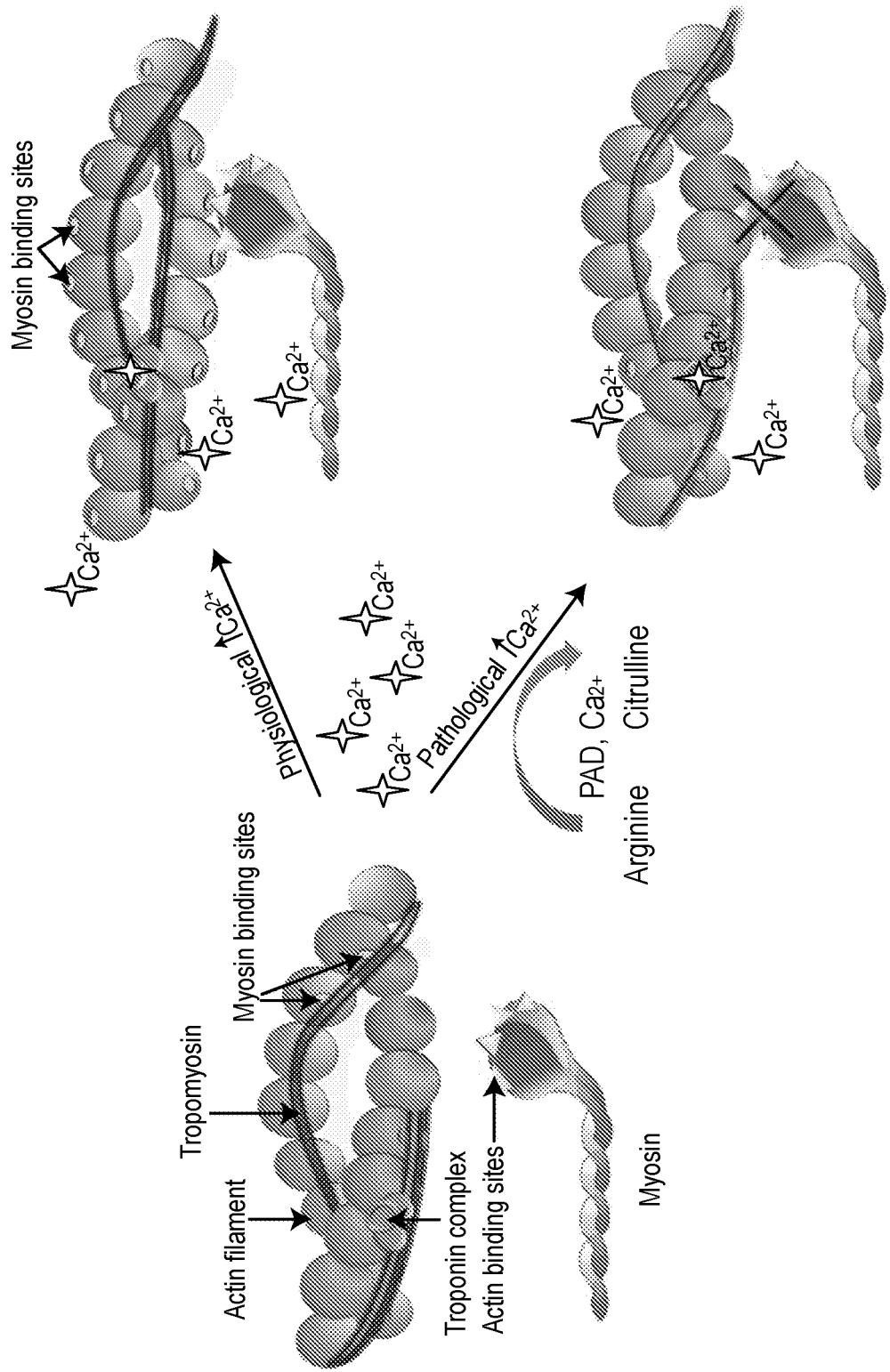
FIG. 7 depicts in accordance with various embodiments of the invention, citrullination of the contractile proteins could affect different aspects of regulatory function. It could either trigger a structural change or stabilizes a conformation that is necessary for actin-activated release of Pi and completion of the ATPase cycle.

First, intrinsic actomyosin HMM-ATPase was inhibited by citrullination, but this was overcome in the presence of F-actin regardless of whether F-actin is citrullinated or not. Citrullinated F-actin was a more potent modulator of MINI enzymatic activity and increased actomyosin HMM-ATPase rate by 55% compared to the unmodified F-actin. This suggests that citrullination of F-actin changes the confirmation of the actin filament to alter the ease of ATP hydrolysis by the myosin once it is bound. The actin-HMM interaction was also affected by the citrullination of TM. Citrullinated TM displayed enhanced binding to F-actin compared to unmodified TM. This was also observed in the presence of HMM (based on the centrifugation assays). This correlated to an inhibition of the citrullinated TM-actin-HMM ATPase activity compared to the non-citrullinated TM, suggesting that citrullinated TM altered the ability of HMM to bind to the actin filament (FIG. 7). Intriguingly, citrullinated TnI, like the unmodified protein complex, bound tightly to actin-TM based on centrifugation studies. FIG. 3C shows that >95% of the unmodified and modified TnI was present in the pellet.

Figure 4C:
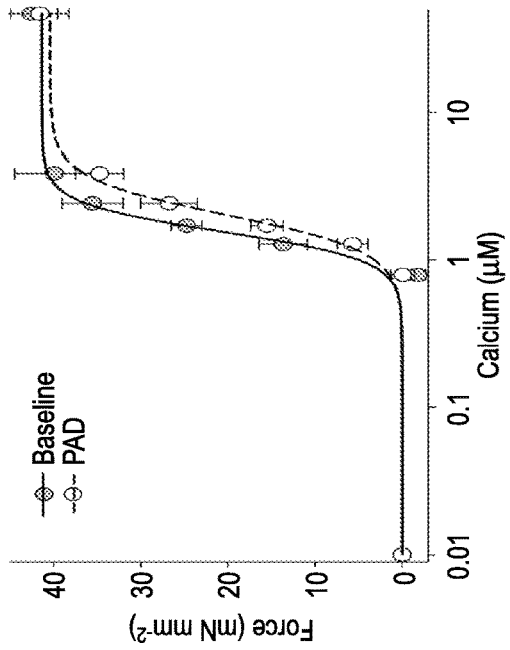
Figure 4D:
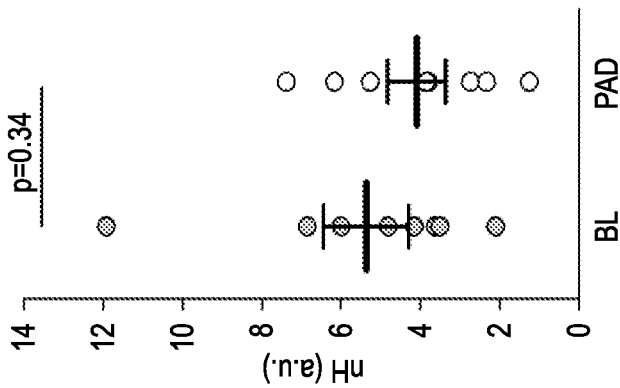
Figure 4E:
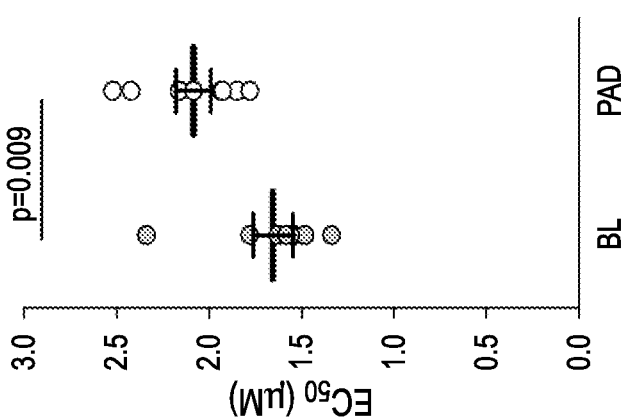
Figure 4F:
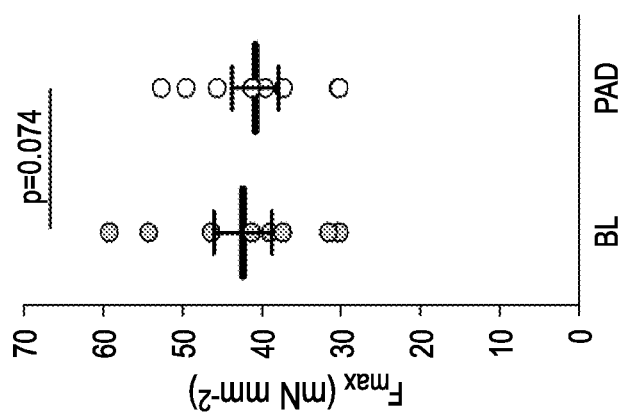

Biochemical results were related to our physiological finding and showed that citrullination of the sarcomeric proteins caused a decrease in $Ca^{2+}$-sensitivity in the skinned cardiac myocyte (FIG. 4C). On TnI, C-terminus residues 191 to 210, which contains the citrullinated residue 203, is primarily responsible for maintaining the TM conformation that prevents cross bridge cycling. Thus, not only does TnI promote the blocked state, but also contributes to the stabilization of TM in the closed state. In mice, cardiac TnI containing cardiomyopathy mutations, R192H or R204H (which are equivalent to the human sequence of 191 and 203 the latter being the same citrullinatable residue as discussed above) increases the binding affinity of Tn for actin-TM. Perhaps this is augmented by the citrullination of TnT at residue 77, which is located in the N-terminal tail (TnT1) that lies along TM and has been shown to be involved in cooperativity of the actin-TM-Tn filament. In addition, binding of $Ca^{2+}$ or myosin to actin-TM-Tn can displace TnI residues 151 and 188, which flank the second citrullinated residue 169, away from the outer domain of F-actin. This is consistent with an azimuthal displacement to TnI-TM by $Ca^{2+}$ that can expose the high affinity-binding site on F-actin for myosin. Studies on familial hypertrophic cardiomyopathic mutations occurring on thick filament proteins (TM, MHC, MyBP-C, ELC, and RLC) show that a change in one amino acid side chain can have an enormous effect on cardiac morphology and function. Furthermore, factors that lead to abnormal contraction and relaxation in the failing heart include metabolic pathway abnormalities that result in decreased energy production, energy transfer and energy utilization.

Finally, to better understand the involvement of citrullinated proteins in the heart, it is important to obtain insight about cell specificity. Previous data acquired by the immunohistochemistry showed that PADs 1-3 and to some degree, PAD6 were detected in cardiomyocytes with PADs 2 and 4 found in endothelial cells and vascular smooth muscle cells. In the present study, we relied not on antibodies and tissue slices, but rather examined the mRNA expression of PAD family members in isolated mouse cardiomyocytes and cardiac fibroblasts. The data showed that PAD2 was primarily expressed in both cardiomyocytes and cardiac fibroblasts whereas PAD1 and PAD4 mRNA were the major forms in the cardiac fibroblasts.

We have presented previously unexplored roles for citrullination in the heart. Ultimately, identification of citrullination of the majority of the sarcomeric proteins and alterations in their biochemical properties suggest that there is potentially a new PTM regulation of cardiac contractility. Since citrullination at some of these residues were increased in the myocardium of individuals with HF compared to the controls, suggest that citrullination could play a role, in the decrease contractile dysfunction in HF.

Example 4: Citrullinated Peptides in Neurodegenerative Diseases

Citrullination is a PTM of arginine residues that is characterized by the oxidization of the side chain. This modification is catalyzed by Peptidyl Arginine Deiminase enzymes (PAD) that causes the conversion of arginine to citrulline. Citrullination, also known as deimination occurs when there is a loss of a positive charge and reduction in hydrogen-bonding ability, ultimately causing a change in the protein's chemical structure. This modification plays both a physiological role, for instance during apoptosis and epigenetics, and a pathological role in cancer or diseases of the central nervous system [3]. Furthermore, anti-citrullinated protein antibodies (ACPAs) are present in ~60% of patients with rheumatoid arthritis (RA) and are associated with aggressive disease and a poor prognosis [4, 5]. Genetic studies of RA have identified many disease-prone SNPs at >100 non-HLA gene loci [6]. Therefore, the investigation to associate citrullination, SNPs and disease can provide an insight to many pathological disorders.

Protocol Overview

The purpose of this protocol is to build citrullinated assay libraries that support accurate detection of citrullinated proteins/peptides in vivo. The protocol covers the sample preparation, the acquisition of high-quality fragment ion spectra in DIA mode, the spectral citrullinated library generation and bioinformatics pipeline for binning the citrullinated peptides based on quality. Furthermore, additional tools were developed to translate the large datasets into knowledge by further annotating the peptide data with known vs. novel, and linkage to disease associated genomic alteration information.

Materials

Reagents: Rabbit skeletal muscle PAD cocktail (PAD) (SignalChem); Sequencing grade Lys-C protease (WAKO); iRT retention time peptides [13]; FASP™ Protein Digestion Kit (Expedeon), Human brain tissue. Healthy control post-mortem human brain tissues corresponding to superior frontal gyms (SFG) (n=10) obtained from NIH NeuroBioBank (NBB). The cases had neither a clinical history nor a neuropathology diagnosis of neurologic disease. Human ALS motor cortex(n=1) and ALS thoracic spinal cord (n=4) with corresponding healthy samples obtained from occipital lobe (n=3). Mouse brains: Alzheimer's model (1. 9 months old, lots of beta-amlyloid, memory deficitis and onset of neurodegeneration, n=5; 2. 9 months old, normal/healthy mouse, with intact memory, n=5; 3. 2 months old, little to no detectable beta-amyloid and intact memory, n=2; 4. 2 months old, healthy mouse, n=2). Stroke mouse (a middle cerebral artery occlusion stroke, n=5 Left side of brain where stroke occurred, right side of brain, corresponding healthy control); Healthy mouse (n=5, brain, aorta, skeletal muscle).

Brain buffer A: Ice-cold low salt buffer: 10 mM Tris, pH 7.5, 5 mM EDTA, 1 mM DTT, 10% sucrose, 10 mM b-glycerophosphate, 10 mM sodium orthovanadate, 10 mM tetrasodium pyrophosphate, 50 mM sodium fluoride, 1×Roche complete protease inhibitor cocktail).

Brain buffer B: 1% Triton, 10 mM Tris, pH 7.5, 5 mM EDTA, 1 mM DTT, 10% sucrose, 10 mM b-glycerophosphate, 10 mM sodium orthovanadate, 10 mM tetrasodium pyrophosphate, 50 mM sodium fluoride, 1× Roche complete protease inhibitor cocktail PAD Buffer: 0.1M tris-HCl, pH7.4, 10 mM $CaCl_2$, 5 mM DTT, 10 ug/ul aprotonin, 10 µg/ul leupeptin, 10 ug/ul pepstatin.

Equipment: High Speed Mixer Mill (MM400) (Retsch); Mixer Mill jar (#22.008.0005 Retsch) and 7 mm stainless steel ball (#22.455.0008 Retsch); Refrigenerated Bench-top centrifuge (Eppendorf 5415R), temperature 4° C. and 20° C.; Beckman Coulter Optima Ultracentrifuge with TLA 100.2 rotor; TripleTof 5600+ mass spectrometer (AB Sciex); TripleTof 6600+ mass spectrometer (AB Sciex); iProXpress (proteininformationresource.org/iproxpress2) [14]; Computer: PC with Microsoft Windows 7 (Microsoft), ≥4 GB of RAM, sufficient hard disk space (for the protocol case study ≥40 GB).

Software: Microsoft Windows 7 (Microsoft); MS Excel (Microsoft); Cytoscape Plugin BiNGO A Biological Network Gene Ontology Tool (baderlab.org/Software/EnrichmentMap/BingoTutorial).

Equipment Setup: Detailed instructions, including screenshots, for the installation of each software module are provided in Supplementary material.

Methods: 1. Brain sample preparation. TIMING 90 min to a few days (depends on number of samples); 2. Weigh tissue and record wet tissue weight. 3. Cut the tissue into small pieces with a scalpel or a tissue slice blade. 4. Transfer the tissue pieces into 3 volumes (w/v) of ice cold Buffer A. 5. Homogenize the tissue on ice using a homogenizer (30 s at 20 Hz using a single 7 mm stainless-steel ball). 6. Centrifuge the sample for 15 min, 30800 rpm, 4° C. using a TLA 100.2 rotor in a Beckman Coulter Optima Ultracentrifuge. 7. Transfer the supernatant into a clean tube. 8. To remaining pellet add buffer B (1:3 tissue to buffer ratio) and homogenized at 30 Hz for 30 s in a cold Mixer Mill MM400. 9. Centrifuge at 100,000 rpm for 20 min in a TLA-100.2 rotor (Beckman). 10. Transfer the supernatant into a clean tube and determine the protein concentration by the Bradford method.

Protein citrullination: Peptides can only be identified by targeted MS if they are included in the assay library. To cover proteins that are expressed in specific biological conditions we needed to prepare the pool of citrullinated peptides that theoretically represents the entire biological space. Most PAD isoforms are exclusively expressed in the cytoplasm, except for PAD4, which contains a nuclear localization signal and is indeed found to reside at least in part in the nucleus. It would therefore be reasonable to assume that the substrate specificity differs between the PAD isotypes [15, 16]. A key step in the process is the treatment of pooled tissue/sample(s) in vitro with a PAD cocktail to induce hypo-citrullination of accessible arginine residues. (1) Pool samples in each fraction in order to obtain 200 ug sample pool. (2) Mix up to 30 µl of a protein pool with 150 µl of PAD Buffer. (3) Add PAD cocktail (Catalog #P312-37C) in an enzyme/substrate (w/w) ratio of 1:25, and incubate the reaction for 2 h at 37C, gentle shacking. Stop citrullination by adding EDTA until 50 mM final concentration. (4) Prepare the negative control the same way but add water instead of PAD cocktail. (5) Keep on ice until use.

Protein digestion. Protein Discovery's FASP Protein Digestion Kit was used in order to digest all samples with LysC in an enzyme/substrate (w/w) ratio of 1:30, and incubate the reaction for 20 h at 37° C., gentle shaking.

SWATH-MS (Sequential Window Acquisition of all Theoretical Fragment Ion Spectra—Mass Spectrometry) Data Acquisition. Generation of SWATH-MS (Sequential Window Acquisition of all Theoretical Fragment Ion Spectra—Mass Spectrometry) maps: Triple-TOF MS analysis in DDA and SWATH (Sequential Window Acquisition of all Theoretical Fragment Ion Spectra) mode. A TripleTOF 6600 mass spectrometer (Sciex) was used for both data dependent acquisition to build peptide spectral ion library and SWATH-MS (Sequential Window Acquisition of all Theoretical Fragment Ion Spectra—Mass Spectrometry) (data independent acquisition) for each individual sample analysis. The raw data was searched with ProteinPilot™ Software 5.0 to create a spectral ion library. Individual SWATH-MS (Sequential Window Acquisition of all Theoretical Fragment Ion Spectra—Mass Spectrometry) runs were matched against the spectral library created in the presence or absence of PAD (plus and minus PAD).

Figure 9:
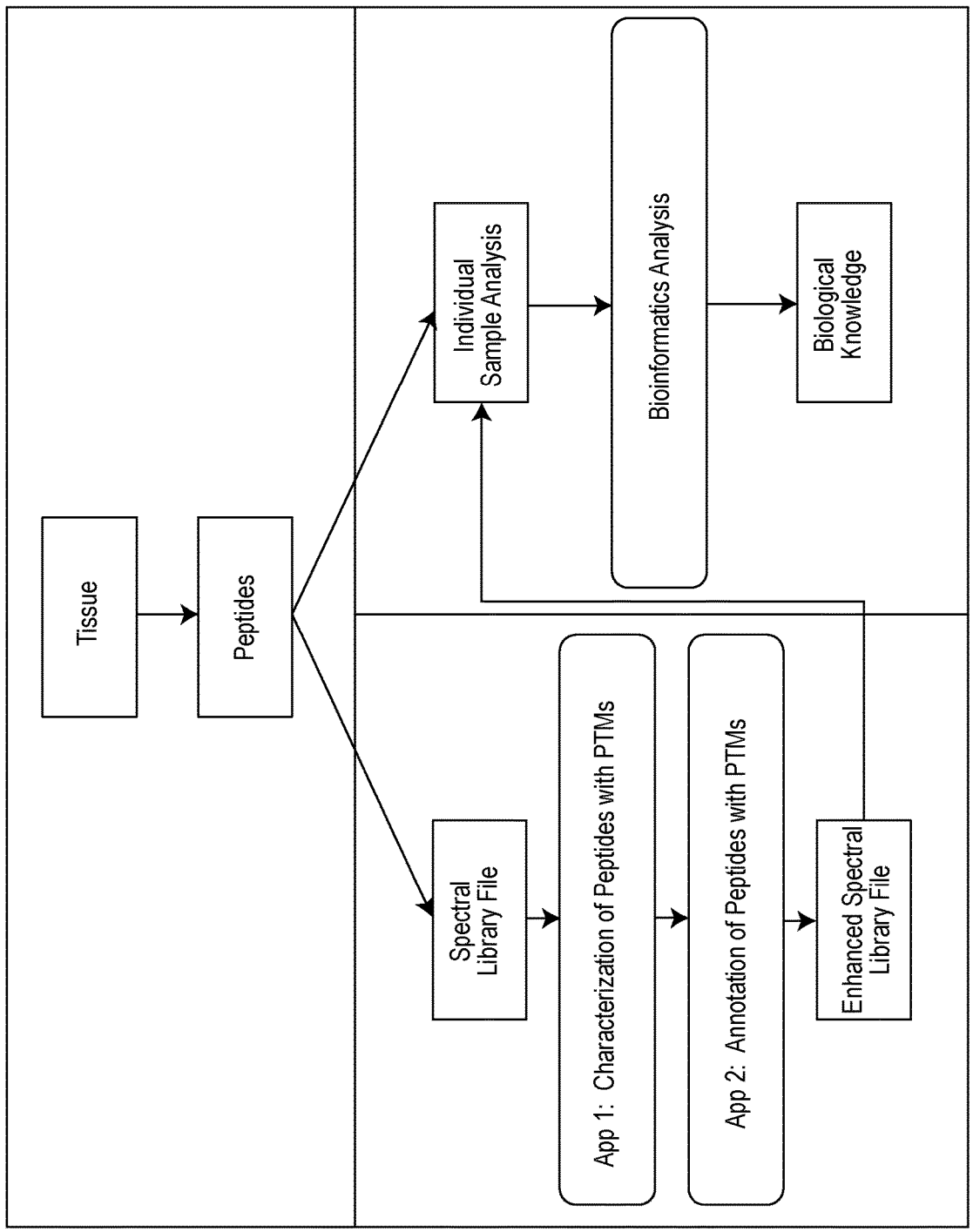
FIG. 9 depicts in accordance with various embodiments of the invention, an overview bioinformatics workflow for processing citrullinated spectra library file.

Extensive identification and analysis of conserved citrullinated peptides. The blast on the peptide level was performed to find human homology (sequence-similar) equivalent of the mouse data obtained from brain stroke mouse model, Alzheimer's and healthy mouse brain, as well as from mouse aorta and mouse skeletal muscle. The matching list only includes the top blastp-short hit, meaning >80% of peptide homology between mouse and human was found. In most cases, if the top hit was an isoform, the other isoforms and canonical protein was also conserved. FIG. 9 shows the overview bioinformatics workflow for processing citrullinated spectra library file. Two different types of tissue sample, heart and brain, were used to develop the presented methodologies. The final SWATH (Sequential Window Acquisition of all Theoretical Fragment Ion Spectra) assay library generated from the human brain consists of 360,202 peptides (16,275 unique). The bioinformatics pipeline extracted 1,530 unique peptides that were considered to be high confident and valid citrullinated peptides (Table 11). An additional 1,571 unique peptides were identified as potentially high confident valid citrullinated peptides, and the other remaining peptides were considered to be low confident (Table 11). It is important to note that a peptide may have more than 1 citrullinated R, and some peptides share the exact citrullinated R site on the full length protein. Therefore, the number of unique peptides does not equal the number of unique citrullinated sites. The total number of unique citrullinated sites (on full length protein) in Output1, 2, and 3 is 2413.

TABLE 11

Summary of output files for brain sample plus and minus PAD treatment for brain samples (confidence threshold used was 0.995) (JF_150402_5600-plus/minusPAD).

| Output File | Description | NG Rule | Total Peptides | | Total Unique Peptides | |
|---|---|---|---|---|---|---|
| | | | minus PAD | plus/minus PAD | minus PAD | plus/minus PAD |
| 1 | delta =>5 min conf >0.95 | Not checked | 1,637 | 36,202 | 58 | 1,530 |
| 2 | delta <5 min OR conf <0.95 OR no matched control | pass | 3,238 | 30,382 | 152 | 1,571 |
| 3 | delta <5 min OR conf <0.95 OR no matched control | fail | 1,370 | 19,450 | 55 | 1,006 |
| 4 | every line without R[Dea] | Not checked | 375,717 | 431,816 | 17,147 | 20,702 |

The citrullinated peptides are binned into 4 different output files based. Output 1 contains the high confidence peptides, which have a >5 min delta in retention time between the modified peptide and the unmodified peptide, plus a confidence score (user input). Output 2 and 3 contains peptides that had a citrullinated R residue; however, no unmodified peptide was found in the dataset limiting the ability to calculate the retention time difference. However, for Output 2 an N/Q residue is not within 5 amino acids on either side of the citrullinated R residue; whereas in Output 3 an N/Q residue is located within 5 amino acids on either side the citrulinated R residue. Output 4 contains all peptides in the original file that did not meet the criteria for Outputs 1-3.

Herein we describe a step-by-step protocol and an integrated, openly accessible computational pipeline to generate high-quality assay libraries for analysis of citrullinated peptides in complex biological samples. Using the high resolution of the time-of-flight mass analyzer (>30,000) that allowing for confident identification of the peptide elution profile and discrimination between near isobaric parent mass tolerance and bioinformatics pipeline that rules the outcomes we were able to identified citrullinated peptides over a dynamic range of 6 orders of magnitude and quantified those with relative abundance.

There are some chemical, proteomic and antibody-based procedures that are currently available for the analysis of citrullination in complex samples [15-17]. However, with the current methods it remains challenging to rapidly, consistently, reproducibly, accurately, and sensitively detect and quantify citrullinated peptides across multiple samples. Here we present a new strategy that systematically queries sample sets for the presence and quantity of citrullinated proteins with exact site of modified residues. It consists of using the information available in fragment ion spectral libraries, like relative intensities, chromatographic concurrence to mine the complete citrullinated fragment ion maps generated using DIA method.

In essence, our tools identify peak groups that uniquely associate with the targeted citrullinated peptide within the comprehensive SWATH MS (Sequential Window Acquisition of all Theoretical Fragment Ion Spectra Mass Spectrometry) signal map, and then compute a probability that the targeted citrullinated peptide has been correctly identified by following the set up rules in bioinformatics pipeline. In order to increase sensitivity a high-quality library of citrullinated assays is a prerequisite for SWATH MS (Sequential Window Acquisition of all Theoretical Fragment Ion Spectra Mass Spectrometry) and similar targeting MS methods. Ideally, the citrullinated peptides in the assay library cover all citrullinated proteins of interest for a particular study, or even an entire proteome. In order to make sure it is true samples on based the library is built on are in vitro citrullinated by PAD cocktail. This step helps improve detection of citrullinated proteins present in lower amounts as well as cover potentially new sites.

We show that SWATH-MS (Sequential Window Acquisition of all Theoretical Fragment Ion Spectra—Mass Spectrometry) can be successfully adopted for PTM analysis. Bioinformatics pipeline added for analysis of citrullinated peptide makes the analysis reliable, robust and quick. We believe that this methodology will increase popularity of analysis of citrullination in the field and shortly will be invaluable to elucidate the importance of this posttranslational modification in vivo.

As described herein, citrullination, the post-translational (PTM) conversion of arginine to citrulline by the family of peptidylarginine deiminase (PADs), has been commonly implicated as abnormal pathological features in neurodegenerative diseases such as prion diseases, multiple sclerosis, and Alzheimer's disease. This PTM could be a target for novel diagnostic or therapeutic agents. Therefore, an unambiguous and efficient method to identify citrullinated proteins and their modified residues is of extreme importance.

ALS, or amyotrophic lateral sclerosis, is a progressive neurodegenerative disease that affects nerve cells in the brain and the spinal cord. The inventors investigated the role of citrullination in ALS disorders, with a focus on identifying a potentially clinically relevant PTM biomarker(s).

Figure 8A:
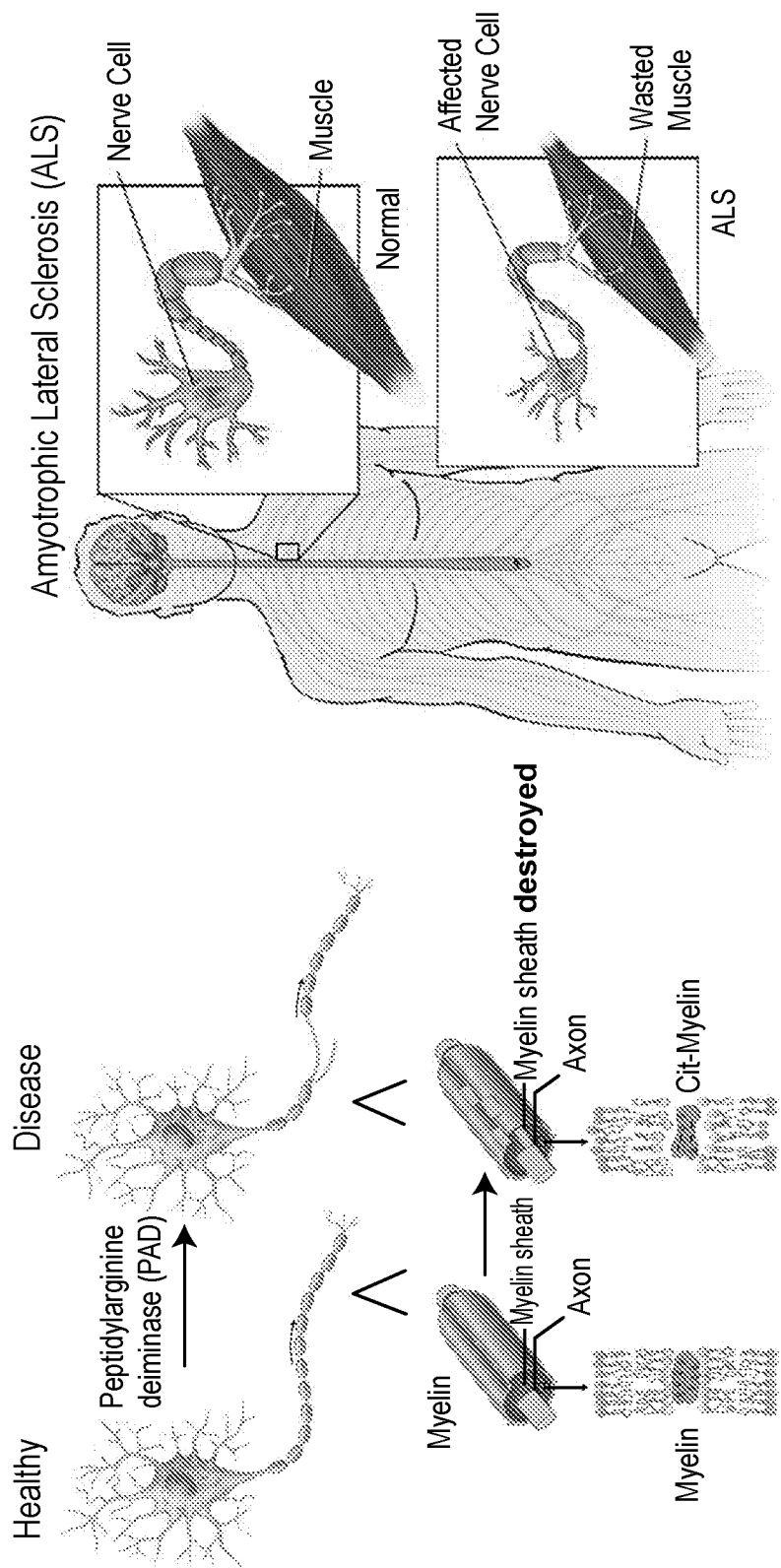
Figure 8B:
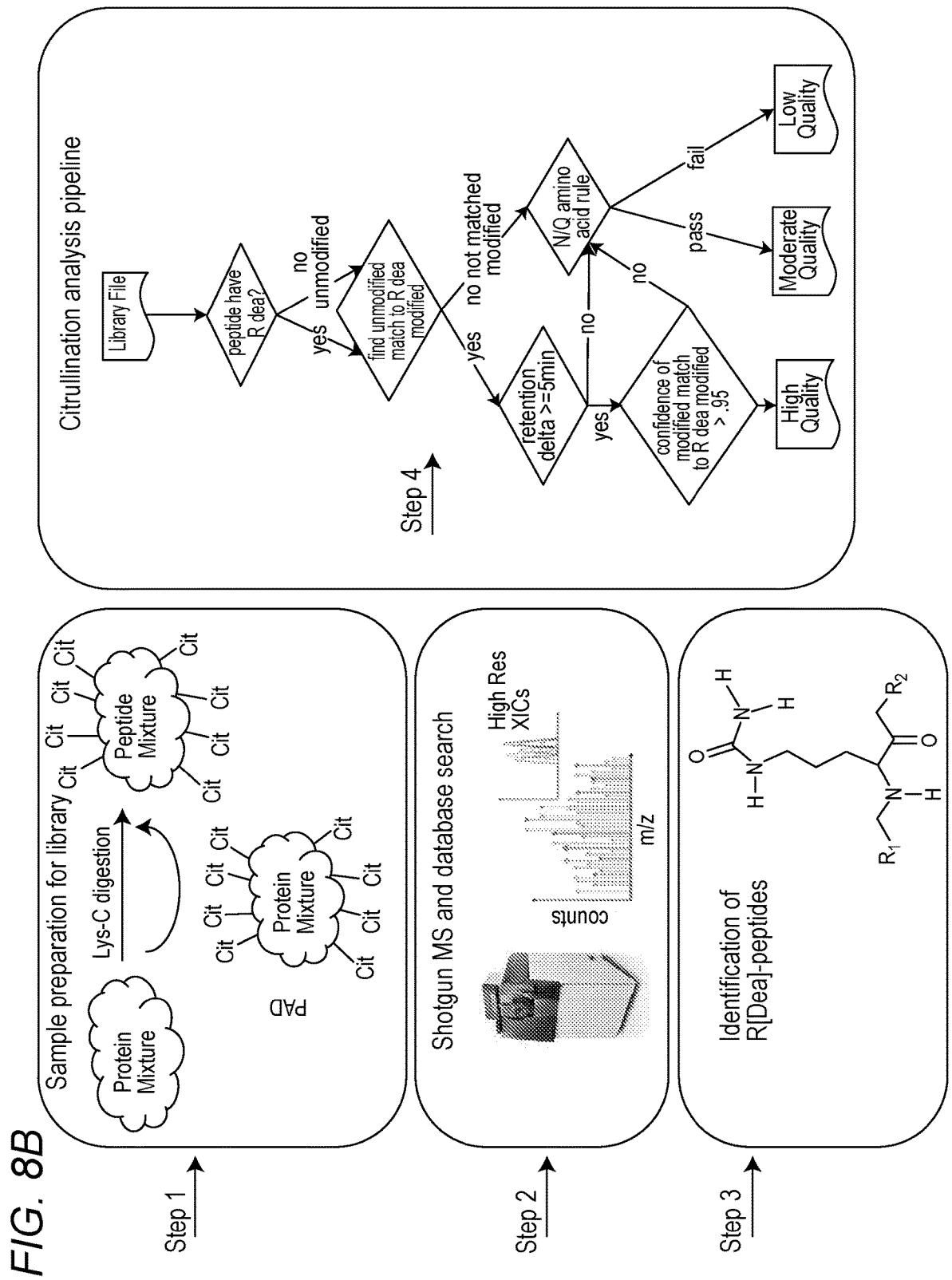
Figure 8C:
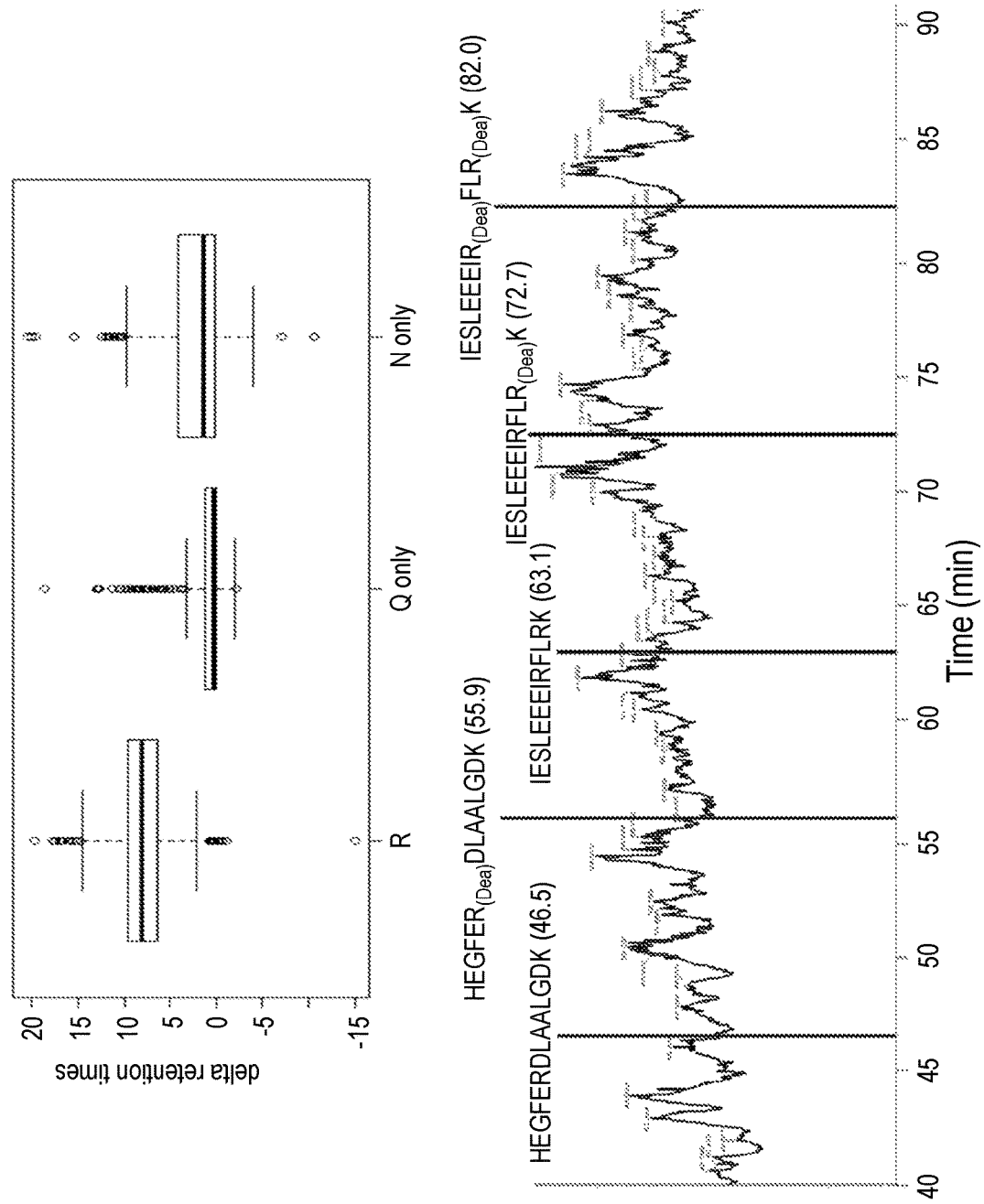
Figure 8D:
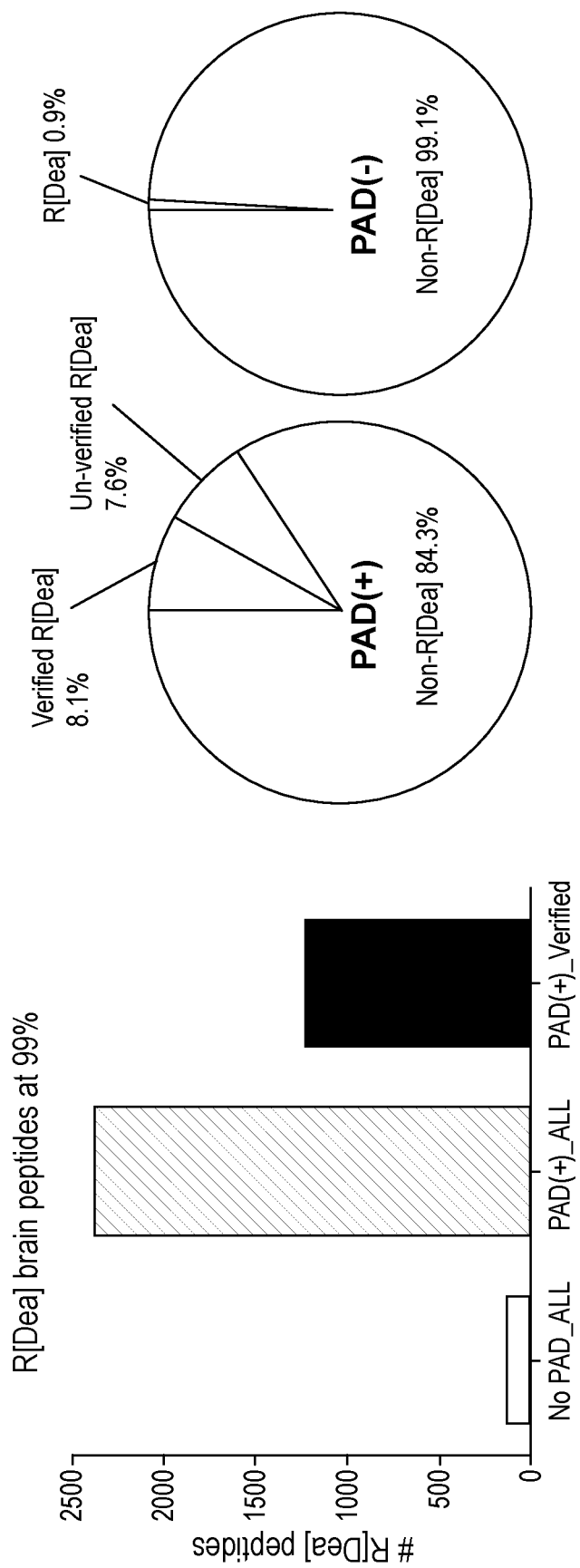
Figure 8G:
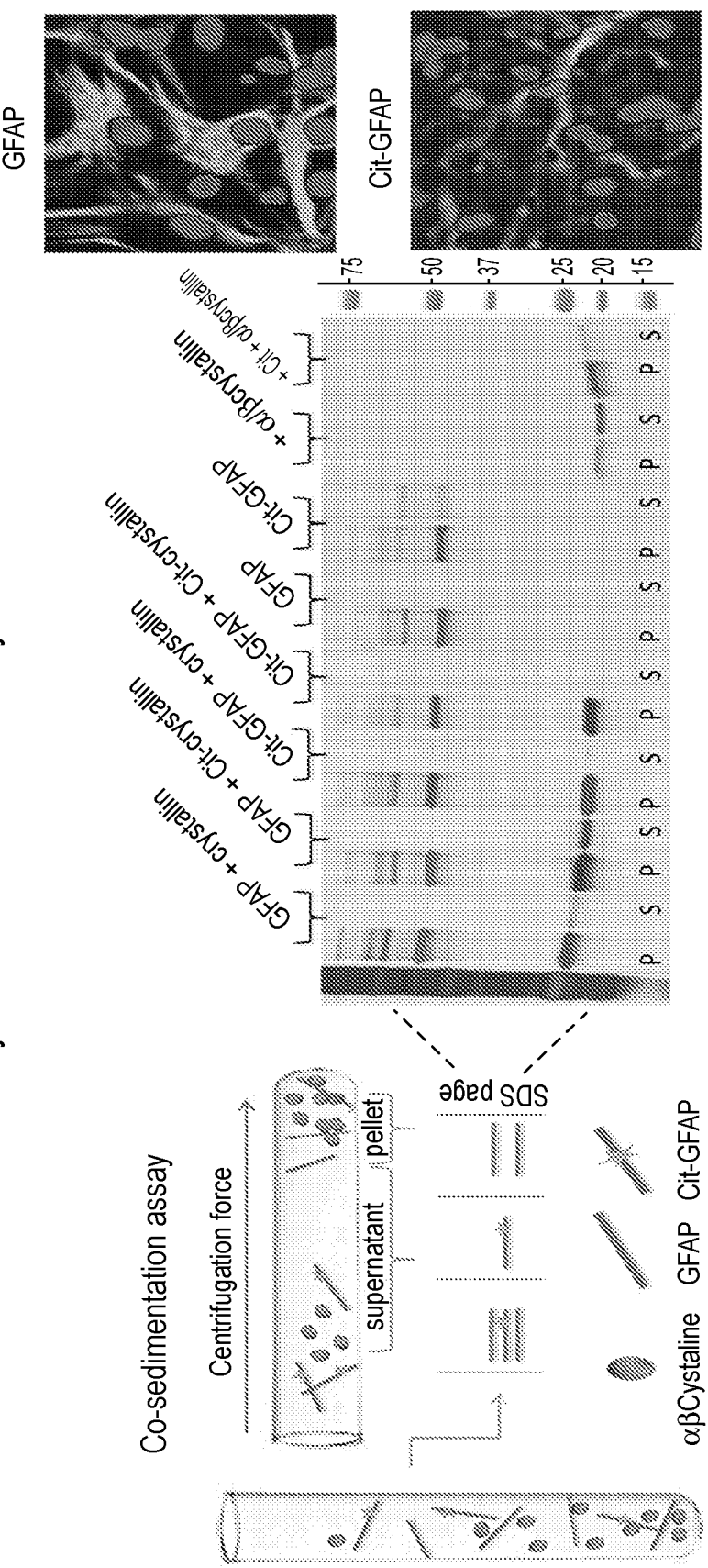

FIG. 8B depicts construction of citrulinated ion library. FIG. 8C depicts delta RT for R[Dea] and N/Q[Dea] compared to unmodified sequence. Respectively, peptide containing citrullinated Arg eluted later compared to unmodified peptides (>5 min difference). The same trend was observed between peptides with citrullinated R and peptides with N and Q deamination.

As shown in FIG. 8F, alteration in citrullination of any one or more of Glial fibrillary acidic protein, Glucose-6-phosphate isomerase, Vimentin, Endophilin-A1, Myelin basic protein, Delta-1-pyrroline-5-carboxylate dehydrogenase, Peroxiredoxin-5, Neurogranin, Dual specificity mitogen-activated protein kinase kinase 1, Tubulin polymerization-promoting protein family member 3, Delta(3,5)-Delta (2,4)-dienoyl-CoA isomerase, Cysteine and glycine-rich protein 1, Cellular retinoic acid-binding protein 1 GMP reductase 2 and/or Guanine nucleotide-binding protein G(I)/G(S)/G(0) subunit gamma-3 may be indicative of ALS.

TABLE 2

Citrullinated peptides as biomarkers for ALS. These peptides detected in subject with ALS but not healthy humans. "Dea" is Citrullination or deamination. "CAM" is carbamidomethylation.

| UniProtKB Accessions | Protein Name | Modified Sequence | Modification position |
| --- | --- | --- | --- |
| Q99962 | SH3 Endophilin-A1 G2 | PSGVQMDPC[CAM]C[CAM]R[Dea]ALYDFEPENEGELGFK (SEQ ID NO: 306) | 296 |
| P49419 | Alpha-aminoadipic semialdehyde dehydrogenase | QYMR[Dea]R[Dea]STC[CAM]TINYSK (SEQ ID NO: 307) | 581, 519 |
| H3BRN4 | 4-aminobutyrate aminotransferase | LILIAR[Dea]NK (SEQ ID NO: 308) | 465 |
| P68402 | Platelet-activating factor acetylhydrolase IB subunit beta | VIVVWVGTNNHENTAEEVAGGIEAIVQLINTR[Dea]QPQAK (SEQ ID NO: 309) | 128 |
| Q13011 | ECH Delta(3,5)-Delta(2,4)-dienoyl-CoA isomerase | EVDVGLAADVGTLQR[Dea]LPK (SEQ ID NO: 310) | 211 |
| P21291 | CSRP1 Cysteine and glycine-rich protein 1 | HEEAPGHR[Dea]PTTNPNASK (SEQ ID NO: 311) | 109 |
| P63215 | GBG Guanine nucleotide-binding protein G(I)/G(S)/G(O) subunit gamma-33 | GETPVNSTMSIGQAR[Dea]K (SEQ ID NO: 312) | 17 |
| F8VVM2 | F Phosphate carrier protein, | VRIQTQPGYANTLR[Dea]DAAPK (SEQ ID NO: 313) | 200 |
| P49588 | SYA Alanine-tRNA ligase | NVGC[CAM]LQEALQLATSFAQLR[Dea]LGDVK (SEQ ID NO: 314) | 962 |

TABLE 3

Citrullinated peptides (from humans) as biomarkers for ALS. "Dea" is Citrullination or deamination. "CAM" is carbamidomethylation.

| UniProtKB Accessions | Protein Name | Modified Sequence | Modification position |
| --- | --- | --- | --- |
| P14136 | Glial fibrillary acidic protein | FADLTDAAAR[Dea]NAELLR[Dea]QAK (SEQ ID NO: 315) | 270, 276 |
| P14136 | Glial fibrillary acidic protein | EIR[Dea]TQYEAMASSNMHEAEEWYRSK (SEQ ID NO: 316) | 239 |
| P14136 | Glial fibrillary acidic protein | MASSNMHEAEEWYR[Dea]SK (SEQ ID NO: 317) | 258 |
| P14136 | Glial fibrillary acidic protein | ASSNMHEAEEWYR[Dea]SK (SEQ ID NO: 318) | 258 |
| P14136 | Glial fibrillary acidic protein | LAR[Dea]LEEEGQSLK (SEQ ID NO: 319) | 330 |
| P06744 | Glucose-6-phosphate isomerase | ILLANFLAQTEALMR[Dea]GK (SEQ ID NO: 320) | 438 |
| P08670 | Vimentin | TVETR[Dea]DGQVINETSQHHDDLE (SEQ ID NO: 321) | 450 |
| P08670 | Vimentin | VELQELNDR[Dea]FANYIDK (SEQ ID NO: 322) | 113 |
| P08670 | Vimentin | SSVPGVR[Dea]LLQDSVDFSLADAINTEFK (SEQ ID NO: 323) | 78 |
| P08670 | Vimentin | ALR[Dea]DVR[Dea]QQYESVAAK (SEQ ID NO: 324) | 270, 273 |

TABLE 3-continued

Citrullinated peptides (from humans) as biomarkers for ALS. "Dea" is Citrullination or deamination. "CAM" is carbamidomethylation.

| UniProtKB Accessions | Protein Name | Modified Sequence | Modification position |
|---|---|---|---|
| P02686 | Myelin basic protein | GAEGQRPGFGYGGR[Dea]ASDYK (SEQ ID NO: 325) | 264 |
| P02686 | Myelin basic protein | SHGR[Dea]TQDENPVVHFF (SEQ ID NO: 326) | 213 |
| P02686 | Myelin basic protein | SRFSWGAEGQRPGFGYGGR[Dea]ASDYK (SEQ ID NO: 327) | 264 |
| P02686 | Myelin basic protein | SR[Dea]FSWGAEGQR[Dea]PGFGYGGR[Dea]ASDYK (SEQ ID NO: 328) | 247, 256, 264 |
| P02686 | Myelin basic protein | SWGAEGQR[Dea]PGFGYGGR[Dea]ASDYK (SEQ ID NO: 329) | 256, 264 |
| P02686 | Myelin basic protein | SHGR[Dea]TQDENPVVHF (SEQ ID NO: 330) | 213 |
| P02686 | Myelin basic protein | LGGR[Dea]DSRSGSPMARR[Dea] (SEQ ID NO: 331) | 293 |
| P02686 | Myelin basic protein | EGQRPGFGYGGR[Dea]ASDYK (SEQ ID NO: 332) | 264 |
| P30038 | Delta-1-pyrroline-5-carboxylate dehydrogenase | AIEAALAAR[Dea]K (SEQ ID NO: 333) | 113 |
| P30044 | Peroxiredoxin-5 | VR[Dea]LLADPTGAFGK (SEQ ID NO: 334) | 148 |
| Q9BW30 | Tubulin polymerization-promoting protein famiyl member 3 | TGGAVDR[Dea]LTDTSR[Dea]YTGSHK (SEQ ID NO: 335) | 124, 130 |
| Q13011 | Delta(3,5)-Delta(2,4)-dienoyl-CoA isomerase | VIGNQSLVNELAFTAR[Dea]K (SEQ ID NO: 336) | 230 |
| P29762 | Cellular retinoic acid-binding protein 1 | MR[Dea]SSENFDELLK (SEQ ID NO: 337) | 11 |
| Q9P2T1 | GMP reductase 2 | YAGGVAEYR[Dea]ASEGK (SEQ ID NO: 338) | 286 |

TABLE 4

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| P69905 | Hemoglobin subunit alpha OS = Homo sapiens GN = HAB1 PE = 1 SV = 2 | R[Dea]MFLSFPTTK (SEQ ID NO: 339) | 32, |
| P66905 | Hemoglobin subunit alpha OS = Homo sapiens GN = HAB1 PE = 1 SV = 3 | VGAHAGEYGAEALER[Dea]MFL (SEQ ID NO: 340) | 32, |
| P46821 | Microtubule-associated protein 1B OS = Homo sapiens GN = MAP1B PE = 1 SV = 2 | TTR[Dea]TSDVGGYYYEK (SEQ ID NO: 341) | 1897, |
| Q15149 | Plectin OS = Homo sapiens GN = PLEC PE = 1 SV = 3 | VPQR[Dea]AGEVER[Dea]DLDK (SEQ ID NO: 342) | 571, 577, |
| Q15149 | Plectin OS = Homo sapiens GN = PLEC PE = 1 SV = 4 | LHVAILER[Dea]EK (SEQ ID NO: 343) | 517, |
| Q14204 | Cytoplasmic dynein 1 heavy chain 1 OS = Homo sapiens GN = DYNC1H1 PE = 1 SV = 5 | R[Dea]VEPLR[Dea]NELQK (SEQ ID NO: 344) | 3408, 3413 |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| Q01484 | Ankyrin-2 OS = Homo sapiens GN = ANK2 PE = 1 SV = 4 | EGHVGLVQELLGR[Dea]GSSVDSATK (SEQ ID NO: 345) | 86, |
| J3KPX8 | MAP1 light chain LC2 OS = Homo sapiens GN = MAP1A PE = 1 SV = 1 | AIVFEIMEAGEPTGPILGAEALPGGLR[Dea]TL PQEPGKPQK (SEQ ID NO: 346) | 1123, |
| Q13385 | Tubulin beta-2A chain OS = Homo sapiens GN = TUBB2A, PE = 1 SV = 1 | IREEYPDR[Dea]IMNTFSVMPSPK (SEQ ID NO: 347) | 162, |
| Q00610 | Clathrin heavy chain 1 OS = Homo sapiens GN = CLTC PE = 1 SV = 5 | GILR[Dea]TPDTIR[Dea]R[Dea]FQSVPAQPG QTSPLLQYFGILLDQGQLNK (SEQ ID NO: 348) | 393, 399, 400, |
| Q00610 | Clathrin heavy chain 1 OS = Homo sapiens GN = CLTC PE = 1 SV = 6 | YESLELC[CAM]R[Dea]PVLQQGR[Dea]K (SEQ ID NO: 349) | 436, 437, 444, |
| Q99798 | Aconitate hydratase, OS = Homo sapiens GN = ACO2 PE = 1 SV = 2 | SYLR[Dea]LR[Dea]PDR[Dea]VAMQDATAQMA MLQFISSGLSK (SEQ ID NO: 350) | 90, 92, 95, |
| E7ESP9 | Neurofilament medium polypeptide OS = Homo sapiens GN = NEFM PE = 1 SV = 1 | SIELESVR[Dea]GTK (SEQ ID NO: 351) | 335, |
| Q9NQC3 | Reticulon-4 OS = Homo sapiens GN = RTN4 PE = 1 SV = 2 | AESAVIVANPR[Dea]EEIIVK (SEQ ID NO: 352) | 320, |
| Q9NQC3 | Reticulon-4 OS = Homo sapiens GN = RTN4 PE = 1 SV = 2 | EAQIR[Dea]ETETFSDSSPIEIIDEFPTLISSK (SEQ ID NO: 353) | 854, |
| Q9NQ66 | 1-phosphatidylinositol 4,5-biphosphate phosphodiesterase beta-1 OS = Homo sapiens GN = PLCB1 PE = 1 SV = 1 | EWTNEVFSLATNLLAQNMSR[Dea]DAFLEK (SEQ ID NO: 354) | 148, |
| P04075 | Fructose-biphosphate aldolase A OS = Homo sapiens GN = ALDOA PE = 1 SV = 2 | ADDGR[Dea]PFPQVIK (SEQ ID NO: 355) | 92, |
| P10809 | 60 kDa heat shock protein, OS = Homo sapiens GN = HSPD1 PE = 1 SV = 2 | LVQDVANNTNEEAGDGTTTATVLAR[Dea]SIAK (SEQ ID NO: 356) | 121, |
| P00558 | Phosphoglycerate kinase OS = Homo sapiens GN = PGK1 PE = 1 SV = 3 | ALESPER[Dea]PFLAILGGAK (SEQ ID NO: 357) | 206, |
| P00558 | Phosphoglycerate kinase OS = Homo sapiens GN = PGK1 PE = 1 SV = 3 | R[Dea]VVMR[Dea]VDFNVPMK (SEQ ID NO: 358) | 18, 22, |
| P13639 | Elongation factor 2 OS = Homo sapiens GN = EEF2 PE = 1 SV = 4 | YEWDVAEAR[Dea]K (SEQ ID NO: 359) | 647, |
| P13639 | Elongation factor 2 OS = Homo sapiens GN = EEF2 PE = 1 SV = 4 | VLENAEGAR[Dea]TTPSVVAFTADGER[Dea]LV GMPAK (SEQ ID NO: 360) | 85, 99, |
| P06744 | Glucose-6-phosphate isomerase OS = Homo sapiens GN = GPI PE = 1 SV = 4 | NLVTEDVMR[Dea]MLVDLAK (SEQ ID NO: 361) | 66, |
| P12277 | Creatine kinase B-type OS = Homo sapiens GN = CKB PE = 1 SV = 1 | DLFDPIIEDR[Dea]HGGYKPSDEHK (SEQ ID NO: 362) | 96, |
| P12277 | Creatine kinase B-type OS = Homo sapiens GN = CKB PE = 1 SV = 2 | DLFDPIIEDR[Dea]HGGYKPSDEHK (SEQ ID NO: 363) | 96, |
| P11216 | Glycogen phosphorylase, brain form OS = Homo sapiens GN = PYGB PE = 1 SV = 5 | QISVR[Dea]GLAGLGDVAEVR[Dea]K (SEQ ID NO: 364) | 17, 29, |
| P49588 | Alanine--tRNA ligase, cytoplasmic OS = Homo sapiens GN = AARS PE = 1 SV = 2 | DVQR[Dea]EIADLGEALATAVIPQWQK (SEQ ID NO: 365) | 793, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| Q01814 | Plasma membrane calcium-transporting ATPase 2 OS = Homo sapiens GN = ATP2B2 PE = 1 SV = 2 | GIIDSTHTEQR[Dea]QVVAVTGDGTNDGPALK (SEQ ID NO: 366) | 812, |
| P09543 | 2',3'-cyclic nucleotide 3'-phosphodiesterase OS = Homo sapiens GN = CNP PE = 1 SV = 2 | ITPGAR[Dea]GAFSEEYK (SEQ ID NO: 367) | 93, |
| P09543 | 2',3'-cyclic nucleotide 3'-phosphodiesterase OS = Homo sapiens GN = CNP PE = 1 SV = 2 | TLFILR[Dea]GLPGSGK (SEQ ID NO: 368) | 56, |
| P09543 | 2',3'-cyclic nucleotide '3-phosphodiesterase OS = Homo sapiens GN = CNP PE = 1 SV = 2 | ELR[Dea]QFVPGDEPREK (SEQ ID NO: 369) | 224, |
| P19367 | Hexokinase-1 OS = Homo sapiens GN = HK1 PE = 1 SV = 3 | MVSGMYLGELVR[Dea]LILVK (SEQ ID NO: 370) | 307, |
| Q9ULC6 | Protein-arginine deiminase type-1 OS = Homo sapiens GN = PADI1 PE = 1 SV = 2 | R[Dea]ELGLAESDIVDIPQLFFLK (SEQ ID NO: 371) | 556, |
| Q8N573 | Oxidation resistance protein 1 OS = Homo sapiens GN = OXR1 PE = 1 SV = 2 | TLYR[Dea]TMTGLDTPVLMVIK (SEQ ID NO: 372) | 754, |
| P15311 | Ezrin OS = Homo sapiens GN = EZR PE = 1 SV = 4 | EELER[Dea]QAVDQIK (SEQ ID NO: 373) | 405, |
| P08238 | Heat shock protein HSP 90-beta OS = Homo sapiens GN = HSP90AB1 PE = 1 SV = 4 | IDIIPNPQER[Dea]TLTLVDTGIGMTK (SEQ ID NO: 374) | 82, |
| P29966 | Myristoylated alanine-rich C-kinase substrate OS = Homo sapiens GN = MARCKS PE = 1 SV = 4 | GEAAAER[Dea]PGEAAVASSPSK (SEQ ID NO: 375) | 18, |
| P49418 | Amphiphysin OS = Homo sapiens GN = AMPH PE = 1 SV = 1 | AEEPLAAVTPAVGLDLGMDTR[Dea]AEEPVEEAVIIPGADADAAVGTLVSAAEGAPGEEAEAEK (SEQ ID NO: 376) | 457, |
| P10636 | Microtubule-associated protein tau OS = Homo sapiens GN = MAPT PE = 1 SV = 5 | SR[Dea]LQTAPVPMPDLK (SEQ ID NO: 377) | 559, |
| P52306 | Rap1 GTPase-GDP dissociation stimulator OS = Homo sapiens GN = RAP1GDS1 PE = 1 SV = 3 | LLGTLR[Dea]MLIDAQAEAAEQLGK (SEQ ID NO: 378) | 427, |
| Q05639 | Elongation factor 1-alpha 2 OS = Homo sapiens GN = EEF1A2 PE = 1 SV = 1 | YYITIIDAPGHR[Dea]DFIK (SEQ ID NO: 379) | 96, |
| Q02252 | Methylmalonate-semialdehyde dehydrogenase [acylating], OS = Homo sapiens GN = ALDH6A1 PE = 1 SV = 2 | YAHLVDVGQVGVNVPIPVPLPMFSFTGSR[Dea]SFR[Dea]GDTNFYGK (SEQ ID NO: 380) | 488, 492, |
| P09972 | Fructose-biphosphate aldolase C OS = Homo sapiens GN = ALDOC PE = 1 SV = 2 | R[Dea]AEVNGLAAQGK (SEQ ID NO: 381) | 331, |
| P40926 | Malate dehydrogenase, OS = Homo sapiens GN = MDH2 PE = 1 SV = 3 | GLDPAR[Dea]VNVPVIGGHAGK (SEQ ID NO: 382) | 191, |
| P48735 | Isocitrate dehydrogenase [NADP], OS = Homo sapiens GN = IDH2 PE = 1 SV = 2 | ATDFVADR[Dea]AGTFK (SEQ ID NO: 383) | 188, |
| F5GXC8 | Succinyl-CoA ligase [ADP-forming] subunit beta, OS = Homo sapiens GN = SUCLA2 PE = 1 SV = 1 | IFDLQDWTQEDER[Dea]DK (SEQ ID NO: 384) | 242, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| P09104 | Gamma-enolase OS = Homo sapiens GN = ENO2 PE = 1 SV = 3 | LAMQEFMILPVGAESFR[Dea]DAMRLGAEVYHTLK (SEQ ID NO: 385) | 179, |
| Q9BPU6 | Dihydropyrimidinase-related protein 5 OS = Homo sapiens GN = DPYSL5 PE = 1 SV = 1 | VR[Dea]GVDR[Dea]TPYLGDVAVVVHPGK (SEQ ID NO: 386) | 485, 489, |
| Q9BPU6 | Dihydropyrimidinase-related protein 5 OS = Homo sapiens GN = DPYSL5 PE = 1 SV = 2 | MDENR[Dea]FVAVTSSNAAK (SEQ ID NO: 387) | 372, |
| Q14195 | Dihydropyrimidinase-related protein 3 OS = Homo sapiens GN = DPYSL3 PE = 1 SV = 1 | SAADLISQAR[Dea]K (SEQ ID NO: 388) | 268, |
| P09471 | Guanine nucleotide-binding protein G(o) subunit alpha OS = Homo sapiens GN = GNAO1 PE = 1 SV = 4 | PVVYSNTIQSLAAIVR[Dea]AMDTLGIEYGDK (SEQ ID NO: 389) | 86, |
| Q9ULU8 | Calcium-dependent secretion activator 1 OS = Homo sapiens GN = CADPS PE = 1 SV = 3 | ELGR[Dea]VILHPTPNSPK (SEQ ID NO: 390) | 479, |
| P49419 | Alpha-aminoadipic semialdehyde dehydrogenase OS = Homo sapiens GN = ALDH7A1 PE = 1 SV = 5 | DLGR[Dea]IFR[Dea]WLGPK (SEQ ID NO: 391) | 466, 469, |
| P38606 | V-type proton ATPase catalytic subunit A OS = Homo sapiens GN = ATP6V1A PE = 1 SV = 2 | TVGMLSNMIAFYDMAR[Dea]R[Dea]AVETTAQSDNK (SEQ ID NO: 392) | 552, 553, |
| H3BRN4 | 4-aminobutyrate aminotransferase OS = Homo sapiens GN = ABAT PE = 1 SV = 1 | EEFR[Dea]PNAPYR[Dea]IFNTWLGDPSK (SEQ ID NO: 393) | 386, 392, |
| P07237 | Protein disulfide-isomerase OS = Homo sapiens GN = P4HB PE = 1 SV = 3 | R[Dea]TGPAATTLPDGAAAESLVESSEVAVIGFFK (SEQ ID NO: 394) | 132, |
| O94760 | N(G), N(G)-dimethylarginine dimethylaminohydrolase 1 | IMQQMSDHR[Dea]YDK (SEQ ID NO: 395) | 208, |
| Q16181 | Septin-7 | DR[Dea]LPLAVVGSNTIIEVNGK (SEQ ID NO: 396) | 243, |
| O75781 | Paralemmin-1 OS = Homo sapiens GN = PALM PE = 1 SV = 2 | R[Dea]RQLEDER[Dea]RQLQHLK (SEQ ID NO: 397) | 32, 39, |
| P30153 | Serine/threonine-protein phosphatase 2A 65 kDa regulatory subunit A alpha isoform OS = Homo sapiens GN = PPP2R1A PE = 1 SV = 4 | HMLPTVLR[Dea]MAGDPVANVR[Dea]FNVAK (SEQ ID NO: 398) | 527, 537, |
| P15121 | Aldose reductase OS = Homo sapiens GN = AKR1B1 PE = 1 SV = 3 | PEDPSLLEDPR[Dea]IK (SEQ ID NO: 400) | 233, |
| P07954 | Fumarate hydratase OS = Homo sapiens GN = FH PE = 1 SV = 3 | IGR[Dea]THTQDAVPLTLGQEFSGYVQQVK (SEQ ID NO: 401) | 233, |
| P24752 | Acetyl-CoA acetyltransferase, OS = Homo sapiens GN = ACAT1 PE = 1 SV = 1 | EVVIVSATR[Dea]TPIGSFLGSLSLLPATK (SEQ ID NO: 402) | 49, |
| E9PFW3 | AP-2 complex subunit mu OS = Homo sapiens GN = AP2M1 PE = 1 SV = 1 | DIILPFR[Dea]VIPLVR[Dea]EVGRTK (SEQ ID NO: 403) | 313, 319, |
| P30086 | Phosphatidylethanolamino-binding protein OS = Homo sapiens GN = PEBP1 PE = 1 SV = 3 | LYTLVLTDPDAPSR[Dea]K (SEQ ID NO: 404) | 76, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| P04350 | Tubulin beta-4A chain OS = Homo sapiens GN = TUBB4A PE = 1 SV = 2 | GHYTEGAELVDAVLDVVR[Dea]K (SEQ ID NO: 405) | 121, |
| Q9UI5 | Transgelin-3 OS = Homo sapiens GN = TAGLN3 PE = 1 SV = 2 | AAETYGVR[Dea]TTDIFQTVDLWEGK (SEQ ID NO: 406) | 106, |
| O43175 | D-3-phosphoglycerate dehydrogenase OS = Homo sapiens GN = PHGDH PE = 1 SV = 4 | VLISDSLPDC[CAM]C[CAM]R[Dea]K (SEQ ID NO: 407) | 18, 19, 20, |
| P00915 | Carbonic anhydrase 1 OS = Homo sapiens GN = CA1 PE = 1 SV = 2 | ESISVSSEQLAQFRSLLSN[Dea]VEGDNAVPMQH NNR[Dea]PTQPLK (SEQ ID NO: 408) | 233, 247, |
| P61981 | 14-3-3 protein gamma OS = Homo sapiens GN = YWHAG PE = 1 SV = 2 | MKGDYYR[Dea]YLAEVATGEK (SEQ ID NO: 409) | 132, |
| P61604 | 10 kDa heat shock protein, OS = Homo sapiens GN = HSPE1 PE = 1 SV = 2 | DYFLFR[Dea]DGDILGK (SEQ ID NO: 410) | 92, |
| P21281 | V-type proton ATPase subunit B, brain isoform OS = Homo sapiens GN = ATP6V1B2 PE = 1 SV = 3 | DIGWQLLR[Dea]IFPK (SEQ ID NO: 411) | 485, |
| B4DKF8 | PH and SEC7 domain-containing protein 3 OS = Homo sapiens GN = PSD3 PE = 1 SV = 1 | FSR[Dea]PLLPATTTK (SEQ ID NO: 412) | 245, |
| P32119 | Peroxiredoxin-2 OS = Homo sapiens GN = PRDX2 PE = 1 SV = 5 | EGGLGPLNIPLLADVTR[Dea]R[Dea]LSEDYGV LK (SEQ ID NO: 413) | 109, 110, |
| P32119 | Peroxiredoxin-2 OS = Homo sapiens GN = PRDX2 PE = 1 SV = 5 | TDEGIAYR[Dea]GLFIIDGK (SEQ ID NO: 414) | 127, |
| P02647 | Apolipoprotein A-I OS = Homo sapiens GN = APOA1 PE = 1 SV = 1 | VEPLR[Dea]AELQEGARQK (SEQ ID NO: 415) | 147, |
| Q12765 | Secernin-1 OS = Homo sapiens GN = SCRN1 PE = 1 SV = 2 | NSAR[Dea]PR[Dea]DEVQEVVYFSAADHEPESK (SEQ ID NO: 416) | 30, 32, |
| Q12765 | Secernin-1 OS = Homo sapiens GN = SCRN1 PE = 1 SV = 2 | AHEWAR[Dea]AIIESDQEQGR[Dea]K (SEQ ID NO: 417) | 355, 366, |
| P00918 | Carbonic anhydrase 2 OS = Homo sapiens GN = CA2 PE = 1 SV = 2 | LNFNGEGEPEELMVDNWR[Dea]PAQPLK (SEQ ID NO: 418) | 245, |
| E9PDE8 | Heat shock 70 kDa protein 4L OS = Homo sapiens GN = HSPA4L PE = 1 SV = 1 | VR[Dea]YLEEER[Dea]PFAIEQVTGMLLAK (SEQ ID NO: 419) | 78, 84, |
| Q9H115 | Beta-soluble NSF attachment protein OS = Homo sapiens GN = NAPB PE = 1 SV = 2 | ER[Dea]EAVQLMAEAEK (SEQ ID NO: 420) | 8, |
| Q9UPY8 | Microtubule-associated protein RP/EB family member 3 OS = Homo sapiens GN = MAPRE3 PE = 1 SV = 1 | LIGTAVPQR[Dea]TSPTGPK (SEQ ID NO: 421) | 160, |
| P00505 | Aspartate aminotransferase, OS = Homo sapiens GN = GOT2 PE = 1 SV = 3 | FSR[Dea]DVFLPK (SEQ ID NO: 422) | 153, |
| Q13509 | Tubulin beta-3 chain OS = Homo sapiens GN = TUBB3 PE = 1 SV = 2 | FWEVISDEHGIDPSGNYVGDSDLQLER[Dea]ISV YYNEASSHK (SEQ ID NO: 423) | 46, |
| O15144 | Actin-related protein 2/3 complex subunit 2 OS = Homo sapiens GN = ARPC2 PE = 1 SV = 1 | DR[Dea]VTVVFSTVFK (SEQ ID NO: 424) | 160, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| P09211 | Glutathione S-transferase P OS = Homo sapiens GN = GSTP1 PE = 1 SV = 2 | FQDGDLTLYQSNTILR[Dea]HLGR[Dea]TLGLY GK (SEQ ID NO: 425) | 71, 75, |
| O95292 | Vesicle-associated membrane protein-associated protein B/C OS = Homo sapiens GN = VAPB PE = 1 SV = 3 | FR[Dea]GPFTDVVTTNLK (SEQ ID NO: 426) | 19, |
| P42765 | 3-ketoacyl-CoA thiolase, OS = Homo sapiens GN = ACAA2 PE = 1 SV = 2 | QTMQVDEHAR[Dea]PQTTLEQLQK (SEQ ID NO: 427) | 224, |
| Q8TAM6 | Ermin OS = Homo sapiens GN = ERMN PE = 2 SV = 1 | GHQAAEIEWLGFR[Dea]K (SEQ ID NO: 428) | 163, |
| Q92686 | Neurogranin OS = Homo sapiens GN = NRGN PE = 1 SV = 1 | GPGPGGPGGAGVAR[Dea]GGAGGGPSGD (SEQ ID NO: 429) | 68, |
| K7ELL7 | Glucosidase 2 subunit beta OS = Homo sapiens GN = PRKCSH PE = 1 SV = 1 | MPPYDEQTQAFIDAAQEAR[Dea]NK (SEQ ID NO: 430) | 381, |
| Q9BY11 | Protein kinase C and casein kinase substrate in neurons protein OS = Homo sapiens GN = PACSIN1 PE = 1 SV = 1 | GPQYGSLER[Dea]AWGAIMTEADK (SEQ ID NO: 431) | 82, |
| O15075 | Serine/threonine-protein kinase DCLK1 OS = Homo sapiens GN = DCLK1 PE = 1 SV = 2 | TTSASR[Dea]AVSSLATAK (SEQ ID NO: 432) | 161, |
| P09622 | Dihydrolipoyl dehydrogenase, OS = Homo sapiens GN = DLD PE = 1 SV = 2 | NLGLEELGIELDPR[Dea]GR[Dea]IPVNTRFQ [Dea]TK (SEQ ID NO: 433) | 334, 336, 344, |
| P25705 | ATP synthase subunit alpha, OS = Homo sapiens GN = APT5A1 PE = 1 SV = 1 | R[Dea]TGAIVDVPGEELLGR[Dea]VVDALGNAI DGK (SEQ ID NO: 434) | 133, 149, |
| Q02750 | Dual specificity mitogen-activated protein kinase kinase 1 OS = Homo sapiens GN = MAP2K1 PE = 1 SV = 2 | AGR[Dea]IPEQILGK (SEQ ID NO: 435) | 160, |
| Q01995 | Transgelin OS = Homo sapiens GN = TAGLN PE = 1 SV = 4 | GPSYGMSR[Dea]EVQSK (SEQ ID NO: 436) | 12, |
| Q16352 | Alpha-internexin OS = Homo sapiens GN = INA PE = 1 SV = 2 | SEMAR[Dea]HLR[Dea]EYQDLLNVK (SEQ ID NO: 437) | 374, 377, |
| Q92752 | Tenascin-R OS = Homo sapiens GN = TNR PE = 1 SV = 3 | R[Dea]HAVLMGLQPATEYIVNLVAVHGTVTSEPI VGSITTGIDPPK (SEQ ID NO: 438) | 827, |
| O94811 | Tubulin polymerization-promoting protein OS = Homo sapiens GN = TPPP PE = 1 SV = 1 | AISSPTVSR[Dea]LTDTTK (SEQ ID NO: 439) | 165, |
| P30048 | Thioredoxin-dependent peroxide reductase, OS = Homo sapiens GN = PRDX3 PE = 1 SV = 3 | HLSVNDLPVGRSVEETLR[Dea]LVK (SEQ ID NO: 440) | 214, |
| Q9Y570 | Protein phosphatase methylesterase 1 OS = Homo sapiens GN = PPME1 PE = 1 SV = 3 | R[Dea]DFSPVPWSQYFESMEDVEVENETGK (SEQ ID NO: 441) | 39, |
| P69891 | Hemoglobin subunit gamma-1 OS = Homo sapiens GN = HBG1 PE = 1 SV = 2 | MVTAVASALSSR[Dea]YH (SEQ ID NO: 442) | 145, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| Q5T9B7 | Adenylate kinase isoenzyme 1 OS = Homo sapiens GN = AK1 PE = 1 SV = 1 | GQLVPLETVLDMLR[Dea]DAMVAK (SEQ ID NO: 443) | 93, |
| F5GXJ9 | CD166 antigen OS = Homo sapiens GN = ALCAM PE = 1 SV = 1 | PDGSPVFIAFR[Dea]SSTK (SEQ ID NO: 444) | 20, |
| Q6PUV4 | Complexin-2 OS = Homo sapiens GN = CPLX1 PE = 1 SV = 2 | AALEQPC[CAM]EGSLTR[Dea]PK (SEQ ID NO: 445) | 90, 96, |
| Q5T6W5 | Heterogeneous nuclear ribonucleoprotein K OS = Homo sapiens GN = HNRNPK PE = 1 SV = 1 | R[Dea]PAEDMEEEQAFK (SEQ ID NO: 446) | 22, |
| Q9NQR4 | Omega-amidase NIT2 OS = Homo sapiens NG = NIT2 PE = 1 SV = 1 | R[Dea]SDLYAVEMK (SEQ ID NO: 447) | 265, |
| P48426 | Phosphatidylinositol 5-phosphate 4-kinasse type-2 alpha OS = Homo sapiens GN = PIP4K2A PE = 1 SV = 2 | R[Dea]FLDFIGHILT (SEQ ID NO: 448) | 396, |
| Q4J6C6 | Prolyl endopeptidase-like OS = Homo sapiens GN = PREPL PE = 1 SV = 1 | LMR[Dea]TAADTPAIMNWDLFFTMK (SEQ ID NO: 449) | 326, |
| P61106 | Ras-related protein Rab-14 OS = Homo sapiens GN = RAB14 PE = 1 SV = 4 | ADLEAQR[Dea]DVTYEEAK (SEQ ID NO: 450) | 132, |
| Q99447 | Ethanolamine-phosphate cytidylyltrasferase OS = Homo sapiens GN = PCYT2 PE = 1 SV = 1 | GPPVFTQEER[Dea]YK (SEQ ID NO: 451) | 76, |
| P48506 | Glutamate--cysteine ligase catalytic subunit OS = Homo sapiens GN = GCLC PE = 1 SV = 2 | SR[Dea]YDSIDSYLSK (SEQ ID NO: 452) | 328, |
| P27361 | Mitogen-activated protein kinase 3 OS = Homo sapiens GN = MAPK3 PE = 1 SV = 4 | R[Dea]ITVEEALAHPYLEQYYDPTDEPVAEEPFT FAMELDDLPK (SEQ ID NO: 453) | 318, |
| B1AKZ3 | Astrocytic phosphoprotein PEA-15 OS = Homo sapiens GN = PEA15 PE = 1 SV = 1 | LTR[Dea]IPSAK (SEQ ID NO: 454) | 122, |
| P12036 | Neurofilament heavy polypeptide OS = Homo sapiens GN = NEFH PE = 1 SV = 4 | EQLQALNDR[Dea]FAGYIDK (SEQ ID NO: 455) | 107, |
| P62333 | 26S protease regulatory subunit 10B OS = Homo sapiens GN = PSMC6 PE = 1 SV = 1 | IHIDLPNEQAR[Dea]LDILK (SEQ ID NO: 456) | 309, |
| P36578 | 60S ribosomal protein L4 OS = Homo sapiens GN = RPL4 PE = 1 SV = 5 | GHR[Dea]IEEVPELPLVVEDK (SEQ ID NO: 457) | 143, |
| P13861 | cAMP-dependent protein kinase type II-alpha regulatory subunit OS = Homo sapiens GN = PRKAR2A PE = 1 SV = 2 | NLDQEQLSQVLDAMFER[Dea]IVK (SEQ ID NO: 4589) | 158, |
| Q8WW12 | PEST proteolytic signal-containing nuclear protein OS = Homo sapiens GN = PNCP PE = 1 SV = 2 | R[Dea]SAEEEAADLPTKPTK (SEQ ID NO: 459) | 52, |
| P50897 | Palmitoyl-1-protein thioesterase 1 OS = Homo sapiens GN = PPT1 PE = 1 SV = 1 | ETIPLQETSLYTQDR[Dea]LGLK (SEQ ID NO: 460) | 268, |
| Q9UJU6 | Drebrin-like protein OS = Homo sapiens GN = DBNL PE = 1 SV = 1 | ESGR[Dea]FQDVGPQAPVGSVYQK (SEQ ID NO: 461) | 148, |

TABLE 4-continued

Correlated citrullinated LysC peptides based on matching mouse sequence to human sequence. "Dea" is Citrullination or deamination. "CAM" is carbamidomethylation.

| UniProtKB Accessions | Protein Name | Modified Sequence | Modification position |
|---|---|---|---|
| Q14019 | Coactosin-like protein OS = Homo sapiens GN = COTL1 PE = 1 SV = 3 | FALITWIGENVSGLQR[Dea]AK (SEQ ID NO: 462) | 91, |
| Q8TEA8 | D-tyrosyl-tRNA(Tyr) deacylase 1 OS = Homo sapiens GN = DTD1 PE = 1 SV = 2 | ILNLR[Dea]VFEDESGK (SEQ ID NO: 463) | 53, |
| H0Y7Q1 | Arf-GAP with dual PH domain-containing protein 1 (Fragment) OS = Homo sapiens GN = ADAP1 PE = 1 SV = 1 | AVDR[Dea]PMLPQEYAVEAHFK (SEQ ID NO: 464) | 340, |
| O00401 | Neural Wiskott-Aldrich syndrome protein OS = Homo sapiens GN = WASL PE = 1 SV = 2 | AALLDQIR[Dea]EGAQLK (SEQ ID NO: 465) | 414, |
| O94772 | Lymphocyte antigen 6H OS = Homo sapiens GN = LY6H PE = 2 SV = 1 | R[Dea]HFFSDYLMGFINSGILK (SEQ ID NO: 466) | 82, |
| A8MX49 | Protein phosphatase 1F OS = Homo sapiens GN = PPM1F PE = 1 SV = 2 | APGTVLSQEEVEGELAELAMGFLGSR[Dea]K (SEQ ID NO: 467) | 69, |
| O95336 | 6-phosphogluconolactonase OS = Homo sapiens GN = PGLS PE = 1 SV = 2 | IVAPISDSPKPPPQR[Dea]VTLTLPVLNAAR [Dea]TVIFVATGEGK (SEQ ID NO: 468) | 185, 197, |
| O43708 | Maleylacetoacetate isomerase OS = Homo sapiens GN = GSTZ1 PE = 1 SV = 3 | R[Dea]ASVR[Dea]MISDLIAGGIQPLQNLSVLK (SEQ ID NO: 469) | 96, 100, |
| Q9UI12 | ATPase inhibitor OS = Homo sapiens GN = ATPIF1 PE = 1 SV = 1 | GSDQSENVDR[Dea]GAGSIR[Dea]EAGGAFGK (SEQ ID NO: 470) | 35, 41, |
| Q9P1F3 | Costars family protein AVRACL OS = Homo sapiens GN = AVRACL PE = 1 SV = 1 | IGVLFR[Dea]KKD (SEQ ID NO: 471) | 35, |
| P62851 | 40S ribosomal protein S25 OS = Homo sapiens GN = RPS25 PE = 1 SV = 1 | IR[Dea]GSLAR[Dea]AALQELLSK (SEQ ID NO: 472) | 80, 85, |
| C9J0K6 | Sorcin OS = Homo sapiens GN = SRI PE = 1 SV = 1 | ALTTMGFR[Dea]LSPQAVNSIAK (SEQ ID NO: 473) | 92, |
| Q9NVJ2 | ADP-ribosylation factor-like protein 8B OS = Homo sapiens GN = ARL8B PE = 1 SV = 1 | R[Dea]DLPNALDEK (SEQ ID NO: 474) | 132, |

TABLE 5A

Citrullinated peptides observed in chronic neurodegenerative disease. These citrullinated peptides are brain specific.

| Peptide | UniProtKB Accessions | Name |
|---|---|---|
| ADDGR[Dea]PFPQVIK (SEQ ID NO: 355) | sp\|P04075-2\| ALDOA_HUMAN | Isoform 2 of Fructose-bisphosphate aldolase A OS = Homo sapiens GN = ALDOA |
| EVVIVSATR[Dea]TPIGSLFLGSLS LLPATK (SEQ ID NO: 402) | sp\|P24752\| THIL_HUMAN | Acetyl-CoA acetyltransferase |
| RGETSGR[Dea]VDDNEETIK (SEQ ID NO: 1) | sp\|P00568\| KAD1_HUMAN | Adenylate kinase isoenzyme 1 OS = Homo sapiens GN = AK1 PE = 1 SV = 3 |
| PGVVHVIDIDR[Dea]GEEK (SEQ ID NO: 475) | sp\|P55087\| AQP4_HUMAN | Aquaporin-4 OS = Homo sapiens GN = AQP4 PE = 1 SV = 2 |

TABLE 5A-continued

Citrullinated peptides observed in chronic neurodegenerative disease.
These citrullinated peptides are brain specific.

| Peptide | UniProtKB Accessions | Name |
|---|---|---|
| IPVGPETLGR[Dea]IMNVIGEPIDERGPIK (SEQ ID NO: 476) | sp\|P06576\| ATPB_HUMAN | ATP synthase subunit beta, OS = Homo sapiens GN = ATP5B PE = 1 SV = 3 |
| SVHR[Dea]GEVPCTVTTASPLDDAVLSELK (SEQ ID NO: 477) | sp\|P48047\| ATPO_HUMAN | ATP synthase subunit O, OS = Homo sapiens GN = ATP5O PE = 1 SV = 1 |
| GILR[Dea]TPDTIR[Dea]R[Dea]FQSVPAQPGQTSPLLQYFGILLDQGQLNK (SEQ ID NO: 348) | sp\|Q00610\| CLH1_HUMAN | Clathrin heavy chain 1 |
| ELEEDFIR[Dea]SELK (SEQ ID NO: 478) | sp\|Q14019\| COTL1_HUMAN | Coactosin-like protein OS = Homo sapiens GN = COTL1 PE = 1 SV = 3 |
| DLFDPIIEDR[Dea]HGGYK (SEQ ID NO: 363) | sp\|P12277\| KCRB_HUMAN | Creatine kinase B-type OS = Homo sapiens GN = CKB PE = 1 SV = 1 |
| EGNASGVSLLEALDTILPPTR[Dea]PTDK (SEQ ID NO: 479) | sp\|Q05639\| EF1A2_HUMAN | Elongation factor 1-alpha OS = Homo sapiens GN = EEF1A2 PE = 1 SV = 1 |
| GHQAAEIEWLGFR[Dea]K (SEQ ID NO: 428) | sp\|Q8TAM6\| ERMIN_HUMAN | Ermin |
| EELER[Dea]QAVDQIK (SEQ ID NO: 373) | sp\|P15311\| ERZI_HUMAN | Ezmin |
| EIR[Dea]TQYEAMASSNMHEAEEWYRSK (SEQ ID NO: 316) | sp\|P14136\| GFAP_HUMAN | Glial fibrillary acidic protein |
| FADLTDAAAR[Dea]NAELLR[Dea]QAK (SEQ ID NO: 315) | sp\|P14136\| GFAP_HUMAN | Glial fibrillary acidic protein |
| GYFEDRR[Dea]PSANCDPYAVTEAIVRTCLLNETGDEPFQYK (SEQ ID NO: 480) | sp\|P15104\| GLNA_HUMAN | Glutamine synthetase OS = Homo sapiens GN = GLUL PE = 1 SV = 4 |
| RLIGRR[Dea]FDDAVVQSDMK (SEQ ID NO: 481) | sp\|P11142\| HSP7C_HUMAN | Heat shock cognate 71 kDa protein OS = Homo sapiens GN = HSPA8 PE = 1 SV = 1 |
| VGAHAGEYGAEALER[Dea]MFL (SEQ ID NO: 340) | sp\|P69905\| HBA_HUMAN | Hemoglobin subunit alpha |
| LGRLLVVYPWTQR[dea]YFDSFGDLSSASAIMGNAK (SEQ ID NO: 482) | sp\|P69892\| HGB2_HUMAN | Hemoglobin subunit gamma-2 OS = Homo sapiens GN = HBG2 PE = 1 SV = 2 |
| ESLLFEGR[Dea]ITPELLTRGK (SEQ ID NO: 483) | sp\|P19367\| HXK1_HUMAN | Hexokinase-1 OS = Homo sapiens GN = HK1 PE = 1 SV = 3 |
| RSTITSR[Dea]EVQTAVR[Dea]LLLPGELAK (SEQ ID NO: 484) | sp\|Q8N257\| H2B3B_HUMAN | Histone H2B type 3-B OS = Homo sapiens GN = HIST3B2BB PE = 1 SV = 3 |
| CR[Dea]EVAENCK (SEQ ID NO: 485) | sp\|P50213\| IDH3A_HUMAN | Isocitrate dehydrogenase [NAD] subunit alpha, OS = Homo sapiens GN = IDH3A PE = 1 SV = 1 |
| CR[Dea]APEVSQYIYQVYDSILK (SEQ ID NO: 486) | sp\|P63010-2\| AP2B1_HUMAN | Isoform 2 of AP-2 complex subunit beta OS = Homo sapiens GN = AP2B1 |
| GILR[Dea]TPDTIR[dea]RFQSVPAQPGQTSPLLQYFGILLDQGQLNK (SEQ ID NO: 487) | sp\|Q00610-2\| CLH1_HUMAN | Isoform 2 of Clathrin heavy chain 1 OS = Homo sapiens GN = CLTC |
| PTIFIQE[Dea]RDPTNIK (SEQ ID NO: 488) | sp\|P04406-2\| G3P_HUMAN | Isoform 2 of Glyceraldehyde-3-phosphate dehydrogenase OS = Homo sapiens GN = GAPDH |
| GCDVVIPAGVPR[Dea]K (SEQ ID NO: 489) | sp\|P40926-2\| MDHM_HUMAN | Isoform 2 of Malate dehydrogenase, OS = Homo sapiens GN = MDH2 |

TABLE 5A-continued

Citrullinated peptides observed in chronic neurodegenerative disease.
These citrullinated peptides are brain specific.

| Peptide | UniProtKB Accessions | Name |
|---|---|---|
| HR[Dea]DTGILDSIGRFFSGDR[Dea]GAPK (SEQ ID NO: 490) | sp\|P02686-2\| MBP_HUMAN | Isoform 2 of Myelin basic protein OS = Homo sapiens GN = MBP |
| ER[Dea]LDQPMTEIVSR[Dea]VSK (SEQ ID NO: 491) | sp\|P22314-2\| UBA1_HUMAN | Isoform 2 of Ubiquitin-like modifier-activating enzyme 1 OS = Homo sapiens GN = UBA1 |
| LLVSSEDYGR[dea]DLTGVQNLRK (SEQ ID NO: 492) | sp\|Q13813-3\| SPTN1_HUMAN | Isoform 3 of Spectrin alpha chain, non-erythrocytic 1 OS = Homo sapiens GN = SPTAN1 |
| VAVTPPGLAR[Dea]EDWK (SEQ ID NO: 493) | sp\|P28331-4\| NDUS1_HUMAN | Isoform 4 of NADH-ubiquinone oxidoreductase 75 kDa subunit, OS = Homo sapiens GN = NDUFS1 |
| VR[Dea]IQTQPGYAN (SEQ ID NO: 494) | sp\|Q00325-2\| MPCP_HUMAN | Isoform B of Phosphate carrier protein, OS = Homo sapiens GN = SLC25A3 |
| RIER[Dea]ELAEAQDDSILK (SEQ ID NO: 495) | sp\|P30530-2\| UFO_HUMAN | Isoform Short of Tyrosine-protein kinase receptor UFO OS = Homo sapiens GN = AXL |
| SR[Dea]LQTAPVPMPDLK (SEQ ID NO: 377) | sp\|P10636\| TAU_HUMAN | Microtubule-associated protein tau |
| KRDTGILDSIGRFFGGDR[Dea]GAPK (SEQ ID NO: 496) | sp\|P02686\| MBP_HUMAN | Myelin basic protein |
| LGGR[Dea]DSRSGSPMARR[Dea] (SEQ ID NO: 331) | sp\|P02686\| MBP_HUMAN | Myelin basic protein |
| SHGR[Dea]TQDENPVVHF (SEQ ID NO: 330) | sp\|P02686\| MBP_HUMAN | Myelin basic protein |
| EGQRPGFGYGGR[Dea]ASDYK (SEQ ID NO: 332) | sp\|P02686\| MBP_HUMAN | Myelin basic protein |
| GAEGQRPGFGYGGR[Dea]ASDYK (SEQ ID NO: 325) | sp\|P02686\| MBP_HUMAN | Myelin basic protein |
| GEAAAER[Dea]PGEAAVASSPSK (SEQ ID NO: 375) | sp\|P29966\| MARCS_HUMAN | Myristoylated alanine-rich C-kinase substrate |
| GPGPGGPGGAGVAR[Dea]GGAGGGPSGD (SEQ ID NO: 429) | sp\|Q92686\| NEUG_HUMAN | Neurogranin |
| TDEGIAYR[Dea]GLFIIDGK (SEQ ID NO: 414) | sp\|P32119\| PRDX2_HUMAN | Peroxiredoxin-2 |
| VRIQTQPGYANTLR[Dea]DAAPK (SEQ ID NO: 313) | sp\|F8VVM2\| F8VVM2_HUMAN | Phosphate carrier protein, |
| GIIDSTHTEQR[Dea]QVVAVTGDGTNDGPALK (SEQ ID NO: 366) | sp\|Q01814\| AT2B2_HUMAN | Plasma membrane calcium-transporting ATPase 2 |
| EAFQNAYLELGGLGER[Dea]VLGFCHYYLPEEQFPK (SEQ ID NO: 497) | sp\|P13637\| AT1A3_HUMAN | Sodium/potassium-transporting ATPase subunit alpha-3 OS = Homo sapiens GN = ATP1A3 PE = 1 SV = 3 |
| VLENAEGAR[Dea]TTPSVVAFTADGER[Dea]LVGMPAK (SEQ ID NO: 360) | s{\|P38646\| GRP75_HUMAN | Stress-70 protein, OS = Homo sapiens GN = HSPA9 PE = 1 SV = 2 |
| RIHVLPIDDTVEGITGNLFEVYLK (SEQ ID NO: 498) | sp\|P55072\| TERA_HUMAN | Transitional endoplasmic reticulum APTase OS = Homo sapiens GN = VCP PE = 1 SV = 4 |
| HVPR[Dea]AVFVDLEPTVIDEIRNGPYRQLFHPEQLITGK (SEQ ID NO: 499) | sp\|P68366\| TBA4A_HUMAN | Tubulin alpha-4A chain OS = Homo sapiens GN = TUBA4A PE = 1 SV = 1 |
| FWEVISDEHGIDPSGNYVGSDLQLER[Dea]ISVYYNEASSHK (SEQ ID NO: 423) | sp\|Q13509\| TBB3_HUMAN | Tubulin beta-3 chain |

TABLE 5A-continued

Citrullinated peptides observed in chronic neurodegenerative disease.
These citrullinated peptides are brain specific.

| Peptide | UniProtKB Accessions | Name |
|---|---|---|
| AILVDLEPGTMDSVRS[Dea]GAFGH LFR[Dea]PDNFIFGQSGAGNNWAK (SEQ ID NO: 500) | sp\|Q13509\| TBB3_HUMAN | Tubulin beta-3 chain OS = Homo sapiens GN = TUBB3 PE = 1 SV = 2 |
| GHYTEGAELVDAVLDVVR[Dea]K (SEQ ID NO: 405) | sp\|P04350\| TBB4A_HUMAN | Tubulin beta |
| AISSPTVSR[Dea]LTDTTK (SEQ ID NO: 439) | sp\|O94811\| TPPP_HUMAN | Tubulin polymerization-promoting protein |
| TVETR[Dea]DGQVINETSQHHDDLE (SEQ ID NO: 321) | sp\|P08670\| VIME_HUMAN | Vimentin |

TABLE 5B

Citrullinated peptides observed in chronic neurodegenerative disease.
These citrullinated peptides are not brain specific.

| Peptide | UniProtKB Accessions | Protein Name |
|---|---|---|
| AVLDVAETGTEAAAATGVIGGIRK (SEQ ID NO: 501) | sp\|Q96P15-3\| SPB11_HUMAN | Isoform 3 of Serpin B11 OS = Homo sapiens GN = SERPINB11 |
| GFPVVLDSPRDGNLK (SEQ ID NO: 502) | sp\|Q9Y2J8\| PADI2_HUMAN | Protein-arginine deiminase type-2 OS = Homo sapiens GN = PADI2 PE = 1 SV = 2 |
| GPDRLPAGYEIVLYISMSDSDK (SEQ ID NO: 503) | sp\|Q9Y2J8\| PADI2_HUMAN | Protein argining deiminase type-2 OS = Homo sapiens GN = PADI2 PE = 1 SV = 2 |
| RFSMVIDNGIVK (SEQ ID NO: 504) | sp\|P30044\| PRDX5_HUMAN | Peroxidoxin-5, OS = Homo sapiens GN = PRDX5 PE = 1 SV = 4 |

TABLE 6A

Citrullinated peptide detected in acquired brain injury in human brains.
These citrullinated peptides are brain specific

| Peptide | UniProtKB Accessions | Protein Name |
|---|---|---|
| AQQRDVDGATLARLDLEK (SEQ ID NO: 505) | sp\|Q16352\| AINX_HUMAN | Alpha-internexin OS = Homo sapiens GN = INA PE = 1 SV = 2 |
| AVTELNEPLSNEDR[Dea]NLLSVAYK (SEQ ID NO: 506) | sp\|Q04917\| 1433F_HUMAN | 14-3-3 protein eta OS = Homo sapiens GN = YWHAH PE = 1 SV = 4 |
| AVTEQGAELSNEER[dea]NLLSVAYK (SEQ ID NO: 507) | sp\|P27348\| 143T_HUMAN | 14-3-3 protein theta OS = Homo sapiens GN = YWHAQ PE = 1 SV = 1 |
| VVR[Dea]TALLDAAGVASLLTTAEVV VTEIPK (SEQ ID NO: 285) | sp\|P10809\| CH60_HUMAN | 50 kDa heat shock protein |
| LEAPDADELPR[Dea]SDFDPGQDTYQ HPPK (SEQ ID NO: 508) | sp\|Q99798\| ACON_HUMAN | Aconitate hydratase, OS = Homo sapiens GN = ACO2 PE = 1 SV = 2 |
| LSEELSGGR[Dea]LK (SEQ ID NO: 509) | sp\|P61158\| ARP3_HUMAN | Actin-related protein 3 OS = Homo sapiens GN = ACTR3 PE = 1 SV = 3 |
| ILIPWLLSPER[Dea]LDIK (SEQ ID NO: 510) | sp\|Q8WXF7\| ATLA1_HUMAN | Atlastin-1 OS = Homo sapiens GN = ATL1 PE = 1 SV = 1 |
| LR[Dea]FPAEDEFPDLSSHNNHMAK (SEQ ID NO: 511) | sp\|P12277\| KCRB_HUMAN | Creatine kinase B-type OS = Homo sapiens GN = CKB PE = 1 SV = 1 |

TABLE 6A-continued

Citrullinated peptide detected in acquired brain injury in human brains.
These citrullinated peptides are brain specific

| Peptide | UniProtKB Accessions | Protein Name |
|---|---|---|
| ITR[Dea]TSFLDDAFRK (SEQ ID NO: 512) | sp\|Q14204\| DYHC1_HUMAN | Cytoplasmic dynein 1 heavy chain 1 OS = Homo sapiens GN = DYNC1H1 PE = 1 SV = 5 |
| DNFTLIPEGTNGTEER[Dea]MSVIWDK (SEQ ID NO: 513) | sp\|Q16555\| YL2_HUMAN | Dihydropyrimidinase-related protein 2 OS = Homo sapiens GN = DPYSL2 PE = 1 SV = 1 |
| MVEGFFDR[Dea]GASIVEDK (SEQ ID NO: 514) | sp\|P49448\| DHE4_HUMAN | Glutamate dehydrogenase 2, OS = Homo sapiens GN = GLUD2 PE = 1 SV = 2 |
| GDYYR[Dea]YLAEVAAGDDK (SEQ ID NO: 515) | sp\|P63104-2\| I433Z_HUMAN | Isoform 2 of 14-3-3 protein zeta/delta OS = Homo sapiens GN = YWHAZ |
| R[Dea]ALVFQPVTELK (SEQ ID NO: 516) | sp\|P08237-2\| PFKAM_HUMAN | Isoform 2 of ATP-dependent 6-phosphofructo-kinase, muscle type OS = Homo sapiens GN = PFKM |
| GVPLYR[Dea]HIADLAGNPEVILPVPAFNVINGGSHAGNK (SEQ ID NO: 517) | sp\|P09104-2\| ENOG_HUMAN | Isoform 2 of Gamma-enolase OS = Homo sapiens GN = ENO2 |
| R[Dea]VIISAPSADAPMFVMGVNHEK (SEQ ID NO: 125) | sp\|P04406-2\| G3P_HUMAN | Isoform 2 of Glyceraldehyde-3-phosphate dehydrogenase OS = Homo sapiens GN = GAPDH |
| NSPLVSR[Dea]LTLYDIAHTPGVAADLSHIETR[Dea]ANVK (SEQ ID NO: 518) | sp\|P40926-2\| MDHM_HUMAN | Isoform 2 of Malate dehydrogenase, OS = Homo sapiens GN = MDH2 |
| HEGFE[Dea]DLAALGDK (SEQ ID NO: 519) | sp\|Q13813-2\| SPTN1_HUMAN | Isoform 2 of Spectrin alpha chain, non-erythrocytic 1 OS = Homo sapiens GN = SPTAN1 |
| LFVTNDAATILR[Dea]ELEVQHPAAK (SEQ ID NO: 520) | sp\|P50990-2\| TCPQ_HUMAN | Isoform 2 of T-complex protein 1 subunit theta OS = Homo sapiens GN = CCT8 |
| GR[Dea]GITGIEDK (SEQ ID NO: 521) | sp\|29401-2\| TKT_HUMAN | Isoform 2 of Transketolase OS = Homo sapiens GN = TKT |
| PHSVSLNDTETR[Dea]K (SEQ ID NO: 522) | sp\|Q9P0L0-2\| VAPA_HUMAN | Isoform 2 of Vesicle-associated membrane protein-associated protein A OS = Homo sapiens GN = VAPA |
| MDIRG[Dea]AVDAAVPTNIIAAK (SEQ ID NO: 523) | sp\|Q9UI12-2\| VATH_HUMAN | Isoform 2 of V-type proton ATPase subunit H OS = Homo sapiens GN = ATP6V1H |
| TDDYGR[Dea]DLSSVQTLLTK (SEQ ID NO: 524) | sp\|Q13813-3\| SPTN1_HUMAN | Isoform 3 of Spectrin alpha chain, non-erythrocytic 1 OS = Homo sapiens GN = SPTAN1 |
| R[Dea]LVPGGGATEIELAK (SEQ ID NO: 525) | sp\|P50990-3\| TCP1_HUMAN | Isoform 3 of T-complex protein 1 subunit theta OS = Homo sapiens GN = CCT8 |
| VR[Dea]LLADPTGAFGK (SEQ ID NO: 265) | sp\|P30044-4\| PRDX5_HUMAN | Isoform 4 of Peroxiredoxin-5, OS = Homo sapiens GN = PRDX5 |
| R[Dea]GFGFVTFDDHDPVDK (SEQ ID NO: 526) | sp\|P2266-2\| ROA2_HUMAN | Isoform A2 of Heterogeneous nuclear ribonucleoproteins A2/B1 OS = Homo sapiens GN = HNRNPA2B1 |
| IATPR[Dea]GAASPAQK (SEQ ID NO: 527) | sp\|P10636-7\| TAU_HUMAN | Isoform Tau-E of Microtubule-associated protein tau OS = Homo sapiens GN = MAPT |
| RVVAEPVELAQEFR[Dea]K (SEQ ID NO: 528) | sp\|O75489\| NDUS3_HUMAN | NADH dehydrogenase [ubiquinone] iron-sulfur protein 3, OS = Homo sapiens GN = NDUFS3 PE = 1 SV = 1 |
| GADEAALAR[Dea]AELEK (SEQ ID NO: 529) | sp\|P07196\| NFL_HUMAN | Neurofilament light polypeptide OS = Homo sapiens GN = NEFL PE = 1 SV = 3 |
| QIVWNGPVGVFEWEAFAR[Dea]GTK (SEQ ID NO: 530) | sp\|P00558\| PGK1_HUMAN | Phosphoglycerate kinase OS = Homo sapiens GN = PGK1 PE = 1 SV = 3 |
| PMQFLGDEETVR[Dea]K (SEQ ID NO: 531) | sp\|P18669\| PGAM1_HUMAN | Phosphoglycerate mutase OS = Homo sapiens GN = PGAM1 PE = 1 SV = 2 |

TABLE 6A-continued

Citrullinated peptide detected in acquired brain injury in human brains.
These citrullinated peptides are brain specific

| Peptide | UniProtKB Accessions | Protein Name |
| --- | --- | --- |
| R[Dea]GFGFVYUFQSHDAADK (SEQ ID NO: 532) | sp\|Q4VXU2\| PAP1L_HUMAN | Polyadenylate-binding protein 1-like OS = Homo sapiens GN = PABPC1L PE = 2 SV = 1 |
| VPDFSDYR[Dea]RAEVLDSTK (SEQ ID NO: 533) | sp\|P9C7P4\| UCRIL_HUMAN | Putative cytochrome b-c1 complex subunit Rieske-like protein 1 OS = Homo sapiens GN = UQCRFS1P1 PE = 5 SV = 1 |
| R[Dea]DVAGDASESALLK (SEQ ID NO: 534) | sp\|P13637\| AT1A3_HUMAN | Sodium/potassium-transporting ATPase subunit alpha-3 OS = Homo sapiens GN = ATP1A3 PE = 1 SV = 3 |
| DLTSVMR[Dea]LLSK (SEQ ID NO: 535) | sp\|Q01082\| SPTB2_HUMAN | Spectrin beta chain, non-erythrocytic 1 OS = Homo sapiens GN = SPTBN1 PE = 1 SV = 2 |
| FMELLEPLSER[Dea]K (SEQ ID NO: 536) | sp\|P38646\| GRP75_HUMAN | Spectrin beta chain, non-erythrocytic 1 OS = Homo sapiens GN = SPTBN1 PE = 1 SV = 2 |
| ER[Dea]VEAVNMAEGIIHDTETK (SEQ ID NO: 537) | sp\|P38646\| GRP75_HUMAN | Stress-70 protein OS = Homo sapiens GN = HSPA9 PE = 1 SV = 2 |
| HVLSGTLGIPEHTYR[Dea]SR[Dea]VTLSNQPYIK (SEQ ID NO: 538) | sp\|P04216\| THY1_HUMAN | Thy-1 membrane glycoprotein OS = Homo sapiens GN = THY1 PE = 1 SV = 2 |
| MIIYR[Dea]DLSIHDELFSDIYK (SEQ ID NO: 539) | sp\|P13693\| TCTP_HUMAN | Translationally-controlled tumor protein OS = Homo sapiens GN = TPT1 PE = 1 SV = 1 |
| TGGAVDR[Dea]LTDTSK (SEQ ID NO: 540) | sp\|Q9BW30\| TPPP3_HUMAN | Tubulin polymerization-promoting protein family member 3 OS = Homo sapiens GN = TPPP3 PE = 1 SV = 1 |
| SSEEAVR[Dea]EVHR[Dea]LIEGRAPVISGVTK (SEQ ID NO: 541) | sp\|O94811\| TPPP_HUMAN | Tubulin polymerization-promoting protein OS = Homo sapiens GN = TPPP PE = 1 SV = 1 |
| LLIIGTTSR[Dea]K (SEQ ID NO: 542) | sp\|P46459\| NSF_HUMAN | Vesicle-fusing ATPase OS = Homo sapiens GN = NSF PE = 1 SV = 3 |
| WGDPVTR[Dea]VLDDGELLVQQTK (SEQ ID NO: 543) | sp\|P46459\| NSF_HUMAN | Vesicle-fusing ATPase OS = Homo sapiens GN = NSF PE = 1 SV = 3 |
| ITR[Dea]VEMLEIIEAIYK (SEQ ID NO: 544) | sp\|P62760\| VISLI_HUMAN | Visinin-like protein 1 OS = Homo sapiens GN = VSNL1 PE = 1 SV = 2 |
| FPR[dea]YAEIVHLTLPDGTK (SEQ ID NO: 545) | sp\|P21281\| VATB2_HUMAN | V-type proton ATPase subunit B, brain isoform OS = Homo sapiens GN = ATP6V1B2 PE = 1 SV = 3 |

TABLE 6B

Citrullinated peptide detected in acquired brain injury in human brains.
These citrullinated peptides are not brain specific

| Peptide | UniProtKB Accessions | Name |
| --- | --- | --- |
| GDARPAEIDSLWEISK (SEQ ID NO: 546) | sp\|P49821\|NDUV1_HUMAN | NADH dehydrogenase [ubiquinone] flavoprotein 1, OS = Homo sapiens GN = NDUFV1 PE = 1 SV = 4 |
| SVVLMSHLGRPDGVPMPDK (SEQ ID NO: 547) | sp\|P00558-2\|PGK1_HUMAN | Isoform 2 of Phosphoglycerate kinase 1 OS = Homo sapiens GN = PGK1 |

TABLE 7

Secreted citrullinated human proteins in chronic brain disease

| UniProtKB Accessions | Protein Name |
| --- | --- |
| P61764 | Syntaxin-binding protein 1; |
| P62805 | Histone H4 |
| Q14204 | Cytoplasmic dynein 1 heavy chain 1; |
| Q05193 | Dynamin-1; |
| P09104 | Gamma-enolase; |
| P14625 | Endoplasmin precursor; |
| O43301 | Heat shock 70 kDa protein 12A |
| P62136 | Serine/threonine-protein phosphatase PP1-alpha catalytic subunit; |
| P27797 | Calreticulin precursor; |
| P31146 | Coronin-1A; |
| P38117 | Electron transfer flavoprotein subunit beta; |
| P68871 | Hemoglobin subunit beta; |
| P28482 | Mitogen-activated protein kinase 1; |
| P27361 | Mitogen-activated protein kinase 3; |
| O00232 | 26S proteasome non-ATPase regulatory subunit 12; |
| P36578 | 60S ribosomal protein L4; |
| P05387 | 60S acidic ribosomal protein P2; |
| Q16181 | Septin-7; |
| P49588 | Alanine--tRNA ligase, cytoplasmic; |

TABLE 8

Non-secreted citrullinated human proteins in chronic brain disease

| UniProtKB Accessions | Protein Name |
| --- | --- |
| P17600 | Synapsin-1; |
| Q99798 | Aconitate hydratase, |
| O14810 | Complexin-1; |
| Q6PUV4 | Complexin-2; |
| Q9Y2J2 | Band 4.1-like protein 3; |
| Q92777 | Synapsin-2; |
| Q2M2I8 | AP2-associated protein kinase 1; |
| P35611 | Alpha-adducin; |
| P63010 | AP-2 complex subunit beta; |
| O15075 | Serine/threonine-protein kinase DCLK1; |
| O94925 | Glutaminase kidney isoform, |
| P50213 | Isocitrate dehydrogenase [NAD] subunit alpha |
| Q08209 | Serine/threonine-protein phosphatase 2B catalytic subunit alpha isoform; |

TABLE 9

Secreted citrullinated human proteins in acute brain disease

| UniProtKB Accessions | Protein Name |
| --- | --- |
| Q86VP6 | Cullin-associated NEDD8-dissociated protein 1; |
| P30044 | Peroxiredoxin-5, |

TABLE 10

Non-secreted citrullinated human proteins in acute brain disease

| UniProtKB Accessions | Protein Name |
| --- | --- |
| P63215 | Guanine nucleotide-binding protein G(I)/G(S)/G(O) subunit gamma-3 precursor |

REFERENCES FOR EXAMPLE 4

1. Ren J, Jiang C, Gao X, Liu Z, Yuan Z, Jin C, et al. PhosSNP for systematic analysis of genetic polymorphisms that influence protein phosphorylation. Mol Cell Proteomics 2010, 9:623-634.
2. Ryu G M, Song P, Kim K W, Oh K S, Park K J, Kim J H. Genome-wide analysis to predict protein sequence variations that change phosphorylation sites or their corresponding kinases. Nucleic Acids Res 2009, 37:1297-1307.
3. Baka Z, Gyorgy B, Geher P, Buzas E I, Falus A, Nagy G. Citrullination under physiological and pathological conditions. Joint Bone Spine 2012, 79:431-436.
4. Demoruelle M K, Deane K. Antibodies to citrullinated protein antigens (ACPAs): clinical and pathophysiologic significance. Curr Rheumatol Rep 2011, 13:421-430.
5. Uysal H, Nandakumar K S, Kessel C, Haag S, Carlsen S, Burkhardt H, et al. Antibodies to citrullinated proteins: molecular interactions and arthritogenicity. Immunol Rev 2010, 233:9-33.
6. Okada Y, Wu D, Trynka G, Raj T, Terao C, Ikari K, et al. Genetics of rheumatoid arthritis contributes to biology and drug discovery. Nature 2014, 506:376-381.
7. De Ceuleneer M, Van Steendam K, Dhaenens M, Deforce D. In vivo relevance of citrullinated proteins and the challenges in their detection. Proteomics 2012, 12:752-760.
8. Raijmakers R, van Beers J J, El-Azzouny M, Visser N F, Bozic B, Pruijn G J, et al. Elevated levels of fibrinogen-derived endogenous citrullinated peptides in synovial fluid of rheumatoid arthritis patients. Arthritis Res Ther 2012, 14:R114.
9. Stahl D C, Swiderek K M, Davis M T, Lee T D. Data-controlled automation of liquid chromatography/tandem mass spectrometry analysis of peptide mixtures. J Am Soc Mass Spectrom 1996, 7:532-540.
10. Yates J R, 3rd, Eng J K, McCormack A L, Schieltz D. Method to correlate tandem mass spectra of modified peptides to amino acid sequences in the protein database. Anal Chem 1995, 67:1426-1436.
11. Gillet LC1 NP TS, Röst H, Selevsek N, Reiter L, Bonner R, Aebersold R. Targeted data extraction of the MS/MS spectra generated by data-independent acquisition: a new concept for consistent and accurate proteome analysis. Mol Cell Proteomics 2012.
12. Liu Y, Huttenhain R, Collins B, Aebersold R. Mass spectrometric protein maps for biomarker discovery and clinical research. Expert Rev Mol Diagn 2013, 13:811-825.
13. Escher C, Reiter L, MacLean B, Ossola R, Herzog F, Chilton J, et al. Using iRT, a normalized retention time for more targeted measurement of peptides. Proteomics 2012, 12:1111-1121.
14. Crowgey E L, Stabley D L, Chen C, Huang H, Robbins K M, Polson S W, et al. An integrated approach for analyzing clinical genomic variant data from next-generation sequencing. J Biomol Tech 2015, 26:19-28.
15. Hensen S M, Boelens W C, Bonger K M, van Cruchten R T, van Delft F L, Pruijn G J. Phenylglyoxal-based visualization of citrullinated proteins on Western blots. Molecules 2015, 20:6592-6600.
16. Hensen S M, Pruijn G J. Methods for the detection of peptidylarginine deiminase (PAD) activity and protein citrullination. Mol Cell Proteomics 2014, 13:388-396.
17. Stensland M, Holm A, Kiehne A, Fleckenstein B. Targeted analysis of protein citrullination using chemical modification and tandem mass spectrometry. Rapid Commun Mass Spectrom 2009, 23:2754-2762.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of detecting a citrullinated protein in a human subject, comprising:

obtaining a biological sample selected from the group consisting of blood, plasma, serum, brain tissue, spinal fluid and combinations thereof from the human subject, wherein the human subject has or is suspected of having Alzheimer's disease (AD);

contacting the biological sample with a protease to obtain a digested sample comprising a citrullinated peptide, wherein the citrullinated peptide is selected from the group consisting of SEQ ID NO: 377, SEQ ID NO: 414, SEQ ID NO: 423, SEQ ID NO: 405, SEQ ID NO: 479, SEQ ID NO: 499, SEQ ID NO: 500, SEQ ID NO: 502, SEQ ID NO: 504, and combinations thereof; and detecting an amount of citrullinated peptide in the digested sample, thereby detecting an amount of citrullinated protein in the human subject; and comparing the amount of citrullinated protein to a reference value, wherein the amount of citrullinated peptide is detected using mass spectrometry, and wherein the citrullinated protein is selected from the group consisting of Microtubule-associated protein tau, Peroxiredoxin-2, Tubulin beta-3 chain, Tubulin beta-4A chain, Elongation factor 1-alpha 2, Tubulin alpha-4A chain, Protein-arginine deiminase type-2, Peroxiredoxin-5, and combinations thereof.

2. The method of claim 1, wherein the biological sample is brain tissue or spinal fluid.

3. The method of claim 1, wherein the mass spectrometry is Sequential Window Acquisition of all Theoretical Fragment Ion Spectra (SWATH) mass spectrometry.

4. The method of claim 1, further comprising administering a treatment to the subject.

5. The method of claim 4, wherein the treatment comprises therapeutic agents, surgical treatments, or both.

6. The method of claim 1, wherein the mass spectrometry is high resolution mass spectrometry.

7. The method of claim 1, wherein the mass spectrometry is tandem mass spectrometry.

* * * * *

SEQUENCE LISTING

```
<160> NUMBER OF SEQ ID NOS: 547

<210> SEQ ID NO 1
<211> LENGTH: 16
<212> TYPE: PRT
<213> ORGANISM: Homo sapiens

<400> SEQUENCE: 1

Arg Gly Glu Thr Ser Gly Arg Val Asp Asp Asn Glu Glu Thr Ile Lys
1               5                   10                  15
```

```
<210> SEQ ID NO 2
<211> LENGTH: 14
<212> TYPE: PRT
<213> ORGANISM: Homo sapiens

<400> SEQUENCE: 2

Ala Ala Gly Ala Ala Arg Ile Ile Ala Val Asp Ile Asn Lys
1               5                   10

<210> SEQ ID NO 3
<211> LENGTH: 13
<212> TYPE: PRT
<213> ORGANISM: Homo sapiens

<400> SEQUENCE: 3

Ser Pro Asp Asp Pro Ala Arg His Ile Thr Gly Glu Lys
1               5                   10

<210> SEQ ID NO 4
<211> LENGTH: 21
<212> TYPE: PRT
<213> ORGANISM: Homo sapiens

<400> SEQUENCE: 4

Asp Ile Arg His Asp Pro Ser Leu Gln Pro Trp Ser Val Ser Tyr Asp
1               5                   10                  15

Gly Gly Ser Ala Lys
            20

<210> SEQ ID NO 5
<211> LENGTH: 18
<212> TYPE: PRT
<213> ORGANISM: Homo sapiens

<400> SEQUENCE: 5

Leu Ile Leu Thr Leu Thr His Gly Thr Ala Val Cys Thr Arg Thr Tyr
1               5                   10                  15

Glu Lys

<210> SEQ ID NO 6
<211> LENGTH: 13
<212> TYPE: PRT
<213> ORGANISM: Homo sapiens

<400> SEQUENCE: 6

Thr Ala Glu Asn Phe Arg Ala Leu Ser Thr Gly Glu Lys
1               5                   10

<210> SEQ ID NO 7
<211> LENGTH: 12
<212> TYPE: PRT
<213> ORGANISM: Homo sapiens

<400> SEQUENCE: 7

Phe Gln His Pro Gly Ser Asp Met Arg Gln Glu Lys
1               5                   10

<210> SEQ ID NO 8
<211> LENGTH: 9
<212> TYPE: PRT
<213> ORGANISM: Homo sapiens

<400> SEQUENCE: 8

Val Ser Pro Leu Thr Phe Gly Arg Lys
```

-continued

```
<210> SEQ ID NO 9
<211> LENGTH: 17
<212> TYPE: PRT
<213> ORGANISM: Homo sapiens

<400> SEQUENCE: 9

Arg His Pro His Thr Glu His Val Gln Gln Thr Phe Arg Thr Glu Ile
1               5                   10                  15

Lys

<210> SEQ ID NO 10
<211> LENGTH: 9
<212> TYPE: PRT
<213> ORGANISM: Homo sapiens

<400> SEQUENCE: 10

Gly Leu Ser Glu Met Arg Leu Glu Lys
1               5

<210> SEQ ID NO 11
<211> LENGTH: 7
<212> TYPE: PRT
<213> ORGANISM: Homo sapiens

<400> SEQUENCE: 11

Cys Asp Ile Asp Ile Arg Lys
1               5

<210> SEQ ID NO 12
<211> LENGTH: 14
<212> TYPE: PRT
<213> ORGANISM: Homo sapiens

<400> SEQUENCE: 12

Gln Glu Tyr Asp Glu Ala Gly Pro Ser Ile Val His Arg Lys
1               5                   10

<210> SEQ ID NO 13
<211> LENGTH: 14
<212> TYPE: PRT
<213> ORGANISM: Homo sapiens

<400> SEQUENCE: 13

Ser Ser Ser Ser Arg Gly Ser Ser Tyr Ser Ser Ile Pro Lys
1               5                   10

<210> SEQ ID NO 14
<211> LENGTH: 13
<212> TYPE: PRT
<213> ORGANISM: Homo sapiens

<400> SEQUENCE: 14

Thr Ser Pro Glu Gly Ala Arg Asp Leu Leu Gly Pro Lys
1               5                   10

<210> SEQ ID NO 15
<211> LENGTH: 18
<212> TYPE: PRT
<213> ORGANISM: Homo sapiens

<400> SEQUENCE: 15

Glu Pro Val Phe Ile Pro Arg Pro Gly Ile Thr Tyr Glu Pro Pro Asn
```

Tyr Lys

<210> SEQ ID NO 16
<211> LENGTH: 11
<212> TYPE: PRT
<213> ORGANISM: Homo sapiens

<400> SEQUENCE: 16

Arg Val Ala Thr Pro Phe Gly Gly Phe Glu Lys
1               5                   10

<210> SEQ ID NO 17
<211> LENGTH: 21
<212> TYPE: PRT
<213> ORGANISM: Homo sapiens

<400> SEQUENCE: 17

Ala Glu Leu Pro Asp Tyr Arg Ser Phe Asn Arg Val Ala Thr Pro Phe
1               5                   10                  15

Gly Gly Phe Glu Lys
            20

<210> SEQ ID NO 18
<211> LENGTH: 12
<212> TYPE: PRT
<213> ORGANISM: Homo sapiens

<400> SEQUENCE: 18

Asn Ile Asp Ala Leu Ser Gly Met Glu Gly Arg Lys
1               5                   10

<210> SEQ ID NO 19
<211> LENGTH: 10
<212> TYPE: PRT
<213> ORGANISM: Homo sapiens

<400> SEQUENCE: 19

Glu Ser Leu Asp Leu Arg Ala His Leu Lys
1               5                   10

<210> SEQ ID NO 20
<211> LENGTH: 12
<212> TYPE: PRT
<213> ORGANISM: Homo sapiens

<400> SEQUENCE: 20

Pro Arg Ser Phe Met Pro Asn Leu Val Pro Pro Lys
1               5                   10

<210> SEQ ID NO 21
<211> LENGTH: 16
<212> TYPE: PRT
<213> ORGANISM: Homo sapiens

<400> SEQUENCE: 21

Glu Thr Arg Ala Glu Phe Ala Glu Arg Ser Val Thr Lys Leu Glu Lys
1               5                   10                  15

<210> SEQ ID NO 22
<211> LENGTH: 19
<212> TYPE: PRT
<213> ORGANISM: Homo sapiens

```
<400> SEQUENCE: 22

Phe Ala Asp Leu Ser Glu Ala Ala Asn Arg Asn Asn Asp Ala Leu Arg
1               5                   10                  15

Gln Ala Lys

<210> SEQ ID NO 23
<211> LENGTH: 21
<212> TYPE: PRT
<213> ORGANISM: Homo sapiens

<400> SEQUENCE: 23

Leu Trp Arg Asp Gly Arg Gly Ala Leu Gln Asn Ile Ile Pro Ala Ser
1               5                   10                  15

Thr Gly Ala Ala Lys
            20

<210> SEQ ID NO 24
<211> LENGTH: 17
<212> TYPE: PRT
<213> ORGANISM: Homo sapiens

<400> SEQUENCE: 24

Ala Glu Glu Thr Gln Arg Ser Val Asn Asp Leu Thr Ser Gln Arg Ala
1               5                   10                  15

Lys

<210> SEQ ID NO 25
<211> LENGTH: 31
<212> TYPE: PRT
<213> ORGANISM: Homo sapiens

<400> SEQUENCE: 25

Ser Tyr Leu Arg Leu Arg Pro Asp Arg Val Ala Met Gln Asp Ala Thr
1               5                   10                  15

Ala Gln Met Ala Met Leu Gln Phe Ile Ser Ser Gly Leu Ser Lys
            20                  25                  30

<210> SEQ ID NO 26
<211> LENGTH: 23
<212> TYPE: PRT
<213> ORGANISM: Homo sapiens

<400> SEQUENCE: 26

Ala Asn Ser Val Arg Asn Ala Val Thr Gln Glu Phe Gly Pro Val Pro
1               5                   10                  15

Asp Thr Ala Arg Tyr Tyr Lys
            20

<210> SEQ ID NO 27
<211> LENGTH: 18
<212> TYPE: PRT
<213> ORGANISM: Homo sapiens

<400> SEQUENCE: 27

Ile Val Tyr Gly His Leu Asp Asp Pro Ala Ser Gln Glu Ile Glu Arg
1               5                   10                  15

Gly Lys

<210> SEQ ID NO 28
<211> LENGTH: 14
<212> TYPE: PRT
```

```
<213> ORGANISM: Homo sapiens

<400> SEQUENCE: 28

Leu Leu Arg Ala Val Ile Leu Gly Pro Pro Gly Ser Gly Lys
1               5                   10

<210> SEQ ID NO 29
<211> LENGTH: 14
<212> TYPE: PRT
<213> ORGANISM: Homo sapiens

<400> SEQUENCE: 29

Val Ala Gly Ala Ser Arg Ile Ile Gly Val Asp Ile Asn Lys
1               5                   10

<210> SEQ ID NO 30
<211> LENGTH: 29
<212> TYPE: PRT
<213> ORGANISM: Homo sapiens

<400> SEQUENCE: 30

Arg Thr Gly Ala Ile Val Asp Val Pro Val Gly Glu Glu Leu Leu Gly
1               5                   10                  15

Arg Val Val Asp Ala Leu Gly Asn Ala Ile Asp Gly Lys
            20                  25

<210> SEQ ID NO 31
<211> LENGTH: 19
<212> TYPE: PRT
<213> ORGANISM: Homo sapiens

<400> SEQUENCE: 31

Ala Ile Glu Glu Gln Val Ala Val Ile Tyr Ala Gly Val Arg Gly Tyr
1               5                   10                  15

Leu Asp Lys

<210> SEQ ID NO 32
<211> LENGTH: 25
<212> TYPE: PRT
<213> ORGANISM: Homo sapiens

<400> SEQUENCE: 32

Gly Ile Arg Pro Ala Ile Asn Val Gly Leu Ser Val Ser Arg Val Gly
1               5                   10                  15

Ser Ala Ala Gln Thr Arg Ala Met Lys
            20                  25

<210> SEQ ID NO 33
<211> LENGTH: 26
<212> TYPE: PRT
<213> ORGANISM: Homo sapiens

<400> SEQUENCE: 33

Gln Gly Gln Tyr Ser Pro Met Ala Ile Glu Glu Gln Val Ala Val Ile
1               5                   10                  15

Tyr Ala Gly Val Arg Gly Tyr Leu Asp Lys
            20                  25

<210> SEQ ID NO 34
<211> LENGTH: 21
<212> TYPE: PRT
<213> ORGANISM: Homo sapiens
```

```
<400> SEQUENCE: 34

Ser Gly Gly Pro Val Asp Ala Ser Ser Glu Tyr Gln Gln Glu Leu Glu
1               5                   10                  15

Arg Glu Leu Phe Lys
            20

<210> SEQ ID NO 35
<211> LENGTH: 8
<212> TYPE: PRT
<213> ORGANISM: Homo sapiens

<400> SEQUENCE: 35

Tyr Arg Asn Phe Asp Ile Pro Lys
1               5

<210> SEQ ID NO 36
<211> LENGTH: 11
<212> TYPE: PRT
<213> ORGANISM: Homo sapiens

<400> SEQUENCE: 36

Glu Glu Arg Ala Asp Leu Ile Ala Tyr Leu Lys
1               5                   10

<210> SEQ ID NO 37
<211> LENGTH: 14
<212> TYPE: PRT
<213> ORGANISM: Homo sapiens

<400> SEQUENCE: 37

Val Leu Arg Asn Ala Ala Gly Asn Phe Tyr Ile Asn Asp Lys
1               5                   10

<210> SEQ ID NO 38
<211> LENGTH: 16
<212> TYPE: PRT
<213> ORGANISM: Homo sapiens

<400> SEQUENCE: 38

Ala Ala Asp Met Leu Ser Gly Pro Arg Arg Ala Glu Ile Leu Ala Lys
1               5                   10                  15

<210> SEQ ID NO 39
<211> LENGTH: 21
<212> TYPE: PRT
<213> ORGANISM: Homo sapiens

<400> SEQUENCE: 39

Val Ala Asn Glu Pro Val Leu Ala Phe Thr Gln Gly Ser Pro Glu Arg
1               5                   10                  15

Asp Ala Leu Gln Lys
            20

<210> SEQ ID NO 40
<211> LENGTH: 15
<212> TYPE: PRT
<213> ORGANISM: Homo sapiens

<400> SEQUENCE: 40

Glu Met Val Leu Thr Gly Asp Arg Ile Ser Ala Gln Asp Ala Lys
1               5                   10                  15

<210> SEQ ID NO 41
```

```
<211> LENGTH: 18
<212> TYPE: PRT
<213> ORGANISM: Homo sapiens

<400> SEQUENCE: 41

Val Leu Arg Gly Val Glu Val Thr Val Gly His Glu Gln Glu Glu Gly
1               5                   10                  15

Gly Lys

<210> SEQ ID NO 42
<211> LENGTH: 17
<212> TYPE: PRT
<213> ORGANISM: Homo sapiens

<400> SEQUENCE: 42

His Leu Glu Ile Asn Pro Asp His Ser Ile Ile Glu Thr Leu Arg Gln
1               5                   10                  15

Lys

<210> SEQ ID NO 43
<211> LENGTH: 9
<212> TYPE: PRT
<213> ORGANISM: Homo sapiens

<400> SEQUENCE: 43

Ala Ala Thr Ile Thr Pro Phe Arg Lys
1               5

<210> SEQ ID NO 44
<211> LENGTH: 18
<212> TYPE: PRT
<213> ORGANISM: Homo sapiens

<400> SEQUENCE: 44

Val Tyr Phe Arg Leu Pro Arg Pro Pro Pro Glu Met Pro Glu Ser
1               5                   10                  15

Leu Lys

<210> SEQ ID NO 45
<211> LENGTH: 23
<212> TYPE: PRT
<213> ORGANISM: Homo sapiens

<400> SEQUENCE: 45

Cys Asp Leu His Arg Leu Glu Glu Gly Pro Pro Val Thr Thr Val Leu
1               5                   10                  15

Thr Arg Glu Asp Gly Leu Lys
                20

<210> SEQ ID NO 46
<211> LENGTH: 10
<212> TYPE: PRT
<213> ORGANISM: Homo sapiens

<400> SEQUENCE: 46

Phe Ala Ile Tyr Arg Trp Asp Pro Asp Lys
1               5                   10

<210> SEQ ID NO 47
<211> LENGTH: 18
<212> TYPE: PRT
<213> ORGANISM: Homo sapiens
```

```
<400> SEQUENCE: 47

Thr Arg Leu Ile Gly Pro Asn Cys Pro Gly Val Ile Asn Pro Gly Glu
1               5                   10                  15

Cys Lys

<210> SEQ ID NO 48
<211> LENGTH: 11
<212> TYPE: PRT
<213> ORGANISM: Homo sapiens

<400> SEQUENCE: 48

Ala Asp Arg Ala Gly Asn Val Ile Phe Arg Lys
1               5                   10

<210> SEQ ID NO 49
<211> LENGTH: 13
<212> TYPE: PRT
<213> ORGANISM: Homo sapiens

<400> SEQUENCE: 49

Ser Arg Val Thr Gln Ser Asn Phe Ala Val Gly Tyr Lys
1               5                   10

<210> SEQ ID NO 50
<211> LENGTH: 15
<212> TYPE: PRT
<213> ORGANISM: Homo sapiens

<400> SEQUENCE: 50

Phe Asp Arg Gly Tyr Ile Ser Pro Tyr Phe Ile Asn Thr Ser Lys
1               5                   10                  15

<210> SEQ ID NO 51
<211> LENGTH: 24
<212> TYPE: PRT
<213> ORGANISM: Homo sapiens

<400> SEQUENCE: 51

Pro Asn Ile Arg Asn Val Val Val Asp Gly Val Arg Thr Pro Phe
1               5                   10                  15

Leu Leu Ser Gly Thr Ser Tyr Lys
            20

<210> SEQ ID NO 52
<211> LENGTH: 14
<212> TYPE: PRT
<213> ORGANISM: Homo sapiens

<400> SEQUENCE: 52

Thr Gly Arg Glu Asp Ile Ala Asn Leu Ala Asp Glu Phe Lys
1               5                   10

<210> SEQ ID NO 53
<211> LENGTH: 10
<212> TYPE: PRT
<213> ORGANISM: Homo sapiens

<400> SEQUENCE: 53

Arg Leu Gln Leu Leu Glu Pro Phe Asp Lys
1               5                   10

<210> SEQ ID NO 54
<211> LENGTH: 26
```

<212> TYPE: PRT
<213> ORGANISM: Homo sapiens

<400> SEQUENCE: 54

```
Leu Gly Ile Thr His Val Leu Asn Ala Ala Glu Gly Arg Ser Phe Met
1               5                   10                  15

His Val Asn Thr Asn Ala Asn Phe Tyr Lys
            20                  25
```

<210> SEQ ID NO 55
<211> LENGTH: 13
<212> TYPE: PRT
<213> ORGANISM: Homo sapiens

<400> SEQUENCE: 55

```
Phe Gly Val Ser Thr Gly Arg Glu Gly Gln Thr Pro Lys
1               5                   10
```

<210> SEQ ID NO 56
<211> LENGTH: 20
<212> TYPE: PRT
<213> ORGANISM: Homo sapiens

<400> SEQUENCE: 56

```
Asp Val Val Phe Leu Leu Asp Gly Ser Glu Gly Val Arg Ser Gly Phe
1               5                   10                  15

Pro Leu Leu Lys
            20
```

<210> SEQ ID NO 57
<211> LENGTH: 19
<212> TYPE: PRT
<213> ORGANISM: Homo sapiens

<400> SEQUENCE: 57

```
Gly Val Asn Thr Gly Ala Val Gly Ser Tyr Ile Tyr Asp Arg Asp Pro
1               5                   10                  15

Glu Gly Lys
```

<210> SEQ ID NO 58
<211> LENGTH: 16
<212> TYPE: PRT
<213> ORGANISM: Homo sapiens

<400> SEQUENCE: 58

```
Arg Gly Glu Thr Ser Gly Arg Val Asp Asp Asn Glu Glu Thr Ile Lys
1               5                   10                  15
```

<210> SEQ ID NO 59
<211> LENGTH: 24
<212> TYPE: PRT
<213> ORGANISM: Homo sapiens

<400> SEQUENCE: 59

```
Tyr Gly Tyr Thr His Leu Ser Thr Gly Asp Leu Leu Arg Ser Glu Val
1               5                   10                  15

Ser Ser Gly Ser Ala Arg Gly Lys
            20
```

<210> SEQ ID NO 60
<211> LENGTH: 14
<212> TYPE: PRT
<213> ORGANISM: Homo sapiens

<400> SEQUENCE: 60

Leu Leu Arg Ser Glu Val Ser Ser Gly Ser Ala Arg Gly Lys
1               5                   10

<210> SEQ ID NO 61
<211> LENGTH: 24
<212> TYPE: PRT
<213> ORGANISM: Homo sapiens

<400> SEQUENCE: 61

Tyr Gly Tyr Thr His Leu Ser Thr Gly Asp Leu Leu Arg Ser Glu Val
1               5                   10                  15

Ser Ser Gly Ser Ala Arg Gly Lys
            20

<210> SEQ ID NO 62
<211> LENGTH: 13
<212> TYPE: PRT
<213> ORGANISM: Homo sapiens

<400> SEQUENCE: 62

Pro Glu Asp Pro Ser Leu Leu Glu Asp Pro Arg Ile Lys
1               5                   10

<210> SEQ ID NO 63
<211> LENGTH: 16
<212> TYPE: PRT
<213> ORGANISM: Homo sapiens

<400> SEQUENCE: 63

Gln Val Ser Gly Pro Glu Arg Thr Ile Pro Ile Thr Arg Glu Glu Lys
1               5                   10                  15

<210> SEQ ID NO 64
<211> LENGTH: 29
<212> TYPE: PRT
<213> ORGANISM: Homo sapiens

<400> SEQUENCE: 64

Tyr Arg Ile Pro Ala Asp Val Asp Pro Leu Thr Ile Thr Ser Ser Leu
1               5                   10                  15

Ser Ser Asp Gly Val Leu Thr Val Asn Gly Pro Arg Lys
            20                  25

<210> SEQ ID NO 65
<211> LENGTH: 28
<212> TYPE: PRT
<213> ORGANISM: Homo sapiens

<400> SEQUENCE: 65

Ser Pro Phe Tyr Leu Arg Pro Pro Ser Phe Leu Arg Ala Pro Ser Trp
1               5                   10                  15

Phe Asp Thr Gly Leu Ser Glu Met Arg Leu Glu Lys
            20                  25

<210> SEQ ID NO 66
<211> LENGTH: 28
<212> TYPE: PRT
<213> ORGANISM: Homo sapiens

<400> SEQUENCE: 66

Ser Pro Phe Tyr Leu Arg Pro Pro Ser Phe Leu Arg Ala Pro Ser Trp

```
                1               5                    10                   15

Phe Asp Thr Gly Leu Ser Glu Met Arg Leu Glu Lys
                20                   25

<210> SEQ ID NO 67
<211> LENGTH: 16
<212> TYPE: PRT
<213> ORGANISM: Homo sapiens

<400> SEQUENCE: 67

Gln Val Ser Gly Pro Glu Arg Thr Ile Pro Ile Thr Arg Glu Glu Lys
1               5                   10                  15

<210> SEQ ID NO 68
<211> LENGTH: 18
<212> TYPE: PRT
<213> ORGANISM: Homo sapiens

<400> SEQUENCE: 68

His Ile Tyr Leu Leu Pro Ser Gly Arg Ile Asn Val Ser Gly Leu Thr
1               5                   10                  15

Thr Lys

<210> SEQ ID NO 69
<211> LENGTH: 11
<212> TYPE: PRT
<213> ORGANISM: Homo sapiens

<400> SEQUENCE: 69

Leu Leu Ala His Val Arg Pro Pro Val Ser Lys
1               5                   10

<210> SEQ ID NO 70
<211> LENGTH: 22
<212> TYPE: PRT
<213> ORGANISM: Homo sapiens

<400> SEQUENCE: 70

Asn Val Leu Gly His Met Gln Gln Gly Gly Ser Pro Thr Pro Phe Asp
1               5                   10                  15

Arg Asn Phe Ala Thr Lys
                20

<210> SEQ ID NO 71
<211> LENGTH: 10
<212> TYPE: PRT
<213> ORGANISM: Homo sapiens

<400> SEQUENCE: 71

Met Asp Ala Asp Asp Ser Arg Ala Pro Lys
1               5                   10

<210> SEQ ID NO 72
<211> LENGTH: 15
<212> TYPE: PRT
<213> ORGANISM: Homo sapiens

<400> SEQUENCE: 72

Glu Leu Phe Asp Pro Ile Ile Ser Asp Arg His Gly Gly Tyr Lys
1               5                   10                  15

<210> SEQ ID NO 73
<211> LENGTH: 22
```

-continued

<212> TYPE: PRT
<213> ORGANISM: Homo sapiens

<400> SEQUENCE: 73

Gly Gly Asp Asp Leu Asp Pro Asn Tyr Val Leu Ser Ser Arg Val Arg
1               5                   10                  15

Thr Gly Arg Ser Ile Lys
            20

<210> SEQ ID NO 74
<211> LENGTH: 15
<212> TYPE: PRT
<213> ORGANISM: Homo sapiens

<400> SEQUENCE: 74

Pro Ile Ile Ser Asp Arg His Gly Gly Tyr Lys Pro Thr Asp Lys
1               5                   10                  15

<210> SEQ ID NO 75
<211> LENGTH: 19
<212> TYPE: PRT
<213> ORGANISM: Homo sapiens

<400> SEQUENCE: 75

Glu Leu Phe Asp Pro Ile Ile Ser Asp Arg His Gly Gly Tyr Lys Pro
1               5                   10                  15

Thr Asp Lys

<210> SEQ ID NO 76
<211> LENGTH: 22
<212> TYPE: PRT
<213> ORGANISM: Homo sapiens

<400> SEQUENCE: 76

Gly Gly Asp Asp Leu Asp Pro Asn Tyr Val Leu Ser Ser Arg Val Arg
1               5                   10                  15

Thr Gly Arg Ser Ile Lys
            20

<210> SEQ ID NO 77
<211> LENGTH: 12
<212> TYPE: PRT
<213> ORGANISM: Homo sapiens

<400> SEQUENCE: 77

Phe Glu Glu Ile Leu Thr Arg Leu Arg Leu Gln Lys
1               5                   10

<210> SEQ ID NO 78
<211> LENGTH: 26
<212> TYPE: PRT
<213> ORGANISM: Homo sapiens

<400> SEQUENCE: 78

Val Ala Ile Gln Leu Asn Asp Thr His Pro Ala Leu Ser Ile Pro Glu
1               5                   10                  15

Leu Met Arg Ile Leu Val Asp Val Glu Lys
            20                  25

<210> SEQ ID NO 79
<211> LENGTH: 18
<212> TYPE: PRT

<400> SEQUENCE: 79

Gln Ile Ser Val Arg Gly Leu Ala Gly Leu Gly Asp Val Ala Glu Val
1               5                   10                  15

Arg Lys

<210> SEQ ID NO 80
<211> LENGTH: 9
<212> TYPE: PRT
<213> ORGANISM: Homo sapiens

<400> SEQUENCE: 80

Leu Arg Val Asp Pro Val Asn Phe Lys
1               5

<210> SEQ ID NO 81
<211> LENGTH: 22
<212> TYPE: PRT
<213> ORGANISM: Homo sapiens

<400> SEQUENCE: 81

Val Gly Ala His Ala Gly Glu Tyr Gly Ala Glu Ala Leu Glu Arg Met
1               5                   10                  15

Phe Leu Ser Phe Pro Thr
            20

<210> SEQ ID NO 82
<211> LENGTH: 12
<212> TYPE: PRT
<213> ORGANISM: Homo sapiens

<400> SEQUENCE: 82

Leu Glu Arg Met Phe Leu Ser Phe Pro Thr Thr Lys
1               5                   10

<210> SEQ ID NO 83
<211> LENGTH: 8
<212> TYPE: PRT
<213> ORGANISM: Homo sapiens

<400> SEQUENCE: 83

Arg Val Asp Pro Val Asn Phe Lys
1               5

<210> SEQ ID NO 84
<211> LENGTH: 42
<212> TYPE: PRT
<213> ORGANISM: Homo sapiens

<400> SEQUENCE: 84

Val Asn Val Asp Glu Val Gly Gly Glu Ala Leu Gly Arg Leu Leu Val
1               5                   10                  15

Val Tyr Pro Trp Thr Gln Arg Phe Phe Glu Ser Phe Gly Asp Leu Ser
            20                  25                  30

Thr Pro Asp Ala Val Met Gly Asn Pro Lys
        35                  40

<210> SEQ ID NO 85
<211> LENGTH: 16
<212> TYPE: PRT
<213> ORGANISM: Homo sapiens

<400> SEQUENCE: 85

Val Asn Val Asp Glu Val Gly Gly Glu Ala Leu Gly Arg Leu Leu Val
1               5                   10                  15

<210> SEQ ID NO 86
<211> LENGTH: 42
<212> TYPE: PRT
<213> ORGANISM: Homo sapiens

<400> SEQUENCE: 86

Val Asn Val Asp Glu Val Gly Gly Glu Ala Leu Gly Arg Leu Leu Val
1               5                   10                  15

Val Tyr Pro Trp Thr Gln Arg Phe Phe Glu Ser Phe Gly Asp Leu Ser
            20                  25                  30

Thr Pro Asp Ala Val Met Gly Asn Pro Lys
        35                  40

<210> SEQ ID NO 87
<211> LENGTH: 20
<212> TYPE: PRT
<213> ORGANISM: Homo sapiens

<400> SEQUENCE: 87

Arg Phe Phe Glu Ser Phe Gly Asp Leu Ser Thr Pro Asp Ala Val Met
1               5                   10                  15

Gly Asn Pro Lys
            20

<210> SEQ ID NO 88
<211> LENGTH: 14
<212> TYPE: PRT
<213> ORGANISM: Homo sapiens

<400> SEQUENCE: 88

Val Asn Val Asp Glu Val Gly Gly Glu Ala Leu Gly Arg Leu
1               5                   10

<210> SEQ ID NO 89
<211> LENGTH: 14
<212> TYPE: PRT
<213> ORGANISM: Homo sapiens

<400> SEQUENCE: 89

Val Leu Thr Asp Pro Asp Ala Pro Ser Arg Lys Asp Pro Lys
1               5                   10

<210> SEQ ID NO 90
<211> LENGTH: 16
<212> TYPE: PRT
<213> ORGANISM: Homo sapiens

<400> SEQUENCE: 90

Cys Asp Glu Pro Ile Leu Ser Asn Arg Ser Gly Asp His Arg Gly Lys
1               5                   10                  15

<210> SEQ ID NO 91
<211> LENGTH: 19
<212> TYPE: PRT
<213> ORGANISM: Homo sapiens

<400> SEQUENCE: 91

Ser Val Val Leu Met Ser His Leu Gly Arg Pro Asp Gly Val Pro Met
1               5                   10                  15

Pro Asp Lys

<210> SEQ ID NO 92
<211> LENGTH: 13
<212> TYPE: PRT
<213> ORGANISM: Homo sapiens

<400> SEQUENCE: 92

Arg Val Val Met Arg Val Asp Phe Asn Val Pro Met Lys
1               5                   10

<210> SEQ ID NO 93
<211> LENGTH: 22
<212> TYPE: PRT
<213> ORGANISM: Homo sapiens

<400> SEQUENCE: 93

Tyr Leu Tyr Glu Ile Ala Arg Arg His Pro Tyr Phe Tyr Ala Pro Glu
1               5                   10                  15

Leu Leu Phe Phe Ala Lys
            20

<210> SEQ ID NO 94
<211> LENGTH: 15
<212> TYPE: PRT
<213> ORGANISM: Homo sapiens

<400> SEQUENCE: 94

Val Pro Gln Val Ser Thr Pro Thr Leu Val Glu Val Ser Arg Asn
1               5                   10                  15

<210> SEQ ID NO 95
<211> LENGTH: 12
<212> TYPE: PRT
<213> ORGANISM: Homo sapiens

<400> SEQUENCE: 95

Trp Ala Val Ala Arg Leu Ser Gln Arg Phe Pro Lys
1               5                   10

<210> SEQ ID NO 96
<211> LENGTH: 7
<212> TYPE: PRT
<213> ORGANISM: Homo sapiens

<400> SEQUENCE: 96

Phe Gly Glu Arg Ala Phe Lys
1               5

<210> SEQ ID NO 97
<211> LENGTH: 10
<212> TYPE: PRT
<213> ORGANISM: Homo sapiens

<400> SEQUENCE: 97

Thr Glu Ser Leu Val Asn Arg Arg Pro Cys
1               5                   10

<210> SEQ ID NO 98
<211> LENGTH: 13
<212> TYPE: PRT
<213> ORGANISM: Homo sapiens

<400> SEQUENCE: 98

```
Ala Trp Ala Val Ala Arg Leu Ser Gln Arg Phe Pro Lys
1               5                   10

<210> SEQ ID NO 99
<211> LENGTH: 30
<212> TYPE: PRT
<213> ORGANISM: Homo sapiens

<400> SEQUENCE: 99

Asp Asp Asn Pro Asn Leu Pro Arg Leu Val Arg Pro Glu Val Asp Val
1               5                   10                  15

Met Cys Thr Ala Phe His Asp Asn Glu Glu Thr Phe Leu Lys
            20                  25                  30

<210> SEQ ID NO 100
<211> LENGTH: 9
<212> TYPE: PRT
<213> ORGANISM: Homo sapiens

<400> SEQUENCE: 100

Thr Pro Val Ser Asp Arg Val Thr Lys
1               5

<210> SEQ ID NO 101
<211> LENGTH: 8
<212> TYPE: PRT
<213> ORGANISM: Homo sapiens

<400> SEQUENCE: 101

Ala Leu Leu Val Arg Tyr Thr Lys
1               5

<210> SEQ ID NO 102
<211> LENGTH: 8
<212> TYPE: PRT
<213> ORGANISM: Homo sapiens

<400> SEQUENCE: 102

Ser Glu Val Ala His Arg Phe Lys
1               5

<210> SEQ ID NO 103
<211> LENGTH: 10
<212> TYPE: PRT
<213> ORGANISM: Homo sapiens

<400> SEQUENCE: 103

Leu Val Glu Val Ser Arg Asn Leu Gly Lys
1               5                   10

<210> SEQ ID NO 104
<211> LENGTH: 22
<212> TYPE: PRT
<213> ORGANISM: Homo sapiens

<400> SEQUENCE: 104

Arg Met Pro Cys Ala Glu Asp Tyr Leu Ser Val Val Leu Asn Gln Leu
1               5                   10                  15

Cys Val Leu His Glu Lys
            20

<210> SEQ ID NO 105
<211> LENGTH: 30
<212> TYPE: PRT
```

<213> ORGANISM: Homo sapiens

<400> SEQUENCE: 105

Asp Asp Asn Pro Asn Leu Pro Arg Leu Val Arg Pro Glu Val Asp Val
1               5                   10                  15
Met Cys Thr Ala Phe His Asp Asn Glu Glu Thr Phe Leu Lys
            20                  25                  30

<210> SEQ ID NO 106
<211> LENGTH: 22
<212> TYPE: PRT
<213> ORGANISM: Homo sapiens

<400> SEQUENCE: 106

Tyr Leu Tyr Glu Ile Ala Arg Arg His Pro Tyr Phe Tyr Ala Pro Glu
1               5                   10                  15
Leu Leu Phe Phe Ala Lys
            20

<210> SEQ ID NO 107
<211> LENGTH: 12
<212> TYPE: PRT
<213> ORGANISM: Homo sapiens

<400> SEQUENCE: 107

Cys Cys Thr Glu Ser Leu Val Asn Arg Arg Pro Cys
1               5                   10

<210> SEQ ID NO 108
<211> LENGTH: 12
<212> TYPE: PRT
<213> ORGANISM: Homo sapiens

<400> SEQUENCE: 108

Arg Glu Phe Thr Glu Ser Gln Leu Gln Glu Gly Lys
1               5                   10

<210> SEQ ID NO 109
<211> LENGTH: 19
<212> TYPE: PRT
<213> ORGANISM: Homo sapiens

<400> SEQUENCE: 109

Met Ile Ile Tyr Arg Asp Leu Ile Ser His Asp Glu Met Phe Ser Asp
1               5                   10                  15
Ile Tyr Lys

<210> SEQ ID NO 110
<211> LENGTH: 15
<212> TYPE: PRT
<213> ORGANISM: Homo sapiens

<400> SEQUENCE: 110

Thr Ser Ala Ala Leu Ser Thr Val Gly Ser Ala Ile Ser Arg Lys
1               5                   10                  15

<210> SEQ ID NO 111
<211> LENGTH: 14
<212> TYPE: PRT
<213> ORGANISM: Homo sapiens

<400> SEQUENCE: 111

Phe Val Glu Gly Leu Pro Ile Asn Asp Phe Ser Arg Glu Lys

```
1               5                   10
```

<210> SEQ ID NO 112
<211> LENGTH: 21
<212> TYPE: PRT
<213> ORGANISM: Homo sapiens

<400> SEQUENCE: 112

Glu Glu Ala Glu Asn Asn Leu Ala Ala Phe Arg Ala Asp Val Asp Ala
1               5                   10                  15

Ala Thr Leu Ala Arg
            20

<210> SEQ ID NO 113
<211> LENGTH: 38
<212> TYPE: PRT
<213> ORGANISM: Homo sapiens

<400> SEQUENCE: 113

Ser Arg Leu Gly Thr Thr Arg Thr Pro Ser Ser Tyr Gly Ala Gly Glu
1               5                   10                  15

Leu Leu Asp Phe Ser Leu Ala Asp Ala Val Asn Gln Glu Phe Leu Thr
            20                  25                  30

Thr Arg Thr Asn Glu Lys
        35

<210> SEQ ID NO 114
<211> LENGTH: 17
<212> TYPE: PRT
<213> ORGANISM: Homo sapiens

<400> SEQUENCE: 114

Asn Phe Arg Glu Thr Ser Pro Glu Gln Arg Gly Ser Glu Val His Thr
1               5                   10                  15

Lys

<210> SEQ ID NO 115
<211> LENGTH: 12
<212> TYPE: PRT
<213> ORGANISM: Homo sapiens

<400> SEQUENCE: 115

Met Ala Leu Asp Val Glu Ile Ala Thr Tyr Arg Lys
1               5                   10

<210> SEQ ID NO 116
<211> LENGTH: 38
<212> TYPE: PRT
<213> ORGANISM: Homo sapiens

<400> SEQUENCE: 116

Ser Arg Leu Gly Thr Thr Arg Thr Pro Ser Ser Tyr Gly Ala Gly Glu
1               5                   10                  15

Leu Leu Asp Phe Ser Leu Ala Asp Ala Val Asn Gln Glu Phe Leu Thr
            20                  25                  30

Thr Arg Thr Asn Glu Lys
        35

<210> SEQ ID NO 117
<211> LENGTH: 16
<212> TYPE: PRT
<213> ORGANISM: Homo sapiens

```
<400> SEQUENCE: 117

Val Asp Val Glu Arg Asp Asn Leu Leu Asp Asp Leu Gln Arg Leu Lys
1               5                   10                  15

<210> SEQ ID NO 118
<211> LENGTH: 17
<212> TYPE: PRT
<213> ORGANISM: Homo sapiens

<400> SEQUENCE: 118

Asn Phe Arg Glu Thr Ser Pro Glu Gln Arg Gly Ser Glu Val His Thr
1               5                   10                  15

Lys

<210> SEQ ID NO 119
<211> LENGTH: 21
<212> TYPE: PRT
<213> ORGANISM: Homo sapiens

<400> SEQUENCE: 119

Thr Ile Glu Thr Arg Asp Gly Glu Val Val Ser Glu Ala Thr Gln Gln
1               5                   10                  15

Gln His Glu Val Leu
            20

<210> SEQ ID NO 120
<211> LENGTH: 13
<212> TYPE: PRT
<213> ORGANISM: Homo sapiens

<400> SEQUENCE: 120

Ser Ser Pro Val Phe Pro Arg Ala Gly Phe Gly Ser Lys
1               5                   10

<210> SEQ ID NO 121
<211> LENGTH: 18
<212> TYPE: PRT
<213> ORGANISM: Homo sapiens

<400> SEQUENCE: 121

Ala Ser Gly Val Gln Val Ala Asp Glu Val Cys Arg Ile Phe Tyr Asp
1               5                   10                  15

Met Lys

<210> SEQ ID NO 122
<211> LENGTH: 17
<212> TYPE: PRT
<213> ORGANISM: Homo sapiens

<400> SEQUENCE: 122

Lys Pro Ile Thr Thr Gly Gly Val Thr Tyr Arg Glu Gln Pro Trp His
1               5                   10                  15

Lys

<210> SEQ ID NO 123
<211> LENGTH: 14
<212> TYPE: PRT
<213> ORGANISM: Homo sapiens

<400> SEQUENCE: 123

Glu Leu Ser Asp Ile Ala His Arg Ile Val Ala Pro Gly Lys
```

```
<210> SEQ ID NO 124
<211> LENGTH: 18
<212> TYPE: PRT
<213> ORGANISM: Homo sapiens

<400> SEQUENCE: 124

Leu Val Ile Asn Gly Asn Pro Ile Thr Ile Phe Gln Glu Arg Asp Pro
1               5                   10                  15

Ser Lys

<210> SEQ ID NO 125
<211> LENGTH: 22
<212> TYPE: PRT
<213> ORGANISM: Homo sapiens

<400> SEQUENCE: 125

Arg Val Ile Ile Ser Ala Pro Ser Ala Asp Ala Pro Met Phe Val Met
1               5                   10                  15

Gly Val Asn His Glu Lys
            20

<210> SEQ ID NO 126
<211> LENGTH: 20
<212> TYPE: PRT
<213> ORGANISM: Homo sapiens

<400> SEQUENCE: 126

Ala Phe Arg Val Pro Thr Ala Asn Val Ser Val Val Asp Leu Thr Cys
1               5                   10                  15

Arg Leu Glu Lys
            20

<210> SEQ ID NO 127
<211> LENGTH: 15
<212> TYPE: PRT
<213> ORGANISM: Homo sapiens

<400> SEQUENCE: 127

Val Ser Val Val Asp Leu Thr Cys Arg Leu Glu Lys Pro Ala Lys
1               5                   10                  15

<210> SEQ ID NO 128
<211> LENGTH: 21
<212> TYPE: PRT
<213> ORGANISM: Homo sapiens

<400> SEQUENCE: 128

Leu Trp Arg Asp Gly Arg Gly Ala Leu Gln Asn Ile Ile Pro Ala Ser
1               5                   10                  15

Thr Gly Ala Ala Lys
            20

<210> SEQ ID NO 129
<211> LENGTH: 13
<212> TYPE: PRT
<213> ORGANISM: Homo sapiens

<400> SEQUENCE: 129

Asp Arg Ser Glu Glu Glu Arg Thr Thr Glu Ala Glu Lys
1               5                   10
```

<210> SEQ ID NO 130
<211> LENGTH: 14
<212> TYPE: PRT
<213> ORGANISM: Homo sapiens

<400> SEQUENCE: 130

His Val Ser Gly Ile Thr Asp Thr Glu Glu Glu Arg Ile Lys
1               5                   10

<210> SEQ ID NO 131
<211> LENGTH: 13
<212> TYPE: PRT
<213> ORGANISM: Homo sapiens

<400> SEQUENCE: 131

Ser Pro Arg Phe Ala Leu Phe Asp Leu Ala Glu Gly Lys
1               5                   10

<210> SEQ ID NO 132
<211> LENGTH: 25
<212> TYPE: PRT
<213> ORGANISM: Homo sapiens

<400> SEQUENCE: 132

Leu Gly Gln Asn Pro Thr Gln Ala Glu Val Leu Arg Val Leu Gly Lys
1               5                   10                  15

Pro Arg Gln Glu Glu Leu Asn Thr Lys
            20                  25

<210> SEQ ID NO 133
<211> LENGTH: 12
<212> TYPE: PRT
<213> ORGANISM: Homo sapiens

<400> SEQUENCE: 133

Leu Gly Lys Pro Arg Gln Glu Glu Leu Asn Thr Lys
1               5                   10

<210> SEQ ID NO 134
<211> LENGTH: 11
<212> TYPE: PRT
<213> ORGANISM: Homo sapiens

<400> SEQUENCE: 134

Glu Ala Phe Met Leu Phe Asp Arg Thr Pro Lys
1               5                   10

<210> SEQ ID NO 135
<211> LENGTH: 11
<212> TYPE: PRT
<213> ORGANISM: Homo sapiens

<400> SEQUENCE: 135

Glu Ala Phe Met Leu Phe Asp Arg Thr Pro Lys
1               5                   10

<210> SEQ ID NO 136
<211> LENGTH: 13
<212> TYPE: PRT
<213> ORGANISM: Homo sapiens

<400> SEQUENCE: 136

Val Leu Gly Lys Pro Arg Gln Glu Glu Leu Asn Thr Lys
1               5                   10

<210> SEQ ID NO 137
<211> LENGTH: 17
<212> TYPE: PRT
<213> ORGANISM: Homo sapiens

<400> SEQUENCE: 137

Ala Leu Gly Gln Asn Pro Thr Gln Ala Glu Val Leu Arg Val Leu Gly
1               5                   10                  15

Lys

<210> SEQ ID NO 138
<211> LENGTH: 25
<212> TYPE: PRT
<213> ORGANISM: Homo sapiens

<400> SEQUENCE: 138

Leu Gly Gln Asn Pro Thr Gln Ala Glu Val Leu Arg Val Leu Gly Lys
1               5                   10                  15

Pro Arg Gln Glu Glu Leu Asn Thr Lys
            20                  25

<210> SEQ ID NO 139
<211> LENGTH: 16
<212> TYPE: PRT
<213> ORGANISM: Homo sapiens

<400> SEQUENCE: 139

Leu Gly Gln Asn Pro Thr Gln Ala Glu Val Leu Arg Val Leu Gly Lys
1               5                   10                  15

<210> SEQ ID NO 140
<211> LENGTH: 11
<212> TYPE: PRT
<213> ORGANISM: Homo sapiens

<400> SEQUENCE: 140

Glu Ala Phe Met Leu Phe Asp Arg Thr Pro Lys
1               5                   10

<210> SEQ ID NO 141
<211> LENGTH: 18
<212> TYPE: PRT
<213> ORGANISM: Homo sapiens

<400> SEQUENCE: 141

Met Leu Asp Phe Glu Thr Phe Leu Pro Ile Leu Gln His Ile Ser Arg
1               5                   10                  15

Asn Lys

<210> SEQ ID NO 142
<211> LENGTH: 17
<212> TYPE: PRT
<213> ORGANISM: Homo sapiens

<400> SEQUENCE: 142

Glu Gln Gly Thr Tyr Glu Asp Phe Val Glu Gly Leu Arg Val Phe Asp
1               5                   10                  15

Lys

<210> SEQ ID NO 143
<211> LENGTH: 16

```
<212> TYPE: PRT
<213> ORGANISM: Homo sapiens

<400> SEQUENCE: 143

Asn Asp Leu Arg Asp Thr Phe Ala Ala Leu Gly Arg Val Asn Val Lys
1               5                   10                  15

<210> SEQ ID NO 144
<211> LENGTH: 16
<212> TYPE: PRT
<213> ORGANISM: Homo sapiens

<400> SEQUENCE: 144

Glu Ala Phe Thr Ile Met Asp Gln Asn Arg Asp Gly Phe Ile Asp Lys
1               5                   10                  15

<210> SEQ ID NO 145
<211> LENGTH: 17
<212> TYPE: PRT
<213> ORGANISM: Homo sapiens

<400> SEQUENCE: 145

Gly Asp Ser Glu Met Ala Val Phe Gly Ala Ala Ala Pro Tyr Leu Arg
1               5                   10                  15

Lys

<210> SEQ ID NO 146
<211> LENGTH: 13
<212> TYPE: PRT
<213> ORGANISM: Homo sapiens

<400> SEQUENCE: 146

Val Arg Glu Leu Glu Asn Glu Leu Glu Ala Glu Gln Lys
1               5                   10

<210> SEQ ID NO 147
<211> LENGTH: 20
<212> TYPE: PRT
<213> ORGANISM: Homo sapiens

<400> SEQUENCE: 147

Arg Tyr Arg Ile Leu Asn Pro Ala Ala Ile Pro Glu Gly Gln Phe Ile
1               5                   10                  15

Asp Ser Arg Lys
            20

<210> SEQ ID NO 148
<211> LENGTH: 12
<212> TYPE: PRT
<213> ORGANISM: Homo sapiens

<400> SEQUENCE: 148

Arg Asn His Leu Arg Val Val Asp Ser Leu Gln Thr
1               5                   10

<210> SEQ ID NO 149
<211> LENGTH: 14
<212> TYPE: PRT
<213> ORGANISM: Homo sapiens

<400> SEQUENCE: 149

Arg Val Arg Glu Leu Glu Asn Glu Leu Glu Ala Glu Gln Lys
1               5                   10
```

```
<210> SEQ ID NO 150
<211> LENGTH: 12
<212> TYPE: PRT
<213> ORGANISM: Homo sapiens

<400> SEQUENCE: 150

Ala Val Phe Gly Ala Ala Ala Pro Tyr Leu Arg Lys
1               5                   10

<210> SEQ ID NO 151
<211> LENGTH: 17
<212> TYPE: PRT
<213> ORGANISM: Homo sapiens

<400> SEQUENCE: 151

Leu Glu Ala Arg Val Arg Glu Leu Glu Asn Glu Leu Glu Ala Glu Gln
1               5                   10                  15

Lys

<210> SEQ ID NO 152
<211> LENGTH: 19
<212> TYPE: PRT
<213> ORGANISM: Homo sapiens

<400> SEQUENCE: 152

Tyr Arg Ile Leu Asn Pro Ala Ala Ile Pro Glu Gly Gln Phe Ile Asp
1               5                   10                  15

Ser Arg Lys

<210> SEQ ID NO 153
<211> LENGTH: 20
<212> TYPE: PRT
<213> ORGANISM: Homo sapiens

<400> SEQUENCE: 153

Arg Tyr Arg Ile Leu Asn Pro Ala Ala Ile Pro Glu Gly Gln Phe Ile
1               5                   10                  15

Asp Ser Arg Lys
            20

<210> SEQ ID NO 154
<211> LENGTH: 23
<212> TYPE: PRT
<213> ORGANISM: Homo sapiens

<400> SEQUENCE: 154

Asp Phe Glu Leu Asn Ala Leu Asn Ala Arg Ile Glu Asp Glu Gln Ala
1               5                   10                  15

Leu Gly Ser Gln Leu Gln Lys
            20

<210> SEQ ID NO 155
<211> LENGTH: 17
<212> TYPE: PRT
<213> ORGANISM: Homo sapiens

<400> SEQUENCE: 155

Ala Glu Glu Thr Gln Arg Ser Val Asn Asp Leu Thr Ser Gln Arg Ala
1               5                   10                  15

Lys
```

```
<210> SEQ ID NO 156
<211> LENGTH: 12
<212> TYPE: PRT
<213> ORGANISM: Homo sapiens

<400> SEQUENCE: 156

Arg Ser Val Asn Asp Leu Thr Ser Gln Arg Ala Lys
1               5                   10

<210> SEQ ID NO 157
<211> LENGTH: 14
<212> TYPE: PRT
<213> ORGANISM: Homo sapiens

<400> SEQUENCE: 157

Arg Val Arg Glu Leu Glu Asn Glu Leu Glu Ala Glu Gln Lys
1               5                   10

<210> SEQ ID NO 158
<211> LENGTH: 19
<212> TYPE: PRT
<213> ORGANISM: Homo sapiens

<400> SEQUENCE: 158

Tyr Arg Ile Leu Asn Pro Ala Ala Ile Pro Glu Gly Gln Phe Ile Asp
1               5                   10                  15

Ser Arg Lys

<210> SEQ ID NO 159
<211> LENGTH: 17
<212> TYPE: PRT
<213> ORGANISM: Homo sapiens

<400> SEQUENCE: 159

Arg Val Ile Gln Tyr Phe Ala Val Ile Ala Ala Ile Gly Asp Arg Ser
1               5                   10                  15

Lys

<210> SEQ ID NO 160
<211> LENGTH: 20
<212> TYPE: PRT
<213> ORGANISM: Homo sapiens

<400> SEQUENCE: 160

Arg Tyr Arg Ile Leu Asn Pro Ala Ala Ile Pro Glu Gly Gln Phe Ile
1               5                   10                  15

Asp Ser Arg Lys
            20

<210> SEQ ID NO 161
<211> LENGTH: 15
<212> TYPE: PRT
<213> ORGANISM: Homo sapiens

<400> SEQUENCE: 161

Val Arg Trp Gln Arg Gly Gly Ser Asp Ile Ser Ala Ser Asn Lys
1               5                   10                  15

<210> SEQ ID NO 162
<211> LENGTH: 9
<212> TYPE: PRT
<213> ORGANISM: Homo sapiens

<400> SEQUENCE: 162
```

```
Pro Arg Pro Gln Val Thr Trp Thr Lys
1               5
```

<210> SEQ ID NO 163
<211> LENGTH: 22
<212> TYPE: PRT
<213> ORGANISM: Homo sapiens

<400> SEQUENCE: 163

```
Ser Gly Glu His Asp Phe Gly Ala Ala Phe Asp Gly Asp Gly Asp Arg
1               5                   10                  15

Asn Met Ile Leu Gly Lys
            20
```

<210> SEQ ID NO 164
<211> LENGTH: 14
<212> TYPE: PRT
<213> ORGANISM: Homo sapiens

<400> SEQUENCE: 164

```
Asp Leu Glu Ala Leu Met Phe Asp Arg Ser Phe Val Gly Lys
1               5                   10
```

<210> SEQ ID NO 165
<211> LENGTH: 19
<212> TYPE: PRT
<213> ORGANISM: Homo sapiens

<400> SEQUENCE: 165

```
Val Asn Asp Asp Ile Ile Val Asn Trp Val Asn Glu Thr Leu Arg Glu
1               5                   10                  15

Ala Lys Lys
```

<210> SEQ ID NO 166
<211> LENGTH: 21
<212> TYPE: PRT
<213> ORGANISM: Homo sapiens

<400> SEQUENCE: 166

```
Cys Ser Val Ile Arg Asp Ser Leu Leu Gln Asp Gly Glu Phe Ser Met
1               5                   10                  15

Asp Leu Arg Thr Lys
            20
```

<210> SEQ ID NO 167
<211> LENGTH: 17
<212> TYPE: PRT
<213> ORGANISM: Homo sapiens

<400> SEQUENCE: 167

```
Cys Asp Val Ser Arg Gly Asp Trp Val Thr Ala Leu Ala Ser Val Thr
1               5                   10                  15

Lys
```

<210> SEQ ID NO 168
<211> LENGTH: 11
<212> TYPE: PRT
<213> ORGANISM: Homo sapiens

<400> SEQUENCE: 168

```
Tyr Arg Ala Tyr Ala Thr Glu Pro His Ala Lys
1               5                   10
```

```
<210> SEQ ID NO 169
<211> LENGTH: 14
<212> TYPE: PRT
<213> ORGANISM: Homo sapiens

<400> SEQUENCE: 169

Gln Glu Leu Glu Arg Glu Ala Glu Glu Arg Gly Glu Lys
1               5                   10

<210> SEQ ID NO 170
<211> LENGTH: 12
<212> TYPE: PRT
<213> ORGANISM: Homo sapiens

<400> SEQUENCE: 170

Gly Glu Arg Val Asp Phe Asp Asp Ile His Arg Lys
1               5                   10

<210> SEQ ID NO 171
<211> LENGTH: 15
<212> TYPE: PRT
<213> ORGANISM: Homo sapiens

<400> SEQUENCE: 171

Glu Ala Glu Asp Gly Pro Met Glu Glu Ser Lys Pro Lys Pro Arg
1               5                   10                  15

<210> SEQ ID NO 172
<211> LENGTH: 20
<212> TYPE: PRT
<213> ORGANISM: Homo sapiens

<400> SEQUENCE: 172

Ala Glu Ala Glu Thr Glu Glu Thr Arg Ala Glu Glu Asp Glu Glu
1               5                   10                  15

Glu Glu Ala Lys
            20

<210> SEQ ID NO 173
<211> LENGTH: 36
<212> TYPE: PRT
<213> ORGANISM: Homo sapiens

<400> SEQUENCE: 173

His Val Pro Arg Ala Val Phe Val Asp Leu Glu Pro Thr Val Ile Asp
1               5                   10                  15

Glu Val Arg Thr Gly Thr Tyr Arg Gln Leu Phe His Pro Glu Gln Leu
            20                  25                  30

Ile Thr Gly Lys
            35

<210> SEQ ID NO 174
<211> LENGTH: 36
<212> TYPE: PRT
<213> ORGANISM: Homo sapiens

<400> SEQUENCE: 174

His Val Pro Arg Ala Val Phe Val Asp Leu Glu Pro Thr Val Ile Asp
1               5                   10                  15

Glu Ile Arg Asn Gly Pro Tyr Arg Gln Leu Phe His Pro Glu Gln Leu
            20                  25                  30
```

```
Ile Thr Gly Lys
        35

<210> SEQ ID NO 175
<211> LENGTH: 12
<212> TYPE: PRT
<213> ORGANISM: Homo sapiens

<400> SEQUENCE: 175

Glu Ile Ile Asp Pro Val Leu Asp Arg Ile Arg Lys
1               5                   10

<210> SEQ ID NO 176
<211> LENGTH: 16
<212> TYPE: PRT
<213> ORGANISM: Homo sapiens

<400> SEQUENCE: 176

Glu Asp Ala Ala Asn Asn Tyr Ala Arg Gly His Tyr Thr Val Gly Lys
1               5                   10                  15

<210> SEQ ID NO 177
<211> LENGTH: 21
<212> TYPE: PRT
<213> ORGANISM: Homo sapiens

<400> SEQUENCE: 177

Thr Val Glu Thr Arg Asp Gly Gln Val Ile Asn Glu Thr Ser Gln His
1               5                   10                  15

His Asp Asp Leu Glu
        20

<210> SEQ ID NO 178
<211> LENGTH: 27
<212> TYPE: PRT
<213> ORGANISM: Homo sapiens

<400> SEQUENCE: 178

Leu Ala Thr Gln Ser Asn Glu Ile Thr Ile Pro Val Thr Phe Glu Ser
1               5                   10                  15

Arg Ala Gln Leu Gly Gly Pro Glu Ala Ala Lys
            20                  25

<210> SEQ ID NO 179
<211> LENGTH: 23
<212> TYPE: PRT
<213> ORGANISM: Homo sapiens

<400> SEQUENCE: 179

Ile Pro Glu Asn Ile Tyr Arg Gly Ile Arg Asn Leu Leu Glu Ser Tyr
1               5                   10                  15

His Val Pro Glu Leu Ile Lys
        20

<210> SEQ ID NO 180
<211> LENGTH: 14
<212> TYPE: PRT
<213> ORGANISM: Homo sapiens

<400> SEQUENCE: 180

Ser Glu Glu Glu Leu Ser Asp Leu Phe Arg Met Phe Asp Lys
1               5                   10
```

```
<210> SEQ ID NO 181
<211> LENGTH: 17
<212> TYPE: PRT
<213> ORGANISM: Homo sapiens

<400> SEQUENCE: 181

Glu Leu Asp Arg Asp Thr Val Phe Ala Leu Val Asn Tyr Ile Phe Phe
1               5                   10                  15

Lys

<210> SEQ ID NO 182
<211> LENGTH: 13
<212> TYPE: PRT
<213> ORGANISM: Homo sapiens

<400> SEQUENCE: 182

Glu Asn Gly Gly Ala Arg Leu Ala Glu Tyr His Ala Lys
1               5                   10

<210> SEQ ID NO 183
<211> LENGTH: 17
<212> TYPE: PRT
<213> ORGANISM: Homo sapiens

<400> SEQUENCE: 183

Asp Ser Gly Arg Asp Tyr Val Ser Gln Phe Glu Gly Ser Ala Leu Gly
1               5                   10                  15

Lys

<210> SEQ ID NO 184
<211> LENGTH: 20
<212> TYPE: PRT
<213> ORGANISM: Homo sapiens

<400> SEQUENCE: 184

Ala Lys Pro Ala Leu Glu Asp Leu Arg Gln Gly Leu Leu Pro Val Leu
1               5                   10                  15

Glu Ser Phe Lys
                20

<210> SEQ ID NO 185
<211> LENGTH: 10
<212> TYPE: PRT
<213> ORGANISM: Homo sapiens

<400> SEQUENCE: 185

Pro Arg Gln Ile Asp Asn Pro Asp Tyr Lys
1               5                   10

<210> SEQ ID NO 186
<211> LENGTH: 12
<212> TYPE: PRT
<213> ORGANISM: Homo sapiens

<400> SEQUENCE: 186

Thr Glu Arg Glu Gln Phe Val Glu Phe Arg Asp Lys
1               5                   10

<210> SEQ ID NO 187
<211> LENGTH: 20
<212> TYPE: PRT
<213> ORGANISM: Homo sapiens

<400> SEQUENCE: 187
```

```
Ile Glu Arg Ala Ile Thr Gln Glu Leu Pro Gly Leu Leu Gly Ser Leu
1               5                   10                  15

Gly Leu Gly Lys
            20

<210> SEQ ID NO 188
<211> LENGTH: 20
<212> TYPE: PRT
<213> ORGANISM: Homo sapiens

<400> SEQUENCE: 188

Thr Ile Glu Gly Ile Val Met Ala Ala Asp Ser Ala Arg Ser Phe Ser
1               5                   10                  15

Pro Leu Glu Lys
            20

<210> SEQ ID NO 189
<211> LENGTH: 10
<212> TYPE: PRT
<213> ORGANISM: Homo sapiens

<400> SEQUENCE: 189

Ile Ser Arg Val Asp Ala Ala Ser Leu Lys
1               5                   10

<210> SEQ ID NO 190
<211> LENGTH: 11
<212> TYPE: PRT
<213> ORGANISM: Homo sapiens

<400> SEQUENCE: 190

Ala Thr Val Val Tyr Gln Gly Glu Arg Val Lys
1               5                   10

<210> SEQ ID NO 191
<211> LENGTH: 11
<212> TYPE: PRT
<213> ORGANISM: Homo sapiens

<400> SEQUENCE: 191

Val Glu Arg Gln Val Phe Gly Glu Ala Thr Lys
1               5                   10

<210> SEQ ID NO 192
<211> LENGTH: 15
<212> TYPE: PRT
<213> ORGANISM: Homo sapiens

<400> SEQUENCE: 192

Tyr Leu Tyr Leu Arg Asn Asn Gln Ile Asp His Ile Asp Glu Lys
1               5                   10                  15

<210> SEQ ID NO 193
<211> LENGTH: 7
<212> TYPE: PRT
<213> ORGANISM: Homo sapiens

<400> SEQUENCE: 193

Ala Leu Glu Leu Phe Arg Lys
1               5

<210> SEQ ID NO 194
<211> LENGTH: 14
```

```
<212> TYPE: PRT
<213> ORGANISM: Homo sapiens

<400> SEQUENCE: 194

Glu Glu Asp Pro Ala Thr Gly Thr Gly Asp Pro Pro Arg Lys
1               5                   10

<210> SEQ ID NO 195
<211> LENGTH: 14
<212> TYPE: PRT
<213> ORGANISM: Homo sapiens

<400> SEQUENCE: 195

Gly Ala Phe Ser Arg Leu Asp Pro Thr Gly Thr Phe Glu Lys
1               5                   10

<210> SEQ ID NO 196
<211> LENGTH: 24
<212> TYPE: PRT
<213> ORGANISM: Homo sapiens

<400> SEQUENCE: 196

Pro Asn Val Ser Glu Ala Leu Arg Ser Ala Gly Leu Pro Ser His Ser
1               5                   10                  15

Ser Val Ile Ser Gln His Ser Lys
            20

<210> SEQ ID NO 197
<211> LENGTH: 10
<212> TYPE: PRT
<213> ORGANISM: Homo sapiens

<400> SEQUENCE: 197

Tyr Ala Leu Gln Ser Gln Gln Arg Trp Lys
1               5                   10

<210> SEQ ID NO 198
<211> LENGTH: 36
<212> TYPE: PRT
<213> ORGANISM: Homo sapiens

<400> SEQUENCE: 198

Val Ser Pro Glu Thr Val Asp Ser Val Ile Met Gly Asn Val Leu Gln
1               5                   10                  15

Ser Ser Ser Asp Ala Ile Tyr Leu Ala Arg His Val Gly Leu Arg Val
            20                  25                  30

Gly Ile Pro Lys
            35

<210> SEQ ID NO 199
<211> LENGTH: 26
<212> TYPE: PRT
<213> ORGANISM: Homo sapiens

<400> SEQUENCE: 199

Glu Val Val Ile Val Ser Ala Thr Arg Thr Pro Ile Gly Ser Phe Leu
1               5                   10                  15

Gly Ser Leu Ser Leu Leu Pro Ala Thr Lys
            20                  25

<210> SEQ ID NO 200
<211> LENGTH: 31
<212> TYPE: PRT
```

```
<213> ORGANISM: Homo sapiens

<400> SEQUENCE: 200

Ser Tyr Leu Arg Leu Arg Pro Asp Arg Val Ala Met Gln Asp Ala Thr
1               5                  10                 15

Ala Gln Met Ala Met Leu Gln Phe Ile Ser Ser Gly Leu Ser Lys
            20                  25                 30

<210> SEQ ID NO 201
<211> LENGTH: 23
<212> TYPE: PRT
<213> ORGANISM: Homo sapiens

<400> SEQUENCE: 201

Phe Arg Gly His Leu Asp Asn Ile Ser Asn Asn Leu Leu Ile Gly Ala
1               5                  10                 15

Ile Asn Ile Glu Asn Gly Lys
            20

<210> SEQ ID NO 202
<211> LENGTH: 19
<212> TYPE: PRT
<213> ORGANISM: Homo sapiens

<400> SEQUENCE: 202

Ala Phe Thr Gly Phe Ile Val Glu Ala Asp Thr Pro Gly Ile Gln Ile
1               5                  10                 15

Gly Arg Lys

<210> SEQ ID NO 203
<211> LENGTH: 15
<212> TYPE: PRT
<213> ORGANISM: Homo sapiens

<400> SEQUENCE: 203

Phe Ala Arg Glu Glu Ile Ile Pro Val Ala Ala Glu Tyr Asp Lys
1               5                  10                 15

<210> SEQ ID NO 204
<211> LENGTH: 22
<212> TYPE: PRT
<213> ORGANISM: Homo sapiens

<400> SEQUENCE: 204

Thr Arg Pro Val Val Ala Ala Gly Ala Val Gly Leu Ala Gln Arg Ala
1               5                  10                 15

Leu Asp Glu Ala Thr Lys
            20

<210> SEQ ID NO 205
<211> LENGTH: 17
<212> TYPE: PRT
<213> ORGANISM: Homo sapiens

<400> SEQUENCE: 205

Lys Arg Gly Glu Thr Ser Gly Arg Val Asp Asp Asn Glu Glu Thr Ile
1               5                  10                 15

Lys

<210> SEQ ID NO 206
<211> LENGTH: 23
<212> TYPE: PRT
```

```
<213> ORGANISM: Homo sapiens

<400> SEQUENCE: 206

Val Ala Phe Thr Gly Ser Thr Glu Ile Gly Arg Val Ile Gln Val Ala
1               5                   10                  15

Ala Gly Ser Ser Asn Leu Lys
            20

<210> SEQ ID NO 207
<211> LENGTH: 11
<212> TYPE: PRT
<213> ORGANISM: Homo sapiens

<400> SEQUENCE: 207

Ser Arg Val Val Gly Asn Pro Phe Asp Ser Lys
1               5                   10

<210> SEQ ID NO 208
<211> LENGTH: 9
<212> TYPE: PRT
<213> ORGANISM: Homo sapiens

<400> SEQUENCE: 208

Pro Tyr Val Leu Pro Ser Val Arg Lys
1               5

<210> SEQ ID NO 209
<211> LENGTH: 26
<212> TYPE: PRT
<213> ORGANISM: Homo sapiens

<400> SEQUENCE: 209

Ile Pro Val Gly Pro Glu Thr Leu Gly Arg Ile Met Asn Val Ile Gly
1               5                   10                  15

Glu Pro Ile Asp Glu Arg Gly Pro Ile Lys
            20                  25

<210> SEQ ID NO 210
<211> LENGTH: 26
<212> TYPE: PRT
<213> ORGANISM: Homo sapiens

<400> SEQUENCE: 210

Ile Pro Val Gly Pro Glu Thr Leu Gly Arg Ile Met Asn Val Ile Gly
1               5                   10                  15

Glu Pro Ile Asp Glu Arg Gly Pro Ile Lys
            20                  25

<210> SEQ ID NO 211
<211> LENGTH: 21
<212> TYPE: PRT
<213> ORGANISM: Homo sapiens

<400> SEQUENCE: 211

Ile Gln Arg Phe Leu Ser Gln Pro Phe Gln Val Ala Glu Val Phe Thr
1               5                   10                  15

Gly His Met Gly Lys
            20

<210> SEQ ID NO 212
<211> LENGTH: 34
<212> TYPE: PRT
<213> ORGANISM: Homo sapiens
```

<400> SEQUENCE: 212

Ala His Gly Gly Tyr Ser Val Phe Ala Gly Val Gly Glu Arg Thr Arg
1               5                   10                  15

Glu Gly Asn Asp Leu Tyr His Glu Met Ile Glu Ser Gly Val Ile Asn
            20                  25                  30

Leu Lys

<210> SEQ ID NO 213
<211> LENGTH: 14
<212> TYPE: PRT
<213> ORGANISM: Homo sapiens

<400> SEQUENCE: 213

Pro Arg Ala Glu Glu Arg Arg Ile Ala Ala Glu Glu Lys
1               5                   10

<210> SEQ ID NO 214
<211> LENGTH: 28
<212> TYPE: PRT
<213> ORGANISM: Homo sapiens

<400> SEQUENCE: 214

Ser Gln Leu Ser Ala Ala Val Thr Ala Leu Asn Ser Glu Ser Asn Phe
1               5                   10                  15

Ala Arg Ala Tyr Ala Gln Gly Ile Ser Arg Thr Lys
            20                  25

<210> SEQ ID NO 215
<211> LENGTH: 19
<212> TYPE: PRT
<213> ORGANISM: Homo sapiens

<400> SEQUENCE: 215

Thr Val Val Gly Gln Ile Thr Val Asp Met Met Tyr Gly Gly Met Arg
1               5                   10                  15

Gly Met Lys

<210> SEQ ID NO 216
<211> LENGTH: 21
<212> TYPE: PRT
<213> ORGANISM: Homo sapiens

<400> SEQUENCE: 216

Leu Arg Phe Pro Ala Glu Asp Glu Phe Pro Asp Leu Ser Ala His Asn
1               5                   10                  15

Asn His Met Ala Lys
            20

<210> SEQ ID NO 217
<211> LENGTH: 21
<212> TYPE: PRT
<213> ORGANISM: Homo sapiens

<400> SEQUENCE: 217

Glu Val Phe Thr Arg Phe Cys Cys Ala Met Thr Gly Leu Thr Gln Ile
1               5                   10                  15

Glu Thr Leu Phe Lys
            20

<210> SEQ ID NO 218

```
<211> LENGTH: 24
<212> TYPE: PRT
<213> ORGANISM: Homo sapiens

<400> SEQUENCE: 218

Cys Cys Ala Met Thr Arg Ala Glu Arg Arg Glu Val Glu Asn Val Ala
1               5                   10                  15

Ile Thr Ala Leu Glu Gly Leu Lys
            20

<210> SEQ ID NO 219
<211> LENGTH: 20
<212> TYPE: PRT
<213> ORGANISM: Homo sapiens

<400> SEQUENCE: 219

Thr Arg Ala Glu Arg Arg Glu Val Glu Asn Val Ala Ile Thr Ala Leu
1               5                   10                  15

Glu Gly Leu Lys
            20

<210> SEQ ID NO 220
<211> LENGTH: 20
<212> TYPE: PRT
<213> ORGANISM: Homo sapiens

<400> SEQUENCE: 220

Glu Val Arg Glu Gln Pro Arg Leu Phe Pro Pro Ser Ala Asp Tyr Pro
1               5                   10                  15

Asp Leu Arg Lys
            20

<210> SEQ ID NO 221
<211> LENGTH: 12
<212> TYPE: PRT
<213> ORGANISM: Homo sapiens

<400> SEQUENCE: 221

Lys Glu Glu Arg Ala Asp Leu Ile Ala Tyr Leu Lys
1               5                   10

<210> SEQ ID NO 222
<211> LENGTH: 30
<212> TYPE: PRT
<213> ORGANISM: Homo sapiens

<400> SEQUENCE: 222

Glu Ile Tyr Pro Tyr Val Ile Gln Glu Leu Arg Pro Thr Leu Asn Glu
1               5                   10                  15

Leu Gly Ile Ser Thr Pro Glu Glu Leu Gly Leu Asp Lys Val
            20                  25                  30

<210> SEQ ID NO 223
<211> LENGTH: 31
<212> TYPE: PRT
<213> ORGANISM: Homo sapiens

<400> SEQUENCE: 223

Ser His Gly Ser Gln Glu Thr Asp Glu Glu Phe Asp Ala Arg Trp Val
1               5                   10                  15

Thr Tyr Phe Asn Lys Pro Asp Ile Asp Ala Trp Glu Leu Arg Lys
            20                  25                  30
```

<210> SEQ ID NO 224
<211> LENGTH: 25
<212> TYPE: PRT
<213> ORGANISM: Homo sapiens

<400> SEQUENCE: 224

Ala Ser Gly Gly Gly Val Pro Thr Asp Glu Glu Gln Ala Thr Gly Leu
1               5                   10                  15

Glu Arg Glu Ile Met Leu Ala Ala Lys
            20                  25

<210> SEQ ID NO 225
<211> LENGTH: 22
<212> TYPE: PRT
<213> ORGANISM: Homo sapiens

<400> SEQUENCE: 225

Thr Val Ile Gln Ala Glu Ile Asp Ala Ala Glu Leu Ile Asp Phe
1               5                   10                  15

Phe Arg Phe Asn Ala Lys
            20

<210> SEQ ID NO 226
<211> LENGTH: 8
<212> TYPE: PRT
<213> ORGANISM: Homo sapiens

<400> SEQUENCE: 226

Asn Phe Gln Arg Ile Leu Gln Lys
1               5

<210> SEQ ID NO 227
<211> LENGTH: 10
<212> TYPE: PRT
<213> ORGANISM: Homo sapiens

<400> SEQUENCE: 227

Val Val Val Ser Gly Gly Arg Gly Leu Lys
1               5                   10

<210> SEQ ID NO 228
<211> LENGTH: 23
<212> TYPE: PRT
<213> ORGANISM: Homo sapiens

<400> SEQUENCE: 228

Val Phe Ser Val Arg Gly Thr Ser Phe Asp Ala Ala Thr Ser Gly
1               5                   10                  15

Gly Ser Ala Ser Ser Glu Lys
            20

<210> SEQ ID NO 229
<211> LENGTH: 36
<212> TYPE: PRT
<213> ORGANISM: Homo sapiens

<400> SEQUENCE: 229

Leu Leu Tyr Asp Leu Ala Asp Gln Leu His Ala Ala Val Gly Ala Ser
1               5                   10                  15

Arg Ala Ala Val Asp Ala Gly Phe Val Pro Asn Asp Met Gln Val Gly
            20                  25                  30

Gln Thr Gly Lys

<210> SEQ ID NO 230
<211> LENGTH: 15
<212> TYPE: PRT
<213> ORGANISM: Homo sapiens

<400> SEQUENCE: 230

Val Glu Arg Glu Ile Asp Gly Gly Leu Glu Thr Leu Arg Leu Lys
1               5                   10                  15

<210> SEQ ID NO 231
<211> LENGTH: 17
<212> TYPE: PRT
<213> ORGANISM: Homo sapiens

<400> SEQUENCE: 231

Leu Ser Val Ile Ser Val Glu Asp Pro Pro Gln Arg Thr Ala Gly Val
1               5                   10                  15

Lys

<210> SEQ ID NO 232
<211> LENGTH: 29
<212> TYPE: PRT
<213> ORGANISM: Homo sapiens

<400> SEQUENCE: 232

Pro Phe Leu Leu Pro Val Glu Ala Val Tyr Ser Val Pro Gly Arg Gly
1               5                   10                  15

Thr Val Val Thr Gly Thr Leu Glu Arg Gly Ile Leu Lys
            20                  25

<210> SEQ ID NO 233
<211> LENGTH: 19
<212> TYPE: PRT
<213> ORGANISM: Homo sapiens

<400> SEQUENCE: 233

Ser Leu Glu Arg Ala Glu Ala Gly Asp Asn Leu Gly Ala Leu Val Arg
1               5                   10                  15

Gly Leu Lys

<210> SEQ ID NO 234
<211> LENGTH: 14
<212> TYPE: PRT
<213> ORGANISM: Homo sapiens

<400> SEQUENCE: 234

Asn Ile Arg Thr Val Val Thr Gly Ile Glu Met Phe His Lys
1               5                   10

<210> SEQ ID NO 235
<211> LENGTH: 29
<212> TYPE: PRT
<213> ORGANISM: Homo sapiens

<400> SEQUENCE: 235

Pro Phe Leu Leu Pro Val Glu Ala Val Tyr Ser Val Pro Gly Arg Gly
1               5                   10                  15

Thr Val Val Thr Gly Thr Leu Glu Arg Gly Ile Leu Lys
            20                  25

```
<210> SEQ ID NO 236
<211> LENGTH: 19
<212> TYPE: PRT
<213> ORGANISM: Homo sapiens

<400> SEQUENCE: 236

Ser Leu Glu Arg Ala Glu Ala Gly Asp Asn Leu Gly Ala Leu Val Arg
1               5                   10                  15

Gly Leu Lys

<210> SEQ ID NO 237
<211> LENGTH: 28
<212> TYPE: PRT
<213> ORGANISM: Homo sapiens

<400> SEQUENCE: 237

Ala Gln Phe Ala Gln Pro Glu Ile Leu Ile Gly Thr Ile Pro Gly Ala
1               5                   10                  15

Gly Gly Thr Gln Arg Leu Thr Arg Ala Val Gly Lys
            20                  25

<210> SEQ ID NO 238
<211> LENGTH: 34
<212> TYPE: PRT
<213> ORGANISM: Homo sapiens

<400> SEQUENCE: 238

Ile Ala Asn Asp Ile Arg Phe Leu Gly Ser Gly Pro Arg Ser Gly Leu
1               5                   10                  15

Gly Glu Leu Ile Leu Pro Glu Asn Glu Pro Gly Ser Ser Ile Met Pro
            20                  25                  30

Gly Lys

<210> SEQ ID NO 239
<211> LENGTH: 14
<212> TYPE: PRT
<213> ORGANISM: Homo sapiens

<400> SEQUENCE: 239

Tyr Tyr Gly Ala Gln Thr Val Arg Ser Thr Met Asn Phe Lys
1               5                   10

<210> SEQ ID NO 240
<211> LENGTH: 13
<212> TYPE: PRT
<213> ORGANISM: Homo sapiens

<400> SEQUENCE: 240

Asp Ser Gly Asn Lys Pro Pro Gly Leu Leu Pro Arg Lys
1               5                   10

<210> SEQ ID NO 241
<211> LENGTH: 21
<212> TYPE: PRT
<213> ORGANISM: Homo sapiens

<400> SEQUENCE: 241

Asp Gln Gln Glu Ala Ala Leu Val Asp Met Val Asn Asp Gly Val Glu
1               5                   10                  15

Asp Leu Arg Cys Lys
            20
```

-continued

```
<210> SEQ ID NO 242
<211> LENGTH: 17
<212> TYPE: PRT
<213> ORGANISM: Homo sapiens

<400> SEQUENCE: 242

Ala Gln Ile His Asp Leu Val Leu Val Gly Gly Ser Thr Arg Ile Pro
1               5                   10                  15

Lys

<210> SEQ ID NO 243
<211> LENGTH: 31
<212> TYPE: PRT
<213> ORGANISM: Homo sapiens

<400> SEQUENCE: 243

Asp Ala Gly Val Ile Ala Gly Leu Asn Val Leu Arg Ile Ile Asn Glu
1               5                   10                  15

Pro Thr Ala Ala Ala Ile Ala Tyr Gly Leu Asp Arg Thr Gly Lys
            20                  25                  30

<210> SEQ ID NO 244
<211> LENGTH: 14
<212> TYPE: PRT
<213> ORGANISM: Homo sapiens

<400> SEQUENCE: 244

Glu Gln Val Ala Asn Ser Ala Phe Val Glu Arg Val Arg Lys
1               5                   10

<210> SEQ ID NO 245
<211> LENGTH: 14
<212> TYPE: PRT
<213> ORGANISM: Homo sapiens

<400> SEQUENCE: 245

Ala Asn Ile Met Arg Met Ser Asp Gly Leu Phe Leu Gln Lys
1               5                   10

<210> SEQ ID NO 246
<211> LENGTH: 17
<212> TYPE: PRT
<213> ORGANISM: Homo sapiens

<400> SEQUENCE: 246

Ile Trp Tyr Glu His Arg Leu Ile Asp Asp Met Val Ala Gln Val Leu
1               5                   10                  15

Lys

<210> SEQ ID NO 247
<211> LENGTH: 10
<212> TYPE: PRT
<213> ORGANISM: Homo sapiens

<400> SEQUENCE: 247

Ser Asn Leu Asp Arg Ala Leu Gly Arg Gln
1               5                   10

<210> SEQ ID NO 248
<211> LENGTH: 13
<212> TYPE: PRT
<213> ORGANISM: Homo sapiens

<400> SEQUENCE: 248
```

```
Ala Thr Asp Phe Val Ala Asp Arg Ala Gly Thr Phe Lys
1               5                   10
```

<210> SEQ ID NO 249
<211> LENGTH: 14
<212> TYPE: PRT
<213> ORGANISM: Homo sapiens

<400> SEQUENCE: 249

```
Pro Ile Thr Ile Gly Arg His Ala His Gly Asp Gln Tyr Lys
1               5                   10
```

<210> SEQ ID NO 250
<211> LENGTH: 20
<212> TYPE: PRT
<213> ORGANISM: Homo sapiens

<400> SEQUENCE: 250

```
Thr Ile Glu Ala Glu Ala Ala His Gly Thr Val Thr Arg His Tyr Arg
1               5                   10                  15

Glu His Gln Lys
            20
```

<210> SEQ ID NO 251
<211> LENGTH: 21
<212> TYPE: PRT
<213> ORGANISM: Homo sapiens

<400> SEQUENCE: 251

```
His Arg Gly Tyr Leu Gly Val Met Pro Ala Tyr Ser Ala Ala Glu Asp
1               5                   10                  15

Ala Leu Thr Thr Lys
            20
```

<210> SEQ ID NO 252
<211> LENGTH: 24
<212> TYPE: PRT
<213> ORGANISM: Homo sapiens

<400> SEQUENCE: 252

```
Pro Gly Ala His Ile Asn Ala Val Gly Ala Ser Arg Pro Asp Trp Arg
1               5                   10                  15

Glu Leu Asp Asp Glu Leu Met Lys
            20
```

<210> SEQ ID NO 253
<211> LENGTH: 17
<212> TYPE: PRT
<213> ORGANISM: Homo sapiens

<400> SEQUENCE: 253

```
Gly Glu Met Met Asp Leu Gln His Gly Ser Leu Phe Leu Arg Thr Pro
1               5                   10                  15

Lys
```

<210> SEQ ID NO 254
<211> LENGTH: 22
<212> TYPE: PRT
<213> ORGANISM: Homo sapiens

<400> SEQUENCE: 254

```
His Arg Val Ile Gly Ser Gly Cys Asn Leu Asp Ser Ala Arg Phe Arg
```

-continued

```
1               5                   10                  15
Tyr Leu Met Ala Glu Lys
                20

<210> SEQ ID NO 255
<211> LENGTH: 28
<212> TYPE: PRT
<213> ORGANISM: Homo sapiens

<400> SEQUENCE: 255

Ile Val Val Val Thr Ala Gly Val Arg Gln Gln Glu Gly Glu Ser Arg
1               5                   10                  15

Leu Asn Leu Val Gln Arg Asn Val Asn Val Phe Lys
                20                  25

<210> SEQ ID NO 256
<211> LENGTH: 12
<212> TYPE: PRT
<213> ORGANISM: Homo sapiens

<400> SEQUENCE: 256

Leu Gln Gln Arg Leu Gly Arg Glu Val Glu Glu Lys
1               5                   10

<210> SEQ ID NO 257
<211> LENGTH: 14
<212> TYPE: PRT
<213> ORGANISM: Homo sapiens

<400> SEQUENCE: 257

Gly Cys Asp Val Val Val Ile Pro Ala Gly Val Pro Arg Lys
1               5                   10

<210> SEQ ID NO 258
<211> LENGTH: 29
<212> TYPE: PRT
<213> ORGANISM: Homo sapiens

<400> SEQUENCE: 258

Asn Ser Pro Leu Val Ser Arg Leu Thr Leu Tyr Asp Ile Ala His Thr
1               5                   10                  15

Pro Gly Val Ala Ala Asp Leu Ser His Ile Glu Thr Lys
                20                  25

<210> SEQ ID NO 259
<211> LENGTH: 20
<212> TYPE: PRT
<213> ORGANISM: Homo sapiens

<400> SEQUENCE: 259

Gln Glu Gly Ile Ile Phe Ile Gly Pro Pro Pro Ser Ala Ile Arg Asp
1               5                   10                  15

Met Gly Ile Lys
                20

<210> SEQ ID NO 260
<211> LENGTH: 23
<212> TYPE: PRT
<213> ORGANISM: Homo sapiens

<400> SEQUENCE: 260

Asn Leu Arg Val Asn Ala Gly Asp Gln Pro Gly Ala Asp Leu Gly Pro
1               5                   10                  15
```

```
Leu Ile Thr Pro Gln Ala Lys
         20

<210> SEQ ID NO 261
<211> LENGTH: 20
<212> TYPE: PRT
<213> ORGANISM: Homo sapiens

<400> SEQUENCE: 261

Ser Met Gly Ala Ile Val Arg Gly Phe Asp Thr Arg Ala Ala Ala Leu
1               5                   10                  15

Glu Gln Phe Lys
         20

<210> SEQ ID NO 262
<211> LENGTH: 11
<212> TYPE: PRT
<213> ORGANISM: Homo sapiens

<400> SEQUENCE: 262

Pro Ile Phe Ser Arg Asp Met Asn Glu Ala Lys
1               5                   10

<210> SEQ ID NO 263
<211> LENGTH: 11
<212> TYPE: PRT
<213> ORGANISM: Homo sapiens

<400> SEQUENCE: 263

Arg Thr Ile Ala Gln Asp Tyr Gly Val Leu Lys
1               5                   10

<210> SEQ ID NO 264
<211> LENGTH: 27
<212> TYPE: PRT
<213> ORGANISM: Homo sapiens

<400> SEQUENCE: 264

Glu Gly Gly Leu Gly Pro Leu Asn Ile Pro Leu Leu Ala Asp Val Thr
1               5                   10                  15

Arg Arg Leu Ser Glu Asp Tyr Gly Val Leu Lys
         20                  25

<210> SEQ ID NO 265
<211> LENGTH: 13
<212> TYPE: PRT
<213> ORGANISM: Homo sapiens

<400> SEQUENCE: 265

Val Arg Leu Leu Ala Asp Pro Thr Gly Ala Phe Gly Lys
1               5                   10

<210> SEQ ID NO 266
<211> LENGTH: 25
<212> TYPE: PRT
<213> ORGANISM: Homo sapiens

<400> SEQUENCE: 266

Leu Pro Phe Pro Ile Ile Asp Asp Arg Asn Arg Glu Leu Ala Ile Leu
1               5                   10                  15

Leu Gly Met Leu Asp Pro Ala Glu Lys
         20                  25
```

```
<210> SEQ ID NO 267
<211> LENGTH: 15
<212> TYPE: PRT
<213> ORGANISM: Homo sapiens

<400> SEQUENCE: 267

Asp Arg Met Val Asn Ser Asn Leu Ala Ser Val Glu Glu Leu Lys
1               5                   10                  15

<210> SEQ ID NO 268
<211> LENGTH: 19
<212> TYPE: PRT
<213> ORGANISM: Homo sapiens

<400> SEQUENCE: 268

His Ser Leu Asp Ala Ser Gln Gly Thr Ala Thr Gly Pro Arg Gly Ile
1               5                   10                  15

Phe Thr Lys

<210> SEQ ID NO 269
<211> LENGTH: 16
<212> TYPE: PRT
<213> ORGANISM: Homo sapiens

<400> SEQUENCE: 269

Ser Ala Ala Val Val Phe Ala Ser Thr Asp Arg Ala Leu Gln Asn Lys
1               5                   10                  15

<210> SEQ ID NO 270
<211> LENGTH: 17
<212> TYPE: PRT
<213> ORGANISM: Homo sapiens

<400> SEQUENCE: 270

Ser Asp Ile Gly Glu Val Ile Leu Val Gly Gly Met Thr Arg Met Pro
1               5                   10                  15

Lys

<210> SEQ ID NO 271
<211> LENGTH: 16
<212> TYPE: PRT
<213> ORGANISM: Homo sapiens

<400> SEQUENCE: 271

Ile Val Arg Ala Ser Asn Gly Asp Ala Trp Val Glu Ala His Gly Lys
1               5                   10                  15

<210> SEQ ID NO 272
<211> LENGTH: 11
<212> TYPE: PRT
<213> ORGANISM: Homo sapiens

<400> SEQUENCE: 272

Val Thr Leu Glu Tyr Arg Pro Val Ile Asp Lys
1               5                   10

<210> SEQ ID NO 273
<211> LENGTH: 12
<212> TYPE: PRT
<213> ORGANISM: Homo sapiens

<400> SEQUENCE: 273

Ile Tyr Gln Arg Ala Phe Gly Gly Gln Ser Leu Lys
```

```
<210> SEQ ID NO 274
<211> LENGTH: 28
<212> TYPE: PRT
<213> ORGANISM: Homo sapiens

<400> SEQUENCE: 274

Pro Val Ser Phe Ile Ala Gly Leu Thr Ala Pro Pro Gly Arg Arg
1               5                   10                  15

Met Gly His Ala Gly Ala Ile Ile Ala Gly Gly Lys
            20                  25

<210> SEQ ID NO 275
<211> LENGTH: 12
<212> TYPE: PRT
<213> ORGANISM: Homo sapiens

<400> SEQUENCE: 275

Ile Asn Phe Asp Ser Asn Ser Ala Tyr Arg Gln Lys
1               5                   10

<210> SEQ ID NO 276
<211> LENGTH: 13
<212> TYPE: PRT
<213> ORGANISM: Homo sapiens

<400> SEQUENCE: 276

Gly Arg Ile Cys Asn Gln Val Leu Val Cys Glu Arg Lys
1               5                   10

<210> SEQ ID NO 277
<211> LENGTH: 15
<212> TYPE: PRT
<213> ORGANISM: Homo sapiens

<400> SEQUENCE: 277

Ile Phe Asp Leu Gln Asp Trp Thr Gln Glu Asp Glu Arg Asp Lys
1               5                   10                  15

<210> SEQ ID NO 278
<211> LENGTH: 23
<212> TYPE: PRT
<213> ORGANISM: Homo sapiens

<400> SEQUENCE: 278

Gly Leu Thr Ala Val Ser Asn Asn Ala Gly Val Asp Asn Phe Gly Leu
1               5                   10                  15

Gly Leu Leu Leu Arg Ser Lys
            20

<210> SEQ ID NO 279
<211> LENGTH: 21
<212> TYPE: PRT
<213> ORGANISM: Homo sapiens

<400> SEQUENCE: 279

His Leu Ser Val Asn Asp Leu Pro Val Gly Arg Ser Val Glu Glu Thr
1               5                   10                  15

Leu Arg Leu Val Lys
            20

<210> SEQ ID NO 280
```

```
<211> LENGTH: 21
<212> TYPE: PRT
<213> ORGANISM: Homo sapiens

<400> SEQUENCE: 280

His Leu Ser Val Asn Asp Leu Pro Val Gly Arg Ser Val Glu Glu Thr
1               5                   10                  15

Leu Arg Leu Val Lys
            20

<210> SEQ ID NO 281
<211> LENGTH: 25
<212> TYPE: PRT
<213> ORGANISM: Homo sapiens

<400> SEQUENCE: 281

Ala Leu Thr Ser Phe Glu Arg Asp Ser Ile Phe Ser Asn Leu Thr Gly
1               5                   10                  15

Gln Leu Asp Tyr Gln Gly Phe Glu Lys
            20                  25

<210> SEQ ID NO 282
<211> LENGTH: 12
<212> TYPE: PRT
<213> ORGANISM: Homo sapiens

<400> SEQUENCE: 282

Ser Asp Ser His Pro Ser Asp Ala Leu Thr Arg Lys
1               5                   10

<210> SEQ ID NO 283
<211> LENGTH: 20
<212> TYPE: PRT
<213> ORGANISM: Homo sapiens

<400> SEQUENCE: 283

Ile Thr Ala Phe Val Val Glu Arg Gly Phe Gly Ile Thr His Gly
1               5                   10                  15

Pro Pro Glu Lys
            20

<210> SEQ ID NO 284
<211> LENGTH: 16
<212> TYPE: PRT
<213> ORGANISM: Homo sapiens

<400> SEQUENCE: 284

Ala Leu Val Glu Arg Gly Gly Val Val Thr Ser Asn Pro Leu Gly Phe
1               5                   10                  15

<210> SEQ ID NO 285
<211> LENGTH: 28
<212> TYPE: PRT
<213> ORGANISM: Homo sapiens

<400> SEQUENCE: 285

Val Val Arg Thr Ala Leu Leu Asp Ala Ala Gly Val Ala Ser Leu Leu
1               5                   10                  15

Thr Thr Ala Glu Val Val Val Thr Glu Ile Pro Lys
            20                  25

<210> SEQ ID NO 286
<211> LENGTH: 29
```

```
<212> TYPE: PRT
<213> ORGANISM: Homo sapiens

<400> SEQUENCE: 286

Leu Val Gln Asp Val Ala Asn Asn Thr Asn Glu Glu Ala Gly Asp Gly
1               5                   10                  15

Thr Thr Thr Ala Thr Val Leu Ala Arg Ser Ile Ala Lys
            20                  25

<210> SEQ ID NO 287
<211> LENGTH: 23
<212> TYPE: PRT
<213> ORGANISM: Homo sapiens

<400> SEQUENCE: 287

Gly Ala Asn Pro Val Glu Ile Arg Arg Gly Val Met Leu Ala Val Asp
1               5                   10                  15

Ala Val Ile Ala Glu Leu Lys
            20

<210> SEQ ID NO 288
<211> LENGTH: 14
<212> TYPE: PRT
<213> ORGANISM: Homo sapiens

<400> SEQUENCE: 288

Gly Arg Thr Val Ile Ile Glu Gln Ser Trp Gly Ser Pro Lys
1               5                   10

<210> SEQ ID NO 289
<211> LENGTH: 23
<212> TYPE: PRT
<213> ORGANISM: Homo sapiens

<400> SEQUENCE: 289

Gly Ala Asn Pro Val Glu Ile Arg Arg Gly Val Met Leu Ala Val Asp
1               5                   10                  15

Ala Val Ile Ala Glu Leu Lys
            20

<210> SEQ ID NO 290
<211> LENGTH: 27
<212> TYPE: PRT
<213> ORGANISM: Homo sapiens

<400> SEQUENCE: 290

Phe Gly Ala Asp Ala Arg Ala Leu Met Leu Gln Gly Val Asp Leu Leu
1               5                   10                  15

Ala Asp Ala Val Ala Val Thr Met Gly Pro Lys
            20                  25

<210> SEQ ID NO 291
<211> LENGTH: 26
<212> TYPE: PRT
<213> ORGANISM: Homo sapiens

<400> SEQUENCE: 291

Pro Ala Arg Val Ile Leu Gln Asp Phe Thr Gly Val Pro Ala Val Val
1               5                   10                  15

Asp Phe Ala Ala Met Arg Asp Ala Val Lys
            20                  25
```

```
<210> SEQ ID NO 292
<211> LENGTH: 14
<212> TYPE: PRT
<213> ORGANISM: Homo sapiens

<400> SEQUENCE: 292

Thr Val Arg Gly Ser Leu Glu Arg Gln Ala Gly Gln Ile Lys
1               5                   10

<210> SEQ ID NO 293
<211> LENGTH: 14
<212> TYPE: PRT
<213> ORGANISM: Homo sapiens

<400> SEQUENCE: 293

Thr Val Arg Gly Ser Leu Glu Arg Gln Ala Gly Gln Ile Lys
1               5                   10

<210> SEQ ID NO 294
<211> LENGTH: 22
<212> TYPE: PRT
<213> ORGANISM: Homo sapiens

<400> SEQUENCE: 294

Ala Ser Gly Val Ser Leu Leu Glu Ala Leu Asp Thr Ile Leu Pro Pro
1               5                   10                  15

Thr Arg Pro Thr Asp Lys
            20

<210> SEQ ID NO 295
<211> LENGTH: 35
<212> TYPE: PRT
<213> ORGANISM: Homo sapiens

<400> SEQUENCE: 295

Ile Gly Gly Ile Gly Thr Val Pro Val Gly Arg Val Glu Thr Gly Ile
1               5                   10                  15

Leu Arg Pro Gly Met Val Val Thr Phe Ala Pro Val Asn Ile Thr Thr
            20                  25                  30

Glu Val Lys
        35

<210> SEQ ID NO 296
<211> LENGTH: 14
<212> TYPE: PRT
<213> ORGANISM: Homo sapiens

<400> SEQUENCE: 296

Val Asn Phe Thr Val Asp Gln Ile Arg Ala Ile Met Asp Lys
1               5                   10

<210> SEQ ID NO 297
<211> LENGTH: 14
<212> TYPE: PRT
<213> ORGANISM: Homo sapiens

<400> SEQUENCE: 297

Val Ala Pro Ala Gln Pro Ser Glu Glu Gly Pro Gly Arg Lys
1               5                   10

<210> SEQ ID NO 298
<211> LENGTH: 12
<212> TYPE: PRT
<213> ORGANISM: Homo sapiens
```

<400> SEQUENCE: 298

Ala Val Arg Leu Leu Pro Gly Glu Leu Ala Lys
1               5                  10

<210> SEQ ID NO 299
<211> LENGTH: 15
<212> TYPE: PRT
<213> ORGANISM: Homo sapiens

<400> SEQUENCE: 299

Leu Pro Phe Gln Arg Leu Val Arg Glu Ile Ala Gln Asp Phe Lys
1               5                  10                  15

<210> SEQ ID NO 300
<211> LENGTH: 15
<212> TYPE: PRT
<213> ORGANISM: Homo sapiens

<400> SEQUENCE: 300

Arg Ile Ser Gly Leu Ile Tyr Glu Glu Thr Arg Gly Val Leu Lys
1               5                  10                  15

<210> SEQ ID NO 301
<211> LENGTH: 18
<212> TYPE: PRT
<213> ORGANISM: Homo sapiens

<400> SEQUENCE: 301

Val Phe Leu Glu Asn Val Ile Arg Asp Ala Val Thr Tyr Thr Glu His
1               5                  10                  15

Ala Lys

<210> SEQ ID NO 302
<211> LENGTH: 17
<212> TYPE: PRT
<213> ORGANISM: Homo sapiens

<400> SEQUENCE: 302

Glu Ser Ser Ser His His Pro Gly Ile Ala Glu Phe Pro Ser Arg Gly
1               5                  10                  15

Lys

<210> SEQ ID NO 303
<211> LENGTH: 9
<212> TYPE: PRT
<213> ORGANISM: Homo sapiens

<400> SEQUENCE: 303

Arg Leu Asp Gly Ser Val Asp Phe Lys
1               5

<210> SEQ ID NO 304
<211> LENGTH: 15
<212> TYPE: PRT
<213> ORGANISM: Homo sapiens

<400> SEQUENCE: 304

Leu Arg Thr Glu Gly Asp Gly Val Tyr Thr Leu Asn Asn Glu Lys
1               5                  10                  15

<210> SEQ ID NO 305
<211> LENGTH: 12

```
<212> TYPE: PRT
<213> ORGANISM: Homo sapiens

<400> SEQUENCE: 305

Asp Tyr Glu Leu Leu Cys Leu Asp Gly Thr Arg Lys
1               5                   10

<210> SEQ ID NO 306
<211> LENGTH: 27
<212> TYPE: PRT
<213> ORGANISM: Homo sapiens

<400> SEQUENCE: 306

Pro Ser Gly Val Gln Met Asp Pro Cys Cys Arg Ala Leu Tyr Asp Phe
1               5                   10                  15

Glu Pro Glu Asn Glu Gly Glu Leu Gly Phe Lys
            20                  25

<210> SEQ ID NO 307
<211> LENGTH: 14
<212> TYPE: PRT
<213> ORGANISM: Homo sapiens

<400> SEQUENCE: 307

Gln Tyr Met Arg Arg Ser Thr Cys Thr Ile Asn Tyr Ser Lys
1               5                   10

<210> SEQ ID NO 308
<211> LENGTH: 8
<212> TYPE: PRT
<213> ORGANISM: Homo sapiens

<400> SEQUENCE: 308

Leu Ile Leu Ile Ala Arg Asn Lys
1               5

<210> SEQ ID NO 309
<211> LENGTH: 37
<212> TYPE: PRT
<213> ORGANISM: Homo sapiens

<400> SEQUENCE: 309

Val Ile Val Val Trp Val Gly Thr Asn Asn His Glu Asn Thr Ala Glu
1               5                   10                  15

Glu Val Ala Gly Gly Ile Glu Ala Ile Val Gln Leu Ile Asn Thr Arg
            20                  25                  30

Gln Pro Gln Ala Lys
        35

<210> SEQ ID NO 310
<211> LENGTH: 18
<212> TYPE: PRT
<213> ORGANISM: Homo sapiens

<400> SEQUENCE: 310

Glu Val Asp Val Gly Leu Ala Ala Asp Val Gly Thr Leu Gln Arg Leu
1               5                   10                  15

Pro Lys

<210> SEQ ID NO 311
<211> LENGTH: 17
<212> TYPE: PRT
<213> ORGANISM: Homo sapiens
```

```
<400> SEQUENCE: 311

His Glu Glu Ala Pro Gly His Arg Pro Thr Thr Asn Pro Asn Ala Ser
1               5                   10                  15

Lys

<210> SEQ ID NO 312
<211> LENGTH: 16
<212> TYPE: PRT
<213> ORGANISM: Homo sapiens

<400> SEQUENCE: 312

Gly Glu Thr Pro Val Asn Ser Thr Met Ser Ile Gly Gln Ala Arg Lys
1               5                   10                  15

<210> SEQ ID NO 313
<211> LENGTH: 19
<212> TYPE: PRT
<213> ORGANISM: Homo sapiens

<400> SEQUENCE: 313

Val Arg Ile Gln Thr Gln Pro Gly Tyr Ala Asn Thr Leu Arg Asp Ala
1               5                   10                  15

Ala Pro Lys

<210> SEQ ID NO 314
<211> LENGTH: 24
<212> TYPE: PRT
<213> ORGANISM: Homo sapiens

<400> SEQUENCE: 314

Asn Val Gly Cys Leu Gln Glu Ala Leu Gln Leu Ala Thr Ser Phe Ala
1               5                   10                  15

Gln Leu Arg Leu Gly Asp Val Lys
            20

<210> SEQ ID NO 315
<211> LENGTH: 19
<212> TYPE: PRT
<213> ORGANISM: Homo sapiens

<400> SEQUENCE: 315

Phe Ala Asp Leu Thr Asp Ala Ala Arg Asn Ala Glu Leu Leu Arg
1               5                   10                  15

Gln Ala Lys

<210> SEQ ID NO 316
<211> LENGTH: 24
<212> TYPE: PRT
<213> ORGANISM: Homo sapiens

<400> SEQUENCE: 316

Glu Ile Arg Thr Gln Tyr Glu Ala Met Ala Ser Ser Asn Met His Glu
1               5                   10                  15

Ala Glu Glu Trp Tyr Arg Ser Lys
            20

<210> SEQ ID NO 317
<211> LENGTH: 16
<212> TYPE: PRT
<213> ORGANISM: Homo sapiens
```

```
<400> SEQUENCE: 317

Met Ala Ser Ser Asn Met His Glu Ala Glu Glu Trp Tyr Arg Ser Lys
1               5                   10                  15

<210> SEQ ID NO 318
<211> LENGTH: 15
<212> TYPE: PRT
<213> ORGANISM: Homo sapiens

<400> SEQUENCE: 318

Ala Ser Ser Asn Met His Glu Ala Glu Glu Trp Tyr Arg Ser Lys
1               5                   10                  15

<210> SEQ ID NO 319
<211> LENGTH: 12
<212> TYPE: PRT
<213> ORGANISM: Homo sapiens

<400> SEQUENCE: 319

Leu Ala Arg Leu Glu Glu Glu Gly Gln Ser Leu Lys
1               5                   10

<210> SEQ ID NO 320
<211> LENGTH: 17
<212> TYPE: PRT
<213> ORGANISM: Homo sapiens

<400> SEQUENCE: 320

Ile Leu Leu Ala Asn Phe Leu Ala Gln Thr Glu Ala Leu Met Arg Gly
1               5                   10                  15

Lys

<210> SEQ ID NO 321
<211> LENGTH: 21
<212> TYPE: PRT
<213> ORGANISM: Homo sapiens

<400> SEQUENCE: 321

Thr Val Glu Thr Arg Asp Gly Gln Val Ile Asn Glu Thr Ser Gln His
1               5                   10                  15

His Asp Asp Leu Glu
            20

<210> SEQ ID NO 322
<211> LENGTH: 16
<212> TYPE: PRT
<213> ORGANISM: Homo sapiens

<400> SEQUENCE: 322

Val Glu Leu Gln Glu Leu Asn Asp Arg Phe Ala Asn Tyr Ile Asp Lys
1               5                   10                  15

<210> SEQ ID NO 323
<211> LENGTH: 26
<212> TYPE: PRT
<213> ORGANISM: Homo sapiens

<400> SEQUENCE: 323

Ser Ser Val Pro Gly Val Arg Leu Leu Gln Asp Ser Val Asp Phe Ser
1               5                   10                  15

Leu Ala Asp Ala Ile Asn Thr Glu Phe Lys
            20                  25
```

<210> SEQ ID NO 324
<211> LENGTH: 15
<212> TYPE: PRT
<213> ORGANISM: Homo sapiens

<400> SEQUENCE: 324

Ala Leu Arg Asp Val Arg Gln Gln Tyr Glu Ser Val Ala Ala Lys
1               5                   10                  15

<210> SEQ ID NO 325
<211> LENGTH: 19
<212> TYPE: PRT
<213> ORGANISM: Homo sapiens

<400> SEQUENCE: 325

Gly Ala Glu Gly Gln Arg Pro Gly Phe Gly Tyr Gly Gly Arg Ala Ser
1               5                   10                  15

Asp Tyr Lys

<210> SEQ ID NO 326
<211> LENGTH: 15
<212> TYPE: PRT
<213> ORGANISM: Homo sapiens

<400> SEQUENCE: 326

Ser His Gly Arg Thr Gln Asp Glu Asn Pro Val Val His Phe Phe
1               5                   10                  15

<210> SEQ ID NO 327
<211> LENGTH: 24
<212> TYPE: PRT
<213> ORGANISM: Homo sapiens

<400> SEQUENCE: 327

Ser Arg Phe Ser Trp Gly Ala Glu Gly Gln Arg Pro Gly Phe Gly Tyr
1               5                   10                  15

Gly Gly Arg Ala Ser Asp Tyr Lys
            20

<210> SEQ ID NO 328
<211> LENGTH: 24
<212> TYPE: PRT
<213> ORGANISM: Homo sapiens

<400> SEQUENCE: 328

Ser Arg Phe Ser Trp Gly Ala Glu Gly Gln Arg Pro Gly Phe Gly Tyr
1               5                   10                  15

Gly Gly Arg Ala Ser Asp Tyr Lys
            20

<210> SEQ ID NO 329
<211> LENGTH: 21
<212> TYPE: PRT
<213> ORGANISM: Homo sapiens

<400> SEQUENCE: 329

Ser Trp Gly Ala Glu Gly Gln Arg Pro Gly Phe Gly Tyr Gly Gly Arg
1               5                   10                  15

Ala Ser Asp Tyr Lys
            20

<210> SEQ ID NO 330

```
<211> LENGTH: 14
<212> TYPE: PRT
<213> ORGANISM: Homo sapiens

<400> SEQUENCE: 330

Ser His Gly Arg Thr Gln Asp Glu Asn Pro Val Val His Phe
1               5                   10

<210> SEQ ID NO 331
<211> LENGTH: 15
<212> TYPE: PRT
<213> ORGANISM: Homo sapiens

<400> SEQUENCE: 331

Leu Gly Gly Arg Asp Ser Arg Ser Gly Ser Pro Met Ala Arg Arg
1               5                   10                  15

<210> SEQ ID NO 332
<211> LENGTH: 17
<212> TYPE: PRT
<213> ORGANISM: Homo sapiens

<400> SEQUENCE: 332

Glu Gly Gln Arg Pro Gly Phe Gly Tyr Gly Gly Arg Ala Ser Asp Tyr
1               5                   10                  15

Lys

<210> SEQ ID NO 333
<211> LENGTH: 10
<212> TYPE: PRT
<213> ORGANISM: Homo sapiens

<400> SEQUENCE: 333

Ala Ile Glu Ala Ala Leu Ala Ala Arg Lys
1               5                   10

<210> SEQ ID NO 334
<211> LENGTH: 13
<212> TYPE: PRT
<213> ORGANISM: Homo sapiens

<400> SEQUENCE: 334

Val Arg Leu Leu Ala Asp Pro Thr Gly Ala Phe Gly Lys
1               5                   10

<210> SEQ ID NO 335
<211> LENGTH: 19
<212> TYPE: PRT
<213> ORGANISM: Homo sapiens

<400> SEQUENCE: 335

Thr Gly Gly Ala Val Asp Arg Leu Thr Asp Thr Ser Arg Tyr Thr Gly
1               5                   10                  15

Ser His Lys

<210> SEQ ID NO 336
<211> LENGTH: 17
<212> TYPE: PRT
<213> ORGANISM: Homo sapiens

<400> SEQUENCE: 336

Val Ile Gly Asn Gln Ser Leu Val Asn Glu Leu Ala Phe Thr Ala Arg
1               5                   10                  15
```

Lys

<210> SEQ ID NO 337
<211> LENGTH: 12
<212> TYPE: PRT
<213> ORGANISM: Homo sapiens

<400> SEQUENCE: 337

Met Arg Ser Ser Glu Asn Phe Asp Glu Leu Leu Lys
1               5                   10

<210> SEQ ID NO 338
<211> LENGTH: 14
<212> TYPE: PRT
<213> ORGANISM: Homo sapiens

<400> SEQUENCE: 338

Tyr Ala Gly Gly Val Ala Glu Tyr Arg Ala Ser Glu Gly Lys
1               5                   10

<210> SEQ ID NO 339
<211> LENGTH: 10
<212> TYPE: PRT
<213> ORGANISM: Mus musculus

<400> SEQUENCE: 339

Arg Met Phe Leu Ser Phe Pro Thr Thr Lys
1               5                   10

<210> SEQ ID NO 340
<211> LENGTH: 18
<212> TYPE: PRT
<213> ORGANISM: Mus musculus

<400> SEQUENCE: 340

Val Gly Ala His Ala Gly Glu Tyr Gly Ala Glu Ala Leu Glu Arg Met
1               5                   10                  15

Phe Leu

<210> SEQ ID NO 341
<211> LENGTH: 14
<212> TYPE: PRT
<213> ORGANISM: Mus musculus

<400> SEQUENCE: 341

Thr Thr Arg Thr Ser Asp Val Gly Gly Tyr Tyr Tyr Glu Lys
1               5                   10

<210> SEQ ID NO 342
<211> LENGTH: 14
<212> TYPE: PRT
<213> ORGANISM: Mus musculus

<400> SEQUENCE: 342

Val Pro Gln Arg Ala Gly Glu Val Glu Arg Asp Leu Asp Lys
1               5                   10

<210> SEQ ID NO 343
<211> LENGTH: 10
<212> TYPE: PRT
<213> ORGANISM: Mus musculus

<400> SEQUENCE: 343

Leu His Val Ala Ile Leu Glu Arg Glu Lys

```
<210> SEQ ID NO 344
<211> LENGTH: 11
<212> TYPE: PRT
<213> ORGANISM: Mus musculus

<400> SEQUENCE: 344

Arg Val Glu Pro Leu Arg Asn Glu Leu Gln Lys
1               5                   10

<210> SEQ ID NO 345
<211> LENGTH: 22
<212> TYPE: PRT
<213> ORGANISM: Mus musculus

<400> SEQUENCE: 345

Glu Gly His Val Gly Leu Val Gln Glu Leu Gly Arg Gly Ser Ser
1               5                   10                  15

Val Asp Ser Ala Thr Lys
            20

<210> SEQ ID NO 346
<211> LENGTH: 38
<212> TYPE: PRT
<213> ORGANISM: Mus musculus

<400> SEQUENCE: 346

Ala Ile Val Phe Glu Ile Met Glu Ala Gly Glu Pro Thr Gly Pro Ile
1               5                   10                  15

Leu Gly Ala Glu Ala Leu Pro Gly Gly Leu Arg Thr Leu Pro Gln Glu
            20                  25                  30

Pro Gly Lys Pro Gln Lys
            35

<210> SEQ ID NO 347
<211> LENGTH: 20
<212> TYPE: PRT
<213> ORGANISM: Mus musculus

<400> SEQUENCE: 347

Ile Arg Glu Glu Tyr Pro Asp Arg Ile Met Asn Thr Phe Ser Val Met
1               5                   10                  15

Pro Ser Pro Lys
            20

<210> SEQ ID NO 348
<211> LENGTH: 40
<212> TYPE: PRT
<213> ORGANISM: Mus musculus

<400> SEQUENCE: 348

Gly Ile Leu Arg Thr Pro Asp Thr Ile Arg Arg Phe Gln Ser Val Pro
1               5                   10                  15

Ala Gln Pro Gly Gln Thr Ser Pro Leu Leu Gln Tyr Phe Gly Ile Leu
            20                  25                  30

Leu Asp Gln Gly Gln Leu Asn Lys
            35                  40

<210> SEQ ID NO 349
<211> LENGTH: 16
<212> TYPE: PRT
```

<213> ORGANISM: Mus musculus

<400> SEQUENCE: 349

Tyr Glu Ser Leu Glu Leu Cys Arg Pro Val Leu Gln Gln Gly Arg Lys
1               5                   10                  15

<210> SEQ ID NO 350
<211> LENGTH: 31
<212> TYPE: PRT
<213> ORGANISM: Mus musculus

<400> SEQUENCE: 350

Ser Tyr Leu Arg Leu Arg Pro Asp Arg Val Ala Met Gln Asp Ala Thr
1               5                   10                  15

Ala Gln Met Ala Met Leu Gln Phe Ile Ser Ser Gly Leu Ser Lys
            20                  25                  30

<210> SEQ ID NO 351
<211> LENGTH: 11
<212> TYPE: PRT
<213> ORGANISM: Mus musculus

<400> SEQUENCE: 351

Ser Ile Glu Leu Glu Ser Val Arg Gly Thr Lys
1               5                   10

<210> SEQ ID NO 352
<211> LENGTH: 17
<212> TYPE: PRT
<213> ORGANISM: Mus musculus

<400> SEQUENCE: 352

Ala Glu Ser Ala Val Ile Val Ala Asn Pro Arg Glu Glu Ile Ile Val
1               5                   10                  15

Lys

<210> SEQ ID NO 353
<211> LENGTH: 29
<212> TYPE: PRT
<213> ORGANISM: Mus musculus

<400> SEQUENCE: 353

Glu Ala Gln Ile Arg Glu Thr Glu Thr Phe Ser Asp Ser Pro Ile
1               5                   10                  15

Glu Ile Ile Asp Glu Phe Pro Thr Leu Ile Ser Ser Lys
            20                  25

<210> SEQ ID NO 354
<211> LENGTH: 26
<212> TYPE: PRT
<213> ORGANISM: Mus musculus

<400> SEQUENCE: 354

Glu Trp Thr Asn Glu Val Phe Ser Leu Ala Thr Asn Leu Leu Ala Gln
1               5                   10                  15

Asn Met Ser Arg Asp Ala Phe Leu Glu Lys
            20                  25

<210> SEQ ID NO 355
<211> LENGTH: 12
<212> TYPE: PRT
<213> ORGANISM: Mus musculus

```
<400> SEQUENCE: 355

Ala Asp Asp Gly Arg Pro Phe Pro Gln Val Ile Lys
1               5                  10

<210> SEQ ID NO 356
<211> LENGTH: 29
<212> TYPE: PRT
<213> ORGANISM: Mus musculus

<400> SEQUENCE: 356

Leu Val Gln Asp Val Ala Asn Asn Thr Asn Glu Glu Ala Gly Asp Gly
1               5                   10                  15

Thr Thr Thr Ala Thr Val Leu Ala Arg Ser Ile Ala Lys
            20                  25

<210> SEQ ID NO 357
<211> LENGTH: 17
<212> TYPE: PRT
<213> ORGANISM: Mus musculus

<400> SEQUENCE: 357

Ala Leu Glu Ser Pro Glu Arg Pro Phe Leu Ala Ile Leu Gly Gly Ala
1               5                   10                  15

Lys

<210> SEQ ID NO 358
<211> LENGTH: 13
<212> TYPE: PRT
<213> ORGANISM: Mus musculus

<400> SEQUENCE: 358

Arg Val Val Met Arg Val Asp Phe Asn Val Pro Met Lys
1               5                   10

<210> SEQ ID NO 359
<211> LENGTH: 10
<212> TYPE: PRT
<213> ORGANISM: Mus musculus

<400> SEQUENCE: 359

Tyr Glu Trp Asp Val Ala Glu Ala Arg Lys
1               5                   10

<210> SEQ ID NO 360
<211> LENGTH: 30
<212> TYPE: PRT
<213> ORGANISM: Mus musculus

<400> SEQUENCE: 360

Val Leu Glu Asn Ala Glu Gly Ala Arg Thr Thr Pro Ser Val Val Ala
1               5                   10                  15

Phe Thr Ala Asp Gly Glu Arg Leu Val Gly Met Pro Ala Lys
            20                  25                  30

<210> SEQ ID NO 361
<211> LENGTH: 16
<212> TYPE: PRT
<213> ORGANISM: Mus musculus

<400> SEQUENCE: 361

Asn Leu Val Thr Glu Asp Val Met Arg Met Leu Val Asp Leu Ala Lys
1               5                   10                  15
```

<210> SEQ ID NO 362
<211> LENGTH: 21
<212> TYPE: PRT
<213> ORGANISM: Mus musculus

<400> SEQUENCE: 362

Asp Leu Phe Asp Pro Ile Ile Glu Asp Arg His Gly Gly Tyr Lys Pro
1               5                   10                  15

Ser Asp Glu His Lys
            20

<210> SEQ ID NO 363
<211> LENGTH: 15
<212> TYPE: PRT
<213> ORGANISM: Mus musculus

<400> SEQUENCE: 363

Asp Leu Phe Asp Pro Ile Ile Glu Asp Arg His Gly Gly Tyr Lys
1               5                   10                  15

<210> SEQ ID NO 364
<211> LENGTH: 18
<212> TYPE: PRT
<213> ORGANISM: Mus musculus

<400> SEQUENCE: 364

Gln Ile Ser Val Arg Gly Leu Ala Gly Leu Gly Asp Val Ala Glu Val
1               5                   10                  15

Arg Lys

<210> SEQ ID NO 365
<211> LENGTH: 23
<212> TYPE: PRT
<213> ORGANISM: Mus musculus

<400> SEQUENCE: 365

Asp Val Gln Arg Glu Ile Ala Asp Leu Gly Glu Ala Leu Ala Thr Ala
1               5                   10                  15

Val Ile Pro Gln Trp Gln Lys
            20

<210> SEQ ID NO 366
<211> LENGTH: 28
<212> TYPE: PRT
<213> ORGANISM: Mus musculus

<400> SEQUENCE: 366

Gly Ile Ile Asp Ser Thr His Thr Glu Gln Arg Gln Val Val Ala Val
1               5                   10                  15

Thr Gly Asp Gly Thr Asn Asp Gly Pro Ala Leu Lys
            20                  25

<210> SEQ ID NO 367
<211> LENGTH: 14
<212> TYPE: PRT
<213> ORGANISM: Mus musculus

<400> SEQUENCE: 367

Ile Thr Pro Gly Ala Arg Gly Ala Phe Ser Glu Glu Tyr Lys
1               5                   10

<210> SEQ ID NO 368

```
<210> SEQ ID NO 368
<211> LENGTH: 13
<212> TYPE: PRT
<213> ORGANISM: Mus musculus

<400> SEQUENCE: 368

Thr Leu Phe Ile Leu Arg Gly Leu Pro Gly Ser Gly Lys
1               5                   10

<210> SEQ ID NO 369
<211> LENGTH: 14
<212> TYPE: PRT
<213> ORGANISM: Mus musculus

<400> SEQUENCE: 369

Glu Leu Arg Gln Phe Val Pro Gly Asp Glu Pro Arg Glu Lys
1               5                   10

<210> SEQ ID NO 370
<211> LENGTH: 17
<212> TYPE: PRT
<213> ORGANISM: Mus musculus

<400> SEQUENCE: 370

Met Val Ser Gly Met Tyr Leu Gly Glu Leu Val Arg Leu Ile Leu Val
1               5                   10                  15

Lys

<210> SEQ ID NO 371
<211> LENGTH: 20
<212> TYPE: PRT
<213> ORGANISM: Mus musculus

<400> SEQUENCE: 371

Arg Glu Leu Gly Leu Ala Glu Ser Asp Ile Val Asp Ile Pro Gln Leu
1               5                   10                  15

Phe Phe Leu Lys
            20

<210> SEQ ID NO 372
<211> LENGTH: 18
<212> TYPE: PRT
<213> ORGANISM: Mus musculus

<400> SEQUENCE: 372

Thr Leu Tyr Arg Thr Met Thr Gly Leu Asp Thr Pro Val Leu Met Val
1               5                   10                  15

Ile Lys

<210> SEQ ID NO 373
<211> LENGTH: 12
<212> TYPE: PRT
<213> ORGANISM: Mus musculus

<400> SEQUENCE: 373

Glu Glu Leu Glu Arg Gln Ala Val Asp Gln Ile Lys
1               5                   10

<210> SEQ ID NO 374
<211> LENGTH: 23
<212> TYPE: PRT
<213> ORGANISM: Mus musculus

<400> SEQUENCE: 374
```

-continued

Ile Asp Ile Ile Pro Asn Pro Gln Glu Arg Thr Leu Thr Leu Val Asp
1               5                   10                  15

Thr Gly Ile Gly Met Thr Lys
            20

<210> SEQ ID NO 375
<211> LENGTH: 19
<212> TYPE: PRT
<213> ORGANISM: Mus musculus

<400> SEQUENCE: 375

Gly Glu Ala Ala Ala Glu Arg Pro Gly Glu Ala Ala Val Ala Ser Ser
1               5                   10                  15

Pro Ser Lys

<210> SEQ ID NO 376
<211> LENGTH: 60
<212> TYPE: PRT
<213> ORGANISM: Mus musculus

<400> SEQUENCE: 376

Ala Glu Glu Pro Leu Ala Ala Val Thr Pro Ala Val Gly Leu Asp Leu
1               5                   10                  15

Gly Met Asp Thr Arg Ala Glu Glu Pro Val Glu Glu Ala Val Ile Ile
            20                  25                  30

Pro Gly Ala Asp Ala Asp Ala Val Gly Thr Leu Val Ser Ala Ala
        35                  40                  45

Glu Gly Ala Pro Gly Glu Ala Glu Ala Glu Lys
    50                  55                  60

<210> SEQ ID NO 377
<211> LENGTH: 14
<212> TYPE: PRT
<213> ORGANISM: Mus musculus

<400> SEQUENCE: 377

Ser Arg Leu Gln Thr Ala Pro Val Pro Met Pro Asp Leu Lys
1               5                   10

<210> SEQ ID NO 378
<211> LENGTH: 21
<212> TYPE: PRT
<213> ORGANISM: Mus musculus

<400> SEQUENCE: 378

Leu Leu Gly Thr Leu Arg Met Leu Ile Asp Ala Gln Ala Glu Ala Ala
1               5                   10                  15

Glu Gln Leu Gly Lys
            20

<210> SEQ ID NO 379
<211> LENGTH: 16
<212> TYPE: PRT
<213> ORGANISM: Mus musculus

<400> SEQUENCE: 379

Tyr Tyr Ile Thr Ile Ile Asp Ala Pro Gly His Arg Asp Phe Ile Lys
1               5                   10                  15

<210> SEQ ID NO 380
<211> LENGTH: 41
<212> TYPE: PRT

<213> ORGANISM: Mus musculus

<400> SEQUENCE: 380

Tyr Ala His Leu Val Asp Val Gly Gln Val Gly Asn Val Pro Ile
1               5                   10                  15

Pro Val Pro Leu Pro Met Phe Ser Phe Thr Gly Ser Arg Ser Ser Phe
            20                  25                  30

Arg Gly Asp Thr Asn Phe Tyr Gly Lys
        35                  40

<210> SEQ ID NO 381
<211> LENGTH: 12
<212> TYPE: PRT
<213> ORGANISM: Mus musculus

<400> SEQUENCE: 381

Arg Ala Glu Val Asn Gly Leu Ala Ala Gln Gly Lys
1               5                   10

<210> SEQ ID NO 382
<211> LENGTH: 18
<212> TYPE: PRT
<213> ORGANISM: Mus musculus

<400> SEQUENCE: 382

Gly Leu Asp Pro Ala Arg Val Asn Val Pro Val Ile Gly Gly His Ala
1               5                   10                  15

Gly Lys

<210> SEQ ID NO 383
<211> LENGTH: 13
<212> TYPE: PRT
<213> ORGANISM: Mus musculus

<400> SEQUENCE: 383

Ala Thr Asp Phe Val Ala Asp Arg Ala Gly Thr Phe Lys
1               5                   10

<210> SEQ ID NO 384
<211> LENGTH: 15
<212> TYPE: PRT
<213> ORGANISM: Mus musculus

<400> SEQUENCE: 384

Ile Phe Asp Leu Gln Asp Trp Thr Gln Glu Asp Glu Arg Asp Lys
1               5                   10                  15

<210> SEQ ID NO 385
<211> LENGTH: 31
<212> TYPE: PRT
<213> ORGANISM: Mus musculus

<400> SEQUENCE: 385

Leu Ala Met Gln Glu Phe Met Ile Leu Pro Val Gly Ala Glu Ser Phe
1               5                   10                  15

Arg Asp Ala Met Arg Leu Gly Ala Glu Val Tyr His Thr Leu Lys
            20                  25                  30

<210> SEQ ID NO 386
<211> LENGTH: 21
<212> TYPE: PRT
<213> ORGANISM: Mus musculus

<400> SEQUENCE: 386

Val Arg Gly Val Asp Arg Thr Pro Tyr Leu Gly Asp Val Ala Val Val
1               5                   10                  15

Val His Pro Gly Lys
            20

<210> SEQ ID NO 387
<211> LENGTH: 16
<212> TYPE: PRT
<213> ORGANISM: Mus musculus

<400> SEQUENCE: 387

Met Asp Glu Asn Arg Phe Val Ala Val Thr Ser Ser Asn Ala Ala Lys
1               5                   10                  15

<210> SEQ ID NO 388
<211> LENGTH: 11
<212> TYPE: PRT
<213> ORGANISM: Mus musculus

<400> SEQUENCE: 388

Ser Ala Ala Asp Leu Ile Ser Gln Ala Arg Lys
1               5                   10

<210> SEQ ID NO 389
<211> LENGTH: 28
<212> TYPE: PRT
<213> ORGANISM: Mus musculus

<400> SEQUENCE: 389

Pro Val Val Tyr Ser Asn Thr Ile Gln Ser Leu Ala Ala Ile Val Arg
1               5                   10                  15

Ala Met Asp Thr Leu Gly Ile Glu Tyr Gly Asp Lys
            20                  25

<210> SEQ ID NO 390
<211> LENGTH: 15
<212> TYPE: PRT
<213> ORGANISM: Mus musculus

<400> SEQUENCE: 390

Glu Leu Gly Arg Val Ile Leu His Pro Thr Pro Asn Ser Pro Lys
1               5                   10                  15

<210> SEQ ID NO 391
<211> LENGTH: 12
<212> TYPE: PRT
<213> ORGANISM: Mus musculus

<400> SEQUENCE: 391

Asp Leu Gly Arg Ile Phe Arg Trp Leu Gly Pro Lys
1               5                   10

<210> SEQ ID NO 392
<211> LENGTH: 28
<212> TYPE: PRT
<213> ORGANISM: Mus musculus

<400> SEQUENCE: 392

Thr Val Gly Met Leu Ser Asn Met Ile Ala Phe Tyr Asp Met Ala Arg
1               5                   10                  15

Arg Ala Val Glu Thr Thr Ala Gln Ser Asp Asn Lys
            20                  25

```
<210> SEQ ID NO 393
<211> LENGTH: 21
<212> TYPE: PRT
<213> ORGANISM: Mus musculus

<400> SEQUENCE: 393

Glu Glu Phe Arg Pro Asn Ala Pro Tyr Arg Ile Phe Asn Thr Trp Leu
1               5                   10                  15

Gly Asp Pro Ser Lys
            20

<210> SEQ ID NO 394
<211> LENGTH: 31
<212> TYPE: PRT
<213> ORGANISM: Mus musculus

<400> SEQUENCE: 394

Arg Thr Gly Pro Ala Ala Thr Thr Leu Pro Asp Gly Ala Ala Ala Glu
1               5                   10                  15

Ser Leu Val Glu Ser Ser Glu Val Ala Val Ile Gly Phe Phe Lys
            20                  25                  30

<210> SEQ ID NO 395
<211> LENGTH: 12
<212> TYPE: PRT
<213> ORGANISM: Mus musculus

<400> SEQUENCE: 395

Ile Met Gln Gln Met Ser Asp His Arg Tyr Asp Lys
1               5                   10

<210> SEQ ID NO 396
<211> LENGTH: 19
<212> TYPE: PRT
<213> ORGANISM: Mus musculus

<400> SEQUENCE: 396

Asp Arg Leu Pro Leu Ala Val Val Gly Ser Asn Thr Ile Ile Glu Val
1               5                   10                  15

Asn Gly Lys

<210> SEQ ID NO 397
<211> LENGTH: 15
<212> TYPE: PRT
<213> ORGANISM: Mus musculus

<400> SEQUENCE: 397

Arg Arg Gln Leu Glu Asp Glu Arg Gln Leu Gln His Leu Lys
1               5                   10                  15

<210> SEQ ID NO 398
<211> LENGTH: 23
<212> TYPE: PRT
<213> ORGANISM: Mus musculus

<400> SEQUENCE: 398

His Met Leu Pro Thr Val Leu Arg Met Ala Gly Asp Pro Val Ala Asn
1               5                   10                  15

Val Arg Phe Asn Val Ala Lys
            20
```

```
<210> SEQ ID NO 399
<211> LENGTH: 4
<212> TYPE: PRT
<213> ORGANISM: Mus musculus

<400> SEQUENCE: 399

Ala Ala Ala Ala
1

<210> SEQ ID NO 400
<211> LENGTH: 13
<212> TYPE: PRT
<213> ORGANISM: Mus musculus

<400> SEQUENCE: 400

Pro Glu Asp Pro Ser Leu Leu Glu Asp Pro Arg Ile Lys
1               5                   10

<210> SEQ ID NO 401
<211> LENGTH: 26
<212> TYPE: PRT
<213> ORGANISM: Mus musculus

<400> SEQUENCE: 401

Ile Gly Arg Thr His Thr Gln Asp Ala Val Pro Leu Thr Leu Gly Gln
1               5                   10                  15

Glu Phe Ser Gly Tyr Val Gln Gln Val Lys
            20                  25

<210> SEQ ID NO 402
<211> LENGTH: 26
<212> TYPE: PRT
<213> ORGANISM: Mus musculus

<400> SEQUENCE: 402

Glu Val Val Ile Val Ser Ala Thr Arg Thr Pro Ile Gly Ser Phe Leu
1               5                   10                  15

Gly Ser Leu Ser Leu Leu Pro Ala Thr Lys
            20                  25

<210> SEQ ID NO 403
<211> LENGTH: 19
<212> TYPE: PRT
<213> ORGANISM: Mus musculus

<400> SEQUENCE: 403

Asp Ile Ile Leu Pro Phe Arg Val Ile Pro Leu Val Arg Glu Val Gly
1               5                   10                  15

Arg Thr Lys

<210> SEQ ID NO 404
<211> LENGTH: 15
<212> TYPE: PRT
<213> ORGANISM: Mus musculus

<400> SEQUENCE: 404

Leu Tyr Thr Leu Val Leu Thr Asp Pro Asp Ala Pro Ser Arg Lys
1               5                   10                  15

<210> SEQ ID NO 405
<211> LENGTH: 19
<212> TYPE: PRT
<213> ORGANISM: Mus musculus
```

```
<400> SEQUENCE: 405

Gly His Tyr Thr Glu Gly Ala Glu Leu Val Asp Ala Val Leu Asp Val
1               5                   10                  15

Val Arg Lys

<210> SEQ ID NO 406
<211> LENGTH: 22
<212> TYPE: PRT
<213> ORGANISM: Mus musculus

<400> SEQUENCE: 406

Ala Ala Glu Thr Tyr Gly Val Arg Thr Thr Asp Ile Phe Gln Thr Val
1               5                   10                  15

Asp Leu Trp Glu Gly Lys
            20

<210> SEQ ID NO 407
<211> LENGTH: 13
<212> TYPE: PRT
<213> ORGANISM: Mus musculus

<400> SEQUENCE: 407

Val Leu Ile Ser Asp Ser Leu Asp Pro Cys Cys Arg Lys
1               5                   10

<210> SEQ ID NO 408
<211> LENGTH: 39
<212> TYPE: PRT
<213> ORGANISM: Mus musculus

<400> SEQUENCE: 408

Glu Ser Ile Ser Val Ser Ser Glu Gln Leu Ala Gln Phe Arg Ser Leu
1               5                   10                  15

Leu Ser Asn Val Glu Gly Asp Asn Ala Val Pro Met Gln His Asn Asn
            20                  25                  30

Arg Pro Thr Gln Pro Leu Lys
        35

<210> SEQ ID NO 409
<211> LENGTH: 17
<212> TYPE: PRT
<213> ORGANISM: Mus musculus

<400> SEQUENCE: 409

Met Lys Gly Asp Tyr Tyr Arg Tyr Leu Ala Glu Val Ala Thr Gly Glu
1               5                   10                  15

Lys

<210> SEQ ID NO 410
<211> LENGTH: 13
<212> TYPE: PRT
<213> ORGANISM: Mus musculus

<400> SEQUENCE: 410

Asp Tyr Phe Leu Phe Arg Asp Gly Asp Ile Leu Gly Lys
1               5                   10

<210> SEQ ID NO 411
<211> LENGTH: 12
<212> TYPE: PRT
<213> ORGANISM: Mus musculus
```

```
<400> SEQUENCE: 411

Asp Ile Gly Trp Gln Leu Leu Arg Ile Phe Pro Lys
1               5                   10

<210> SEQ ID NO 412
<211> LENGTH: 12
<212> TYPE: PRT
<213> ORGANISM: Mus musculus

<400> SEQUENCE: 412

Phe Ser Arg Pro Leu Leu Pro Ala Thr Thr Thr Lys
1               5                   10

<210> SEQ ID NO 413
<211> LENGTH: 27
<212> TYPE: PRT
<213> ORGANISM: Mus musculus

<400> SEQUENCE: 413

Glu Gly Gly Leu Gly Pro Leu Asn Ile Pro Leu Leu Ala Asp Val Thr
1               5                   10                  15

Arg Arg Leu Ser Glu Asp Tyr Gly Val Leu Lys
            20                  25

<210> SEQ ID NO 414
<211> LENGTH: 16
<212> TYPE: PRT
<213> ORGANISM: Mus musculus

<400> SEQUENCE: 414

Thr Asp Glu Gly Ile Ala Tyr Arg Gly Leu Phe Ile Ile Asp Gly Lys
1               5                   10                  15

<210> SEQ ID NO 415
<211> LENGTH: 15
<212> TYPE: PRT
<213> ORGANISM: Mus musculus

<400> SEQUENCE: 415

Val Glu Pro Leu Arg Ala Glu Leu Gln Glu Gly Ala Arg Gln Lys
1               5                   10                  15

<210> SEQ ID NO 416
<211> LENGTH: 25
<212> TYPE: PRT
<213> ORGANISM: Mus musculus

<400> SEQUENCE: 416

Asn Ser Ala Arg Pro Arg Asp Glu Val Gln Glu Val Val Tyr Phe Ser
1               5                   10                  15

Ala Ala Asp His Glu Pro Glu Ser Lys
            20                  25

<210> SEQ ID NO 417
<211> LENGTH: 18
<212> TYPE: PRT
<213> ORGANISM: Mus musculus

<400> SEQUENCE: 417

Ala His Glu Trp Ala Arg Ala Ile Ile Glu Ser Asp Gln Glu Gln Gly
1               5                   10                  15

Arg Lys
```

<210> SEQ ID NO 418
<211> LENGTH: 24
<212> TYPE: PRT
<213> ORGANISM: Mus musculus

<400> SEQUENCE: 418

Leu Asn Phe Asn Gly Glu Gly Glu Pro Glu Glu Leu Met Val Asp Asn
1               5                   10                  15

Trp Arg Pro Ala Gln Pro Leu Lys
            20

<210> SEQ ID NO 419
<211> LENGTH: 22
<212> TYPE: PRT
<213> ORGANISM: Mus musculus

<400> SEQUENCE: 419

Val Arg Tyr Leu Glu Glu Arg Pro Phe Ala Ile Glu Gln Val Thr
1               5                   10                  15

Gly Met Leu Leu Ala Lys
            20

<210> SEQ ID NO 420
<211> LENGTH: 13
<212> TYPE: PRT
<213> ORGANISM: Mus musculus

<400> SEQUENCE: 420

Glu Arg Glu Ala Val Gln Leu Met Ala Glu Ala Glu Lys
1               5                   10

<210> SEQ ID NO 421
<211> LENGTH: 16
<212> TYPE: PRT
<213> ORGANISM: Mus musculus

<400> SEQUENCE: 421

Leu Ile Gly Thr Ala Val Pro Gln Arg Thr Ser Pro Thr Gly Pro Lys
1               5                   10                  15

<210> SEQ ID NO 422
<211> LENGTH: 9
<212> TYPE: PRT
<213> ORGANISM: Mus musculus

<400> SEQUENCE: 422

Phe Ser Arg Asp Val Phe Leu Pro Lys
1               5

<210> SEQ ID NO 423
<211> LENGTH: 39
<212> TYPE: PRT
<213> ORGANISM: Mus musculus

<400> SEQUENCE: 423

Phe Trp Glu Val Ile Ser Asp Glu His Gly Ile Asp Pro Ser Gly Asn
1               5                   10                  15

Tyr Val Gly Asp Ser Asp Leu Gln Leu Glu Arg Ile Ser Val Tyr Tyr
            20                  25                  30

Asn Glu Ala Ser Ser His Lys
        35

```
<210> SEQ ID NO 424
<211> LENGTH: 12
<212> TYPE: PRT
<213> ORGANISM: Mus musculus

<400> SEQUENCE: 424

Asp Arg Val Thr Val Phe Ser Thr Val Phe Lys
1               5                   10

<210> SEQ ID NO 425
<211> LENGTH: 27
<212> TYPE: PRT
<213> ORGANISM: Mus musculus

<400> SEQUENCE: 425

Phe Gln Asp Gly Asp Leu Thr Leu Tyr Gln Ser Asn Thr Ile Leu Arg
1               5                   10                  15

His Leu Gly Arg Thr Leu Gly Leu Tyr Gly Lys
            20                  25

<210> SEQ ID NO 426
<211> LENGTH: 14
<212> TYPE: PRT
<213> ORGANISM: Mus musculus

<400> SEQUENCE: 426

Phe Arg Gly Pro Phe Thr Asp Val Val Thr Thr Asn Leu Lys
1               5                   10

<210> SEQ ID NO 427
<211> LENGTH: 20
<212> TYPE: PRT
<213> ORGANISM: Mus musculus

<400> SEQUENCE: 427

Gln Thr Met Gln Val Asp Glu His Ala Arg Pro Gln Thr Thr Leu Glu
1               5                   10                  15

Gln Leu Gln Lys
            20

<210> SEQ ID NO 428
<211> LENGTH: 14
<212> TYPE: PRT
<213> ORGANISM: Mus musculus

<400> SEQUENCE: 428

Gly His Gln Ala Ala Glu Ile Glu Trp Leu Gly Phe Arg Lys
1               5                   10

<210> SEQ ID NO 429
<211> LENGTH: 24
<212> TYPE: PRT
<213> ORGANISM: Mus musculus

<400> SEQUENCE: 429

Gly Pro Gly Pro Gly Gly Pro Gly Gly Ala Gly Val Ala Arg Gly Gly
1               5                   10                  15

Ala Gly Gly Gly Pro Ser Gly Asp
            20

<210> SEQ ID NO 430
<211> LENGTH: 21
<212> TYPE: PRT
<213> ORGANISM: Mus musculus
```

-continued

<400> SEQUENCE: 430

Met Pro Pro Tyr Asp Glu Gln Thr Gln Ala Phe Ile Asp Ala Ala Gln
1               5                   10                  15

Glu Ala Arg Asn Lys
            20

<210> SEQ ID NO 431
<211> LENGTH: 20
<212> TYPE: PRT
<213> ORGANISM: Mus musculus

<400> SEQUENCE: 431

Gly Pro Gln Tyr Gly Ser Leu Glu Arg Ala Trp Gly Ala Ile Met Thr
1               5                   10                  15

Glu Ala Asp Lys
            20

<210> SEQ ID NO 432
<211> LENGTH: 15
<212> TYPE: PRT
<213> ORGANISM: Mus musculus

<400> SEQUENCE: 432

Thr Thr Ser Ala Ser Arg Ala Val Ser Ser Leu Ala Thr Ala Lys
1               5                   10                  15

<210> SEQ ID NO 433
<211> LENGTH: 26
<212> TYPE: PRT
<213> ORGANISM: Mus musculus

<400> SEQUENCE: 433

Asn Leu Gly Leu Glu Glu Leu Gly Ile Glu Leu Asp Pro Arg Gly Arg
1               5                   10                  15

Ile Pro Val Asn Thr Arg Phe Gln Thr Lys
            20                  25

<210> SEQ ID NO 434
<211> LENGTH: 29
<212> TYPE: PRT
<213> ORGANISM: Mus musculus

<400> SEQUENCE: 434

Arg Thr Gly Ala Ile Val Asp Val Pro Val Gly Glu Glu Leu Leu Gly
1               5                   10                  15

Arg Val Val Asp Ala Leu Gly Asn Ala Ile Asp Gly Lys
            20                  25

<210> SEQ ID NO 435
<211> LENGTH: 11
<212> TYPE: PRT
<213> ORGANISM: Mus musculus

<400> SEQUENCE: 435

Ala Gly Arg Ile Pro Glu Gln Ile Leu Gly Lys
1               5                   10

<210> SEQ ID NO 436
<211> LENGTH: 13
<212> TYPE: PRT
<213> ORGANISM: Mus musculus

```
<400> SEQUENCE: 436

Gly Pro Ser Tyr Gly Met Ser Arg Glu Val Gln Ser Lys
1               5                   10

<210> SEQ ID NO 437
<211> LENGTH: 17
<212> TYPE: PRT
<213> ORGANISM: Mus musculus

<400> SEQUENCE: 437

Ser Glu Met Ala Arg His Leu Arg Glu Tyr Gln Asp Leu Leu Asn Val
1               5                   10                  15

Lys

<210> SEQ ID NO 438
<211> LENGTH: 42
<212> TYPE: PRT
<213> ORGANISM: Mus musculus

<400> SEQUENCE: 438

Arg His Ala Val Leu Met Gly Leu Gln Pro Ala Thr Glu Tyr Ile Val
1               5                   10                  15

Asn Leu Val Ala Val His Gly Thr Val Thr Ser Glu Pro Ile Val Gly
            20                  25                  30

Ser Ile Thr Thr Gly Ile Asp Pro Pro Lys
        35                  40

<210> SEQ ID NO 439
<211> LENGTH: 15
<212> TYPE: PRT
<213> ORGANISM: Mus musculus

<400> SEQUENCE: 439

Ala Ile Ser Ser Pro Thr Val Ser Arg Leu Thr Asp Thr Thr Lys
1               5                   10                  15

<210> SEQ ID NO 440
<211> LENGTH: 21
<212> TYPE: PRT
<213> ORGANISM: Mus musculus

<400> SEQUENCE: 440

His Leu Ser Val Asn Asp Leu Pro Val Gly Arg Ser Val Glu Glu Thr
1               5                   10                  15

Leu Arg Leu Val Lys
            20

<210> SEQ ID NO 441
<211> LENGTH: 26
<212> TYPE: PRT
<213> ORGANISM: Mus musculus

<400> SEQUENCE: 441

Arg Asp Phe Ser Pro Val Pro Trp Ser Gln Tyr Phe Glu Ser Met Glu
1               5                   10                  15

Asp Val Glu Val Glu Asn Glu Thr Gly Lys
            20                  25

<210> SEQ ID NO 442
<211> LENGTH: 14
<212> TYPE: PRT
<213> ORGANISM: Mus musculus
```

```
<400> SEQUENCE: 442

Met Val Thr Ala Val Ala Ser Ala Leu Ser Ser Arg Tyr His
1               5                   10

<210> SEQ ID NO 443
<211> LENGTH: 20
<212> TYPE: PRT
<213> ORGANISM: Mus musculus

<400> SEQUENCE: 443

Gly Gln Leu Val Pro Leu Glu Thr Val Leu Asp Met Leu Arg Asp Ala
1               5                   10                  15

Met Val Ala Lys
            20

<210> SEQ ID NO 444
<211> LENGTH: 15
<212> TYPE: PRT
<213> ORGANISM: Mus musculus

<400> SEQUENCE: 444

Pro Asp Gly Ser Pro Val Phe Ile Ala Phe Arg Ser Ser Thr Lys
1               5                   10                  15

<210> SEQ ID NO 445
<211> LENGTH: 15
<212> TYPE: PRT
<213> ORGANISM: Mus musculus

<400> SEQUENCE: 445

Ala Ala Leu Glu Gln Pro Cys Glu Gly Ser Leu Thr Arg Pro Lys
1               5                   10                  15

<210> SEQ ID NO 446
<211> LENGTH: 13
<212> TYPE: PRT
<213> ORGANISM: Mus musculus

<400> SEQUENCE: 446

Arg Pro Ala Glu Asp Met Glu Glu Glu Gln Ala Phe Lys
1               5                   10

<210> SEQ ID NO 447
<211> LENGTH: 10
<212> TYPE: PRT
<213> ORGANISM: Mus musculus

<400> SEQUENCE: 447

Arg Ser Asp Leu Tyr Ala Val Glu Met Lys
1               5                   10

<210> SEQ ID NO 448
<211> LENGTH: 11
<212> TYPE: PRT
<213> ORGANISM: Mus musculus

<400> SEQUENCE: 448

Arg Phe Leu Asp Phe Ile Gly His Ile Leu Thr
1               5                   10

<210> SEQ ID NO 449
<211> LENGTH: 21
<212> TYPE: PRT
```

<213> ORGANISM: Mus musculus

<400> SEQUENCE: 449

Leu Met Arg Thr Ala Ala Asp Thr Pro Ala Ile Met Asn Trp Asp Leu
1               5                   10                  15

Phe Phe Thr Met Lys
            20

<210> SEQ ID NO 450
<211> LENGTH: 15
<212> TYPE: PRT
<213> ORGANISM: Mus musculus

<400> SEQUENCE: 450

Ala Asp Leu Glu Ala Gln Arg Asp Val Thr Tyr Glu Glu Ala Lys
1               5                   10                  15

<210> SEQ ID NO 451
<211> LENGTH: 12
<212> TYPE: PRT
<213> ORGANISM: Mus musculus

<400> SEQUENCE: 451

Gly Pro Pro Val Phe Thr Gln Glu Glu Arg Tyr Lys
1               5                   10

<210> SEQ ID NO 452
<211> LENGTH: 12
<212> TYPE: PRT
<213> ORGANISM: Mus musculus

<400> SEQUENCE: 452

Ser Arg Tyr Asp Ser Ile Asp Ser Tyr Leu Ser Lys
1               5                   10

<210> SEQ ID NO 453
<211> LENGTH: 40
<212> TYPE: PRT
<213> ORGANISM: Mus musculus

<400> SEQUENCE: 453

Arg Ile Thr Val Glu Glu Ala Leu Ala His Pro Tyr Leu Glu Gln Tyr
1               5                   10                  15

Tyr Asp Pro Thr Asp Glu Pro Val Ala Glu Glu Pro Phe Thr Phe Ala
                20                  25                  30

Met Glu Leu Asp Asp Leu Pro Lys
            35                  40

<210> SEQ ID NO 454
<211> LENGTH: 8
<212> TYPE: PRT
<213> ORGANISM: Mus musculus

<400> SEQUENCE: 454

Leu Thr Arg Ile Pro Ser Ala Lys
1               5

<210> SEQ ID NO 455
<211> LENGTH: 16
<212> TYPE: PRT
<213> ORGANISM: Mus musculus

<400> SEQUENCE: 455

Glu Gln Leu Gln Ala Leu Asn Asp Arg Phe Ala Gly Tyr Ile Asp Lys
1               5                   10                  15

<210> SEQ ID NO 456
<211> LENGTH: 16
<212> TYPE: PRT
<213> ORGANISM: Mus musculus

<400> SEQUENCE: 456

Ile His Ile Asp Leu Pro Asn Glu Gln Ala Arg Leu Asp Ile Leu Lys
1               5                   10                  15

<210> SEQ ID NO 457
<211> LENGTH: 17
<212> TYPE: PRT
<213> ORGANISM: Mus musculus

<400> SEQUENCE: 457

Gly His Arg Ile Glu Glu Val Pro Glu Leu Pro Leu Val Val Glu Asp
1               5                   10                  15

Lys

<210> SEQ ID NO 458
<211> LENGTH: 20
<212> TYPE: PRT
<213> ORGANISM: Mus musculus

<400> SEQUENCE: 458

Asn Leu Asp Gln Glu Gln Leu Ser Gln Val Leu Asp Ala Met Phe Glu
1               5                   10                  15

Arg Ile Val Lys
            20

<210> SEQ ID NO 459
<211> LENGTH: 16
<212> TYPE: PRT
<213> ORGANISM: Mus musculus

<400> SEQUENCE: 459

Arg Ser Ala Glu Glu Ala Ala Asp Leu Pro Thr Lys Pro Thr Lys
1               5                   10                  15

<210> SEQ ID NO 460
<211> LENGTH: 19
<212> TYPE: PRT
<213> ORGANISM: Mus musculus

<400> SEQUENCE: 460

Glu Thr Ile Pro Leu Gln Glu Thr Ser Leu Tyr Thr Gln Asp Arg Leu
1               5                   10                  15

Gly Leu Lys

<210> SEQ ID NO 461
<211> LENGTH: 20
<212> TYPE: PRT
<213> ORGANISM: Mus musculus

<400> SEQUENCE: 461

Glu Ser Gly Arg Phe Gln Asp Val Gly Pro Gln Ala Pro Val Gly Ser
1               5                   10                  15

Val Tyr Gln Lys
            20

<210> SEQ ID NO 462
<211> LENGTH: 18
<212> TYPE: PRT
<213> ORGANISM: Mus musculus

<400> SEQUENCE: 462

Phe Ala Leu Ile Thr Trp Ile Gly Glu Asn Val Ser Gly Leu Gln Arg
1               5                   10                  15

Ala Lys

<210> SEQ ID NO 463
<211> LENGTH: 13
<212> TYPE: PRT
<213> ORGANISM: Mus musculus

<400> SEQUENCE: 463

Ile Leu Asn Leu Arg Val Phe Glu Asp Glu Ser Gly Lys
1               5                   10

<210> SEQ ID NO 464
<211> LENGTH: 18
<212> TYPE: PRT
<213> ORGANISM: Mus musculus

<400> SEQUENCE: 464

Ala Val Asp Arg Pro Met Leu Pro Gln Glu Tyr Ala Val Glu Ala His
1               5                   10                  15

Phe Lys

<210> SEQ ID NO 465
<211> LENGTH: 14
<212> TYPE: PRT
<213> ORGANISM: Mus musculus

<400> SEQUENCE: 465

Ala Ala Leu Leu Asp Gln Ile Arg Glu Gly Ala Gln Leu Lys
1               5                   10

<210> SEQ ID NO 466
<211> LENGTH: 18
<212> TYPE: PRT
<213> ORGANISM: Mus musculus

<400> SEQUENCE: 466

Arg His Phe Phe Ser Asp Tyr Leu Met Gly Phe Ile Asn Ser Gly Ile
1               5                   10                  15

Leu Lys

<210> SEQ ID NO 467
<211> LENGTH: 27
<212> TYPE: PRT
<213> ORGANISM: Mus musculus

<400> SEQUENCE: 467

Ala Pro Gly Thr Val Leu Ser Gln Glu Glu Val Glu Gly Glu Leu Ala
1               5                   10                  15

Glu Leu Ala Met Gly Phe Leu Gly Ser Arg Lys
                20                  25

<210> SEQ ID NO 468
<211> LENGTH: 38
<212> TYPE: PRT

<213> ORGANISM: Mus musculus

<400> SEQUENCE: 468

Ile Val Ala Pro Ile Ser Asp Ser Pro Lys Pro Pro Gln Arg Val
1               5                   10                  15

Thr Leu Thr Leu Pro Val Leu Asn Ala Ala Arg Thr Val Ile Phe Val
            20                  25                  30

Ala Thr Gly Glu Gly Lys
        35

<210> SEQ ID NO 469
<211> LENGTH: 25
<212> TYPE: PRT
<213> ORGANISM: Mus musculus

<400> SEQUENCE: 469

Arg Ala Ser Val Arg Met Ile Ser Asp Leu Ile Ala Gly Gly Ile Gln
1               5                   10                  15

Pro Leu Gln Asn Leu Ser Val Leu Lys
            20                  25

<210> SEQ ID NO 470
<211> LENGTH: 24
<212> TYPE: PRT
<213> ORGANISM: Mus musculus

<400> SEQUENCE: 470

Gly Ser Asp Gln Ser Glu Asn Val Asp Arg Gly Ala Gly Ser Ile Arg
1               5                   10                  15

Glu Ala Gly Gly Ala Phe Gly Lys
            20

<210> SEQ ID NO 471
<211> LENGTH: 9
<212> TYPE: PRT
<213> ORGANISM: Mus musculus

<400> SEQUENCE: 471

Phe Gly Val Leu Phe Arg Asp Asp Lys
1               5

<210> SEQ ID NO 472
<211> LENGTH: 16
<212> TYPE: PRT
<213> ORGANISM: Mus musculus

<400> SEQUENCE: 472

Ile Arg Gly Ser Leu Ala Arg Ala Ala Leu Gln Glu Leu Leu Ser Lys
1               5                   10                  15

<210> SEQ ID NO 473
<211> LENGTH: 19
<212> TYPE: PRT
<213> ORGANISM: Mus musculus

<400> SEQUENCE: 473

Ala Leu Thr Thr Met Gly Phe Arg Leu Ser Pro Gln Ala Val Asn Ser
1               5                   10                  15

Ile Ala Lys

<210> SEQ ID NO 474
<211> LENGTH: 10

<212> TYPE: PRT
<213> ORGANISM: Mus musculus

<400> SEQUENCE: 474

Arg Asp Leu Pro Asn Ala Leu Asp Glu Lys
1               5                   10

<210> SEQ ID NO 475
<211> LENGTH: 15
<212> TYPE: PRT
<213> ORGANISM: Homo sapiens

<400> SEQUENCE: 475

Pro Gly Val Val His Val Ile Asp Ile Asp Arg Gly Glu Glu Lys
1               5                   10                  15

<210> SEQ ID NO 476
<211> LENGTH: 26
<212> TYPE: PRT
<213> ORGANISM: Homo sapiens

<400> SEQUENCE: 476

Ile Pro Val Gly Pro Glu Thr Leu Gly Arg Ile Met Asn Val Ile Gly
1               5                   10                  15

Glu Pro Ile Asp Glu Arg Gly Pro Ile Lys
            20                  25

<210> SEQ ID NO 477
<211> LENGTH: 26
<212> TYPE: PRT
<213> ORGANISM: Homo sapiens

<400> SEQUENCE: 477

Ser Val His Arg Gly Glu Val Pro Cys Thr Val Thr Thr Ala Ser Pro
1               5                   10                  15

Leu Asp Asp Ala Val Leu Ser Glu Leu Lys
            20                  25

<210> SEQ ID NO 478
<211> LENGTH: 12
<212> TYPE: PRT
<213> ORGANISM: Homo sapiens

<400> SEQUENCE: 478

Glu Leu Glu Glu Asp Phe Ile Arg Ser Glu Leu Lys
1               5                   10

<210> SEQ ID NO 479
<211> LENGTH: 25
<212> TYPE: PRT
<213> ORGANISM: Homo sapiens

<400> SEQUENCE: 479

Glu Gly Asn Ala Ser Gly Val Ser Leu Leu Gly Ala Leu Asp Thr Ile
1               5                   10                  15

Leu Pro Pro Thr Arg Pro Thr Asp Lys
            20                  25

<210> SEQ ID NO 480
<211> LENGTH: 38
<212> TYPE: PRT
<213> ORGANISM: Homo sapiens

<400> SEQUENCE: 480

-continued

Gly Tyr Phe Glu Asp Arg Arg Pro Ser Ala Asn Cys Asp Pro Tyr Ala
1               5                   10                  15

Val Thr Glu Ala Ile Val Arg Thr Cys Leu Leu Asn Glu Thr Gly Asp
            20                  25                  30

Glu Pro Phe Gln Tyr Lys
        35

<210> SEQ ID NO 481
<211> LENGTH: 17
<212> TYPE: PRT
<213> ORGANISM: Homo sapiens

<400> SEQUENCE: 481

Arg Leu Ile Gly Arg Arg Phe Asp Asp Ala Val Val Gln Ser Asp Met
1               5                   10                  15

Lys

<210> SEQ ID NO 482
<211> LENGTH: 32
<212> TYPE: PRT
<213> ORGANISM: Homo sapiens

<400> SEQUENCE: 482

Leu Gly Arg Leu Leu Val Val Tyr Pro Trp Thr Gln Arg Tyr Phe Asp
1               5                   10                  15

Ser Phe Gly Asp Leu Ser Ser Ala Ser Ala Ile Met Gly Asn Ala Lys
            20                  25                  30

<210> SEQ ID NO 483
<211> LENGTH: 18
<212> TYPE: PRT
<213> ORGANISM: Homo sapiens

<400> SEQUENCE: 483

Glu Ser Leu Leu Phe Glu Gly Arg Ile Thr Pro Glu Leu Leu Thr Arg
1               5                   10                  15

Gly Lys

<210> SEQ ID NO 484
<211> LENGTH: 23
<212> TYPE: PRT
<213> ORGANISM: Homo sapiens

<400> SEQUENCE: 484

Arg Ser Thr Ile Thr Ser Arg Glu Val Gln Thr Ala Val Arg Leu Leu
1               5                   10                  15

Leu Pro Gly Glu Leu Ala Lys
            20

<210> SEQ ID NO 485
<211> LENGTH: 9
<212> TYPE: PRT
<213> ORGANISM: Homo sapiens

<400> SEQUENCE: 485

Cys Arg Glu Val Ala Glu Asn Cys Lys
1               5

<210> SEQ ID NO 486
<211> LENGTH: 19
<212> TYPE: PRT

-continued

<213> ORGANISM: Homo sapiens

<400> SEQUENCE: 486

Cys Arg Ala Pro Glu Val Ser Gln Tyr Ile Tyr Gln Val Tyr Asp Ser
1               5                   10                  15

Ile Leu Lys

<210> SEQ ID NO 487
<211> LENGTH: 40
<212> TYPE: PRT
<213> ORGANISM: Homo sapiens

<400> SEQUENCE: 487

Gly Ile Leu Arg Thr Pro Asp Thr Ile Arg Arg Phe Gln Ser Val Pro
1               5                   10                  15

Ala Gln Pro Gly Gln Thr Ser Pro Leu Leu Gln Tyr Phe Gly Ile Leu
            20                  25                  30

Leu Asp Gln Gly Gln Leu Asn Lys
        35                  40

<210> SEQ ID NO 488
<211> LENGTH: 14
<212> TYPE: PRT
<213> ORGANISM: Homo sapiens

<400> SEQUENCE: 488

Pro Ile Thr Ile Phe Gln Glu Arg Asp Pro Thr Asn Ile Lys
1               5                   10

<210> SEQ ID NO 489
<211> LENGTH: 14
<212> TYPE: PRT
<213> ORGANISM: Homo sapiens

<400> SEQUENCE: 489

Gly Cys Asp Val Val Ile Pro Ala Gly Val Pro Arg Lys
1               5                   10

<210> SEQ ID NO 490
<211> LENGTH: 22
<212> TYPE: PRT
<213> ORGANISM: Homo sapiens

<400> SEQUENCE: 490

His Arg Asp Thr Gly Ile Leu Asp Ser Ile Gly Arg Phe Phe Ser Gly
1               5                   10                  15

Asp Arg Gly Ala Pro Lys
            20

<210> SEQ ID NO 491
<211> LENGTH: 16
<212> TYPE: PRT
<213> ORGANISM: Homo sapiens

<400> SEQUENCE: 491

Glu Arg Leu Asp Gln Pro Met Thr Glu Ile Val Ser Arg Val Ser Lys
1               5                   10                  15

<210> SEQ ID NO 492
<211> LENGTH: 20
<212> TYPE: PRT
<213> ORGANISM: Homo sapiens -continued

```
<400> SEQUENCE: 492

Leu Leu Val Ser Ser Glu Asp Tyr Gly Arg Asp Leu Thr Gly Val Gln
1               5                   10                  15

Asn Leu Arg Lys
            20

<210> SEQ ID NO 493
<211> LENGTH: 14
<212> TYPE: PRT
<213> ORGANISM: Homo sapiens

<400> SEQUENCE: 493

Val Ala Val Thr Pro Pro Gly Leu Ala Arg Glu Asp Trp Lys
1               5                   10

<210> SEQ ID NO 494
<211> LENGTH: 11
<212> TYPE: PRT
<213> ORGANISM: Homo sapiens

<400> SEQUENCE: 494

Val Arg Ile Gln Thr Gln Pro Gly Tyr Ala Asn
1               5                   10

<210> SEQ ID NO 495
<211> LENGTH: 16
<212> TYPE: PRT
<213> ORGANISM: Homo sapiens

<400> SEQUENCE: 495

Arg Ile Glu Arg Glu Leu Ala Glu Ala Gln Asp Asp Ser Ile Leu Lys
1               5                   10                  15

<210> SEQ ID NO 496
<211> LENGTH: 22
<212> TYPE: PRT
<213> ORGANISM: Homo sapiens

<400> SEQUENCE: 496

His Arg Asp Thr Gly Ile Leu Asp Ser Ile Gly Arg Phe Phe Gly Gly
1               5                   10                  15

Asp Arg Gly Ala Pro Lys
            20

<210> SEQ ID NO 497
<211> LENGTH: 32
<212> TYPE: PRT
<213> ORGANISM: Homo sapiens

<400> SEQUENCE: 497

Glu Ala Phe Gln Asn Ala Tyr Leu Glu Leu Gly Gly Leu Gly Glu Arg
1               5                   10                  15

Val Leu Gly Phe Cys His Tyr Tyr Leu Pro Glu Gln Phe Pro Lys
            20                  25                  30

<210> SEQ ID NO 498
<211> LENGTH: 24
<212> TYPE: PRT
<213> ORGANISM: Homo sapiens

<400> SEQUENCE: 498

Arg Ile His Val Leu Pro Ile Asp Asp Thr Val Glu Gly Ile Thr Gly
1               5                   10                  15
```

Asn Leu Phe Glu Val Tyr Leu Lys
            20

<210> SEQ ID NO 499
<211> LENGTH: 36
<212> TYPE: PRT
<213> ORGANISM: Homo sapiens

<400> SEQUENCE: 499

His Val Pro Arg Ala Val Phe Val Asp Leu Pro Thr Val Ile Asp
1               5                   10                  15

Glu Ile Arg Asn Gly Pro Tyr Arg Gln Leu Phe His Pro Glu Gln Leu
            20                  25                  30

Ile Thr Gly Lys
        35

<210> SEQ ID NO 500
<211> LENGTH: 41
<212> TYPE: PRT
<213> ORGANISM: Homo sapiens

<400> SEQUENCE: 500

Ala Ile Leu Val Asp Leu Glu Pro Gly Thr Met Asp Ser Val Arg Ser
1               5                   10                  15

Gly Ala Phe Gly His Leu Phe Arg Pro Asp Asn Phe Ile Phe Gly Gln
            20                  25                  30

Ser Gly Ala Gly Asn Asn Trp Ala Lys
        35                  40

<210> SEQ ID NO 501
<211> LENGTH: 24
<212> TYPE: PRT
<213> ORGANISM: Homo sapiens

<400> SEQUENCE: 501

Ala Val Leu Asp Val Ala Glu Thr Gly Thr Glu Ala Ala Ala Thr
1               5                   10                  15

Gly Val Ile Gly Gly Ile Arg Lys
            20

<210> SEQ ID NO 502
<211> LENGTH: 15
<212> TYPE: PRT
<213> ORGANISM: Homo sapiens

<400> SEQUENCE: 502

Gly Phe Pro Val Val Leu Asp Ser Pro Arg Asp Gly Asn Leu Lys
1               5                   10                  15

<210> SEQ ID NO 503
<211> LENGTH: 22
<212> TYPE: PRT
<213> ORGANISM: Homo sapiens

<400> SEQUENCE: 503

Gly Pro Asp Arg Leu Pro Ala Gly Tyr Glu Ile Val Leu Tyr Ile Ser
1               5                   10                  15

Met Ser Asp Ser Asp Lys
            20

<210> SEQ ID NO 504

```
<211> LENGTH: 12
<212> TYPE: PRT
<213> ORGANISM: Homo sapiens

<400> SEQUENCE: 504

Arg Phe Ser Met Val Ile Asp Asn Gly Ile Val Lys
1               5                   10

<210> SEQ ID NO 505
<211> LENGTH: 18
<212> TYPE: PRT
<213> ORGANISM: Homo sapiens

<400> SEQUENCE: 505

Ala Gln Gln Arg Asp Val Asp Gly Ala Thr Leu Ala Arg Leu Asp Leu
1               5                   10                  15

Glu Lys

<210> SEQ ID NO 506
<211> LENGTH: 22
<212> TYPE: PRT
<213> ORGANISM: Homo sapiens

<400> SEQUENCE: 506

Ala Val Thr Glu Leu Asn Glu Pro Leu Ser Asn Glu Asp Arg Asn Leu
1               5                   10                  15

Leu Ser Val Ala Tyr Lys
            20

<210> SEQ ID NO 507
<211> LENGTH: 22
<212> TYPE: PRT
<213> ORGANISM: Homo sapiens

<400> SEQUENCE: 507

Ala Val Thr Glu Gln Gly Ala Glu Leu Ser Asn Glu Glu Arg Asn Leu
1               5                   10                  15

Leu Ser Val Ala Tyr Lys
            20

<210> SEQ ID NO 508
<211> LENGTH: 26
<212> TYPE: PRT
<213> ORGANISM: Homo sapiens

<400> SEQUENCE: 508

Leu Glu Ala Pro Asp Ala Asp Glu Leu Pro Arg Ser Asp Phe Asp Pro
1               5                   10                  15

Gly Gln Asp Thr Tyr Gln His Pro Pro Lys
            20                  25

<210> SEQ ID NO 509
<211> LENGTH: 11
<212> TYPE: PRT
<213> ORGANISM: Homo sapiens

<400> SEQUENCE: 509

Leu Ser Glu Glu Leu Ser Gly Gly Arg Leu Lys
1               5                   10

<210> SEQ ID NO 510
<211> LENGTH: 15
<212> TYPE: PRT
```

```
<213> ORGANISM: Homo sapiens

<400> SEQUENCE: 510

Ile Leu Ile Pro Trp Leu Leu Ser Pro Glu Arg Leu Asp Ile Lys
1               5                   10                  15

<210> SEQ ID NO 511
<211> LENGTH: 21
<212> TYPE: PRT
<213> ORGANISM: Homo sapiens

<400> SEQUENCE: 511

Leu Arg Phe Pro Ala Glu Asp Glu Phe Pro Asp Leu Ser Ser His Asn
1               5                   10                  15

Asn His Met Ala Lys
            20

<210> SEQ ID NO 512
<211> LENGTH: 13
<212> TYPE: PRT
<213> ORGANISM: Homo sapiens

<400> SEQUENCE: 512

Ile Thr Arg Thr Ser Phe Leu Asp Asp Ala Phe Arg Lys
1               5                   10

<210> SEQ ID NO 513
<211> LENGTH: 23
<212> TYPE: PRT
<213> ORGANISM: Homo sapiens

<400> SEQUENCE: 513

Asp Asn Phe Thr Leu Ile Pro Glu Gly Thr Asn Gly Thr Glu Glu Arg
1               5                   10                  15

Met Ser Val Ile Trp Asp Lys
            20

<210> SEQ ID NO 514
<211> LENGTH: 16
<212> TYPE: PRT
<213> ORGANISM: Homo sapiens

<400> SEQUENCE: 514

Met Val Glu Gly Phe Phe Asp Arg Gly Ala Ser Ile Val Glu Asp Lys
1               5                   10                  15

<210> SEQ ID NO 515
<211> LENGTH: 16
<212> TYPE: PRT
<213> ORGANISM: Homo sapiens

<400> SEQUENCE: 515

Gly Asp Tyr Tyr Arg Tyr Leu Ala Glu Val Ala Ala Gly Asp Asp Lys
1               5                   10                  15

<210> SEQ ID NO 516
<211> LENGTH: 12
<212> TYPE: PRT
<213> ORGANISM: Homo sapiens

<400> SEQUENCE: 516

Arg Ala Leu Val Phe Gln Pro Val Thr Glu Leu Lys
1               5                   10
```

```
<210> SEQ ID NO 517
<211> LENGTH: 36
<212> TYPE: PRT
<213> ORGANISM: Homo sapiens

<400> SEQUENCE: 517

Gly Val Pro Leu Tyr Arg His Ile Ala Asp Leu Ala Gly Asn Pro Glu
1               5                   10                  15

Val Ile Leu Pro Val Pro Ala Phe Asn Val Ile Asn Gly Gly Ser His
            20                  25                  30

Ala Gly Asn Lys
        35

<210> SEQ ID NO 518
<211> LENGTH: 33
<212> TYPE: PRT
<213> ORGANISM: Homo sapiens

<400> SEQUENCE: 518

Asn Ser Pro Leu Val Ser Arg Leu Thr Leu Tyr Asp Ile Ala His Thr
1               5                   10                  15

Pro Gly Val Ala Ala Asp Leu Ser His Ile Glu Thr Arg Ala Asn Val
            20                  25                  30

Lys

<210> SEQ ID NO 519
<211> LENGTH: 13
<212> TYPE: PRT
<213> ORGANISM: Homo sapiens

<400> SEQUENCE: 519

His Glu Gly Phe Glu Asp Leu Ala Ala Leu Gly Asp Lys
1               5                   10

<210> SEQ ID NO 520
<211> LENGTH: 22
<212> TYPE: PRT
<213> ORGANISM: Homo sapiens

<400> SEQUENCE: 520

Leu Phe Val Thr Asn Asp Ala Ala Thr Ile Leu Arg Glu Leu Glu Val
1               5                   10                  15

Gln His Pro Ala Ala Lys
            20

<210> SEQ ID NO 521
<211> LENGTH: 10
<212> TYPE: PRT
<213> ORGANISM: Homo sapiens

<400> SEQUENCE: 521

Gly Arg Gly Ile Thr Gly Ile Glu Asp Lys
1               5                   10

<210> SEQ ID NO 522
<211> LENGTH: 13
<212> TYPE: PRT
<213> ORGANISM: Homo sapiens

<400> SEQUENCE: 522

Pro His Ser Val Ser Leu Asn Asp Thr Glu Thr Arg Lys
1               5                   10
```

<210> SEQ ID NO 523
<211> LENGTH: 19
<212> TYPE: PRT
<213> ORGANISM: Homo sapiens

<400> SEQUENCE: 523

Met Asp Ile Arg Gly Ala Val Asp Ala Val Pro Thr Asn Ile Ile
1               5                   10                  15

Ala Ala Lys

<210> SEQ ID NO 524
<211> LENGTH: 17
<212> TYPE: PRT
<213> ORGANISM: Homo sapiens

<400> SEQUENCE: 524

Thr Asp Asp Tyr Gly Arg Asp Leu Ser Ser Val Gln Thr Leu Leu Thr
1               5                   10                  15

Lys

<210> SEQ ID NO 525
<211> LENGTH: 15
<212> TYPE: PRT
<213> ORGANISM: Homo sapiens

<400> SEQUENCE: 525

Arg Leu Val Pro Gly Gly Gly Ala Thr Glu Ile Glu Leu Ala Lys
1               5                   10                  15

<210> SEQ ID NO 526
<211> LENGTH: 16
<212> TYPE: PRT
<213> ORGANISM: Homo sapiens

<400> SEQUENCE: 526

Arg Gly Phe Gly Phe Val Thr Phe Asp Asp His Asp Pro Val Asp Lys
1               5                   10                  15

<210> SEQ ID NO 527
<211> LENGTH: 13
<212> TYPE: PRT
<213> ORGANISM: Homo sapiens

<400> SEQUENCE: 527

Ile Ala Thr Pro Arg Gly Ala Ala Ser Pro Ala Gln Lys
1               5                   10

<210> SEQ ID NO 528
<211> LENGTH: 15
<212> TYPE: PRT
<213> ORGANISM: Homo sapiens

<400> SEQUENCE: 528

Arg Val Val Ala Glu Pro Val Glu Leu Ala Gln Glu Phe Arg Lys
1               5                   10                  15

<210> SEQ ID NO 529
<211> LENGTH: 14
<212> TYPE: PRT
<213> ORGANISM: Homo sapiens

<400> SEQUENCE: 529

Gly Ala Asp Glu Ala Ala Leu Ala Arg Ala Glu Leu Glu Lys
1               5                   10

<210> SEQ ID NO 530
<211> LENGTH: 21
<212> TYPE: PRT
<213> ORGANISM: Homo sapiens

<400> SEQUENCE: 530

Gln Ile Val Trp Asn Gly Pro Val Gly Val Phe Glu Trp Glu Ala Phe
1               5                   10                  15

Ala Arg Gly Thr Lys
            20

<210> SEQ ID NO 531
<211> LENGTH: 13
<212> TYPE: PRT
<213> ORGANISM: Homo sapiens

<400> SEQUENCE: 531

Pro Met Gln Phe Leu Gly Asp Glu Glu Thr Val Arg Lys
1               5                   10

<210> SEQ ID NO 532
<211> LENGTH: 16
<212> TYPE: PRT
<213> ORGANISM: Homo sapiens

<400> SEQUENCE: 532

Arg Gly Phe Gly Phe Val Tyr Phe Gln Ser His Asp Ala Ala Asp Lys
1               5                   10                  15

<210> SEQ ID NO 533
<211> LENGTH: 17
<212> TYPE: PRT
<213> ORGANISM: Homo sapiens

<400> SEQUENCE: 533

Val Pro Asp Phe Ser Asp Tyr Arg Arg Ala Glu Val Leu Asp Ser Thr
1               5                   10                  15

Lys

<210> SEQ ID NO 534
<211> LENGTH: 14
<212> TYPE: PRT
<213> ORGANISM: Homo sapiens

<400> SEQUENCE: 534

Arg Asp Val Ala Gly Asp Ala Ser Glu Ser Ala Leu Leu Lys
1               5                   10

<210> SEQ ID NO 535
<211> LENGTH: 11
<212> TYPE: PRT
<213> ORGANISM: Homo sapiens

<400> SEQUENCE: 535

Asp Leu Thr Ser Val Met Arg Leu Leu Ser Lys
1               5                   10

<210> SEQ ID NO 536
<211> LENGTH: 12
<212> TYPE: PRT
<213> ORGANISM: Homo sapiens

```
<400> SEQUENCE: 536

Phe Met Glu Leu Leu Glu Pro Leu Ser Glu Arg Lys
1               5                   10

<210> SEQ ID NO 537
<211> LENGTH: 19
<212> TYPE: PRT
<213> ORGANISM: Homo sapiens

<400> SEQUENCE: 537

Glu Arg Val Glu Ala Val Asn Met Ala Glu Gly Ile Ile His Asp Thr
1               5                   10                  15

Glu Thr Lys

<210> SEQ ID NO 538
<211> LENGTH: 27
<212> TYPE: PRT
<213> ORGANISM: Homo sapiens

<400> SEQUENCE: 538

His Val Leu Ser Gly Thr Leu Gly Ile Pro Glu His Thr Tyr Arg Ser
1               5                   10                  15

Arg Val Thr Leu Ser Asn Gln Pro Tyr Ile Lys
            20                  25

<210> SEQ ID NO 539
<211> LENGTH: 19
<212> TYPE: PRT
<213> ORGANISM: Homo sapiens

<400> SEQUENCE: 539

Met Ile Ile Tyr Arg Asp Leu Ile Ser His Asp Glu Leu Phe Ser Asp
1               5                   10                  15

Ile Tyr Lys

<210> SEQ ID NO 540
<211> LENGTH: 13
<212> TYPE: PRT
<213> ORGANISM: Homo sapiens

<400> SEQUENCE: 540

Thr Gly Gly Ala Val Asp Arg Leu Thr Asp Thr Ser Lys
1               5                   10

<210> SEQ ID NO 541
<211> LENGTH: 25
<212> TYPE: PRT
<213> ORGANISM: Homo sapiens

<400> SEQUENCE: 541

Ser Ser Glu Glu Ala Val Arg Glu Val His Arg Leu Ile Glu Gly Arg
1               5                   10                  15

Ala Pro Val Ile Ser Gly Val Thr Lys
            20                  25

<210> SEQ ID NO 542
<211> LENGTH: 10
<212> TYPE: PRT
<213> ORGANISM: Homo sapiens

<400> SEQUENCE: 542
```

```
Leu Leu Ile Ile Gly Thr Thr Ser Arg Lys
1               5                   10

<210> SEQ ID NO 543
<211> LENGTH: 20
<212> TYPE: PRT
<213> ORGANISM: Homo sapiens

<400> SEQUENCE: 543

Trp Gly Asp Pro Val Thr Arg Val Leu Asp Asp Gly Glu Leu Val
1               5                   10                  15

Gln Gln Thr Lys
            20

<210> SEQ ID NO 544
<211> LENGTH: 15
<212> TYPE: PRT
<213> ORGANISM: Homo sapiens

<400> SEQUENCE: 544

Ile Thr Arg Val Glu Met Leu Glu Ile Ile Glu Ala Ile Tyr Lys
1               5                   10                  15

<210> SEQ ID NO 545
<211> LENGTH: 17
<212> TYPE: PRT
<213> ORGANISM: Homo sapiens

<400> SEQUENCE: 545

Phe Pro Arg Tyr Ala Glu Ile Val His Leu Thr Leu Pro Asp Gly Thr
1               5                   10                  15

Lys

<210> SEQ ID NO 546
<211> LENGTH: 16
<212> TYPE: PRT
<213> ORGANISM: Homo sapiens

<400> SEQUENCE: 546

Gly Asp Ala Arg Pro Ala Glu Ile Asp Ser Leu Trp Glu Ile Ser Lys
1               5                   10                  15

<210> SEQ ID NO 547
<211> LENGTH: 19
<212> TYPE: PRT
<213> ORGANISM: Homo sapiens

<400> SEQUENCE: 547

Ser Val Val Leu Met Ser His Leu Gly Arg Pro Asp Gly Val Pro Met
1               5                   10                  15

Pro Asp Lys
```